US010787676B2

(12) United States Patent
Li et al.

(10) Patent No.: US 10,787,676 B2
(45) Date of Patent: *Sep. 29, 2020

(54) METHODS OF CONTROLLING SEED SIZE IN PLANTS

(71) Applicant: Institute of Genetics and Developmental Biology Chinese Academy of Sciences, Beijing (CN)

(72) Inventors: Yunhai Li, Beijing (CN); Wenjuan Fang, Beijing (CN); Zhibiao Wang, Beijing (CN); Rongfeng Cui, Beijing (CN)

(73) Assignee: Institute of Genetics and Development Biology Chinese Academy of Sciences, Beijing (CN)

( * ) Notice: Subject to any disclaimer, the term of this patent is extended or adjusted under 35 U.S.C. 154(b) by 107 days.

This patent is subject to a terminal disclaimer.

(21) Appl. No.: 15/628,101

(22) Filed: Jun. 20, 2017

(65) Prior Publication Data

US 2017/0298377 A1 Oct. 19, 2017

Related U.S. Application Data

(62) Division of application No. 14/372,582, filed as application No. PCT/GB2013/050072 on Jan. 15, 2013, now Pat. No. 9,708,625.

(60) Provisional application No. 61/588,792, filed on Jan. 20, 2012.

(30) Foreign Application Priority Data

Feb. 9, 2012 (GB) .................................. 1202258.8

(51) Int. Cl.
*C12N 15/82* (2006.01)
*C12N 9/02* (2006.01)

(52) U.S. Cl.
CPC ....... *C12N 15/8261* (2013.01); *C12N 9/0071* (2013.01); *C12N 9/0077* (2013.01); *C12N 15/827* (2013.01); *C12N 15/8218* (2013.01); *Y02A 40/146* (2018.01)

(58) Field of Classification Search
None
See application file for complete search history.

(56) References Cited

U.S. PATENT DOCUMENTS

2003/0092014 A1* 5/2003 Coleman .............. C12N 9/0073
435/6.12

FOREIGN PATENT DOCUMENTS

| KR | 100877729 | 1/2009 |
| WO | 02099063 | 12/2002 |
| WO | 09047525 | 4/2009 |

OTHER PUBLICATIONS

Li et al, Genes Dev. 22, 1331-1336, 2008 (Year: 2008).*
Ito, Toshiro et al., "Overexpression of a Gene Encoding a Cytochrome P450, CYP78A9, Induces Large and Seedless Fruit in *Arabidopsis*", The Plant Cell, vol. 12, 1541-1550, Sep. 2000.
Ma, Meng et al., "Expression of TaCYP78A3, a gene encoding cytochrome P450 CYP78A3 protein in wheat (*Triticum aestivum* L.), affects seed size", The Plant Jounal (2015) 83, 312-325.
Ma, Meng et al., "TaCYP78A5 regulates seed size in wheat (*Triticum aestivum*)" Journal of Experimental Botany, vol. 27, No. 5 pp. 1397-1410, 2016. 2016.
Wang, Xiaobo et al., "Evolution and association analysis of GmCYP78A10 gene with seed size/weight and pod number in soybean", Mol Biol Rep (2015) 42:489-496.
Yang, Weibing et al., "Control of Rice Embryo Development, Shoot Apical Meristem Maintenance, and Grain Yield by a Novel Cytochrome P450", Molecular Plant, vol. 6, No. 6, pp. 1945-1960, Nov. 2013.
Zhang, Xiangqian et al., "Epigenetic Mutation of RAV6 Affects Leaf Angle and Seed Size in Rice", Plant Physiology, Nov. 2015, vol. 169, pp. 2118-2128.
Zhao, Boatian et al., *Arabidopsis* KLU homologue GmCYP78A72 regulates seed size in soybean, Plant Mol Biol (2016) 90:33-47.
International Search Report for PCT/GB2013/050072 dated Jun. 26, 2013.
Adamski et al., "Local Maternal Control of Seed Size by Kluh/CYP78A5-Dependent Growth Signaling", Proceedings of the National Academy of Science of the United States of America, vol. 106, No. 47, Nov. 2009, pp. 20115-20120.
Fang et al., "Maternal Control of Seed Size by EOD3/CYP78A6 in *Arabidopsis thaliana*", Plant Journal vol. 70, No. 6, Jun. 2012, pp. 929-939.
Zondlo et al., "CYP78AS Encodes a Cytochrome P450 That Marks the Shoot apical meristem boundary in *Arabidopsis*" The Plant Journal, vol. 19, No. 3, Aug. 1999, pp. 259-268.

* cited by examiner

*Primary Examiner* — Elizabeth F McElwain
(74) *Attorney, Agent, or Firm* — McKee, Voorhees & Sease, PLC

(57) ABSTRACT

This invention relates to the identification of a regulator protein (termed CYP78A6, or EOD3) which controls the size of plant seeds and organs in *Arabidopsis* and other plants. Manipulation of CYP78A protein expression may useful, for example, in improving crop yield and increasing plant biomass.

15 Claims, 19 Drawing Sheets
Specification includes a Sequence Listing.

SEQUENCE LISTING

<160> NUMBER OF SEQ ID NOS: 131

<210> SEQ ID NO 1
<211> LENGTH: 1593
<212> TYPE: DNA
<213> ORGANISM: Arabidopsis thaliana

<400> SEQUENCE: 1

```
atggctacga aactcgaaag ctccttaatc tttgcccttt tgtccaaatg cagcgttcta      60
agccaaacca accttgcctt ctccctcctc gccgtcacaa tcatctggct cgccatatct     120
ctcttcttat ggacctatcc cggtggacct gcttggggga atacctctt cggccggtta      180
atatccggtt catacaaaac cggaaacgtt attcccggtc aaaaggctt ccctttggtt      240
ggaagcatgt cactcatgtc aagcactcta gctcaccgac gaatcgctga tgcagctgag     300
aaattcggag ccaagaggct catggctttc agcttaggag agactcgcgt gatcgtcacg     360
tgcaatcccg acgtagcgaa agagattctg aatagcccgg ttttttgctga tcgaccggtt     420
aaagaatcgg cttactcact gatgtttaac agagcaattg gttttgcacc acacggtgtt     480
tactggcgaa cgcttcgccg tatcgcttcg aaccatctct ttagtacaaa acaaatcaga     540
agagccgaga cgcaacgacg agtgatctca agccagatgg ttgagtttct tgaaaaacag     600
agtagtaacg aaccctgttt tgttcgtgag ttgcttaaaa cggcgtcgct taacaacatg     660
atgtgctctg tattcggaca agagtatgag cttgaaaaaa accatgttga gttacgtgaa     720
atggtcgaag aaggttatga tttgctcgga acgttgaatt ggactgatca ccttccttgg     780
ctatcggagt ttgatcctca aagactccgg tctagatgtt ccacactcgt accaaaggta     840
aaccggtttg tatcccggat tatatccgaa caccgtaatc aaaccggtga tttgcctcgt     900
gatttcgtcg acgttttgct ctccctccat ggttcagata aattatccga cccggacata     960
```

```
atcgccgttc tttgggagat gatattcaga ggaacagaca cagttgcggt cttaatcgag    1020
tggatcctcg ctaggatggt ccttcatcca gatatgcaat caacggtaca aaacgagctg    1080
gatcaagtag tcgggaaatc aagagcccta gatgaatctg acttggcttc acttccatat    1140
ctaacggctg tggtgaaaga agtattgagg cttcatcctc caggcccact tctatcatgg    1200
gcccgtttgg ccataacaga cacgatcgtt gatggtcgtc ttgttccggc agggaccaca    1260
gcaatggtga acatgtgggc cgtatcgcat gatccacacg tgtgggttga tccttttggag   1320 tttaaacctg agaggttcgt ggcaaaagaa ggtgaggtgg agttttcggt tcttgggtcg    1380
gatttgagac ttgcaccttt cgggtcgggt cgtcggattt ccccgggaa gaatcttggt    1440 tttactaccg ttatgttttg gacggcgatg atgttacatg agtttgaatg gggaccgtcc    1500
gatggtaacg gcgttgactt atctgagaaa ctgaggcttt cttgcgagat ggctaatcct    1560
cttcctgcta aattgcgccg taggcgcagt taa                                  1593

<210> SEQ ID NO 2
<211> LENGTH: 1668
<212> TYPE: DNA
<213> ORGANISM: Arabidopsis thaliana

<400> SEQUENCE: 2
atggccacca agctcgacac cagtagctta cttttggccc tcttgtccaa atgtagcctc      60
cttactcaaa ccaatcttgc tctctctctc ctcgtagcct ccctagcttc tctcgctctt     120
tctctcttct tctggtctca tcccggagga cccgcatggg gaaagtactt cctccaccgc     180
cgccgtcaaa ccaccgtgat acccgggcca agaggcttac cttttgtcgg aagcatgtct     240
ctcatgtcaa acactctggc tcaccgttgc atagccgcaa ccgcagagaa atttagagcc     300
gaacggttaa tggcgtttag tttgggagaa actcgcgtga tcgtcacgtg caatcctgat     360
gtagctaaag agattctaaa cagtccggtt ttcgctgacc gcccggttaa ggaatcagct     420
tattccctca tgtttaaccg tgctatcggt ttcgctcctt acggcgttta ctggcgaacc     480
ttgagaaaaa tcgcgtctaa tcatcttttc agcccgaaac agattaaacg ttccgaaacg     540
cagagaagcg tgatcgcgaa tcaaatcgtg aagtgtctca caaaacagag taacaccaaa     600
ggtctctgtt tcgcacgtga cttgatcaaa acggcatcgc ttaataacat gatgtgctct     660
gttttcggaa agaatacga gcttgaggaa gagcatgaag aagtgagtga gctacgtgaa     720 tggtggaag aaggttatga tttactcggt acactgaatt ggaccgatca tctcccatgg     780
ctctctgaat tgatcctca agaatccgg tctagatgct ctaatctcgt cccaaaagta     840
aaccggtttg tgaaccggat tatctctgac caccgtgaac aaactcgtga ctcaccgagt     900
gacttcgttg acgtattgct ctctctcgat ggtcctgata attatccga ccctgatatc     960 atcgccgttc tatgggaaat gatattcaga ggaactgaca cggtggctgt tttgatcgag    1020
tggattcttg ctaggatggt ccttcatcca gatattcaat cgacggttca caatgagctt    1080
gatcaaatcg tgggacgatc aagggctgtc gaagagtctg acgtggtgtc tctagtatat    1140
ctaacggctg tggtgaaaga agtcttgagg cttcacccgc caggcccact actctcatgg    1200
gcccgtttag caatcacaga cacgatcatc gacggtcgtc gtgttccggc ggggaccacc    1260
gcaatggtga acatgtgggc tattgcacac gatccacacg tgtgggagaa tccgttggag    1320
tttaaacccg aacgttttgt agccaaggaa ggtgaggttg agttctcggt tcttgggtct    1380
gatttgaggc ttgcaccgtt cgggtccggt cgtcgggttt ccccgggaa gaatcttggt    1440 ttgaccaccg tgacgttttg gactgcgacg cttttgcatg agtttgaatg gctgacgccg    1500
```

```
tccgatgaga agaccgttga cttgtccgag aaactgaggc tctcgtgtga gatggctaat    1560
cctcttgctg ctaaattacg ccccaggcgc agttttagtc aaaagaataa aataaagaac    1620
aaagaaagta aaggaaacaa aaaaaaagaa tcatacaaaa aatactaa                 1668
```

<210> SEQ ID NO 3
<211> LENGTH: 1608
<212> TYPE: DNA
<213> ORGANISM: Arabidopsis thaliana

<400> SEQUENCE: 3

```
atgagaaccg aaatagaaag tttgtgggta tttgctcttg catcaaaatt caatatttac     60
atgcaacaac attttgcttc ccttctcgtc gccattgcta tcacttggtt taccataacc    120
atcgtatttt ggtctactcc gggtggaccg gcttggggaa atacttctt cactcgccgg     180 tttatttctc tcgattacaa ccgaaaatac aagaatctca ttcccggtcc tagagggttt    240
ccacttgtgg gaagcatgag ccttaggtca agccacgtgg ctcatcagcg catagcgtct    300
gtggctgaga tgagtaacgc caagcggctc atggcgttta gcctcggtga tactaaggtg    360
gtggtgacgt gtcatcctgc cgtggcaaag agatactaa acagttcggt ttttgctgac    420
cgaccggttg acgaaaccgc ttacggtttg atgtttaacc gagccatggg atttgctccc    480
aatggtactt attggcgtac gctgcgtcgg ttaggctcga accatctttt taacccgaag    540
caaatcaaac aatcggagga tcagagacgg gtgatagcga ctcagatggt gaatgcgttt    600
gcacgtaacc ctaaatccgc gtgtgcagtg cgtgatttgc tcaaaacagc gtcgttgtgt    660
aacatgatgg gtttggtttt cgggagagag tatgaattgg agtcaaataa caacttggaa    720
tctgaatgct aaagggtttt ggttgaagaa gggtacgatc ttctaggtac gttaaattgg    780
accgaccatc ttccttggtt agccggttta gatttccaac aaatccggtt taggtgctcg    840
cagctcgtac cgaaagtaaa tctgttattg agccgtatca tacatgaaca acgtgctgcc    900
acgggtaact ttcttgacat gttactttct cttcaaggtt cagaaaaatt atcagaatcc    960
gacatggttg ctgttctttg ggaaatgata tttaggggaa cggacactgt tgcggttttg   1020
gtcgagtggg tgctagcgag gattgtgatg catcccaaag ttcaattaac ggtccacgat   1080
gagcttgacc gagtcgttgg cagatcaaga accgtggatg agtcagacct tccatcactc   1140
acgtatctaa cggctatgat caaagaagtg ttgaggctgc atccaccagg tccactgctt   1200
tcttgggcac gactgtctat aacagacact tccgtagatg gatatcacgt gccggctggg   1260
accaccgcga tggtcaacat gtgggctata gcacgtgacc cacacgtgtg gaggatcct    1320 ttagagttta gcctgagag gttcgtggct aaagagggtg aagctgagtt ctctgttttc    1380
gggtcggatc tgaggttggc accgttcggg tcgggtaaga gggtttgccc tggaaagaat   1440
ttgggactta caacggtgtc gttttgggtt gcaacgctct tgcatgagtt tgagtggctt   1500
cctagcgtcg aagctaaccc tccagatctc tcggaggttt tgaggctctc gtgtgagatg   1560
gcttgtccac tcatcgttaa cgtaagctca aggcgtaaga taatgtaa               1608
```

<210> SEQ ID NO 4
<211> LENGTH: 1611
<212> TYPE: DNA
<213> ORGANISM: Arabidopsis thaliana

<400> SEQUENCE: 4

```
atggagttga tgaatttggc ttcaaaagaa acaagctatt ggatgattgc actgcctgcc     60
```

| | |
|---|---|
| ggttttggat cccaaaacct acatgatgtt tccaccctag ctatctatt ccttgccgtc | 120 |
| gtttttctct ctatagtcac gtgggctctc gccggaggcg gtggtgtcgc ttggaagaac | 180 |
| ggccgtaacc ggttgggtcg tgtcgcgatc cctggtcctc gtggcatacc agtattcggc | 240 |
| agtcttttca ctctcagccg aggcttggct catcggacgt tagcagccat ggcttggagc | 300 |
| cgagccaaca ctgagattat ggcttttagc cttggttcaa cgccggttat cgtggcttct | 360 |
| gaaccaaaca tagctcgtga gattctgatg tcgcctcact tcgcggaccg gccggttaag | 420 |
| cagtctgcta agagcctcat gttcagccga gccataggtt tcgccccaaa cgggacttac | 480 |
| tggcgcatgt taagaaggat cgcatcgact cacctatttg ctcctcggcg tatcttagca | 540 |
| cacgaagctg gcgccagct agactgcgct gaaatggtga agctgtgtc agtggagcaa | 600 |
| aacggcgctg gatcagtcgt tttaaggaaa cacttacaac tagccgcctt gaacaacatc | 660 |
| atgggaagtg ttttgggag aagatacgat cctctggctc agaaagagga tcttgatgag | 720 |
| cttacatcaa tggttaggga agggttcgag cttttgggtg cttttaattg gtctgattat | 780 |
| cttccatggc tcggttattt ctacgactca attcgtttaa accaacgttg ctcagatctc | 840 |
| gtccctcgaa ttagaaccct cgtcaagaaa atcatcgacg aacatcgagt tagtaactct | 900 |
| gagaagaaaa gagacattgg agattttgtt gatgtcttat tgtctttaga cggtgatgag | 960 |
| aaacttcaag aagatgacat gatcgccgtt ttatgggaga tgattttcg agggacagat | 1020 |
| acaacggcgt tattaacgga gtggaccatg gccgagctag tactgaaccc taacgtgcaa | 1080 |
| accaagttac gagacgagat tttaactgct gtgggcgacg gcgccgacgg agacgtggca | 1140 |
| gatgctgacc tggcaaaaact cccgtaccta aacgcagtgg tgaaggaaac tctaaggctg | 1200 |
| catcctcctg gaccactgct ttcatgggct cgtcttttcca cgtcagacgt ccagctcagc | 1260 |
| aatggcatgt tgattccaaa gggaactaca gcgatggtca acatgtgggc tataacccac | 1320 |
| gaccagactg tatggtccga cccgctaaag tttgacccgg agagattcac tgggaatgct | 1380 |
| gacatggata ttcgtggtgg ggatctaagg cttgcaccgt ttggagccgg taggagagtg | 1440 |
| tgtccgggga agaacatggg gctagctact gtgactcggt gggtggctga gttggtacga | 1500 |
| cggttcgagt ggggtcagga tcagaccgag ccagttgatc ttggtgaggt cttgaagctt | 1560 |
| tcttgtgaga tggagcatcc gttacgtgcc gttgtaacgg aaatattta a | 1611 |

<210> SEQ ID NO 5
<211> LENGTH: 1554
<212> TYPE: DNA
<213> ORGANISM: Arabidopsis thaliana

<400> SEQUENCE: 5

| | |
|---|---|
| atgtctccgg aagcttacgt tctgttcttt aacagtttta acctcgtaac cttcgaagcc | 60 |
| tttgcttcag tctcacttat catagccaca gttgctttct tgctctcacc aggtgggctc | 120 |
| gcatgggcct ggaccgggtc atccaagagt cgggtttcga ttccaggacc atctggttct | 180 |
| ctttccgtct tctccggctc caatccccac cgtgttctcg ccgctcttgc taaacgcttc | 240 |
| aaggcctctc cgttgatggc gttctcagtt gggttttcgc gtttcgttat ctctagtgaa | 300 |
| ccggagacgg ctaaagagat tttgagcagc tctgcttttg ctgaccggcc ggttaaggag | 360 |
| tcagcttacg agcttttgtt tcaccgtgcc atgggattcg caccgtatgg tgagtattgg | 420 |
| aggaatctga ggagaatctc ctccactcat cttttcagtc caagaagaat cgcgagtttt | 480 |
| gagggtgtta gagttggcat cggtatgaag atggtcaaga agattaaaag ccttgttacg | 540 |
| tctgatgctt gtggtgaagt tgaagtgaaa aagatcgttc actttggttc tttgaataat | 600 |

```
gtaatgacga cagtgtttgg tgaaagctac gattttgatg aagttaatgg aaaagggtgt    660 ttttggaga ggctggtgag tgaaggctac gagttgcttg ggattttaa ctggagtgat      720 cacttttggt ttcttcgttg gtttgacttc caaggagtga ggaagaggtg tagagctttg    780
gtctctgaag tcaacacttt tgtcggcgga ataattgaga acacaagat gaagaagggt     840 aataatctca atggagagga aaatgacttc gttgatgtct tgcttggctt gcaaaaggat    900
gaaaagttgt ctgattctga catgattgct gttctttggg aaatgatatt tagagggaca    960
gatacagttg cgattctagt ggaatgggtg cttgcaagaa tggttttgca tcaagacatc   1020
caagataaac tctacagaga gatagcttct gctacaagta acaatattag atccttgtct   1080
gattccgaca tcccaaaact gccgtacctt caagctattg tcaaagaaac cctaaggctc   1140 cacccctg gtccacttct ctcttgggct cgtctcgcta tccatgacgt ccacgtaggt     1200
cctaaccttg tccctgctgg aaccatagct atggtcaaca tgtggtccat cacacacaac   1260
gctaaaatct ggaccgaccc tgaagcgttt atgcctgaaa ggttcattag tgaggatgtg   1320
agcatcatgg gctcggatct tagattggct ccattcggat ccggtcgtcg ggtttgtccc   1380
ggtaaagcaa tgggtctagc tactgttcat ctctggattg gtcaactaat tcagaatttt   1440
gaatgggtga agggttcttg tgatgttgag ctcgctgagg ttctgaagct gtctatggag   1500
atgaagaatc cgttgaagtg caaggctgtt ccaaggaatg ttggtttcgc ttga         1554

<210> SEQ ID NO 6
<211> LENGTH: 1614
<212> TYPE: DNA
<213> ORGANISM: Arabidopsis thaliana

<400> SEQUENCE: 6
atgactattg atatgtatct ttccttcgct tctcgttctg gatcttctcc atttccaagt     60
ctcgagcttt gtctcagcat tttcctcttc atctcccttt tcgttttctg gttgactcca    120
ggtggctttg cttgggcact ctacaaagct cgtttccata cccgacctga gtccaaaacc    180
ggacctgcca ttcccggccc gtctggtctc cccatctttg gctcctctt ggcttttgtc     240 aacaacgcct taacacacag aatcctcgcc aatattgcta cacttgcaa agcaaaagct     300 ctcatggcgt ctccgtagg gtcaacccgg tttgttataa ccagcgaacc agagaccgcg    360
aaagagcttc taaacagctc tgcttttgca gaccggccag tgaaagagtc tgcttacgag    420
ctgctctttg atagagccat ggggtttgct ccctttggtg attactggag agagttgagg    480
agaatctctt ctacccatct cttcagcct aagaggatct tcagttctgg cgagtcccgc     540
cgaaaaatcg ggcaaaacat ggtaggagag atcaagaacg caatggagtg ttatggagaa    600
gtgcatataa aaaagatctt gcatttcgga tcactcaaca acgtgatgtc tagcgttttc    660
ggtaaaacat acaacttcaa cgaaggtatt gtctactcga aagagagcaa tgagttggag    720
catttggtgt ctgaaggcta tgagctgctc ggaatcttca actggagtga tcatttccct    780
ggaatgagat ggttagattt acaaggtgtg aggagaagat gtcgtagttt ggtcggtaga    840
gtgaatgtgt tcgtcggtaa gataatcaat gaccacaaat caaagaggtc acttcgtgat    900
aatcctgaag agagcactta tgatgatgac tttgtagatg tcttacttgg catgcacggc    960
aacagcaaac tttctgactc cgatatgatc gcagtccttt gggaaatgat ttttagggga   1020
acagacacgg tggcgattct cttggaatgg atccttgcga ggatggttct tcaccctgac   1080
attcaagcca aggcgcaggc cgagatcgat tgtatcgtgg gtgactcggg acgtcaagtc   1140
```

| | |
|---|---|
| acagactcag acctccccaa gctcccatac gttcgtgcca ttgtcaagga aaccctaagg | 1200 |
| atgcacccac ctggtcctct cctctcatgg gctcgtctct ccattcacga tactcagatc | 1260 |
| gggactcact ttatacccgc aggaaccact gcgatggtta acatgtgggc tataacccac | 1320 |
| gatgaaaagg tctggccgga agctcatgag tataaaccag agaggtttct tggtgcgcaa | 1380 |
| gaaagtaata acttccccat catgggatct gatctgaggc ttgctcccttt cggtgctgga | 1440 |
| cgtagggtct gtcccggcaa gtcaatgggt ctagccaccg tggagctatg gctagctcag | 1500 |
| ttgctaggaa gctataagtg ggtctcatgt ggtgaagtgg atttgagtga gactttgaag | 1560 |
| ctatctttgg agatgaagaa cactcttgtc tgcaaggcaa tccctagggg ttaa | 1614 |

<210> SEQ ID NO 7
<211> LENGTH: 1668
<212> TYPE: DNA
<213> ORGANISM: Oryza sativa

<400> SEQUENCE: 7

| | |
|---|---|
| atggcaatgg ccaccgccac cgcctcctcc tgcgtcgacg ccacgtggtg ggcgtacgcc | 60 |
| ctcccggcgc tcctcggcgc cgacaccctc tgcgcccacc cggcgctgct cgccggcgcc | 120 |
| gtcctcctgg ccttcgccac cgccgcgtgt ctcgcctggg ccgcgtcccc cggcggggccg | 180 |
| gcgtgggcgc acggccgcgg ccgcctcggc gcgacgccca tcgagggggcc ccggggggctc | 240 |
| cccgtgttcg gcagcatctt cgcgctctcc cggggcctcc cgcaccgcgc gctcgacgcg | 300 |
| atgtcgcgcg acgcggcggc gccacggggcg agggagctca tggcgttctc cgtcggggag | 360 |
| acgccggcgg tggtgtcgtc gtgcccggcg acggcgaggg aggtgctcgc cacccgtcg | 420 |
| ttcgccgacc gccgctgaa gcgctcggcg cgggagctgc tgttcgcgcg cgccatcggg | 480 |
| ttcgcccccca gcggcgagta ctggcgcctc tccgccgca tcgcctccac ccacctcttc | 540 |
| tcccctcgcc gcgtcgccgc gcacgagccg gggcgccagg ccgacgccac ggcgatgctg | 600 |
| tccgccatgg ccgccgagca gtccgccacc ggcgccgtcg tgctccgccc ccacctccag | 660 |
| gccgccgcgc tcaacaacat catgggcagc gtgttcggcc ggcgctacga cgtctcctcc | 720 |
| tcctccggcg ccgccgccga cgaggccgag cagctcaaga gcatggtgcg cgaggggttc | 780 |
| gagctcctcg gcgcgttcaa ctggtccgac cacctcccat ggctcgccca cctctacgac | 840 |
| cccaaccacg tcgcccgccg ctgcgccgcg ctcgtccccc gcgtccaggc gttcgtccgc | 900 |
| ggcgtcatcc gcgaccaccg cctccgccgc gactcctcct ccaccgccgc cgacaatgcc | 960 |
| gacttcgtcg acgtcctcct ctccctcgag gcccacgaga acctcgccga ggacgacatg | 1020 |
| gtcgccgtcc tctgggagat gatatttcgt gggacggaca cgacggcgtt ggtgacggag | 1080 |
| tggtgcatgg cggaggtggt gaggaacccg gcggtgcagg cgaggctgag gcggaggtg | 1140 |
| gacgcggcgg tgggcggcga cgggtgtccc agcgacggcg acgtggcgcg gatgccgtac | 1200 |
| ctgcaggcgg tggtgaagga gacgctgagg gcgcacccgc cggggccgct gctgagctgg | 1260 |
| gcgcggctgg ccaccgccga cgtggggctc gccaacggca tggtggtgcc ggcgggcacg | 1320 |
| acggcgatgg tgaacatgtg ggccatcacc cacgacggcg aggtgtgggc cgacccggag | 1380 |
| gcgttcgcgc cggagcggtt catcccgtcg gagggcggcc cgacgtcga cgtccgcgac | 1440 |
| ggcgacctcc gcctggcgcc gttcggcgcc gggcgccgcg tctgccccgg caagaacctc | 1500 |
| ggcctcgcca ccgtctccct ctgggtcgcc cgcctcgtcc acgccttcga ctggttcctc | 1560 |
| cccgacgcgt cgccgccggt gtccctcgac gaggtcctca gctctcccct cgagatgaag | 1620 |
| accctctcg ccgccgccgc cacccccgc cgccgccgcg ccgcctga | 1668 |

<210> SEQ ID NO 8
<211> LENGTH: 2133
<212> TYPE: DNA
<213> ORGANISM: Zea mays

<400> SEQUENCE: 8

| | | | | | |
|---|---|---|---|---|---|
| acccattcac | tcactcatct | caaggcctag | gtagcaccgt | agcagctact | agaagcagct | 60 |
| agccagaaca | actcgtccat | ggcgatggcc | tccgcggctt | gctcatgcac | ggacggcacg | 120 |
| tggtgggtgt | acgcgctccc | ggcgctgctc | ggctccgaca | ccctgtgcgc | ccacccggcc | 180 |
| ctcctggctg | gcctgatctt | tctgccacc | gtctcggtgg | ctctgctggc | gtgggccacg | 240 |
| tcgccgggcg | gtccggcgtg | gacgaacggc | cgcggccgcc | tcggcgtcac | tcctatcgtg | 300 |
| ggaccccgtg | gtctgcccgt | gttcggcagc | atcttcgcgc | tgtcccgcgg | gctgccgcac | 360 |
| cgcgccctcg | ccgagatggc | ccgcgccgca | gggccccggg | ccaaggagct | catggcgttc | 420 |
| tccgtcggtg | acacgcccgc | ggtcgtgtcg | tcctgcccgg | ccacggcacg | tgaggtgctc | 480 |
| gcgcacccgt | cattcgccga | ccgccctgtg | aagcggtcgg | cccgggagct | catgttcgcg | 540 |
| cgtgccatcg | ggttcgcgcc | caacggcgag | tactggcgcc | gctccgccg | cgtcgcgtcc | 600 |
| acgcacctct | tttccccgcg | ccgggtcgcc | tcgcacgagc | cgggacgcca | aggtgacgcg | 660 |
| gaggccatgc | tccgctccat | cgccgccgag | cagtcggcct | ctggcgccgt | cgccctccgc | 720 |
| ccgcacctcc | aggccgccgc | tctcaacaac | atcatgggca | gcgtcttcgg | cacgcggtac | 780 |
| gacgtcacat | caggcgccgg | cgccgcggag | gccgagcatc | tcaagagcat | ggtgcgcgag | 840 |
| gggttcgagc | tcctcggcgc | cttcaactgg | tccgaccacc | tccctggct | cgcccacctg | 900 |
| tacgacccaa | gcaacgtcac | ccgccggtgc | gccgcgctcg | tgccgcgcgt | ccagaccttc | 960 |
| gtccgtggcg | tcatcgacga | gcaccggcgc | cgccgccaaa | actccgccgc | cctcaacgac | 1020 |
| aatgctgact | tcgtcgacgt | gctcctctcc | ctcgagggtg | acgagaagct | cggcgacgac | 1080 |
| gacatggtcg | ccatcctctg | ggagatggtc | ttccgcggta | cggacacgac | gacgcttctg | 1140 |
| accgagtggt | gcatggcgga | gctggtgcgc | caccggcgg | tgcaggcgag | ggtgcgcgcc | 1200 |
| gaggtcgacg | cggctgtcgg | tgccggaggt | tgccccaccg | acgccgacgt | ggcgcgcatg | 1260 |
| ccgtacctgc | aggcggttgt | gaaggagacg | ctgcgcgccc | accgcctgg | cccgctgctg | 1320 |
| agctgggctc | gcctcgccac | cgccgacgtg | ccactctgca | acggcatggt | ggtccccggct | 1380 |
| ggcaccacgg | cgatggtgaa | tatgtgggcc | ataacccacg | atgccgccgt | gtgggccgac | 1440 |
| ccggacgcgt | tcgcgccgga | gcggttcctg | ccctccgggg | gcggcgccga | cgtggacgtc | 1500 |
| cgcggcgtcg | acctccgcct | ggccccgttc | ggcgccgggc | gtcgcgtctg | ccccggcaag | 1560 |
| aacctgggcc | tcaccaccgt | gggcctctgg | gttgcccgcc | tcgtgcacgc | cttccagtgg | 1620 |
| gccctgcctg | acggcgcggc | ggccgtttgc | ctcgacgagg | tcctcaagct | ctccctggag | 1680 |
| atgaagacgc | cgctcgtcgc | cgcagccatc | ccccgcaccg | cctgatccgt | cctgccgccg | 1740 |
| acgcgtcacg | tcacgcgttg | tttgcatgga | tgatggtatc | tttgtctgtc | tgtgtggtct | 1800 |
| tcgctaaagt | ttgcttcttc | tcgatcgtcg | gttcgttcgt | gcctccacct | tagcctaggg | 1860 |
| tttggtttct | tgcaaggtag | tgagtgtgtc | ttagtctcac | catcaccggg | gctccaattt | 1920 |
| tggaaagctg | cgtgttagga | gttaacccct | agacatgttt | gcgtcttgat | cgccaccacc | 1980 |
| catcagtatc | agcgcagaaa | ctacatatag | atcagtgttt | gtcgaccagt | catggaagtc | 2040 |
| gtgtgctctc | aagtctgatg | tattatatac | atatatatgt | attgtaatgt | gattatcaag | 2100 | aaccgtgcta tttacaaaaa aaaaaaaaaa aaa                                    2133

<210> SEQ ID NO 9
<211> LENGTH: 1799
<212> TYPE: DNA
<213> ORGANISM: Phalaenopsis sp. SM9108

<400> SEQUENCE: 9
cggcaccact cctctctgtt cctctaatat ctggttaaaa atgacaatgt catccatgga        60
ttcatcttca ataatattaa cttatctctc cccaacactt tctccagcta tcgccgcttc       120
tatcatcatc atctcagctc tactactctt tcccggcggt ctggcgtggg cccttttccct     180
caagcgccca acattctccg ggcccaccgg aattgttttt gctctcgcca gctctgctgc       240
tcataagtca cttgccgccc tagctcgctc cgttcgacgc cctccgcctc atggctttct       300
cggtcggcct cactcgcttc atcgtttcaa gccacccgaa aaccgcaaaa gagattcttt       360
caagcccagc cttcgctgat cggcccatta agaatcagc atacgaactt ctgtttaatc        420
gcgctatggg ttttgcccca tttggggatt actggagaaa cctgagaagg atttcgtcca      480
catatctttt cagtccgcgg cgagtttcat cgttcgagaa gcaacggagt gagattggcg       540
aaggaatggt gcgggatatg aaaagaatga tggagagaaa tggagttgta gaagtgagga       600
gaatgttgca ctacgggtct ttgaataaca tcatgttgac tgttttttggg aaaaagtttg     660
attttgcaaa ggatgagggg ttggagcttg agttgatcct taaggaagga tatgagttac       720
ttgggatctt caactggggt gatcatttgc ctcttttggg atggttagat ttgcaaggtg       780
tgaggagaag atgcagaaca cttgtggcta aggtcaatgt atttgtgaag aagatcatag       840
acgagcataa gaggagagcc aacggcgtag ggattgatga gggtgaaggt gaagattttg       900
ttgatgtgct tcttggtttg gaggagaaag atagactctc agaatctgat atggtcgcag       960
ttctttggga aatgatcttt agaggaactg atactgttgc catcctattg gaatggacgt      1020
tggctagaat ggttcttcat cctgatattc aatcgaaggc acaagttgag attgattctg      1080
tcgttgactc ttcaaggcca gtattggatt ctgatatcca acgacttcct tatctccaat      1140
ctatagtaaa agaaaccctt cgaatgcatc ctcctgggcc tctattgtca tgggctcgcc      1200
tagctatcca tgacgttcct gttgatggtc acatgattcc tgctgggacg actgcaatgg      1260
tgaacatgtg ggcaataaca catgacgaat gcaactgggc tgagcctaac aaattcaatc      1320
ctgatcgatt catcgatgaa gatgtcaata ttcttggttc cgatttaagg ttggcaccct      1380
ttggctccgg taaaagagtt tgccctggca aaacgatggc attggctgca gttcatcttt      1440
ggttggctca gttgctgaaa agcttcaaat tgcttccttc gagaaatggt gtagatttgt      1500
ctgagtgcct aaagatgtct ctcgagatga agaatccttt ggtatgtgtg gctgttccaa      1560
ggttcgagta gtcctgctaa gatgacgtct agttataaga aatttgttct ttgcaaattg      1620
tggccaacat aaatgatttc gtaagctagc aacttatgga taatgtcggt acatgttcgt      1680
ttaaagtgtc aactttgttt ggttgaattt taaaatttga cattgtaata aagattctct      1740
ggttctatgt aaatattgta attcagctta taatataaga aagaaatgaa tttgttgct        1799

<210> SEQ ID NO 10
<211> LENGTH: 1611
<212> TYPE: DNA
<213> ORGANISM: Glycine max

<400> SEQUENCE: 10
aagcactatc cctcccacca tgacaagcca cattgacgac aacctctgga taatagccct        60

```
gacctcgaaa tgcacccaag aaaaccttgc atgggtcctt ttgatcatgg gctcactctg     120
gttaaccatg actttctatt actggtcaca ccccggtggt cctgcctggg gcaagtacta     180
cacctactct cccccccttt caatcattcc cggtcccaaa ggcttccctc ttattggaag     240
catgggcctc atgactttcc ctggcccatca ccgtatcgca gccgcggccg ccacatgcag     300
agccaagcgc tcatggcct ttagtctcgg cgacacacgt gtcatcgtca cgtgccaccc      360
cgacgtggcc aaggagattc tcaacagctc cgtcttcgcc gatcgtcccg tcaaagaatc     420
cgcatacagc ctcatgttta accgcgccat cggcttcgcc tcttacggag tttactggcg     480
aagcctcagg agaatcgcct ctaatcacct cttctgcccc cgccagataa aagcctctga     540
gctccaacgc tctcaaatcg ccgcccaaat ggttcacatc ctaaataaca agcgccaccg     600
cagcttacgt gttcgccaag tgctgaaaaa ggcttcgctc agtaacatga tgtgctccgt     660
gtttggacaa gagtataagc tgcacgaccc aaacagcgga atggaagacc ttggaatatt     720
agtggaccaa ggttatgacc tgttgggcct gtttaattgg ccgaccacc ttccttttct      780 tgcacatttc gacgcccaaa atatccggtt caggtgctcc aacctcgtcc ccatggtgaa     840
ccgtttcgtc ggcacaatca tcgctgaaca ccgagctagt aaaaccgaaa ccaatcgtga     900
ttttgttgac gtcttgctct ctctcccgga acctgatcaa ttatcagact ccgacatgat     960
cgctgtactt tgggaaatga tattcagagg aacggacacg gtagcggttt tgatagagtg    1020
gatactcgcg aggatggcgc ttcatcctca tgtgcagtcc aaagttcaag aggagctaga    1080
tgcagttgtc ggaaaagcac gcgccgtcgc agaggatgac gtggcagtga tgacgtacct    1140
accagcggtg gtgaaggagg tgctgcggct gcacccgccg ggcccacttc tatcatgggc    1200
ccgcttgtcc atcaatgata cgaccattga tgggtatcac gtacctgcgg ggaccactgc    1260
tatggtcaac acgtgggcta tttgcaggga cccacacgtg tggaaggacc cactcgaatt    1320
tatgcccgag aggtttgtca ctgcgggtgg agatgccgaa ttttcgatac tcgggtcgga    1380
tccaagactt gctccatttg ggtcgggtag agagcgtgc ccagggaaga ctcttggatg     1440
ggctacggtg aacttttggg tggcgtcgct cttgcatgag ttcgaatggg taccgtctga    1500
tgagaagggt gttgatctga cggaggtgct gaagctctct agtgaaatgg ctaaccctct    1560
caccgtcaaa gtgcgcccca ggcgtggata agagagagtt gaagcttta t              1611
```

<210> SEQ ID NO 11
<211> LENGTH: 1885
<212> TYPE: DNA
<213> ORGANISM: Glycine max

<400> SEQUENCE: 11

```
ggcactcact gaagcactat ccctcccacc atgacaagcc acattgacga caacctctgg      60
ataatagccc tgacctcgaa atgcacccaa gaaaaccttg catgggtcct tttgatcatg     120
ggctcactct ggttaaccat gactttctat tactggtcac accccggtgg tcctgcctgg     180
ggcaagtact acacctactc tccccccctt tcaatcattc ccggtcccaa aggcttccct     240
cttattggaa gcatgggcct catgattttcc ctggcccatc accgtatcgc agccgcggcc     300
gccacatgca gagccaagcg cctcatggcc tttagtctcg gcgacacacg tgtcatcgtc     360
acgtgccacc ccgacgtggc caaggagatt ctcaacagct ccgtcttcgc cgatcgtccc     420
gtcaaagaat ccgcatacag cctcatgttt aaccgcgcca tcggcttcgc ctcttacgga     480
gtttactggc gaagcctcag gagaatcgcc tctaatcact cttctgcccc cgccagata     540
```

-continued

```
aaagcctctg agctccaacg ctctcaaatc gccgcccaaa tggttcacat cctaaataac      600
aagcgccacc gcagcttacg tgttcgccaa gtgctgaaaa aggcttcgct cagtaacatg      660
atgtgctccg tgtttggaca agagtataag ctgcacgacc caaacagcgg aatggaagac      720
cttggaatat tagtggacca aggttatgac ctgttgggcc tgtttaattg gccgaccac       780 cttcctttc ttgcacattt cgacgcccaa aatatccggt tcaggtgctc caacctcgtc       840
cccatggtga accgtttcgt cggcacaatc atcgctgaac accgagctag taaaaccgaa      900
accaatcgtg attttgttga cgtcttgctc tctctcccgg aacctgatca attatcagac      960
tccgacatga tcgctgtact ttgggaaatg atattcagag aacggacac ggtagcggtt      1020 ttgatagagt ggatactcgc gaggatggcg cttcatcctc atgtgcagtc caaagttcaa     1080
gaggagctag atgcagttgt cggaaaagca cgcgccgtcg cagaggatga cgtggcagtg     1140
atgacgtacc taccagcggt ggtgaaggag gtgctgcggc tgcacccgcc gggcccactt     1200
ctatcatggg cccgcttgtc catcaatgat acgaccattg atgggtatca cgtacctgcg     1260
gggaccactg ctatggtcaa catgtgggct atttgcaggg acccacacgt gtggaaggac     1320
ccactcgaat ttatgcccga gaggtttgtc actgcgggtg gagatgccga attttcgata     1380
ctcgggtcgg atccaagact tgctccattt gggtcgggta ggagagcgtg cccagggaag     1440
actcttggat gggctacggt gaacttttgg gtggcgtcgc tcttgcatga gttcgaatgg     1500
gtaccgtctg atgagaaggg tgttgatctg acggaggtgc tgaagctctc tagtgaaatg     1560
gctaaccctc tcaccgtcaa agtgcgcccc aggcgtggat aagagagagt tgaagctttt     1620
attaaaaagg gaacaagaaa aaagaaaat gaaatatata gaaataaaac agacaagaaa      1680
gtaaagtaaa gattatgcat gttgctgcat gtaggttggt ggttggtggc aggtgtgcag     1740
ccacacaatg gtaatatggt ggaagggatg ggttaggctc tcttttttt ttttagtggt     1800 caagtattaa gtcttctcag cttgtcttct tattacaaaa aaagtactgt tgccagtgta     1860
aataaactta atacgttttt agttg                                           1885
```

<210> SEQ ID NO 12
<211> LENGTH: 1686
<212> TYPE: DNA
<213> ORGANISM: Glycine max

<400> SEQUENCE: 12

```
atgtcaaccc acattgaaag cctgtgggtg ttggccttag cctcaaaatg cattcaagag       60
aacattgcat ggtcactctt gatcatcatg gtcactctct ggctcaccat gaccttcttc     120
tactggtctc accctggtgg tcctgcttgg ggcaaatact actactttaa ttactggaaa     180 aaaccacct caaccaacac aaacatcaac cttaaaatga ttatccctgg tcctagaggc     240
taccctttca ttgggagtat gagtctcatg acatccctcg cacaccaccg tattgctgcg     300 gcggggaag catgcaacgc caccaggctc atggcttttt ccatgggtga cacgcgcc      360 atagtaacgt gcaaccccga tgtcgctaaa gagattctca atagttccac ttttgctgat     420
cgtcccataa aggaatcagc ttacagcctc atgttcaacc gcgccatcgg cttcgcccct     480
tacggcgtct actggcgtac cctccgccgc atcgccgcca cgcacctctt ctgccccaaa    540
caaatcaaag cctccgagct ccagcgcgct gaaatcgccg cccaaatgac aaactcattc    600
cgaaatcacc gttgcagcgg cggtttcgga atccgcagcg tgctcaagag agcgtcactg    660
aacaacatga tgtggtcggt gtttggacaa aagtacaacc ttgacgagat aaacaccgca    720
atggacgagc tatccatgtt ggtggaacaa ggctatgact tgttgggcac ccttaattgg    780
```

```
ggagaccata tcccttttcct gaaagacttt gacctacaga aaatccggtt cacctgctcc    840
aaattagtcc ctcaagtgaa ccggttcgtt ggttcaatca tcgccgacca ccaggccgac    900
acaacccaaa ccaaccgcga tttcgttcat gttttgctct ctctccaagg tcccgataaa    960
ttgtctcact ccgacatgat tgctgtcctc tgggaaatga tatttagggg gaccgacacg   1020
gtggcggttt tgattgagtg gatactggcg aggatggtgc ttcatccgga ggtgcaaagg   1080
aaggtacaag aggagttgga cgcggtggtt agggtggcg cttgacgga gaggtcgtg   1140 gcggcgacgg cgtatcttgc ggcggtggtg aaagaggttc tgaggctgca cccgccgggc   1200
ccgcttctct cgtgggcccg cttggccatc actgatacga ccattgatgg gtatcacgtg   1260
cctgcgggga ccaccgctat ggttaatatg tgggccatag caagggaccc ggaggtgtgg   1320
ctggacccac ttgagttcaa gcccgagagg ttcatgggtc tggaaaacga gttttctgtt   1380
ttcgggtcgg atctgagact cgctccattc ggttcgggtc ggagaacatg ccccgggaag   1440 actttggggtt tgagcaccgt aaccttctgg gtggcttggc ttttgcatga gtttgaatgg   1500
ctaccgtctg atgaagccaa ggttgatcta acggaggtgc tgaggctctc gtgtgaaatg   1560
gctaacccac tcattgttaa agttcgccct aggcatggat taagcactta atgataatat   1620
aattaagcct atctacgtta ttaacttgaa atgtttaat gggaaggaaa aaaaaaaaa   1680 agagag                                                             1686

<210> SEQ ID NO 13
<211> LENGTH: 2100
<212> TYPE: DNA
<213> ORGANISM: Oryza sativa

<400> SEQUENCE: 13
aactcaaact gcacttccct tttcagctct tctccaacct caatttcacc ccattttttcc     60 atatcctctc tgcacacgta cgtacaggta aacgtgcctg atcatggaca tggactcgtc    120
gccgtcgaca caggactgtg cggctggct gctgtacgtc tccctcgctg ccaaatgcgg    180
cggcgaccct tgccgcgtcg tcggcttcgt cgccgttgcc gtcgtcgcct tcgccgtcac    240
gtcgctcctg cactggctgt cgcccggtgg cccggcgtgg gggaggtatt ggtggaacag    300 gagggggtggt ctgggcattg ctgccgccat tcctgggccc cgtgggttgc ccgtgctcgg    360
cagcatgtcg ctcatggcgg gactcgcgca ccggaagctc gccgcggcgg cgggggggctc    420 gccggcgagg cggcgcctca tggcgctgtc tctcggggag acacgggtgg tggtcaccgc    480
cgaccccggc gtcgcgcggg agctcctcgc cagcgcggcg ttcgccgacc ggccggtgaa    540
ggagtccgcg tacgggatgc tgttccaccg cgccatcggg ttcgcgccct acggcacgta    600
ctggcgcgcg ctccgccgcg tcgcgtccac gcacctcttc tcgccgaggc aggtgtccgc    660
ctccgccgcg cagcgcgcgg tgatcgcgcg ccagatggtg gaggccatga ggtccgccgc    720
cgccgccgcc gccggtggcg gcgtggcggc gaggccgttc ctgaagcgcg cgtcgctgca    780
caacgtgatg tggtcggtgt tcgggaggaa gtacgagctg gcggcgccgg agagcgagga    840
gacggcggag ctgaggagca tggtggacga aggctacgac ctcctcggcc agctcaactg    900
gtccgaccac ctcccatggc tcgcaccctt tgacctcaag aagacgcggt caaggtgctc    960
gtcccttgtc ccccgcgtca accgcttcgt cacccgcatc atcgacgagc accgtgctcg   1020
cctcagcctc gccgtcgacg ccgccgtcga cttcaccgac gtccttctct ccctccacgg   1080
cggcgacaag ctctccgacg ccgacatggt cgccgtcctc tgggagatga tctttcgagg   1140
```

```
gacggacacg gtggcggtcc tgatcgagtg ggtggcggcg aggctggtgc tgcaccagga      1200
cgtgcaggcc agggtccatg acgagctgga ccgagtggtc gggtcggacc gggcagtgac      1260
cgagtcggac gcgtccaagc tggtctacct ccaagcggtg atcaaagagg tcctgcgcct      1320
ccacccgccg ggcccactgc tctcgtgggc acgcctcgcc acgtcggatg tacacgtcgg      1380
cgggttcctc ataccctctg gaccaccgc catggtgaac atgtgggcca taacccatga      1440
ccctgccgtt tggcccgacc cgaacgagtt caaaccagag aggttcgtcg cagggccctc      1500
gtcggaccag gccacggagt ttccgataat ggggtcggat ctcaggctcg cgccgttcgg      1560
gtcaggaagg cgaagctgcc ccggcaagtc gctcgccatc gccactgtcg gattctgggt      1620
tgccacgttg ctacacgagt tcgattggct tcccttgtca gataagtcgc gcggcgtcga      1680
tctgtcggag gtgctgaagc tgtcgtgcga gatggcaacc ccgctggagg caaggctaag      1740
gccgcgacgc aaggtgtgat gacgtgtcac caccgtcacg tgggactaag acgaggagag      1800
ggaagccgac ttccacttcc ttctagtgct tgttgagatg tgtaaatgtc cctaaatgta      1860
aagtgttacg ctttgagtag aaatgcccct acgttgtagt gcgtagtatt gtacacttgt      1920
agtatgtaat gcttgtattt ttgtgtgttt tgcacgtcct aagtagtgga gtagtagctg      1980
ataatagtta gttaattact ctgctattta gtcatagtta actacctacc tgcaggtgat      2040
gagagtgaca gttttttttt gtttaattaa ctgcaggtga tgagtgtaga atagctcggt      2100

<210> SEQ ID NO 14
<211> LENGTH: 1861
<212> TYPE: DNA
<213> ORGANISM: Brachypodium distachyon

<400> SEQUENCE: 14
atggcgaccc ctgaggactg tggcagctgg ttgctgtacc tgtcgctggc cgccaaatgc        60
ggcggcgacg gcgaccaccc gcgccgcctg ccgggctcc ttgccgtctg cgccgccgct       120
ttcctcgtca cctgcctcct gcactggtgc ttccccggcg gccggcgtg gggccgctgg       180 tggtggacgc ggcgggcct gggccgcggg cccgtcgtcc ctgggccgag gggcctgccg       240
gtgatcggca gcatgtggct catgactggc ctcgcccacc gcaagctcgc cgcggaggct       300
gcccgcctgc gaggcggcgg gcgccggctg atggccttct ccctcggcga cgcgcgtg       360 gtcgtggcgg gccatcccga cgtggcccgg gagatcctga ccagcccggc cttcgccgac       420
cggcccgtca aggagtccgc ctacgggctc atgttccacc gcgccatcgg cttcgcgcgc       480 cacgcgcct actggcgcgc gctccgccgc gttgcttcca cgcacctctt ctcgccctgg       540
caggtcgccg cgtccggcgc ccagcgcgcg gtgatcgcgc ccagatggt ggccgccctc       600 gccggggcg ccgaggtccg gcgcgtcctg cgtcgcgcgt cgctgcacaa cgtgatgtgg       660
tcggtgttcg gccgccgcta cgacctggag ctggaccctg gcaaggaggt ccgcgagctg       720
ggccagctcg tggacgaagg ctacgacctg ctgggccagc tcaactggtc cgaccacctc       780
ccctggctcg cccgcttcga cctgcaggc acccgggccc ggtgcgccag cctagtgccc       840
cgcgtgaacc gcttcgtcgg cggcatcatc gatgaccacc gggtcaaagc tccgtccgcc       900
gtcaaggact tcacggacgt cctgctgggc ctgcaaggcg cgacaggct cgccgactcc       960 gacatggtcg cggtgctctg ggagatggtg ttccgtggca cggacacggt ggccgtgctg      1020
atggagtggg tgctggcccg gctcgtgctg caccaggacg tgcaggcccg ggtgcacgag      1080
gagctggacc gcgtcgtcgg gcgcgaccgg gccgtggccg agtccgacgc ggcctcgctc      1140
gcctacctcc acgccgtggt caaggaggtc ctgcgcctcc acccgccagg cccgctgctg      1200
```

```
tcctgggccc gcctggccac gtcggacgtg cacgtggacg ggttcctcat ccccgctggc    1260
accaccgcca tggtgaacat gtgggccatc acccacgacg cgacgtctg  ggccgagccc    1320 atggagttcc ggcccgagcg gttcgtcggg ccggggctg  aggagttctc cgtcatgggc    1380
tctgatctcc ggctggcgcc gtttggggcc ggccggagga gctgccccgg aagagcctg    1440 gccatggcga ccgtggcgtt ctggctcgcc acgctgctcc acgagttcga cctgcttcct    1500
tcctccgacc cggcacgtgg cgtgcaactg tcggagaccc tgaggctgtc gtgcgagatg    1560 gccacccgc  tggccctgac gccgagggct cgtcgacgcc cggcggtttg aatttgaatt    1620
gatgacgtat catgcctacg ccaccactgg ctagctagct agaaccctag tattgttgct    1680
gctttgtttt tgagacgttg tcgcctaccg gtcggccgcc ggctcgctac cacgcacgca    1740
cgtacgggca taacgctggc ttatctcgtc cagagctagc aaatgaatcg tttggacttt    1800
tatatatcga gacgtgccag ctgatgacag cgatgttttt tgccttcttg ttccccggt    1860 c                                                                   1861

<210> SEQ ID NO 15
<211> LENGTH: 1755
<212> TYPE: DNA
<213> ORGANISM: Glycine max

<400> SEQUENCE: 15
atgacaaccc acattgataa cctgtggggtg ttggccttgg tctcaaaatg cacacaagag      60
aacattgcat ggtcactctt gaccatcatg gtcactctct ggctctccat gaccttcttc     120
tgctggtctc atcccggtgg tcctgcttgg ggcaagtact actccttca  ttactggaaa     180 aaaacaacca caaccacaac ctcaacctca acaacacaa  actccaacaa ccttaaaatg     240
attcccggtc ccaaaggcta tccttttcatt ggaagcatga gcctcatgac atcccttgca     300
caccaccgta ttgctgccgc tgctcaagca tgcaaagcca ccaggctcat ggccttctcc     360
atgggtgaca cgcgtgtcat cgtcacgtgc cacccccacg tggccaagga gattcttaac     420
agctccgtct tcgccgatcg tcccataaag gaatcagcct acagcctcat gttcaaccgc     480
gccatcggct ttgccccctta cggcgtttac tggcgcaccc tccgccgcat cgccgccacg     540
cacctcttct gccccaaaca aatcaaggcc tcggagctcc agcgcgccga aatcgccgcc     600
cagatgaccc actcgttccg aaaccgccgc ggcggtttcg gaatccgcag cgttctcaag     660
agagcgtcgc tcaacaacat gatgtggtcg gtgtttggac aaagatatga ccttgacgag     720
acaaacactt cagtggacga gttatcccgg ttagtggaac aaggctatga cttgttgggt     780
acccttaatt ggggagacca tatcccttt  ctgaaagact ttgaccttca aaaaatccgg     840
tttacctgct ccaaactcgt ccccaagtg  aaccggttcg taggttcaat catcgccgac     900
caccaaaccg acacaaccca aaccaaccgc gatttcgttc atgttttgct ctctctccaa     960
ggtcccgata aattgtctca ctccgacatg attgctgtcc tctgggaaat gatatttagg    1020
gggaccgaca cggtggcggt tttgattgag tggattatgg caaggatggt gcttcatccg    1080
gaggtacaaa ggagggtgca agaggagctg gacgcggtgg ttggaggtgg tgcgcgcgct    1140
ttgaaggagg aggacgtggc ggcgacggcg tatcttctgg cggtggtgaa ggaggttctg    1200
aggctgcacc ctccaggccc gcttctctcg tgggcccgct tggccatcac cgatacgacc    1260
attgatgggt ataacgtgcc cgcgggaacc accgccatgg ttaatatgtg gccatagga    1320 agggacccgg aggtgtggct ggacccactt gatttcaagc ccgagaggtt catgggcctg    1380
```

```
gaggcggagt tttctgttct cgggtcggat ctgaggctgg ctccattcgg gtcgggtaga      1440
agaacctgcc ccggaaagac tttgggtttg agcaccgtga ctttctgggt ggcgaggctt      1500
ttgcacgagt ttgaatggct accatctgat gaggggaagg ttgatctaac ggaggtgctg      1560
aggctctcgt gtgaaatggc taacccgctc tatgttaaag ttcgccctag cgtggatta      1620 agtacttaat aataataata ataataataa taataataat aataatgtta agtagcaggt      1680
gcatggccct ttggagccac taaatgttaa gtgaatccat gaatcaaggt agaaagtttg      1740
agttggctct gtctc                                                      1755
```

<210> SEQ ID NO 16
<211> LENGTH: 1662
<212> TYPE: DNA
<213> ORGANISM: Oryza sativa

<400> SEQUENCE: 16

```
atggcgactc cggaggacac tggcagctgg ctgctctacc tctccttggc ggctaaatgc       60
tccggcgatg gcgacggcca gcctcaccgg cttcttgggt tcgtcgtggt ttgcgccgtc      120
gctggtctgg ttacatgtct gctgcactgg tccttccccg gagggccggc gtggggagg       180 tggtggtgga cgcggcggcg cgtcggggg tcgccgtgcg gtgtggcggc tgttcctggg      240 ctgaggggc tgccggtgat cggcagcatg tggctcatga ccgggctggc gccaccggaag      300 ctcgccgcgg cggcggaggc ggcggggggcg gggcggctga tggcgctgtc gctcggggag      360
acgcgggtgg tcgtggcggc gcacccggac gtggcgaggg agatcctgca cggcgcggcg      420
ttcgccgacc gccccgtgaa ggagtccgcg tacgggctgc tgttccaccg cgccatcggg      480
ttcgcgcccc acggcgcgta ctggcgcgcg ctgcggcggg tggcgtccac gcacctcttc      540 tcccgtggc aggtcgcggc gtccgcgccc cagcgcgcgg tcatcgcgcg ccagatggtc       600
cgcgccatca agctgcagca gcggagccgg agcggcgatt ccgccgccgg cgccgccgtc      660
gaggtccgcc gcgtcctgcg ccgcgcgtcg ctccacaacg tgatgtggtc ggtgttcggc      720
cggcggtacg agctgcagct ggaccccggc aaggagagcg acgaggtccg ggagctgagg      780
gccctcgtcg acgaaggcta cgacctgctc ggccagctca actggtccga ccacctccca      840
tggctcgccc gcttcgacct gcagagcacc ccgcgcccgct gctcccgcct cgtccccgc       900 gtcaaccgct tcgtcacccg catcatcgac gagcatcgct catctgctcc cgtcgcagcc      960
gccatcgact tcaccgacgt cttgctctcc ctgcagggca gcgacaagct cgccgactcc     1020
gacatggtcg ccgttctctg ggagatggtg tttcgcggga cggacacggt ggccgtgctg     1080
atcgagtggg tcttagcccg gctcgtgctg cagcaggacg tgcaggctcg ggtgcacgac     1140
gagctgggcc gggtggttgg gctggaccgg gacgtgaccg agtccgacac ggcctcactc     1200
gtctacctcc acgccgtcat caaggagacg ctgaggctgc acccaccggg cccactcctc     1260
tcatgggccc gcctggccac gtcggacgta cacgtggacg ggtacctgat ccccgctggc     1320
accaccgcga tggtgaacat gtgggccata gcacacgacc ccgacgtgtg ggccgagccg     1380
atggagtttc ggcccgagcg gttcatcggg aaggcggcgg agttcagtgt aatgggttcg     1440
gatctcaggc tcgcgccgtt cggatcgggt cggcggagct gccccgggaa gagcctcgcc     1500
atggccacgg tggcattctg gcttgccacg ctgttgcacg agttcgccct cctcccctcg     1560
cccgacccgg cacacggcgt cgacttgtcg gaggtgctaa ggctgtcgtg cgagatggcc     1620
accccgctgg cggtgacagc gtggcctcgg cgtgtggtgt ga                        1662
```

<210> SEQ ID NO 17
<211> LENGTH: 1672
<212> TYPE: DNA
<213> ORGANISM: Glycine max

<400> SEQUENCE: 17

| | | | | | |
|---|---|---|---|---|---|
| acaccatcca | ctactcttct | tagttccagc | acaacaagct | cttcatttct | cccacacttt | 60 |
| cttttctttc | accaaaaatg | tcaccagatt | tcacactttt | gttcttcccg | gaactcatgc | 120 |
| agtcccctat | gatcactttc | caagccaccc | tctgcgtcct | tctcttcacc | ctcatgttca | 180 |
| cgctgctctt | cactcctggt | gggcttcctt | gggcctgggc | ccggcccaga | cccatcatcc | 240 |
| ctggcccagt | aactgccctg | ttagggatct | ttactggctc | cacgcctcac | cgtgctttat | 300 |
| ccaaactcgc | ccgtaattac | cacgcggaaa | aactcatggc | tttctccatc | ggtttaaccc | 360 |
| gtttcgtcat | ctccagcgaa | ccggagaccc | taaggagat | tctcggcagc | ccagtttcg | 420 |
| ctgataggcc | ggtgaaggaa | tccgcctatg | agcttctctt | ccaccgcgca | atgggttttg | 480 |
| caccgtatgg | ggagtactgg | aggaatttga | ggagaatctc | agccctacat | ctcttctccc | 540 |
| cgaagagaat | caccggctct | gaatccttca | ggagcgaggt | tggattaaaa | atggttgaac | 600 |
| aagttaagaa | aaccatgagt | gagaaccaac | atgttgaggt | taagaaaatt | ctacacttta | 660 |
| gttcgttgaa | caatgtgatg | atgacggtgt | ttggtaagtc | ttatgagttt | tacgagggtg | 720 |
| agggtttgga | gcttgagggt | ttggtgagtg | aagggtatga | gttgttgggt | gtttttaact | 780 |
| ggagtgacca | ttttccggtt | ttggggtggt | tggatttgca | gggtgtgagg | aagaggtgta | 840 |
| ggtgtttggt | tgaaaaggtt | aatgttttg | ttggaggggt | tattaaggag | catagggtga | 900 |
| agagggagag | gggtgagtgt | gtgaaggatg | aaggaactgg | ggattttgtt | gatgttttgc | 960 |
| ttgatttgga | gaaggaaaac | aggctcagtg | aagctgacat | gatcgctgtt | ctttgggaaa | 1020 |
| tgatatttag | gggaactgac | acggtggcaa | ttctgctaga | gtggactctg | gctcggatgg | 1080 |
| ttctccaccc | tgaaatccaa | gcaaaggcac | agcgcgaaat | agacttcgtt | tgcggatcct | 1140 |
| ccaggcccgt | atccgaagca | gacattccga | acctgcgcta | ccttcagtgc | atagtaaaag | 1200 |
| aaaccctccg | tgtgcaccca | ccaggcccgc | tactctcgtg | ggctcgcctt | gctgtgcacg | 1260 |
| acgttaccgt | gggcggcaag | cacgtgattc | ccaagggcac | caccgcgatg | gtgaacatgt | 1320 |
| gggccataac | ccacgacgag | agggtgtggg | ccgagcccga | aagtttagg | cccgagcggt | 1380 |
| ttgtggagga | ggatgtgagc | ataatggggt | ctgatttgag | gttggcacct | ttcgggtctg | 1440 |
| gaagaagagt | gtgccctggg | aaggcccttg | gtttggcctc | ggttcatctt | tggctcgctc | 1500 |
| agttgcttca | aaattttcat | tgggtttcat | ctgatggtgt | ttctgtggag | ttggatgagt | 1560 |
| ttcttaagct | ttctatggag | atgaagaagc | cactgtcttg | caaggctgtg | cctagggttt | 1620 |
| ctgtttaggt | ttatgtgtgt | tgttgggttg | agttggtttg | gtttgtctgc | tt | 1672 |

<210> SEQ ID NO 18
<211> LENGTH: 1635
<212> TYPE: DNA
<213> ORGANISM: Glycine max

<400> SEQUENCE: 18

| | | | | | |
|---|---|---|---|---|---|
| tcagcacaac | ctcttcatct | ctcccaggct | ttcttttctt | tgcaacaaca | ctaccaaaaa | 60 |
| tgtcaccaga | tttcacactt | tgttctcccc | ggaactcat | gcagtcccct | atcatcactt | 120 |
| tccaagccac | tttctgtgtc | cttctcttca | ccctcatgtt | cacgccgttc | ttcactcctg | 180 |
| gtgggcttcc | ttgggcctgg | gcccggccca | gaaccatcat | ccctggccca | gtaactgccc | 240 |

```
tgctcggggt cttcacgggt tccacacctc acagcgcttt atccaaactg gcccgcactt      300
atcacgcgga aaagctcatg gctttctcca tcggtttaac ccggttcgtt atctccagcg      360
aaccggaaac cgcaaaggag attctcggca gccccggttt tgcggacagg ccggtgaagg      420
aatccgccta tgagcttctc ttccaccgtg caatgggttt cgcaccgtac ggagagtact      480
ggagaaacct gaggagaatc tcagccctac atctcttctc cccgaagaga atcaccagct      540
ctgagtcctt caggagcaag gttgggttaa aaatggttga acaagttaag aaaaccatga      600
gtgagaacca acacgtcgag gttaagaaaa ttctacactt tagttcgttg aacaatgtga      660
tgatgacggt gtttggtaag tgttatgagt tttacgaggg tgagggtttg gagcttgagg      720
gtttggtgag tgaagggtat gagttgttgg gtgtttttaa ctggagtgac cattttccgg      780
ttttggggtg gttggatttg caggggggtga ggaagaggtg taggtgtttg gttgaaaagg      840
ttaatgtttt tgttggaggg gttattaagg agcataggggt gaagagggag aggggtgact      900
gtgtgaagga tgaaggagct gaggattttg ttgatgtttt gcttgatttg gagaaggaaa      960
acaggctcag tgaagctgac atgattgctg ttctttggga aatgatattc aggggaactg     1020
acacggtagc aattctgcta gagtggattc tggctcgcat ggttctccac cctgaaatcc     1080
aagcaaaggc acagcgcgaa atagacttcg tttgcggatc ctccaggctc gtatccgaag     1140
cagacattcc gaacctgcgc taccttcagt gcatagtaaa agaaaccctc cgtgtgcacc     1200
caccaggccc gctactctcg tgggctcgcc ttgctgtgca cgacgttacg gttggcggca     1260
agcacgtgat tcccaagggc accaccgcga tggtgaacat gtgggccata acccacgacg     1320
agagggtgtg ggccgagccc gagaagttta ggcccgagcg gtttgtggaa gaggatgtga     1380
gcataatggg gtctgatttg aggttggcac ctttcgggtc tggaagaaga gtgtgtcctg     1440
ggaaggccct tggtttggcc tcggttcatc tttggctcgc tcagttgctt caaaattttc     1500
attgggtttc atctgatggt gtttctgtgg aattggatga gtttctcaag ctttctatgg     1560
agatgaagaa gccactgtct tgcaaggctg tgcctagggt ttctgtttag gtttatgtgt     1620
gttgttgggt tgagg                                                      1635
```

<210> SEQ ID NO 19
<211> LENGTH: 2158
<212> TYPE: DNA
<213> ORGANISM: Zea mays

<400> SEQUENCE: 19

```
cccgaatcgg gagtagtagt agtagtgcat ccaatcgaca cacacacaaa aaaaaaggtt       60
agttagccat ggcgccgcca acagaggact gcggctggct gctgtacctt tccctggccg      120
ccaaatgcgg cgaccctcag cgcctgctcg gcttcgccgc ggtcttcgtc gcggcctgcg      180
tagtcacgtc gctcctgcac tgggcgtccc cgggcggccc cgcctggggg tggtactggt      240
ggaccaggcg ggccgggctg ggcatcgtcc gtgccgccat cccgggaccc cggggcctgc      300
cggtggtcgg cagcatgggc ctgatgaccg gcctggcgca ccgcaagctc tcggcggcgg      360
ccgagagaca ggccagcagg cgccgcctca tggcgttctc gcttggcgag acccgggtgg      420
tggtcaccgc cgacccccgac gtcgcgcggg agctgctcgc cagcgccgcc ttcgccgacc      480
gccccgtcaa ggagtccgcg tacgggctcc tgttccaccg cgccatcggc tttgccccgc      540
acggcgccta ctggcgcgcg ctccggcgcg tcgtccgc gcacctcttc tcgccgcgcc      600
agatcgcggg ctccgcggcg cagcgcgcgg ccatcgcgcg ccagatggtg acgccacga      660 cgaccgccgc ggcccacgcc cccgtcgtcg tggcgcgccg gttcctgaag cgcgcgtcgc      720
```

```
tgcacaacgt catgtggtcg gtgttcggcc gcaggtacga cctgatggcg gacagccggg    780
aggccgagga gctcaaggcc ctggtagacg aaggctacga cctgcttggg cagctcaact    840
ggtccgacca cctcccgtgg ctcgcccgct tcgacctgca gaagacccgg gccaggtgct    900
gcgcgctcgt cccgcgggtg aaccgcttcg ttggcaacat catcggcgag caccgtgccc    960
gcctcggccg cggcgtcgac accgccgtca tggacttcac ggacgtcctg ctctccctcc   1020
agggcgacga caagctctcc gacgccgaca tgatcgccgt tctgtgggag atgatcttcc   1080
gaggcacgga cacggtggca gtcctgatcg agtgggtgct ggcccgtctg gtgctgcacc   1140
aggacgtgca gagcaaggtc caggaggagc tggaccgggt ggtcgggctg gccaggccg    1200
tgacggagtc ggacacggcc tcgctgccct acctccaggc ggtcatcaag gaagtgctac   1260
gcctgcaccc gccaggccca ctgctctcct gggcgcgcct cgccacctca gacgtgcacg   1320
taggcgggta ccttgtgccc gcgggcacca ccgccatggt gaacatgtgg gccataaccc   1380
atgaccccag cctgtggcct gagccaatgg agttcaggcc cgagaggttc atgggccctg   1440
ccgccgagga cgtcccgata tgggttcgg atctccggct cgcgcctttc gggtccggca    1500
ggcggagctg ccccggcaag tcactcgcgg tggctaccgt cggattctgg gtcgccaccc   1560
tgctgtacga gttcaaatgg ctgccgccgt ccgacgagcc acgggccggc ggcgtcgacc   1620
tatccgaagt gctgaggctg tcgtgtgaga tggctgcacc gctggaggcg agggtggtgc   1680
cacgtcacgc ggtgtgctga gggggctgag acacgtggcc tgcaggggtg gggatcagag   1740
gaggaaagct cgaccgatcg tcttctagct tctactacta cgtaatacct taccttgtag   1800
cagaacgtaa cgtggtcgat atgagatgtg taaagaaaga aaaaaaaga acgcccagtt    1860
gcaccatgca tgctagctgc tggtgtggag tcagtacgta gtagcagcac ccggtttgat   1920
cgatgcttat gtgtgtaatg taatacctac ctgcagttgc aagtaaatgt gtgcctgtta   1980
ttagtctagc taggtagtgt agtgtagtgt accggatggt gagcgagcgt gacagttacc   2040
tttccttttc agtactgcct agctagctag acctagatgt attattatat attgtgtact   2100
cccttcttac gtacgtgcgt tccataataa atgtattctg tagttgtctt tttctact     2158
```

<210> SEQ ID NO 20
<211> LENGTH: 2176
<212> TYPE: DNA
<213> ORGANISM: Sorghum bicolor

<400> SEQUENCE: 20

```
cactcaaccc gagcgccact tctccaaagc atcagcgaac gagcgagctg agggagcgag     60
agagagaaaa ggatagtgaa acacgagaga gctaggagcc atggcggtgg cggcgacccc    120
cgatgactgc ggcagctggt tgctgtacct gtccctagcc gccaaatgcg ccggcggcga    180
ccagcctcac cgcctggccg gtttcctggc ggtctgcgcc gtggccttcg tcgtcacttg    240
cctcctccac tggtgcttcc ctggaggtcc ggcgtgggga aggtggtggt ggacgacgca    300
ggcgcggcgg gtcgcggcgg ccgccgttcc ggggccgagg ggcctgcccg tggtcgggag    360
catgtggctc atgacgggcc tggcgcaccg caagctggcg gcggcggcgg acagcctccg    420
cgccaggcgc ctgatggcgt tctccctcgg cggcacgcgg gtggtggtgg ccgcgcaccc    480
ggacgtggcg cgggagatcc tcaacagccc ggcgttcgcg gaccgtccca tcaaggagtc    540
cgcgtacggg ctcctgttcc accgcgccat cggcttcgcg ccctacggcg cctactggcg    600
cgcgctccgc cgcgtggcgt ccacgcacct cttctccccg tggcaggtcg ccgcctccgc    660
```

```
cgcgcagcgc gccgtcatcg cgcgccagat ggtcgccgcc atgaagcagg agctgtcgtc    720
gtcgtcgtcg gcctcggccg gcttcgaggt ccgccgcgtc ctgcgccgcg ggtccctgca    780
caacgtgatg tggtcggtgt tcggccggcg gtacgacctg gagctggacc cggccaagga    840
gagccccgag acgcgggagc tgaggagcct cgtggacgaa ggctacgacc tgctgggcca    900
gctcaactgg tccgaccacc tccctggct cgcgcgcttc gacctgcaga gcaccaggtc    960
caggtgcgac cgcctcgtcc cgctcgtgaa ccgcttcgtc ggcggcatca tcgacgcgca    1020
ccgcgcccgg aacgacctcc gctccgctcc accacacgcc gtcatggact tcaccgacgt    1080
gctcctctcg ctgccggccg acgacaggct caccgactct gacatgatcg ccgtcctctg    1140
ggaaatggtg ttccgtggaa ctgacaccgt tgccgtgctg atcgagtggg tgctggcgag    1200
gctcgtgctg caccctgacg tgcaggcccg tgtccacgac gagctggacc gcgtggtcgg    1260
gcgtgaccgg gccgtgaccg agtccgactc ggggtcactg gtctacctgc acgccgtgat    1320
caaggaggtg ctcaggatgc acccgccggg cccactgctg tcgtgggcgc gcctggccac    1380
gtcggacgtg caggtggacg ggcacctcat ccccgccggc accaccgcca tggtgaacat    1440
gtgggccata acgcacgacc cggacgtgtg ggcggagccg gcggagttcc agccggagag    1500
gttcatggga tccaccaccg gcggcgagtt cccgataatg gggtcggacc tgaggctcgc    1560
gccgttcggg gcgggccggc gcagctgccc cgggaagagc ctcgccatgg ccaccgtggc    1620
tctctggctc gcgacgctgc tgcacagagtt cgagctgctc ccggcgcgcg cgtctacct    1680 gtcggaggtg ctcaagctgt cgtgcgagat ggccgtcccg ctggccgtga cggcgaggcc    1740
ccggcaagcg gtgtgatgac gcgtcacggc ggctgggacg acgagcagg caggcaggca    1800 gtcagttggg gtatcagtct cactgtgagc attataccac aactactagt agtactacta    1860
ctgtacacgg aatggaaaag cgcttgtgct tttgggagac gttgctaccg gtcacagctt    1920
gcaagttgct actactgggt cgacatgggg tatatgcttt tcatgttact atcttcgata    1980
tgtatcgaga tcaggttgcc gaatgtgata ctttggcttg tactgttagc ttttgtctgg    2040 gtgctcttttt attgcttttt ttttaagtag taatcgctgt aagactcgta aaatgtatat    2100
gctggtttgg atggttttgg attgtagctc acaaactagt attacgcagt tcaatgcctt    2160
aatatgctat ctgttc                                                   2176
```

<210> SEQ ID NO 21
<211> LENGTH: 1587
<212> TYPE: DNA
<213> ORGANISM: Glycine max

<400> SEQUENCE: 21

```
atgtcatcat cggaactctc ctctttcttt cttctccgtc tatcagacat actcagtttc     60
gatgttttgc tcggagttat gtttctagtt gccgtgttcg gctactggct ggttcccggc    120
ggtcttgctt gggcttttc caagttcaag cccgcgattc ccgggccttc cggttacccg    180
gtggtgggtc tggtttgggc tttcataggg cctcttactc acagggtcct tgctaagttg    240
gctgaaacct tgatgcaaa gcccttgatg gcgttctctg tggggttcac tcgtttcatc    300
atctcttctc accccgacac cgccaaagag atcttgaaca gttccgcttt cgcggatcgt    360
cccgttaagg aatctgctta tgaacttctc tttcaccgtg cgatggggtt tgcaccctac    420
ggtgagtact ggaggaacct gaggaggatc tccgcaactc acatgttctc tccgaggaga    480
atcgcagccc aaggagtgtt tcgggcccgg attggagccc aaatggtgag agacatcgtg    540
ggcctgatgg ggagggacgg tgtggtggag gtgaggaagg tgttgcattt tgggtcgttg    600
```

```
aataacgtga tgaagagcgt gtttgggagg agttatgtgt ttggtgaggg gggtgatggg      660
tgtgagctcg aggggttggt gagcgagggg tatcatttgc ttggggtgtt taactggagt      720
gaccactttc cactcttggg ttggttggat ttgcaaggtg tgaggaagag ctgtaggagt      780
ttggttgata gagtgaatgt ttatgttggg aaaatcattt tggagcatag agtgaagagg      840
gttgctcaag gtgaggataa taaggccatt gatactgata gttctggtga ctttgttgat      900
gtgctgctgg atttggagaa agagaatagg ctaaaccact ctgatatggt tgctgttttg      960
tgggaaatga tatttagagg gactgatacg gtagctatcc ttctagagtg gattctagca     1020
agaatggttc ttcatccaga aatacaagca aaggcacaat ctgaaataga ctctgtggtt     1080
gggtctgggc gtagtgtgag tgatgatgac cttccaaacc ttccttacgt tcgagccata     1140
gtgaaggaaa ccttaaggat gcacccacca ggccctcttc tttcatgggc cagactttct     1200
attcatgaca cacaaattgg caatcacttt gttccagctg gcaccactgc tatggtaaac     1260
atgtgggcca taactcacga ccaagaagtg tggtatgagc aaaaacagtt caagccggag     1320
cgttttttga aggacgagga cgtgccaatc atgggatctg atcttaggtt ggcaccttttt    1380 ggctctggga ggagagtgtg ccctggaaaa gccatgggct tggccactgt tgagctttgg     1440
cttgctatgt tcttacaaaa attcaaatgg atgccctgtg atgattctgg tgttgacttg     1500
tctgagtgtt tgaagctctc catggagatg aaacactctc tcaaaaccaa agttgttgca     1560
aggcctgtag tttctcttgc aatgtaa                                         1587

<210> SEQ ID NO 22
<211> LENGTH: 2074
<212> TYPE: DNA
<213> ORGANISM: Zea mays

<400> SEQUENCE: 22
aaagacttga accacgcaac cctctctggt ctctggtcgt cctactttct tccacagcag       60
aaggaaactt gagtcgtgag cgcagtggtg catccaatcc acaaagagct gaggttagtc      120
agccatggcg gcaccgccga ccgaggactg cggctggctg ctgtacctct ccctggccgc      180
caaatgcggc gaccctagcc gcctgctcgg cttggcggcg gtcttcgtcg gcgcctgcgt      240
cgtaacgtcg ctcctgcact gggcgtgccc gggcggcccc gcctgggggc ggtactggtg      300
gaccaggcga ggcgggctgg gcatcgtccg cgccgccatc ccgggacccc ggggcctgcc      360
agtggtcggc agcatggggc tgatgaccgg cctggcgcac cgcaagctcg gcggcggcgg      420 gcggcggcc ggggtcagg gcagcagcag gcgccgccgt ctcatggcgc tctccctcgg      480
cgagacccgg gcggtggtga ccggcgaccc ggacgtcgcg agggagctgc tcggcagcgc      540
cgccttcgcc gaccgccccg tcaaggagtc gcgtacgggg ctcctcttcc accgcgccat      600
cggcttcgcc ccgcacggcg cctactggcg cgcgctccgc cgcgtggcgt cggcgcacct      660
cttctcgccg cgccaggtcg cggcctcctc cgcgcagcgc gcggtcatcg cgcgccagat      720
ggtggacgcc gtgaccacgg ccgcccccgc cccgccccc gccgtcgtgg tggcgcgccg      780
gttcctgaag cgcgcgtcgc tgcacaacgt catgtggtcg gtgttcgggc gcaggtacga      840
cctgctgctg ctggcggcgg acggcgagga gctgaaggcg ctggtggacg aaggctacga      900
cctcctcggg cagctgaact ggtccgacca cctcccgtgg ctggcccgct cgacctgca      960 gaggacccgg gccaggtgct ccgcgctcgt ccgcggggtg aaccgcttcg ttggcaacat     1020
catcgacgag caccgtgcgc gcctcggcct cggcgacacc ggcggcgtca cggacttcac     1080
```

```
cgacgtcctg ctctccctcc agggcgtcga caagctctcc gacgccgaca tggtcgccgt    1140
tctctgggag atgatcttcc gaggcacgga cacggtggcc gtcctaatgg agtgggtgct    1200
ggcgcgtctc gtgctgcacc aggacgtgca gagcaaggtc caggaggagc tggaccgggt    1260
ggtggggcca ccgggccagg ccgcatccgt gacggagtcg acaccgcct cgctcgtcta     1320 cctccaggcg gtcatcaagg aagtgctgcg cctgcacccg ccaggcccgc tgctctcctg    1380
ggcgcgcctg gccacgtcgg acgcgcgcgt aggcgggtac cacgtgcccg cgggcaccac    1440
cgccatggtg aacatgtggg ccataacgca tgaccccagc gtgtgggccg agccgacgga    1500
gttcaggccc gagaggttcg tgggcgcctc tgctggtgct ggtgctggtg ctggtgccga    1560
ggacgttccg atgataatgg gctcggatct ccggctcgcg cccttcgggt ccggcaggcg    1620
gagctgcccc ggcaagtcgc tcgcgctggc taccgtcggg ttctgggtgg ccaccctgct    1680
ccacgagttc aaatggttgc cgccgtgccg cggcgtcgac ctgtccgagg tgctgaggct    1740
gtcgtgtgag atggctgcac cgctggaggc gagggtggtt ccacgtcacg cggtgtgaga    1800
tgacgaggat gagacacgtg gcctgggat aggagaagtt gcccgatcgt ctgtctagat     1860
tgtactgtac tatatatctt atcttagctt tccttacctt gtagcagaga acgtaacgtg    1920
gcccggcggc gatggatgat gagaatgaga tgtgtaaaag aagaaaaaga gcatgcccga    1980
gtgccatatg ctttagagtg gactgtgtat atatgatgat gctattgcta aaaaaaaaa     2040 aaaaaaaaa aaaaaaaaa aaaaaaaaaa aaaa                                  2074
```

<210> SEQ ID NO 23
<211> LENGTH: 2061
<212> TYPE: DNA
<213> ORGANISM: Brachypodium distachyon

<400> SEQUENCE: 23

```
atggcgccgg cgacttctgc ttccgaggac tgcgcggggt ggctgctgta cgcgtccctg      60
gccgcgagat gcaacgacgg cggtgaggcc taccggccg ccgtcttcgc catgccctg      120 ctggccacca gtttcatcct cacctcgctc ctccactggg cctccacccc ggcggcccg     180 gcctggggac gctaccgctg gacttccacc acctctcggg ccgccattag cactagccct    240
cgcatccccg gcccgcgcgg gctgccggtg tcggcagca tgggcctcat gacgggcctg     300
gcccaccgca agctcgccgc ggctgtcgcc gccggggag acgacgaaga ggagaggtcc     360
cagcggaggc ggctgatggc gttctcgatg gcgagacgc gggccgtggt gagctcggac     420
ccggccgtgg cccgcgagct gctgtcgagc ccggcgttcg cggaccggcc cgtcaaggag    480
tccgcctacg ggctcctctt ccaccgcgcc atcggcttcg cgcccacgg cgcctactgg     540 cgctcccctcc gccgcgtcgc ctcggcgcac ctcttctcgc cgcgccaggt cgccgcctcc   600
gccgcccacc gcgccgccat cgcccgcagc atggttggct ccgtctccgc catcgccatg    660
ggctccggcg aggtcgaggt ccgccggttc ctgaagcggg cggcgctgca cggggtcatg    720
tggtccgtgt cgccggag gtacgacggc acggcggcgc ggagctggg aagaaggag       780 gaggaagagc tgaggagcat ggtggaagaa ggatacgagc tcctcggcaa gctcaactgg    840
gccgaccacc tgccatggct ggcccgcttc gacctccagg ggatacgggc ccggtgcgcc    900
gccctcgtgc cacgcgtcaa ccgcttcgtc ggcaagatcg tcgacgacca ccgcgccgct    960
gctgccgccg acgccggcga tcgtgtcgtg gacttcaccg acgttctgct atcccttcaa   1020
ggcgccgaca agctctccga cgccgacatg atcgcggttc tctgggagat ggtgttccgt   1080
ggcacggaca cgatggcggt ggtgatggag tgggtgctgg cccggctggt gatgcaccag   1140
```

```
gacgtgcagg ccagggtcca ggaggagctg gaccgggtgg tcgggccggg ccaagccgtc   1200
tccgaatcgg acgcggcccg gctcgtctac ctccaggccg ttattaagga gacgatgcgg   1260
ctgcacccgc caggccccct gctctcatgg gcccggctcg ccacatcgga cgttcatgtg   1320
ggcgggttcc tcgtgccagc tggcaccacc gccatggtta acatgtgggc catcaccat    1380 gacccgaccg tgtgggcgga tccgctggag ttcaaccccg acaggttcat tgtcggagcc   1440
gttccgttgt cggaaggtca tcataatgcc gttccgggcg ctgagttctc cataatgggc   1500
tcggatctca ggctcgcgcc attcggatcg ggcaggcgga tctgccccgg gaagccactg   1560
gcgatggcca gcatcgggtt ttgggtcgcg acgctcctcc atgagttcaa gtggacctcg   1620
gcgccacgtg gtgacgtcga cctgtcggag gtgctgaggc tgtcatgcga gatggccgcc   1680
ccgctcaagg cgaggctcac accaaggcgc cctgtgtgat gatatgccgg agccaccgac   1740
cacttcttca ccggactagt cctgtctatc ttctttgctt attttctctc taccgatgcc   1800
tgtagtgaaa aaaagaagt aatgtcccgg tttggaaacg tgcctgctgc tataataggt    1860
ccggtcctgg tcgtacttct ctagtccttt tgctgtactt agcttagcta aaagagatgc   1920
taaattaggt acttatgaac tactagtatt ataaggaaat gagtgtgaca gttttcttgt   1980
gtgttttccc tttgctgcct agctagaggt ttctatgcat gtaaatacct ttatatttcc   2040
caatgcaagc ctttgtttgc t                                             2061

<210> SEQ ID NO 24
<211> LENGTH: 1716
<212> TYPE: DNA
<213> ORGANISM: Glycine max

<400> SEQUENCE: 24
acaccacagt ttcaaagccc ttctaaaacg ccttactctg tatcttcttt catcatccaa     60
aaaaaaccat tcacacaaag aaaacctttg ggtttcccaa gatgtcatca tcggaactct    120
cttctttctt tctcctgccc ctatcagcca tactcagttt cgatgctttg ctcggagtta    180
tgtttctagt ggccgtgttc ggctactggc tggttcccgg tggtcttgct tgggctttgt    240
ccaaattcaa gcctgcgatt cccgggcctt gcggttaccc ggtggtgggc ctggtttggg    300 cttttcatagg gcctcttact cacagggtcc ttgcaaagtt ggctgaaacc ttcgatgcaa    360
agcccctgat ggcattctcg gtagggttta ctcgctttat catctcttct caccccgaca    420
ctgccaaaga gatcttgaac agttctgctt ttgcggatcg tcctgttaag gaatccgctt    480
atgagcttct ctttcaccgc gcaatggggt tcgcacccta cggtgagtac tggaggaatc    540
tgaggaggat ttcagcgact cacatgttct ctccgaagag aattgcggcc caaggagtgt    600
tccgggcccg ggttgggggcc caaatggtga gagaaatcgt gggcctgatg ggaagaatg     660 atgtcgtgga ggtgagaaag gtgttgcatt ttggatcgtt gaataacgtg atgaagagtg    720
tgtttgggag gagctatgtg tttggtgagg ggggtgatgg gtgtgagctt gaggagttgg    780
tgagtgaggg gtatgatttg cttgggctgt ttaactggag tgaccacttt cctctcttgg    840
gttggttgga ttttcaagga gtgaggaaga ggtgcaggag tctggtggat agagtgaatg    900 ttttttgttgg gaaaatcatt atggagcata gagtgaagag ggatgctgaa agtggtgact   960 tgttgatgt gctgttggat ttggagaaag aggataggct aaaccactct gatatggttg    1020 ctgtttgtg ggaaatgata tttaggggga ctgatacagt ggcaattctt ctagagtgga   1080
ttctagcaag gatggtactg catccagaaa tacaagcaaa ggctcagtgt gaaatagact   1140
```

| | |
|---|---|
| ctgtggttgg gtctgggtgc agtgtgactg atgatgacct tcctaacctc ccttacgtgc | 1200 |
| gagctatagt gaaggaaacc cttaggatgc acccaccggg ccctcttctt tcatgggcca | 1260 |
| ggctttccat tcacgagaca caaattggca accactttgt tccagctggc acaactgcta | 1320 |
| tggtcaactt gtgggccatc actcatgacc aacaagtgtg gtccgagcca gaacaattca | 1380 |
| agcccgagcg gtttctgaag gacgaggacg tgccaatcat ggggtctgat cttaggttgg | 1440 |
| cacctttgg cgctggtagg agagtgtgcc ctggaaaagc catgggcttg gccactgttg | 1500 |
| agctttggct tgctgtgttc cttcaaaagt tcaaatggat gccttgtgat gattctggtg | 1560 |
| tggacttgtc tgagtgcttg aagctctcca tggagatgaa acactccctc atcaccaaag | 1620 |
| ctgttgcaag gcctacatct tctcttgcaa tgtaatgggt tggagtatcc catcatttta | 1680 |
| ctccccttaa taataatatt tctttccttt taaaaa | 1716 |

<210> SEQ ID NO 25
<211> LENGTH: 1578
<212> TYPE: DNA
<213> ORGANISM: Oryza sativa

<400> SEQUENCE: 25

| | |
|---|---|
| atggcgctct cctccatggc cgcggcgcaa gagagctccc tcctcctctt cctcctcccg | 60 |
| acgtcggccg cctccgtgtt cccgccgctc atctccgtgg tcgtcctcgc cgcgctcctc | 120 |
| ctgtggctct cgccgggtgg ccccgcgtgg gcgctgtccc gttgccgtgg cacgccgccg | 180 |
| ccgccgggcg tggcggggg cgcggccagc gcgctgtccg ccctgccgc gcaccgcgtg | 240 |
| ctcgccggga tttcgcgcgc cgtcgagggc ggcgcggcgg tgatgtcgct ctccgtcggc | 300 |
| ctcacccgcc tcgtcgtggc gagccggccg gagacggcga gggagatcct cgtcagcccg | 360 |
| gcgttcggcg accgcccgt gaaggacgcg gcgaggcagc tgctgttcca ccgcgccatg | 420 |
| gggttcgccc cgtcgggcga cgcgcactgg cgcgggctcc gccgcgcctc cgcggcgcac | 480 |
| ctcttcggcc cgcgccgcgt ggccgggtcc gcgcccgagc gcgaggccat cggcgcccgc | 540 |
| atagtcggcg acgtcgcctc cctcatgtcc cgccgcggcg aggtccccct ccgccgcgtc | 600 |
| cttcacgccg cgtcgctcgg ccacgtcatg gcgaccgtct tcggcaagcg gcacggcgac | 660 |
| atctcgatcc aggacggcga gctcctggag gagatggtca ccgaagggta cgacctcctc | 720 |
| ggcaagttca actgggccga ccacctgcca ttgctcaggt ggctcgacct caggggcatc | 780 |
| cgccgccggt gcaacaggct agtccagaag gtggaggtgt tcgtcggaaa gatcatacag | 840 |
| gagcacaagg cgaagcgagc tgccggaggc gtcgccgtcg ccgacggcgt cttgggcgac | 900 |
| ttcgtcgacg tcctcctcga cctccaggga gaggagaaga tgtcagactc cgacatgatc | 960 |
| gctgttcttt gggagatgat ctttagaggg acggacacgg tggcgatctt gatggagtgg | 1020 |
| gtgatggcga ggatggtgat gcacccggag atccaggcga aggcgcaggc ggaggtggac | 1080 |
| gccgccgtgg ggggacgccg cggccgcgtc gccgacggcg acgtggcgag cctcccctac | 1140 |
| atccagtcca tcgtgaagga gacgctgcgc atgcacccgc cgggccgct cctgtcgtgg | 1200 |
| gcgcgcctcg ccgtgcacga cgcgcgcgtc ggtggccacg ccgtccccgc cgggacgacg | 1260 |
| gcgatggtga acatgtgggc gatcgcccac gacgccgccg tctggccgga gccggatgcg | 1320 |
| ttccgcccgg agcgcttctc ggagggggag gacgtcggcg tgctcggcgg cgacctccgc | 1380 |
| ctcgcgccgt tcggcgccgg ccgcgcgtc tgcctggca ggatgctggc gctcgccacc | 1440 |
| gcccacctct ggctcgccca gctgctgcac gccttcgact ggtcccccac cgccgccggc | 1500 |
| gtcgacctgt ccgagcgcct cggcatgtcg ctggagatgg cggcgccgct cgtgtgcaag | 1560 |

-continued

```
gccgtggcta gggcctga                                              1578
```

<210> SEQ ID NO 26
<211> LENGTH: 1611
<212> TYPE: DNA
<213> ORGANISM: Glycine max

<400> SEQUENCE: 26

```
atgtcaccag attttacact cttgttcttc ccggaactca tccaaccccc tatcgtcacc    60
ctccaagccg ccctatgcat ccttctctta accttcctcc tcacgttttt cctcactcca   120
ggcgggcttg cgtgggcctg ggccaccaag tcctcgaccc ggcccatcat tccgggccca   180
gtaatggccc tgctcagcgt cttcaccggc tccaccccgc accgcaggtt atccatgctc   240
gcccgctctt accacgcaga aaagctcatg gctttttcaa tcggtctgac ccggttcgtc   300
atctcgagtg aaccggaaac cgcaaaggag attctcggca gccccggttt tgctgacaga   360
ccagtgaagg aatcggccta ccagcttctc ttccaccgcg caatggggtt tgcaccatac   420
ggagaatact ggagaaacct gaggagaatc tccgcccttc atctcttctc tccaagaga   480
atcaccggct cggaagcctt taggaacgag gtggggttga aaatggtaga tgaagttaag   540
aaggttatga aggataaccg acacgtggag gttaagagga ttttgcacta cgggtcgttg   600
aacaatgtga tgatgacggt gttcggtaag tgttatgagt tctacagggg tgagggtgtt   660
gagcttgagg ctttggtgag cgaagggtat gagctgttgg gtgtttttaa ctggagcgac   720
cattttccgg ttctggggtg gttggatttg cagggtgtga ggaagaggtg taggtgtttg   780
gttgaaaagg ttaatgcgtt tgttgggggt gttattgagg agcatagagt gaagagggtg   840
agaggtgggt gtgtgaagga tgaagggact ggggattttg ttgatgtttt gcttgatttg   900
gagaacgaga acaagcttag tgaggctgac atgatcgctg ttctttggga aatgatattt   960
aggggaactg acacggtggc aattctgctg gagtggatct tggctcggat ggttctccac  1020
cccgacatcc aagccaaagc acagcgcgaa atagactccg tctgcggacc ctacaggctc  1080
gtatccgaag cagacatgcc gaacctgcgc taccttcagg gcatagtaaa agaaactctc  1140
cgcgtgcacc ctccaggccc gctactctcg tgggctcgcc tggcggtgca cgacgttacc  1200
gtgggcggca agcacgtgat tcccaagggc accaccgcga tggtgaacat gtgggccata  1260
acgcacgacg agaggttttg ggccgagccc gagaggttca ggcccgagcg gtttgtggag  1320
gaggaggatg tgaacataat ggggtctgat ttgaggttgg caccttttcgg gtctgggaga  1380
agagtgtgcc ctgggaaggc cttgggcttg gcctcggttc atctttggct cgctcagttg  1440
ctacaaaatt ttcattgggt tcaatttgat ggtgtctctg ttgagttgga tgagtgtctt  1500
aagctttcta tggagatgaa gaagccactt gcttgcaagg ctgtgcctag ggttgctgtt  1560
tagtttatgg gtgttgttgg gttacttggg tgggtttggg ttatttgcta a           1611
```

<210> SEQ ID NO 27
<211> LENGTH: 1603
<212> TYPE: DNA
<213> ORGANISM: Sorghum bicolor

<400> SEQUENCE: 27

```
ccttctcacc tccctccccc acgccgtcgc catggacgcc accacccagg actccctcct    60
cttcctcttc ccggccgccg ccaccttcct ctccccgctc ctcgccgtgc tcctcgtagc   120
gctctcgctg ctctggctcg tcccaggcgg gcccgcgtgg gcgctcatct ccacctccag   180
```

| | | | | |
|---|---|---|---|---|
| gtcccgcgcg | accccgccgc | cgggcgcgcc | gggcgtggtc | accgcgctct cgggccccgc | 240 |
| agcgcaccgc | gccctggcgt | ccctgtcgcg | gtcgcttccc | ggcggcgccg cgctgtcggc | 300 |
| gttctccgtc | ggactcacgc | gcctcgtcgt | tgccagccag | ccggacacgg cgcgggagct | 360 |
| cctggccagc | gccgccttcg | ccgaccgccc | cgtcaaggac | gcggcccggg gctcctcttt | 420 |
| ccaccgcgcc | atgggcttcg | caccctccgg | cgactactgg | cgcgcgctgt gccgcatcag | 480 |
| ctccgcctac | ctcttcagcc | cgcgcagcga | gtccgccacg | gcaccccgac gcgtcaccat | 540 |
| cggcgagcgc | atgctgcgtg | acctctccga | cgccatcggc | cgcctgaggc ggagcctggt | 600 |
| gagcagggtg | aacgtgttcg | tggcgaggat | catcgaagag | cacaggcaga agaagaagga | 660 |
| cgacgtcgcc | aacaatggcg | agtcggccgc | cggagacttc | gtcgacgtct tgctcggact | 720 |
| ggagggcgag | gagaagctgt | cggactccga | catgatcgct | gtcctctggg agatgatctt | 780 |
| tcgagggacc | gacacggtgg | cgatcctgct | ggagtgggtg | atggcgcgga tggtgctgca | 840 |
| cccggggatc | cagtccaagg | cgcaggcgga | gctggacgcc | gtcgtgggcc gcggcggcgc | 900 |
| cgtctccgac | gccgacgtgt | cccggctgcc | ctacctgcag | cgcgtcgtga aggagacgct | 960 |
| ccgcgtgcac | ccgccgggcc | cgctgctgtc | gtgggcgcgc | ctcgccgtgc acgacgcggt | 1020 |
| ggtcggcggc | cacctcgtcc | cggcgggcac | cacggccatg | gtcaacatgt gggccatcgc | 1080 |
| gcgcgacccc | gcggtgtggg | cggaccccac | cgcgttccgg | cccgagcggt tcgaggagga | 1140 |
| ggacgtgagc | gtgctgggcg | ggaccctccg | gctcgcgccg | ttcggcgccg gcggcgcgt | 1200 |
| gtgccccggc | aagacgctgg | cgctcgccac | cgtccacctc | tggctcgcgc agctgctgca | 1260 |
| ccgcttccag | tgggcgccgg | cagacggcgg | cgtcgacctg | gcggagcgcc tcggcatgtc | 1320 |
| gctggagatg | gagaagccgc | tcgtgtgcaa | gcccacgccg | aggtggtgat ccctgaaagc | 1380 |
| acaaccgagt | tccaatgcat | gatcatgtta | ctattactag | cgtttcatta cgccgcataa | 1440 |
| tttgtttctt | ctgagtcgag | tggatcggtg | ttcaatctgc | ataagtggtt ttgtctatgt | 1500 |
| tattgtttct | gtttgtgatt | gatgggatta | ggtgaagagt | gttcacagtg ctccatttgt | 1560 |
| taggagtacc | agaaatatgt | gaaaaacgcc | tgatgagaaa | cta | 1603 |

<210> SEQ ID NO 28
<211> LENGTH: 1647
<212> TYPE: DNA
<213> ORGANISM: Oryza sativa

<400> SEQUENCE: 28

| | | | | |
|---|---|---|---|---|
| atggatgcca | ctctcggcgc | ctccactacc | catggctacc | tcctcctcct cccggccaac | 60 |
| tccaccacct | tcttctcccc | gctcctcgct | gccctcctcg | ccgtcacctc gctgctctgg | 120 |
| ctcgtcccgg | gcggccccgc | gtgggcgctc | tcccgctgcc | gccggccccc gcccggcgcg | 180 |
| ccgggcgcgc | tcgccgcgct | cgccggcccc | gccgcgcacc | gcgcgctcgc ggccatgtcg | 240 |
| aggtccgtgc | ctggcggcgc | cgccctggcg | tccttctccg | tcggcctcac gcgtttcgtc | 300 |
| gtggccagcc | gccccgacac | ggcgcgggag | ctcctgtcca | gcgccgcgtt cgccgaccgc | 360 |
| cccgtgaagg | acgcggcgcg | gggtttgctc | ttccaccgcg | ccatggggtt cgcgccctcc | 420 |
| ggcgactact | ggcgcgcgct | ccgccgcgtc | agcgccaacc | acctcttcac ccctcgccgc | 480 |
| gtcgccgcct | cggccccgcg | acgcctcgcc | atcggcgagc | gcatgctaga ccgcctgtcc | 540 |
| gccctcgccg | gcgcgagat | cggcatgagg | cgcgtgctcc | acgcggcgtc cctggaccac | 600 |
| gtcatggaca | ccgtcttcgg | gacgcgctac | gacggcgaca | gccaggaggg cgccgagctc | 660 |
| gaggccatgg | tgaaggaagg | gtacgacctc | ctcgggatgt | tcaactgggg agaccacctg | 720 |

```
ccgctgctca aatggctcga cctgcaaggc gtgaggagga ggtgcaggac gctggtgcaa      780
cgagtcgacg tgttcgtccg aagcatcatc gacgagcaca ggcagaggaa gcgccgcacc      840
ggcggcaatg gcggaggcga ggagctcccc ggcgacttcg tcgacgtgtt gctcgggttg      900
caggggaggg agaagatgac ggagtccgac atggtcgccg ttctctgggt aaccaaggat      960
ccatctgaca tgcatgcatc tattcgatcg atcttgtgca ttgcgatcaa cggattcatg     1020
gatatatttg atcttgcgcg cgtgcaggag atgatctttc gggggacgga cacggtggcg     1080
attctgctgg aatggatcat ggcgaggatg gtgctgcacc cggacatcca ggcgaaggcg     1140
caggcggagc tcgacgccgt cgtcggccgc gggcgcgccg tgtcggacgg cgacgtcgcc     1200
ggcctgcgct acctccagtg cgtcgtgaag gaggcgctcc gcgtgcaccc gccgggcccg     1260
ctcctgtcgt gggcgcgcct cgccgtgcgc gacgcgcacg tcggcggcca cgtggtcccc     1320
gcgggcacca cggccatggt caacatgtgg gccatcgcgc acgacccgga gctctggccg     1380
gagcccgacg agttccggcc ggagcggttc gcggaggagg acgtcagcgt gctcggcggc     1440
gacctccgcc tcgcgccgtt cggcgcgggg cggcgcgcct gcccgggcaa gacgctcgcg     1500
ctcgccaccg tccacctctg gctcgcgcag ctgctgcacc gcttcgagtg ggcaccggtc     1560
ggcggcggcg tccacttgtt ggagcgcctg aacatgtcgc tggagatgga gaagcctctc     1620
gtgtgcaagg ctaaacctag gtggtga                                         1647

<210> SEQ ID NO 29
<211> LENGTH: 1905
<212> TYPE: DNA
<213> ORGANISM: Glycine max

<400> SEQUENCE: 29
cattagtatc atcttccctc gtatacttcc cctcctcaac tttgttttgt ttttcatgta       60 cgcttttga atcatcttac gtgctcctaa tcatgattcc aacacttgtt tgtattggca      120
caacaatatt ccaaagcacc ctctcttctt actcattgtc tttcatctct cttttctct      180 ccacgtcact cgcccttctt gctatttccc tcaactattg gcttgtcccc ggaggttttg      240
catggaggaa atatcacagt cgttacaaag gccatgcaaa agtctctggc ccaatgggct      300
ggcccatatt gggaacttta cctgcgatgg gccctctagc ccacaggaaa cttgctgcca      360
tggccacttc accaaaagca aaaaagctca tgacattgag tctaggaaca aatccagttg      420
ttatcagcag tcacccagaa accgcaagag aaattctttg tgggtcgaac ttcgctgacc      480
gacccgttaa agaatcggcc cgaatgctca tgtttgagcg tgccattgga tttgctccat      540
atgggactta ttggcgccac ctacgtaaag tggcaatcac ccacatgttc tctccaagga      600
ggatttctga cttggagagt ctccgacaac atgtggttgg tgaaatggtg atgaggatat      660
ggaaggagat gggggacaaa ggggtggtag aggttcgagg catattgtat gaagggtctt      720
tgagccacat gttggagtgt gtgtttggta ttaataattc tctaggatca caaacaaagg      780
aggcgttggg tgatatggtt gaggaagggt atgacttgat tgccaagttt aattgggcag      840
actattttcc tttcgggttt ttggactttc acggggtcaa gagaaggtgt cacaaattgg      900
caactaaggt caatagtgtg gtgggtaaaa ttgtggaaga agaaaaaaat tcaggaagt      960 acgttggaca aaatgatttt cttagtgcct tgttattgtt gcctaaagag gaaagcatag     1020
gtgattcaga tgtagtggct atcttatggg aaatgatatt tcgggaaca gacacaattg     1080 ctatactttt agaatggatc atggccatga tggttttaca ccaagacgta caaatgaaag     1140
```

| | |
|---|---|
| ctcgtcaaga gatcgactca tgcatcaagc aaaacggtta catgcgagac tcagacattc | 1200 |
| caaacctccc ttacctccag gccatagtga aggaggttct ccgattgcac ccaccaggcc | 1260 |
| cattactttc ctgggctcgc ctcgcaatcc atgatgtcca cgtggacaag gtcatcgtgc | 1320 |
| cagctggcac aactgcaatg gttaacatgt gggctatatc acatgactca tccatttggg | 1380 |
| aggacccgtg ggcctttaag cccgaaagat tcatgaaaga agatgtgtcg atcatggggt | 1440 |
| cggacatgag acttgcacca tttggtgcag gacgtagggt gtgcccagga aaaacattag | 1500 |
| gcttagccac agttcatcta tggcttgcac aacttcttca ccatttcata tggattccag | 1560 |
| tgcaacccgt ggatctttca gaatgcctaa agctctcgct cgaaatgaaa aagcctttac | 1620 |
| gatgccaagt gattcgcagg ttcaacacca taagctcttg aactcaacaa gataaattaa | 1680 |
| tgcacaataa aggatatcat tatcgatgta actgttgtga taaaaaaaaa ttaaagtctt | 1740 |
| tgatttgggt ggaagttatg taatgttgta aaaatatatc aagtatgtag tatgcgttga | 1800 |
| gctcaagata gtccaagaaa tgggctaatg aatggattga tactatctct ctttgaaagt | 1860 |
| acaccacgta caatattgga tctaataaag tcgcatggtt tttgt | 1905 |

<210> SEQ ID NO 30
<211> LENGTH: 1894
<212> TYPE: DNA
<213> ORGANISM: Zea mays

<400> SEQUENCE: 30

| | |
|---|---|
| ggagagatca gctgagagct ggtgggtgct tcccatgacc ttgataccgg ccatctccgg | 60 |
| cgagcaacac ggtaacatgg caaccgtagc cactagcttc gcctacctcg ccatcttcgc | 120 |
| atgcctcgca tgggtgggcg cgtccctgct ctactgggct cacccaggcg gccctgcgtg | 180 |
| gggcaagtac tggagggcga gggggaagaa gccgtcggcg gcgatcccgg ggcctaaggg | 240 |
| gctcccggtg gtcggcagcc tcggcctcat gtccgggctg gcgcaccgct cgctggccga | 300 |
| cgaggcgtcg cgccgcccgg gggccaagcg gctcatggcg ctgtcgctcg gccccgtccg | 360 |
| cgcggtcgtc acgtcccacc cggacgtggc caaggagatc cttgatagcc ggcgttcgc | 420 |
| cgcccgcccc ctgaaccacg ccgcgtacgg cctcatgttc caccgctcca tcggcttcgc | 480 |
| cgagcacggc ccgtactggc gcgcgctccg gcgcgtcgcc gcgggccacc tgttcggccc | 540 |
| gaggcaggtc gaagccttcg cgccgtaccg cgcggccgtc gccgagggca tcgtcgcggc | 600 |
| cctgctgcgc gccggctccg gcggcgccgt cgtccaggtg cgcggcctcc tgcggcgggc | 660 |
| gtcgctctac tacatcatgc ggttcgtgtt cggcaaggag tacgacgtgt cacgcgtggt | 720 |
| gccgccgtcc ggcggggagg aggtggagga gctgctcgag atggtgcacg aggggtacga | 780 |
| gctcctgggc atggagaacc tgtgcgacta cttcccgggg ctcgccgccc tcgacccgca | 840 |
| gggcgtgggc gcacgatgcg ccgagctcat gccgcgggtg aaccggttcg tgcacggcgt | 900 |
| catccaggag caccgtgcca aggcggtcgc cggtggagac gcgcgtgact tcgtcgacat | 960 |
| cttgctctcc ctgcaggaga gtgaggggct cgccgacgcc gacatagcct ctgtgctctg | 1020 |
| ggagatgatc ttcagaggaa cggacgccat ggcggtgctc atggagtgga ccctagctcg | 1080 |
| cctcgtcctc caccgcgacg tccaagccaa ggcgcaccgt gagctcgaca aggtcgtcgg | 1140 |
| cgcggacagc cagaccaccg agtccgcggc gccgtacctg caggcgttgc taaaggaggc | 1200 |
| tctccggatg caccgccggg ggcccctcct gtcgtggcgc cacagggcca tatccgacac | 1260 |
| gtacgtcgac ggccacctcg tcccggcggg caccacggcc atggtgaacc agtgggccat | 1320 |
| cagccgcgac cccgaggtgt gggacgcgcc gctcgagttc cggcccgagc ggttcctccc | 1380 |

| | |
|---|---:|
| cggcggcgag ggccaggacg tgtccgtgct cggcgccgac ggccgcctcg tgccgttcgg | 1440 |
| gtccggcagg aggagctgcc ccggaaagtc cctggccatg accaccgtga cctcctggat | 1500 |
| ggccacgctg ctgcacgagt tcgagtggct gccagcgtca gacgacacag gcgacgtcga | 1560 |
| cctctcggag gtgctccgtc tgtcctgcga gatggcagtg ccgctggagg tccgcgtgcg | 1620 |
| cccgaggagc agcgtgtgaa tgaagtgctg cctgccgata gccatgacac accccccattg | 1680 |
| tgcaatgtgt agcagtgagc ctaagcgttc tgttagtgaa ctgtgaataa gcagctggtg | 1740 |
| aggactgtgc acaccagctc agctcagcct ttggttcagg gtttcaactt gcccgtgtat | 1800 |
| atcgtatatt tagtgtgacc gtgagtatta agttatccgc aaaaggtgta caaatcacaa | 1860 |
| aagctatcga atgaagattg tgtgaagtgg tgtc | 1894 |

<210> SEQ ID NO 31
<211> LENGTH: 1914
<212> TYPE: DNA
<213> ORGANISM: Glycine max

<400> SEQUENCE: 31

| | |
|---|---:|
| tttcgataaa caccatttttt tctcttcctc ttttgaccaa acatgaaacc cacggcaaca | 60 |
| ttcttctttc tcctatccac aacaacactc cttgtttgtc tttgcctcgg aacaacaacg | 120 |
| ttccaaacca ctctctttat aaccttcttc actatttccc ttaactactg gcttgtccct | 180 |
| ggaggctttg catggagaaa ctatcactct tatcacacca acgaaaaacc aaacaaaaaa | 240 |
| cttactgggc ctatgggctg gcccatactt gggtctctgc ctctcatggg ctctttagcc | 300 |
| caccaaaaac tcgctgcctt agccgcgacg ttaaacgcga agaggttaat ggcactgagt | 360 |
| ctgggaccca ctcccgttgt tataagcagc accccgaga ccgccagaga aatcttactc | 420 |
| ggttcctcgt tttcggatcg tccgataaaa gaatccgcac gcgctctcat gttcgagcgt | 480 |
| gccattggct tcgctccatc cggaacctac tggcgacacc tacgtaggat cgcggcgttc | 540 |
| cacatgttct ctccgaggag gattcagggc ctggagggtc tccgacagcg cgtgggtgac | 600 |
| gacatggtga agagcgcgtg gaaggagatg gagatgaaag gcgtggtgga ggttcgcggt | 660 |
| gtgtttcagg aagggtctct ttgtaatatt ctggaaagtg tttttgggag taatgataag | 720 |
| agtgaggagt tgggggatat ggttaggaa gggtacgagc tgattgcgat gttgaacttg | 780 |
| gaggattatt ttcctttgaa gttttttggac tttcatgggg tgaagagaag gtgccacaag | 840 |
| ttggcggcta aggttggtag cgtggtgggg caaattgtgg aggatcgaaa aagagaaggg | 900 |
| agttttgttg tcaagaatga tttttcttagc actttgctat ccttgcccaa agaagaaagg | 960 |
| ttggctgatt cagatatggc ggctattttg tgggaaatgg tgtttcgagg aacagacaca | 1020 |
| gttgcaatac tccttgaatg ggtcatggcc aggatggttt tacaccaaga cgtacaaaag | 1080 |
| aaagcccgcg aagaaatcga cacgtgcatc ggccaaaaca gtcacgtgcg agactcggat | 1140 |
| attgcaaatc tcccatacct ccaggctata gtaaaagaag ttctccggct gcacccaccc | 1200 |
| ggcccactcc tatcatgggc ccgtcttgca gtcaatgatg tccacgttga caaagttctt | 1260 |
| gtgccagctg gtacaacagc aatggttaac atgtgggcca tatcacatga ctcatccatc | 1320 |
| tgggaagacc catgggcttt caagcccgag aggttcctca agaagatgt ttctatcatg | 1380 |
| ggatcggact tgaggcttgc acccttcggg gctggacgta gggtgtgtcc gggccgggcc | 1440 |
| ttggggtttgg ccacgaccca tctctggctc gcgcaacttc ttcgccactt catatggctt | 1500 |
| cccgcgcaac ccgtggatct ttcggagtgt cttaggcttt ccatggaaat gaagacacct | 1560 |

| | |
|---|---|
| ctgcgatgtc tagttgttcg tagataaaaa atataataac gtaagccttt tagctgaact | 1620 |
| atgtttgatg tgcaattata gaatgatcga gcttgtatct gatgtttgat gttaaagatg | 1680 |
| gtactcaaat atttagtgaa atatttagag atgagttatc gtataattat ggaacttatc | 1740 |
| tctaagcttt atttcacttt attttttaagg gtatcaaatt attaaaataa atatctagtg | 1800 |
| ccaggactag aggtggatgt aagaaaagat tggatcgatt aagaaggttt tatgtctctt | 1860 |
| taaatcgtaa aatgtaaatt gctgtaatgt aatgaagttg cttccgtacg tatg | 1914 |

<210> SEQ ID NO 32
<211> LENGTH: 1310
<212> TYPE: DNA
<213> ORGANISM: Sorghum bicolor

<400> SEQUENCE: 32

| | |
|---|---|
| atggacttca ccgacgtcct gctctccctc aacggcgacg acaagctctc cgacgccgac | 60 |
| atgatcgccg tcctctggga gatgatcttc cgaggcacgg acacggtggc ggtgctgatc | 120 |
| gagtgggtgc tggcacgtct ggtgctgcac caggacgtga agcgcaaggt gcacgacgag | 180 |
| ctggaccggg tggtcgggcc gggcgaggcc gtgacggagt cggacaccgc ctcactggtg | 240 |
| tacctgcagg cggtcatcaa ggaagtgctg cgcctgcacc cgccgggccc actgctgtcc | 300 |
| tgggcgcggc tggccacgtc ggacgtgaac gtcggcgggc acctggtccc cgcgggcacc | 360 |
| accgccatgg tgaacatgtg ggccataacc acgacgccca gcgtgtggcc tgagccgacg | 420 |
| gagttcaggc ccgagaggtt cgtcgccgcc gccggcggcg aggacgtcgt cccgataatg | 480 |
| ggttcggacc tccggctcgc gccgttcggg tccggcaggc ggagctgccc cgggaagtcg | 540 |
| ctcgcggtgg ccaccgtcgg gttctgggtc gccaccctgc tgcacgagtt cgaatggttg | 600 |
| ccgtgcggcg gcggcggcgg cgtggacctg tccgaagtgc tgaggctgtc gtgtgagatg | 660 |
| gccgcgccgc tggaggcgag ggtggtgcca cgtcgtcacg cggtgtgatg atgacgaggc | 720 |
| agctgagaca cacgtggacg tggctgggga gaggggacgg agtggctagc ttcttctact | 780 |
| actactacct taccaccttc tagcagaacg taacgtacgt ggccccggac gacgatcgat | 840 |
| gagcgagatg cgtaaaaaaa aaatcgccca agtgccatgc tttagagctg atgctggtgt | 900 |
| ggacttccag taatttcctg tgtatgatgg taggtgctgg tggaaggact acgtagtaac | 960 |
| caccagccgg tttgatgctt aattatgtgt gtgtgtgtgt gtgtgtgtgt gtgtgtgtgt | 1020 |
| gtgtgtgtgt gtgtgtgtgt gtgtgtgtgt gtgtgtgtgt gtgtgtgtgt gtgtgtgtgt | 1080 |
| gtgtgtaatg taacttacta gctgctgctg ctgcatgtaa tatctgcctg ctgttagtcg | 1140 |
| actactaggt agtgtagtgt accagatgat gagtgtgaca gttatctttt cctttttcagt | 1200 |
| aatgcgtagc tagctagagc tagatgtgta ttattgtgta ataataatcc tatgtgtgta | 1260 |
| tatatctctc tatagtttct atcctaatgc aagcgtgcgt gtgtgtacgt | 1310 |

<210> SEQ ID NO 33
<211> LENGTH: 1852
<212> TYPE: DNA
<213> ORGANISM: Glycine max

<400> SEQUENCE: 33

| | |
|---|---|
| atgaaaccca cggcaacatt cttctttctc cttccttcaa caacactcgt tgtttgtctt | 60 |
| tgccttggaa ttggaacaac caccctcttt ataaccctcc tcgcaatttc ccttaactac | 120 |
| tggcttgtcc ctggaggctt tgcatggaga aactatgact attatcaaac caaaaaaaaa | 180 |
| cttactgggc ctatgggctg gcccatactc gggactctgc ctctcatggg ctctttagct | 240 |

```
caccaaaaac ttgcggcttt agccacttcg ctgaacgcaa agaggttaat ggcgctgagt        300
ctgggcccca ctcccgttgt tataagcagc caccccgaga ccgctagaga aatcttgttg        360
ggttcatcgt tttcggatcg tccgataaaa gaatcggcac gcgctctcat gttcgagcgt        420
gccattggtt tcgctcattc aggaacctac tggcggcacc tacgtaggat cgcggcgttt        480
catatgttct ctccgaggag gattcatggc ttggagggtc tccgacaacg cgtaggtgac        540
gacatggtga agagcgcgtg gagggagatg ggggagaagg gggtggtgga ggttcggagg        600
gtatttcagg aagggtcact ttgtaatatt ttggagagtg ttttttggaag taacgataag        660 agtgaggagt tgagggatat ggttagggaa gggtacgagt tgattgcgat gtttaacttg        720
gaggattatt ttcccttcaa gttttttggat tttcatgggg tgaagagaag gtgccacaag        780
ttggcggcta aggttggtag tgtggtgggc caaattgtgg aggaacgaaa aagagatggt        840
ggttttgttg gaagaatga ttttcttagc actttgctat ccttgcccaa agaagaaga        900 ttggctgatt cagatctggt ggctattctg tgggaaatgg tatttcgagg aacagacaca        960
gttgcaatac tccttgaatg ggttatggca aggatggttt tacaccaaga cttacaaaag       1020
aaagcccgcg aagaaatcga cacgtgcgtc ggccaaaaca gtcacgtgcg agactcggat       1080
attgcgaatc tcccttacct ccaggccata gtgaaagaag ttctccggct gcacccacca       1140
ggcccgctac tatcatgggc tcgccttgcg gtccatgatg tccatgcgga caaagtcctc       1200
gtgccagctg gcacaacagc aatggttaac atgtgggcca tttcgcatga ctcgtccatc       1260
tgggaagacc catgggcttt caagcccgag aggttcctca agaagatgt ttccatcatg       1320 ggatcggact tgaggcttgc acccttcggg gctggacgta gggtgtgtcc gggccgggcc       1380
ttgggcttgg ccacggccca tctctggctc gcgcaacttc ttcgccactt catatggctt       1440
cccgcacaaa ccgtggatct ttccgaatgc cttaggcttt ccatggaaat gaagacacct       1500
ctgcgatgcc tagtggttcg tagataaata aataaaaaat cgtaagccct tgaaccgaac       1560
catgtttaat gtgcaattag gatgatcgag cttgtatct gttgtttgat gttaaatttg       1620
gtactcaaat atctagtgaa atatttagag atgagtttat cgtataatta gggagcttat       1680
ctctaagttt tatttcactt tattttttaaa gggtatcaaa ttattaaaat aaatatctag       1740
tgccagttga ctagaggtgg gtgtaagaag agagtggctt aagaaggctt tatgtatctt       1800
taaattgtaa aatgtaaatt actgtaatgt aatgcatgca ttttttcttct tg              1852
```

<210> SEQ ID NO 34
<211> LENGTH: 1554
<212> TYPE: DNA
<213> ORGANISM: Sorghum bicolor

<400> SEQUENCE: 34

```
atggtgctca ccatggccac cggccaagag gactccctcc tcctgctcct cctccccacc         60
acctccccac tcccgcccct catggccgtg ttcatcctag ccgccgtcct cctgtggctc        120
tcccccggtg gtcctgcgtg ggcgctctcc cgctgccgcc gcccgccgtc cggcccaacg        180
ggcgtggtca ccgcgctctc aagcccccgtg gcgcaccgca cctggcggc gctgtcccac        240 gccgtagacg gcggcaaagc actgatggcc ttctcggtcg ggctcacccg cctcgtcgtg        300
tcgagccagc ccgacacggc gcgagagatc ctcgtcaacc ccgcgttcag cgaccgcccc        360
atcaaggacg cggctcgcca cctgctcttc caccgcgcca tgggcttcgc gccctccgga        420
gacgcgcact ggcgcgggct ccgccgcctc gccgccaacc acctgttcgg cccgcgccgc        480
```

```
gtggcggcgg ccgcgcacca ccgcgtctcc atcggcgagg ccatggtcgc cgacgtcgcc      540
gctgccatgg cccgccacgg cgaggtctcc ctgaagcgcg tgctgcatat cgcgtctctc      600
aaccacatca tggccaccgt cttcggcaag cactacgaca tggacagcca agagggcgtc      660
cttctggaag agatggtcac cgagggctac gacctcctgg gcacgttcaa ctgggctgac      720
cacctgccgt tgatcaagca tctcgacctc cagggcgtgc gccgccggtg caacaggtta      780
gtccaaaagg ttgaagtgtt cgttggaaag atcatccagg agcacagggc gaggcgcgcg      840
aatggaggag tcgacgatga gtacatgggt gacttcgtcg acgtccttct tgacctcgag      900
ggagaggaga agctgtccga atccgacatg atcgctgttc tttgggagat gatcttcaga      960
ggcgccgaca ctgtggcgat cttgatggag tggatcatgg cgaggatggc gctgcaccct     1020
gaaatccagt ccaaggccca ggcggagctg acggcgtcg tcgtgggcgg cgtggcggac     1080
gccgacgtgg gcaacctccc ctacatccag tgcatcgtga aggagacgct gcggatgcac     1140
cctccgggcc cgctcctgtc gtgggcgcgc ctcgccatcc acgacgcgca cgtcggcggc     1200
cacctggtcc ccgccggcac cacggccatg gtgaacatgt ggtccatcgc gcatgacccc     1260
gccatctggg cagagccgga gaagttccgc cccgagcgct tccaggagga ggacgtgagc     1320
gtcctcggga gcgacctccg cctggcccg ttcggcgccg gacgccgcgt ctgcccggc      1380 aagatgctgg ccctcgccac cacacacctc tggatcgccc agctgctgca cgagttcgag     1440
tgggcacccg cggccgccaa cggcggcgtc gacctgtccg agcgcctcaa catgtcgctg     1500
gagatggcca cgccgctggt gtgcaaggcc gtccccaggg cccagctggc ctaa           1554

<210> SEQ ID NO 35
<211> LENGTH: 1882
<212> TYPE: DNA
<213> ORGANISM: Sorghum bicolor

<400> SEQUENCE: 35
cgcaacgcaa cagctagcag caagctctga aagtcgcaat ggagagctca gttgagagct       60
ggtgggtgct tcccatgacc ttgatcccgg ccatctccgg ccagcagcac gagaacatgg      120
ccaccatagc cactagcttc gtctacctcg ccatcttcgc atgccttgca tgggcaggcg      180
cgtccctgct ctactgggct cacccaggcg gccctgcgtg gggcaagtac tggagggcga      240
agggaaagcc gtcgtcgacg atcccgggc ccaaggggct cccggtcgtc ggcagcctcg      300
gcctcatgtc cgggctggcg cactgctcgc tggccgacga ggcgtcgcgc cggccggggg      360
ccaagcggct catggcgctg tcgctcggcc ccgtccgcgc ggtggtcacg tcccacccgg      420
acgtggccaa ggagatcctc gacaacccgg cgttcgccga ccgccccctc aaccacgccg      480
cgtacgccct catgttccac cgctccatcg gcttcgccga gcacgcccg tactggcgcg      540 cgctccggcg cgtcgccgcg ggacacctgt tcggcccgag gcaggtcgag gccttcgcgc      600
cgtaccgtgc cgccgtcggg aagggatcg tcgcggccct gcacggcgcc ggcggcggcg      660
tcgtccaggt gcgcggcctc ctgcgccgag cttcgctcta ctacatcatg cggttcgtgt      720
tcggcaagga gtacgacgtg tcgcgcgccg tgccggcgtc cgggaaggag gaggtggagg      780
agctgctcga gatggtgcac gagggtgtacg agctcctggg catggagaac tggtgcgact      840
acttcccggg gctcgccgcc ctcgacccgc agggcgtcgg agcacggtgc gccgagctca      900
tgccacgggt gaaccggttc gtgcatggca tcatccagga gcgccgtgcc aaggcgatcg      960
ccggaggaga cgcgcgtgac ttcgttgaca tcttgctctc cctgcaggag agcgagaggc     1020
tcgccgacgc cgacatagcc gctgtgctct gggagatgat cttcagagga acggacgcca     1080
```

```
tggccgtgct catggagtgg accctagctc gcctcgtcct ccaccgtgac gtccaagcca    1140
aggcgcaccg tgagctcgac gaggtcgtcg gcgggaacag ccaggtcgtc accgagtcgg    1200
cagcggcgcc gtcgctgcct tacctgcagg cgttgctaaa ggaggctctc cggatgcacc    1260
cgccggggcc cctcctgtcg tggcgccaca gggcgatatc cgacacgtac gtcgacgggc    1320
acctcgtccc ggcaggcacc accgccatgg tgaaccagtg ggcaatcagc cgcgaccccg    1380
aggtgtggga cgcgccgctc gagttccggc ccgagcggtt cctccctggc ggcgagggcc    1440
aggacgtgtc cgtgctcggc gccgacggcc gcctcgtgcc gttcgggtcc ggtcggagga    1500
gctgccccgg caagtccctg ctatgaccac ccgtgaccac ctggatggcc accctgctga    1560
acgagttcga gtggctgccg gcgtcagacg atacaggcgg cgacgtcgac ctctcggagg    1620
tgctccgtct gtcctgcgag atggctgtgc cgctggaggt ccgcgtgcgc ccgaggagcg    1680
gcatgtgaat gaagtatctg ccgatagcca tggcaccccc attgtgcaat gtgtagcagt    1740
aaccctaagc gttgtgttag taaactgtga ataagcagca gctggtgagg actgtgcata    1800
ccagctcagc tcagttcagt atttggttca gggtttcaac ttgcctatgt atcatatata    1860
tagtgtgacc gtgagtacaa gt                                              1882
```

<210> SEQ ID NO 36
<211> LENGTH: 2085
<212> TYPE: DNA
<213> ORGANISM: Sorghum bicolor

<400> SEQUENCE: 36

```
gtgcccactt cttccaactt ataatccaag caaccaacta tagctcaaca catctctcct     60
tgtgttctca tctatagcca tctaagtagc aattgcatta gcaaccatag tagcacctgc    120
tatgcactag tcagtaatca gtaccacaca tagtttacac acacacaaca cacacaaacg    180
cacacacaaa aaagacttta cacacttagg ttaactatac atatagccat gaagactgaa    240
gtaatcacca ccatgatctc cttggtcttc ctcgtgcatt tcgctatcac catcagccct    300
aacgcacaac cttcatggct cttctctctc atgtctctct cccttgccgt ggtggcggtc    360
atagtgccat tagtagtcac caccacttgc catgcacgta agaataccga cgctaccacc    420
accatcccgg ggccacgagg gtggccgctg gtaggctccc tgctggtcgt gtcgggccca    480
ctcatgcacc gtcgcctagc cgcgctggcc gacgcgcata gcgcacgtcg cctcatgtcg    540
ctcaccctcg gtgccacccc cgtggtgatc agcagccacc cagaaacggc gcgagacatc    600
ctctcaggtg ccgccttcgt ggaccgcccg cctaaggccg cagcccggga actcatgttt    660
tgccgtgcca tcgggtttgc ccccactggg gagtattggc gtcgcctccg tcgcatcacg    720
ggcgctggca tgctctcccc gcgtcgcatg gccatgctca ggggtcttcg ctgccgtgtt    780
gccgacagca tgatccagcg tgtcgcggac cagatggaga ggtccgggga ggtggccatg    840
agagccttgc tccaaagggc ctccctagag agcatggtgg gtagcgtgct aggcctcgag    900
ggtgacgctg tttgtgagga gctgggtgag atggtgaggg aagggtatga gctcgtgggc    960
atgttcaacc tagaagacca ctactacaag acatcatggg gcccgttgat ggacctttgg   1020
ggggtgaggc ccatgtgcag ggagctggct gctatggtta gagggtattt tgggaagatc   1080
attcaggaga ggaggctggc aggggactgc cacgagaggg ccgacttgct tagctatatg   1140
ctttcacttc cagaggagga gaagttggag gactctgatg tgattgctgt gctgtgggag   1200
atgattttcc gtggcgtgga cgtcgtggcg attctcctgg agtgggccat ggcccgcatg   1260
```

```
tcactgcacc cagacatcca atccaaggcc caggaggaga tggacgcagc ggtgggcgtc    1320
cgtcgtcgtc gtgccatcac cgactccgac gtccccaacc ttgccttcct ccaatggatc    1380
ctcaaggaga cgctccggat gcacccgccg ggcccgctgc tctcctgggc gcgcctggcg    1440
gtgcaggacg cgcgggtggg caagcacgtg gtgccggcgg ggacgacggc catggtgaac    1500
atgtgggcca tctcgcacga cgaggccatc tggggagacc cctgggtgtt ccggccggag    1560
aggttcgcgg cggcggcggc cggggaggag gtgagcgtgc tcgggtccga cctcaggctg    1620
gcgccgttcg ggtccggccg gagggtgtgc cctggcagga tgatgggcct cgccaccgcg    1680
cagctctggc tcggacgcct cctgcaggag taccggtggc tgccgccgcc ggccaataag    1740
cccgtcgagc tcgccgagtg cctccgcctg tccatggaga tgaagacgcc cctcgtctgc    1800
cgcgcggttc ctcgtcgtcg cggaggacgg cctcctgctg cagcttgatg gccactgtg    1860 atgatgagct ccttcggtgc tgtggccact gttgggcacc agtgtaaaat taaatccttg    1920
tgtgtttgcc tactactcgt ttacagtgtt gtttgtacgt acaatcaaag attattgtat    1980
gtatgtgatg tgatgtgatg tatctgtgcc cggccggcct atagctacgt ggctagacac    2040
atgagtatag tttgcactac tctgatatat atatatgtgt tatac                   2085
```

<210> SEQ ID NO 37
<211> LENGTH: 1500
<212> TYPE: DNA
<213> ORGANISM: Oryza sativa

<400> SEQUENCE: 37

```
atggcggtcg tcgccttgcc gccgcttctt gcgaaacgcc atggacatgc acgccgggtt      60
aatggcggcg gcgctgccat tcccgggccg cggggtggc cgctgctggg gtcgctcccg     120
gtggtgtccg gtccgctcat gcaccgccgc ctcgccgcgc tggccgacgc gcacggcggc     180
ggcgcgcggc gcctgatgtc gctgacgctc ggcgcgacgc ccgtggtggt gagcagccac     240
ccggacacgt gcgggagat cctcgccggc gccgcgttcc gcgaccgtcc cgccagggcc     300
gcggcgcggg agctcatgtt cctccgcgcc gtcggcttcg ccccggcctc cggagacgac     360
ggcggcgcct actggcgccg cctccgccgc gccgcgggcg cgggcatgct ctccccgcgc     420
cgcgccgccg cgctcgccgc gctgcgcgcc cgcgtcgcgc gccgcacgtc cgaggccgtg     480
tcccgcggca tggccgtgcc gccggccgc gtcgccatgc gcgccctcct ccacgccgcc     540
tccctcgaca acatggttgg cagcgtgcta gggctcgaac accatgacca ccatggcggc     600
gtcatcagcg acatgggtga catggtgagg aagggtacg agctggttgg caagttcaac     660
ctaggagact actacagtac tacacagtac cagtgcctgt gggggttgct ggatttccat     720
ggggtggggc ccaggtgtca gaggctggca gctagggtta gggagcagtt tgggagggtg     780
atggaggaga ggaggaaggt gagtgacctg cacaagaggg atgatcttct tagctacatg     840
ctctccatgc cacaggagga gaggattgag gactctgatg tcattgctgt cctctgggag     900
atgatctttc gtgggacaga tgtagttgca atactcctgg aatgggccat ggccggatg      960 gtactccacc cagacatcca gtccaaggtg caagaagaac tagataggc ggtgggccac    1020 cggcccatga ccgactcgga catccccaac cttcgcttcc tccattgtgt catcaaggaa    1080
accctccgca tgcacccgcc tggcccactt ctctcatggg cccgcttggc ggtgcatgat    1140
acctatgtgg gcaagcacct agtcccgca gggactacgg caatggtgaa tatgtgggcc    1200
atatcccatg atgagacgat atgggtgac ccatgggtgt ttcgacccga aaggtttatg    1260
gaagaggata tcaatgtgtt gggatcagat ttaaggttgg caccgtttgg atcaggtcgt    1320
```

```
cgggtgtgcc ctggacggat gatgggtctc tccactgcct atctatggtt tggccggatg    1380
ttgcaagagt ataagtgggc agcggctcag ccggttaaac ttacgagtg cctccgtctt    1440 tctatggaga tgaagaaacc tttggtttgt catgcagttc ctcgtagcaa aactggctaa   1500
```

<210> SEQ ID NO 38
<211> LENGTH: 1668
<212> TYPE: DNA
<213> ORGANISM: Oryza sativa

<400> SEQUENCE: 38

```
atggcaatgg ccaccgccac cgcctcctcc tgcgtcgacg ccacgtggtg ggcgtacgcc     60
ctcccggcgc tcctcggcgc cgacaccctc tgcgccacc cggcgctgct cgccggcgcc    120
gtcctcctgg ccttcgccac cgccgcgtg ctcgcctggg ccgcgtcccc cggcggggccg    180 gcgtgggcgc acggccgcgg ccgcctcggc gcgacgccca tcgaggggcc ccggggggctc   240 cccgtgttcg gcagcatctt cgcgctctcc cggggcctcc cgcaccgcgc gctcgacgcg    300
atgtcgcgcg acgcggcggc gccacggcg agggagctca tggcgttctc cgtcggggag    360
acgccggcgg tggtgtcgtc gtgcccggcg acggcgaggg aggtgctcgc caccccgtcg    420
ttcgccgacc gcccgctgaa gcgctcggcg cgggagctgc tgttcgcgcg cgccatcggg    480 ttcgcccca gcggcgagta ctggcgcctc tccgccgca tcgcctccac ccacctcttc      540 tccctcgcc gcgtcgccgc gcacgagccg gggcgccagg ccgacgccac ggcgatgctg    600
tccgccatgg ccgccgagca gtccgccacc ggcgccgtcg tgctccgccc ccacctccag    660
gccgccgcgc tcaacaacat catgggcagc gtgttcggcc ggcgctacga cgtctcctcc   720
tcctccggcg ccgccgccga cgaggccgag cagctcaaga gcatggtgcg cgaggggttc   780
gagctcctcg gcgcgttcaa ctggtccgac cacctcccat ggctcgccca cctctacgac   840
cccaaccacg tcgcccgccg ctgcgccgcg ctcgtccccc gcgtccaggc gttcgtccgc   900
ggcgtcatcc gcgaccaccg cctccgccgc gactcctcct ccaccgccgc cgacaatgcc    960
gacttcgtcg acgtcctcct ctccctcgag gcccacgaga acctcgccga ggacgacatg   1020
gtcgccgtcc tctgggagat gatatttcgt gggacggaca cgacggcgtt ggtgacggag   1080
tggtgcatgg cggaggtggt gaggaacccg gcggtgcagg cgaggctgag ggcggaggtg   1140
gacgcggcgg tgggcggcga cgggtgtccc agcgacggcg acgtggcgcg gatgccgtac   1200
ctgcaggcgg tggtgaagga gacgctgagg gcgcacccgc cggggccgct gctgagctgg   1260
gcgcggctgc ccaccgccga cgtggggctc gccaacggca tggtggtgcc ggcgggcacg   1320
acggcgatgg tgaacatgtg ggccatcacc cacgacggcg aggtgtgggc cgacccggag   1380
gcgttcgcgc cggagcggtt catcccgtcg gagggcggcc ccgacgtcga cgtccgcggc   1440
ggcgacctcc gcctggcgcc gttcggcgcc gggcgccgcg tctgccccgg caagaacctc   1500
ggcctcgcca ccgtcaccct ctgggtcgcc cgcctcgtcc acgccttcga ctggttcctc   1560
cccgacggct cgccgccggt gtccctcgac gaggtcctca agctctccct cgagatgaag   1620 accccctctcg ccgccgccgc caccccccgc cgccgccgcg ccgcctga              1668
```

<210> SEQ ID NO 39
<211> LENGTH: 525
<212> TYPE: DNA
<213> ORGANISM: Sorghum bicolor

<400> SEQUENCE: 39

| | |
|---|---|
| cgtgacggac gccgacgtgg cgaacctccc ctacgtgcag agcgtcgtga aggagacgct | 60 |
| gcgcatgcac ccgccagggc ccgctgctgt cgtgggcgcg cctggccatc cacgacgcgc | 120 |
| acgtcggcgg ccaccctggt ccccgccggc accacggcca tggtgaacat gtgggcgatc | 180 |
| gcgcacgacc ccgccatctg gcggagccg gaggagttcc gccccgagcg gttccaggag | 240 |
| gaggaggagg acgtgagcgt cctcggcggc gacctccgcc tggcccctt cggtgccggc | 300 |
| cgccgcgtat gccccgacaa gatgctcgcc ctcgccacca cccacctctg gtcgcccag | 360 |
| ctgctgcacc ggttcgagtg ggcccctgcg gcgccgcca gcagcggcgg cggcggcgtc | 420 |
| gacctgtcgg agcgcctcaa catgtcgctg gagatggcca cgccgctggt gtgcaaggcc | 480 |
| gtgcccaggt cagcccccca gctgcatgca ggcctagcta gctaa | 525 |

<210> SEQ ID NO 40
<211> LENGTH: 2076
<212> TYPE: DNA
<213> ORGANISM: Sorghum bicolor

<400> SEQUENCE: 40

| | |
|---|---|
| atggcgatgg cctccgcagt ttcgtcgtgc acggacagca cgtggtgggt gtacgcgctc | 60 |
| ccgacgctgc tcggctcgga caccctgtgc gcccacccgg ccctcctggc cggcctgctc | 120 |
| ttcctgacca ccgtcacggc ggctctgctg gcgtgggccg cgtcgccggg agggcctgcg | 180 |
| tgggcgcacg gccgcggccg cctcggcgcc actcctatcg tgggtccccg ggtctcccc | 240 |
| gtgttcggca gcatcttcgc gctctcccgc ggtctgccgc accgtaccct cgccgcgatg | 300 |
| gcccgcgcg cggggcccg ggccaaggag ctcatggcgt tctccgtcgg ggacacgccg | 360 |
| gcggtcgtgt cgtcgtgccc ggccacggcg cgtgaggtgc tcgcgcaccc gtccttcgcc | 420 |
| gaccgccccg tgaagcggtc ggcgcgggag ctcatgttcg cgcgcgccat cgggttcgcg | 480 |
| cccaacggcg agtactggcg ccgcctccgc cgcgtcgcgt ccacgcacct cttctccccg | 540 |
| cgccgcgtcg ccgcgcacga gccgggacgc cagggcgacg cggaggccat gctccgctcc | 600 |
| gtcgccgccg agcagtccgc ctcgggcacc gtcgtcctcc gcccgcacct ccaggccgcc | 660 |
| gctctcaaca acatcatggg cagcgtcttc ggcacgcgat acgacgtcac atccggcgcc | 720 |
| accgccggcg ccgcggaggc cgagcagctc aagagcatgg tgcgcgaggg gttcgagctc | 780 |
| ctcggcgcct tcaactggtc cgaccacctc ccctggctcg cccacctgta cgaccccagc | 840 |
| aacgtcaccc gccgctgcgc cgcgctcgtc ccgcgcgtcc agaccttcgt ccgtggcgtc | 900 |
| atcgacgagc accggcgccg ccgccaaaac tccgccgccc tcgacctcaa cgacaatgct | 960 |
| gacttcgtct acgtgctcct ctccctcgac ggcgacgaga agctccgcga cgacgacatg | 1020 |
| gtcgccatcc tctgggagat gatcttccgc ggtacggaca cgacggcgct tctgacggag | 1080 |
| tggtgcatgg cggagctggt gcgccacccg gcggtgcagg cgaggctgcg ggccgaggtg | 1140 |
| gacgcagctg tcggcgccgg cggtcgcccc accgacgccg acgtggcgcg catgccgtac | 1200 |
| ctgcaggcg tcgtgaagga cgcgctgcga gcgcacccgc ctggcccgct gctgagctgg | 1260 |
| gcgcgcctcg ccaccgccga cgtgcccctc tccaacggca tggtggtccc ggccggcacc | 1320 |
| acggcgatgg tgaacatgtg gccatcacc acgacgccg cgtgtgggc cgacccggac | 1380 |
| gcgttcgcgc cggagcggtt cctgccctcc gagggcggcg ccgacgtgga cgtccgcggc | 1440 |
| gtcgacctcc gcctggcacc gttcggcgcc gggcgccgcg tctgccccgg caagaacctg | 1500 |
| gggctcacca ccgtgggcct ctgggtcgcc cgcctcgtgc acgccttcga gtgggcgctg | 1560 |
| cctgatggcg cgccgcccgt ctgcctcgac gaggtcctca agctctcct ggagatgaag | 1620 |

```
acgccgctcg ccgccgcggc catcccgcgc accgcatgat ccatcctgcc gctgccgccg    1680
acgcgtgcaa caagaaccga ttatgctttg tcacgtcacg tcacgcgttc tttgtctgtg    1740
tgtgtgtggt tctaagctag tgtgcttctt cttgtcgatc gtcggttcgt tctcgtgcct    1800
gcctttgcct agggtttcgt ttcttgcaaa gtagtgacag tgtctccctt agagtcatca    1860
acggggctcc aattttggaa aggtgcgtgt taggagttaa ccccctagaca tgtctgcgtc    1920 tcgatcacca cctactatgt cattatcagc gcagcaccta tatatagatc agtgtctgtc    1980
gatcagtcat ggaagtcgat cgtgtgctca agtctgctgt attatatata atgtattgta    2040
atgtgattat caagaaccgt gctatctata tgttgc                              2076
```

<210> SEQ ID NO 41
<211> LENGTH: 1937
<212> TYPE: DNA
<213> ORGANISM: Brachypodium distachyon

<400> SEQUENCE: 41

```
atggagagct cagtcgagag cagctggtgg gtgctgcccc tgaccttgat tcctgccatc      60
tccggccagc agcagcagca cgatcaaagc acggccgccg ccatagccac cagcttcgtc     120
tacctcgcca tcctcgcctg cctcgcctgg gcggccaagt ccctgctcta ctgggctcac     180
ccgggcgggc tgcatgggg ccggcggtac tggacgagcc cgtgcgcgaa gacggctccg     240
gctccggcgc cgatccccgg gccgagaggg ctcccggtgg tgggcagcct gggcctgatg     300
tccggactag cccacagcac gctggccgcc gaggcggcaa ggacgccggg cgcgaagcgg     360
ctcatggcgc tgtctctcgg cccagtcccc gccgtcgtca cggcccaccc ggacgtggcc     420
aaggagatcc tcgacaaccc ggcgttcgcg gaccggcccg tgaaccacgc cgcctacggc     480
ctcatgttcc accgctccat cggcttcgcg gagcacggcc cctactggcg cgcgctccgg     540
cgcgtggcat cggcgcacct gttcgcgccc aggcaggtcg acgccttcgc cccttaccgc     600
gcgcgcgtcg gggaagacgt cgtggccgcg ctccgccatg ccggggggcgg cgtcgtgaac     660 gtgcgcggcg tgctccggcg cgcgtcgctc tactacatca tgcgcttcgt gttcggggaaa    720 gagtacgacg tgtcgtcgga ctcggggaag aaggatcagg gggaagtgga ggagctgctg     780
gagatggtgc atgagggtta tgagctgctg gggaaggaga actggtgcga ctacttcccg     840 gggctggcg ggttcgaccc gcagggcgtc ggggcgcggt gcgccgagct catgccgcgg     900
gtgaaccgct tcgtgcacgg catcatcgat gagcaccgcg gcaaggcgat gatagccgga     960
ggagaaggag aggcgcagcc gctggacttt gtggacatac tgctttcgtt gcaggagagc    1020
gaggggctcg ccgacgccga catcgccgcc gtgctctggg agatgatctt cagaggaaca    1080
gacgccatgg cggtgctgat ggagtggacc atggcacgcc tcgtcctgca ccccggcgtc    1140
caagccaacg tgcacaagga gctggacgag gtggtcggca agagcagcca cgtcaccgag    1200
tcagccgtgc tctcactgcc ttacctgcag gcgctgctca aggaggcgct ccgcgtgcac    1260
ccgccggggc cgctgctgtc gtggcgccac agggccatgt gggacaccta cgtggacggc    1320
cacctggtcc cggcgggcac cacgccatg gtgaaccagt gggccatgag ccggacccg     1380 gaggtttggg ccgagccgct cgagttccgg cccgaacggt tcctcccggg cggcgaggcc    1440
ggcccgggag tctccgtgct cggctcggac ggccggctcg tgccgttcgg gtctggacgg    1500
aggagctgcc ccgggaagaa cctgccatg accaccgtca cggcgtggat ggccacgctg    1560
atgcacgagt tcgagtggat gccggccaag accggcgccc ccgtcgacat gtcggaggtg    1620
```

```
ctccgcctgt catgcgagat ggcgacgccg ctccaggtcc gggtgcgccc caggcgcggc    1680
gtttgaaagt ctgaggctgc tttcgacggc catatatgac ttcaccgtgt agtttctttc    1740
ttactagccg tgaccctggg ttgtgcttcc tgtttgtgaa taagctggct gggatgaaca    1800
aaagtgtgca ccggctcagc ttcagtgttt ggttcagagt tttctttttg aacttcgtca    1860
gaagtatcat caggtgtgag cttgaggttc cacgttggtg tacagattgc aagaagaaaa    1920
tctataaagg attgtgc                                                   1937
```

<210> SEQ ID NO 42
<211> LENGTH: 530
<212> TYPE: PRT
<213> ORGANISM: Arabidopsis thaliana

<400> SEQUENCE: 42

```
Met Ala Thr Lys Leu Glu Ser Ser Leu Ile Phe Ala Leu Leu Ser Lys
1               5                   10                  15

Cys Ser Val Leu Ser Gln Thr Asn Leu Ala Phe Ser Leu Leu Ala Val
            20                  25                  30

Thr Ile Ile Trp Leu Ala Ile Ser Leu Phe Leu Trp Thr Tyr Pro Gly
        35                  40                  45

Gly Pro Ala Trp Gly Lys Tyr Leu Phe Gly Arg Leu Ile Ser Gly Ser
    50                  55                  60

Tyr Lys Thr Gly Asn Val Ile Pro Gly Pro Lys Gly Phe Pro Leu Val
65                  70                  75                  80

Gly Ser Met Ser Leu Met Ser Ser Thr Leu Ala His Arg Ile Ala
                85                  90                  95

Asp Ala Ala Glu Lys Phe Gly Ala Lys Arg Leu Met Ala Phe Ser Leu
            100                 105                 110

Gly Glu Thr Arg Val Ile Val Thr Cys Asn Pro Asp Val Ala Lys Glu
        115                 120                 125

Ile Leu Asn Ser Pro Val Phe Ala Asp Arg Pro Val Lys Glu Ser Ala
    130                 135                 140

Tyr Ser Leu Met Phe Asn Arg Ala Ile Gly Phe Ala Pro His Gly Val
145                 150                 155                 160

Tyr Trp Arg Thr Leu Arg Arg Ile Ala Ser Asn His Leu Phe Ser Thr
                165                 170                 175

Lys Gln Ile Arg Arg Ala Glu Thr Gln Arg Val Ile Ser Ser Gln
            180                 185                 190

Met Val Glu Phe Leu Glu Lys Gln Ser Ser Asn Glu Pro Cys Phe Val
        195                 200                 205

Arg Glu Leu Leu Lys Thr Ala Ser Leu Asn Asn Met Met Cys Ser Val
    210                 215                 220

Phe Gly Gln Glu Tyr Glu Leu Glu Lys Asn His Val Glu Leu Arg Glu
225                 230                 235                 240

Met Val Glu Glu Gly Tyr Asp Leu Leu Gly Thr Leu Asn Trp Thr Asp
                245                 250                 255

His Leu Pro Trp Leu Ser Glu Phe Asp Pro Gln Arg Leu Arg Ser Arg
            260                 265                 270

Cys Ser Thr Leu Val Pro Lys Val Asn Arg Phe Val Ser Arg Ile Ile
        275                 280                 285

Ser Glu His Arg Asn Gln Thr Gly Asp Leu Pro Arg Asp Phe Val Asp
    290                 295                 300

Val Leu Leu Ser Leu His Gly Ser Asp Lys Leu Ser Asp Pro Asp Ile
305                 310                 315                 320
```

```
Ile Ala Val Leu Trp Glu Met Ile Phe Arg Gly Thr Asp Thr Val Ala
                325                 330                 335

Val Leu Ile Glu Trp Ile Leu Ala Arg Met Val Leu His Pro Asp Met
            340                 345                 350

Gln Ser Thr Val Gln Asn Glu Leu Asp Gln Val Val Gly Lys Ser Arg
        355                 360                 365

Ala Leu Asp Glu Ser Asp Leu Ala Ser Leu Pro Tyr Leu Thr Ala Val
    370                 375                 380

Val Lys Glu Val Leu Arg Leu His Pro Pro Gly Pro Leu Leu Ser Trp
385                 390                 395                 400

Ala Arg Leu Ala Ile Thr Asp Thr Ile Val Asp Gly Arg Leu Val Pro
                405                 410                 415

Ala Gly Thr Thr Ala Met Val Asn Met Trp Ala Val Ser His Asp Pro
            420                 425                 430

His Val Trp Val Asp Pro Leu Glu Phe Lys Pro Glu Arg Phe Val Ala
        435                 440                 445

Lys Glu Gly Glu Val Glu Phe Ser Val Leu Gly Ser Asp Leu Arg Leu
    450                 455                 460

Ala Pro Phe Gly Ser Gly Arg Arg Ile Cys Pro Gly Lys Asn Leu Gly
465                 470                 475                 480

Phe Thr Thr Val Met Phe Trp Thr Ala Met Met Leu His Glu Phe Glu
                485                 490                 495

Trp Gly Pro Ser Asp Gly Asn Gly Val Asp Leu Ser Glu Lys Leu Arg
            500                 505                 510

Leu Ser Cys Glu Met Ala Asn Pro Leu Pro Ala Lys Leu Arg Arg Arg
        515                 520                 525

Arg Ser
    530

<210> SEQ ID NO 43
<211> LENGTH: 534
<212> TYPE: PRT
<213> ORGANISM: Arabidopsis thaliana

<400> SEQUENCE: 43

Met Ala Thr Lys Leu Asp Thr Ser Ser Leu Leu Ala Leu Leu Ser
1               5                   10                  15

Lys Cys Ser Leu Leu Thr Gln Thr Asn Leu Ala Leu Ser Leu Leu Val
                20                  25                  30

Ala Ser Leu Ala Ser Leu Ala Leu Ser Leu Phe Phe Trp Ser His Pro
            35                  40                  45

Gly Gly Pro Ala Trp Gly Lys Tyr Phe Leu His Arg Arg Arg Gln Thr
        50                  55                  60

Thr Val Ile Pro Gly Pro Arg Gly Leu Pro Phe Val Gly Ser Met Ser
65                  70                  75                  80

Leu Met Ser Asn Thr Leu Ala His Arg Cys Ile Ala Ala Thr Ala Glu
                85                  90                  95

Lys Phe Arg Ala Glu Arg Leu Met Ala Phe Ser Leu Gly Glu Thr Arg
                100                 105                 110

Val Ile Val Thr Cys Asn Pro Asp Val Ala Lys Glu Ile Leu Asn Ser
            115                 120                 125

Pro Val Phe Ala Asp Arg Pro Val Lys Glu Ser Ala Tyr Ser Leu Met
        130                 135                 140

Phe Asn Arg Ala Ile Gly Phe Ala Pro Tyr Gly Val Tyr Trp Arg Thr
```

-continued

```
            145                 150                 155                 160

Leu Arg Lys Ile Ala Ser Asn His Leu Phe Ser Pro Lys Gln Ile Lys
                165                 170                 175

Arg Ser Glu Thr Gln Arg Ser Val Ile Ala Asn Gln Ile Val Lys Cys
                180                 185                 190

Leu Thr Lys Gln Ser Asn Thr Lys Gly Leu Cys Phe Ala Arg Asp Leu
                195                 200                 205

Ile Lys Thr Ala Ser Leu Asn Asn Met Met Cys Ser Val Phe Gly Lys
    210                 215                 220

Glu Tyr Glu Leu Glu Glu His Glu Val Ser Glu Leu Arg Glu
225                 230                 235                 240

Leu Val Glu Glu Gly Tyr Asp Leu Leu Gly Thr Leu Asn Trp Thr Asp
                245                 250                 255

His Leu Pro Trp Leu Ser Glu Phe Asp Pro Gln Arg Ile Arg Ser Arg
                260                 265                 270

Cys Ser Asn Leu Val Pro Lys Val Asn Arg Phe Val Asn Arg Ile Ile
                275                 280                 285

Ser Asp His Arg Glu Gln Thr Arg Asp Ser Pro Ser Asp Phe Val Asp
    290                 295                 300

Val Leu Leu Ser Leu Asp Gly Pro Asp Lys Leu Ser Asp Pro Asp Ile
305                 310                 315                 320

Ile Ala Val Leu Trp Glu Met Ile Phe Arg Gly Thr Asp Thr Val Ala
                325                 330                 335

Val Leu Ile Glu Trp Ile Leu Ala Arg Met Val Leu His Pro Asp Ile
                340                 345                 350

Gln Ser Thr Val His Asn Glu Leu Asp Gln Ile Val Gly Arg Ser Arg
                355                 360                 365

Ala Val Glu Glu Ser Asp Val Val Ser Leu Val Tyr Leu Thr Ala Val
    370                 375                 380

Val Lys Glu Val Leu Arg Leu His Pro Pro Gly Pro Leu Leu Ser Trp
385                 390                 395                 400

Ala Arg Leu Ala Ile Thr Asp Thr Ile Ile Asp Gly Arg Arg Val Pro
                405                 410                 415

Ala Gly Thr Thr Ala Met Val Asn Met Trp Ala Ile Ala His Asp Pro
                420                 425                 430

His Val Trp Glu Asn Pro Leu Glu Phe Lys Pro Glu Arg Phe Val Ala
                435                 440                 445

Lys Glu Gly Glu Val Glu Phe Ser Val Leu Gly Ser Asp Leu Arg Leu
    450                 455                 460

Ala Pro Phe Gly Ser Gly Arg Arg Val Cys Pro Gly Lys Asn Leu Gly
465                 470                 475                 480

Leu Thr Thr Val Thr Phe Trp Thr Ala Thr Leu Leu His Glu Phe Glu
                485                 490                 495

Trp Leu Thr Pro Ser Asp Glu Lys Thr Val Asp Leu Ser Glu Lys Leu
                500                 505                 510

Arg Leu Ser Cys Glu Met Ala Asn Pro Leu Ala Ala Lys Leu Arg Pro
                515                 520                 525

Arg Arg Ser Phe Ser Val
    530

<210> SEQ ID NO 44
<211> LENGTH: 535
<212> TYPE: PRT
<213> ORGANISM: Arabidopsis thaliana
```

<400> SEQUENCE: 44

```
Met Arg Thr Glu Ile Glu Ser Leu Trp Val Phe Ala Leu Ala Ser Lys
1               5                   10                  15

Phe Asn Ile Tyr Met Gln Gln His Phe Ala Ser Leu Leu Val Ala Ile
            20                  25                  30

Ala Ile Thr Trp Phe Thr Ile Thr Ile Val Phe Trp Ser Thr Pro Gly
        35                  40                  45

Gly Pro Ala Trp Gly Lys Tyr Phe Phe Thr Arg Arg Phe Ile Ser Leu
    50                  55                  60

Asp Tyr Asn Arg Lys Tyr Lys Asn Leu Ile Pro Gly Pro Arg Gly Phe
65                  70                  75                  80

Pro Leu Val Gly Ser Met Ser Leu Arg Ser Ser His Val Ala His Gln
                85                  90                  95

Arg Ile Ala Ser Val Ala Glu Met Ser Asn Ala Lys Arg Leu Met Ala
            100                 105                 110

Phe Ser Leu Gly Asp Thr Lys Val Val Thr Cys His Pro Ala Val
        115                 120                 125

Ala Lys Glu Ile Leu Asn Ser Ser Val Phe Ala Asp Arg Pro Val Asp
130                 135                 140

Glu Thr Ala Tyr Gly Leu Met Phe Asn Arg Ala Met Gly Phe Ala Pro
145                 150                 155                 160

Asn Gly Thr Tyr Trp Arg Thr Leu Arg Arg Leu Gly Ser Asn His Leu
            165                 170                 175

Phe Asn Pro Lys Gln Ile Lys Gln Ser Glu Asp Gln Arg Arg Val Ile
        180                 185                 190

Ala Thr Gln Met Val Asn Ala Phe Ala Arg Asn Pro Lys Ser Ala Cys
    195                 200                 205

Ala Val Arg Asp Leu Leu Lys Thr Ala Ser Leu Cys Asn Met Met Gly
210                 215                 220

Leu Val Phe Gly Arg Glu Tyr Glu Leu Glu Ser Asn Asn Asn Leu Glu
225                 230                 235                 240

Ser Glu Cys Leu Lys Gly Leu Val Glu Glu Gly Tyr Asp Leu Leu Gly
            245                 250                 255

Thr Leu Asn Trp Thr Asp His Leu Pro Trp Leu Ala Gly Leu Asp Phe
        260                 265                 270

Gln Gln Ile Arg Phe Arg Cys Ser Gln Leu Val Pro Lys Val Asn Leu
    275                 280                 285

Leu Leu Ser Arg Ile Ile His Glu Gln Arg Ala Ala Thr Gly Asn Phe
290                 295                 300

Leu Asp Met Leu Leu Ser Leu Gln Gly Ser Glu Lys Leu Ser Glu Ser
305                 310                 315                 320

Asp Met Val Ala Val Leu Trp Glu Met Ile Phe Arg Gly Thr Asp Thr
            325                 330                 335

Val Ala Val Leu Val Glu Trp Leu Ala Arg Ile Val Met His Pro
        340                 345                 350

Lys Val Gln Leu Thr Val His Asp Glu Leu Asp Arg Val Val Gly Arg
    355                 360                 365

Ser Arg Thr Val Asp Glu Ser Asp Leu Pro Ser Leu Thr Tyr Leu Thr
370                 375                 380

Ala Met Ile Lys Glu Val Leu Arg Leu His Pro Pro Gly Pro Leu Leu
385                 390                 395                 400

Ser Trp Ala Arg Leu Ser Ile Thr Asp Thr Ser Val Asp Gly Tyr His
```

```
            405                 410                 415
Val Pro Ala Gly Thr Thr Ala Met Val Asn Met Trp Ala Ile Ala Arg
            420                 425                 430

Asp Pro His Val Trp Glu Asp Pro Leu Glu Phe Lys Pro Glu Arg Phe
            435                 440                 445

Val Ala Lys Glu Gly Glu Ala Glu Phe Ser Val Phe Gly Ser Asp Leu
            450                 455                 460

Arg Leu Ala Pro Phe Gly Ser Gly Lys Arg Val Cys Pro Gly Lys Asn
465                 470                 475                 480

Leu Gly Leu Thr Thr Val Ser Phe Trp Val Ala Thr Leu His Glu
            485                 490                 495

Phe Glu Trp Leu Pro Ser Val Glu Ala Asn Pro Pro Asp Leu Ser Glu
            500                 505                 510

Val Leu Arg Leu Ser Cys Glu Met Ala Cys Pro Leu Ile Val Asn Val
            515                 520                 525

Ser Ser Arg Arg Lys Ile Met
            530                 535

<210> SEQ ID NO 45
<211> LENGTH: 536
<212> TYPE: PRT
<213> ORGANISM: Arabidopsis thaliana

<400> SEQUENCE: 45

Met Glu Leu Met Asn Leu Ala Ser Lys Glu Thr Ser Tyr Trp Met Ile
1               5                   10                  15

Ala Leu Pro Ala Gly Phe Gly Ser Gln Asn Leu His Asp Val Ser Thr
            20                  25                  30

Leu Gly Tyr Leu Phe Leu Ala Val Val Phe Leu Ser Ile Val Thr Trp
        35                  40                  45

Ala Leu Ala Gly Gly Gly Gly Val Ala Trp Lys Asn Gly Arg Asn Arg
    50                  55                  60

Leu Gly Arg Val Ala Ile Pro Gly Pro Arg Gly Ile Pro Val Phe Gly
65                  70                  75                  80

Ser Leu Phe Thr Leu Ser Arg Gly Leu Ala His Arg Thr Leu Ala Ala
                85                  90                  95

Met Ala Trp Ser Arg Ala Asn Thr Glu Ile Met Ala Phe Ser Leu Gly
            100                 105                 110

Ser Thr Pro Val Ile Val Ala Ser Glu Pro Asn Ile Ala Arg Glu Ile
            115                 120                 125

Leu Met Ser Pro His Phe Ala Asp Arg Pro Val Lys Gln Ser Ala Lys
        130                 135                 140

Ser Leu Met Phe Ser Arg Ala Ile Gly Phe Ala Pro Asn Gly Thr Tyr
145                 150                 155                 160

Trp Arg Met Leu Arg Arg Ile Ala Ser Thr His Leu Phe Ala Pro Arg
                165                 170                 175

Arg Ile Leu Ala His Glu Ala Gly Arg Gln Leu Asp Cys Ala Glu Met
            180                 185                 190

Val Lys Ala Val Ser Val Glu Gln Asn Gly Ala Gly Ser Val Val Leu
        195                 200                 205

Arg Lys His Leu Gln Leu Ala Ala Leu Asn Asn Ile Met Gly Ser Val
    210                 215                 220

Phe Gly Arg Arg Tyr Asp Pro Leu Ala Gln Lys Glu Asp Leu Asp Glu
225                 230                 235                 240
```

```
Leu Thr Ser Met Val Arg Glu Gly Phe Glu Leu Leu Gly Ala Phe Asn
                245                 250                 255

Trp Ser Asp Tyr Leu Pro Trp Leu Gly Tyr Phe Tyr Asp Ser Ile Arg
            260                 265                 270

Leu Asn Gln Arg Cys Ser Asp Leu Val Pro Arg Ile Arg Thr Leu Val
        275                 280                 285

Lys Lys Ile Ile Asp Glu His Arg Val Ser Asn Ser Glu Lys Lys Arg
    290                 295                 300

Asp Ile Gly Asp Phe Val Asp Val Leu Leu Ser Leu Asp Gly Asp Glu
305                 310                 315                 320

Lys Leu Gln Glu Asp Asp Met Ile Ala Val Leu Trp Glu Met Ile Phe
                325                 330                 335

Arg Gly Thr Asp Thr Thr Ala Leu Leu Thr Glu Trp Thr Met Ala Glu
            340                 345                 350

Leu Val Leu Asn Pro Asn Val Gln Thr Lys Leu Arg Asp Glu Ile Leu
        355                 360                 365

Thr Ala Val Gly Asp Gly Ala Asp Gly Asp Val Ala Asp Ala Asp Leu
    370                 375                 380

Ala Lys Leu Pro Tyr Leu Asn Ala Val Val Lys Glu Thr Leu Arg Leu
385                 390                 395                 400

His Pro Pro Gly Pro Leu Leu Ser Trp Ala Arg Leu Ser Thr Ser Asp
                405                 410                 415

Val Gln Leu Ser Asn Gly Met Val Ile Pro Lys Gly Thr Thr Ala Met
            420                 425                 430

Val Asn Met Trp Ala Ile Thr His Asp Gln Thr Val Trp Ser Asp Pro
        435                 440                 445

Leu Lys Phe Asp Pro Glu Arg Phe Thr Gly Asn Ala Asp Met Asp Ile
    450                 455                 460

Arg Gly Gly Asp Leu Arg Leu Ala Pro Phe Gly Ala Gly Arg Arg Val
465                 470                 475                 480

Cys Pro Gly Lys Asn Met Gly Leu Ala Thr Val Thr Arg Trp Val Ala
                485                 490                 495

Glu Leu Val Arg Arg Phe Glu Trp Gly Gln Asp Gln Thr Glu Pro Val
            500                 505                 510

Asp Leu Gly Glu Val Leu Lys Leu Ser Cys Glu Met Glu His Pro Leu
        515                 520                 525

Arg Ala Val Val Thr Glu Ile Phe
    530                 535

<210> SEQ ID NO 46
<211> LENGTH: 517
<212> TYPE: PRT
<213> ORGANISM: Arabidopsis thaliana

<400> SEQUENCE: 46

Met Ser Pro Glu Ala Tyr Val Leu Phe Phe Asn Ser Phe Asn Leu Val
1               5                   10                  15

Thr Phe Glu Ala Phe Ala Ser Val Ser Leu Ile Ile Ala Thr Val Ala
            20                  25                  30

Phe Leu Leu Ser Pro Gly Gly Leu Ala Trp Ala Trp Thr Gly Ser Ser
        35                  40                  45

Lys Ser Arg Val Ser Ile Pro Gly Pro Ser Gly Ser Leu Ser Val Phe
    50                  55                  60

Ser Gly Ser Asn Pro His Arg Val Leu Ala Ala Leu Ala Lys Arg Phe
65                  70                  75                  80
```

```
Lys Ala Ser Pro Leu Met Ala Phe Ser Val Gly Phe Ser Arg Phe Val
                85                  90                  95

Ile Ser Ser Glu Pro Glu Thr Ala Lys Glu Ile Leu Ser Ser Ser Ala
                100                 105                 110

Phe Ala Asp Arg Pro Val Lys Glu Ser Ala Tyr Glu Leu Leu Phe His
                115                 120                 125

Arg Ala Met Gly Phe Ala Pro Tyr Gly Glu Tyr Trp Arg Asn Leu Arg
                130                 135                 140

Arg Ile Ser Ser Thr His Leu Phe Ser Pro Arg Arg Ile Ala Ser Phe
145                 150                 155                 160

Glu Gly Val Arg Val Gly Ile Gly Met Lys Met Val Lys Lys Ile Lys
                165                 170                 175

Ser Leu Val Thr Ser Asp Ala Cys Gly Glu Val Glu Val Lys Lys Ile
                180                 185                 190

Val His Phe Gly Ser Leu Asn Asn Val Met Thr Thr Val Phe Gly Glu
                195                 200                 205

Ser Tyr Asp Phe Asp Glu Val Asn Gly Lys Gly Cys Phe Leu Glu Arg
                210                 215                 220

Leu Val Ser Glu Gly Tyr Glu Leu Leu Gly Ile Phe Asn Trp Ser Asp
225                 230                 235                 240

His Phe Trp Phe Leu Arg Trp Phe Asp Phe Gln Gly Val Arg Lys Arg
                245                 250                 255

Cys Arg Ala Leu Val Ser Glu Val Asn Thr Phe Val Gly Gly Ile Ile
                260                 265                 270

Glu Lys His Lys Met Lys Lys Gly Asn Asn Leu Asn Gly Glu Glu Asn
                275                 280                 285

Asp Phe Val Asp Val Leu Leu Gly Leu Gln Lys Asp Glu Lys Leu Ser
                290                 295                 300

Asp Ser Asp Met Ile Ala Val Leu Trp Glu Met Ile Phe Arg Gly Thr
305                 310                 315                 320

Asp Thr Val Ala Ile Leu Val Glu Trp Val Leu Ala Arg Met Val Leu
                325                 330                 335

His Gln Asp Ile Gln Asp Lys Leu Tyr Arg Glu Ile Ala Ser Ala Thr
                340                 345                 350

Ser Asn Asn Ile Arg Ser Leu Ser Asp Ser Asp Ile Pro Lys Leu Pro
                355                 360                 365

Tyr Leu Gln Ala Ile Val Lys Glu Thr Leu Arg Leu His Pro Pro Gly
                370                 375                 380

Pro Leu Leu Ser Trp Ala Arg Leu Ala Ile His Asp Val His Val Gly
385                 390                 395                 400

Pro Asn Leu Val Pro Ala Gly Thr Ile Ala Met Val Asn Met Trp Ser
                405                 410                 415

Ile Thr His Asn Ala Lys Ile Trp Thr Asp Pro Glu Ala Phe Met Pro
                420                 425                 430

Glu Arg Phe Ile Ser Glu Asp Val Ser Ile Met Gly Ser Asp Leu Arg
                435                 440                 445

Leu Ala Pro Phe Gly Ser Gly Arg Arg Val Cys Pro Gly Lys Ala Met
450                 455                 460

Gly Leu Ala Thr Val His Leu Trp Ile Gly Gln Leu Ile Gln Asn Phe
465                 470                 475                 480

Glu Trp Val Lys Gly Ser Cys Asp Val Glu Leu Ala Glu Val Leu Lys
                485                 490                 495
```

```
Leu Ser Met Glu Met Lys Asn Pro Lys Cys Lys Ala Val Pro Arg
            500                 505                 510

Asn Val Gly Phe Ala
            515

<210> SEQ ID NO 47
<211> LENGTH: 537
<212> TYPE: PRT
<213> ORGANISM: Arabidopsis thaliana

<400> SEQUENCE: 47

Met Thr Ile Asp Met Tyr Leu Ser Phe Ala Ser Arg Ser Gly Ser Ser
1               5                   10                  15

Pro Phe Pro Ser Leu Glu Leu Cys Leu Ser Ile Phe Leu Phe Ile Ser
            20                  25                  30

Leu Phe Val Phe Trp Leu Thr Pro Gly Gly Phe Ala Trp Ala Leu Tyr
        35                  40                  45

Lys Ala Arg Phe His Thr Arg Pro Glu Ser Lys Thr Gly Pro Ala Ile
    50                  55                  60

Pro Gly Pro Ser Gly Leu Pro Ile Phe Gly Leu Leu Ala Phe Val
65              70                  75                  80

Asn Asn Ala Leu Thr His Arg Ile Leu Ala Asn Ile Ala Asp Thr Cys
                85                  90                  95

Lys Ala Lys Ala Leu Met Ala Phe Ser Val Gly Ser Thr Arg Phe Val
            100                 105                 110

Ile Thr Ser Glu Pro Glu Thr Ala Lys Glu Leu Leu Asn Ser Ser Ala
        115                 120                 125

Phe Ala Asp Arg Pro Val Lys Glu Ser Ala Tyr Glu Leu Leu Phe Asp
    130                 135                 140

Arg Ala Met Gly Phe Ala Pro Phe Gly Asp Tyr Trp Arg Glu Leu Arg
145                 150                 155                 160

Arg Ile Ser Ser Thr His Leu Phe Ser Pro Lys Arg Ile Phe Ser Ser
                165                 170                 175

Gly Glu Ser Arg Arg Lys Ile Gly Gln Asn Met Val Gly Glu Ile Lys
            180                 185                 190

Asn Ala Met Glu Cys Tyr Gly Glu Val His Ile Lys Lys Ile Leu His
        195                 200                 205

Phe Gly Ser Leu Asn Asn Val Met Ser Val Phe Gly Lys Thr Tyr
    210                 215                 220

Asn Phe Asn Glu Gly Ile Val Tyr Ser Lys Glu Ser Asn Glu Leu Glu
225                 230                 235                 240

His Leu Val Ser Glu Gly Tyr Glu Leu Leu Gly Ile Phe Asn Trp Ser
                245                 250                 255

Asp His Phe Pro Gly Met Arg Trp Leu Asp Leu Gln Gly Val Arg Arg
            260                 265                 270

Arg Cys Arg Ser Leu Val Gly Arg Val Asn Val Phe Val Gly Lys Ile
        275                 280                 285

Ile Asn Asp His Lys Ser Lys Arg Ser Leu Arg Asp Asn Pro Glu Glu
    290                 295                 300

Ser Thr Tyr Asp Asp Phe Val Asp Val Leu Leu Gly Met His Gly
305                 310                 315                 320

Asn Ser Lys Leu Ser Asp Ser Asp Met Ile Ala Val Leu Trp Glu Met
                325                 330                 335

Ile Phe Arg Gly Thr Asp Thr Val Ala Ile Leu Leu Glu Trp Ile Leu
            340                 345                 350
```

```
Ala Arg Met Val Leu His Pro Asp Ile Gln Ala Lys Ala Gln Ala Glu
        355                 360                 365

Ile Asp Cys Ile Val Gly Asp Ser Gly Arg Gln Val Thr Asp Ser Asp
    370                 375                 380

Leu Pro Lys Leu Pro Tyr Val Arg Ala Ile Val Lys Glu Thr Leu Arg
385                 390                 395                 400

Met His Pro Pro Gly Pro Leu Leu Ser Trp Ala Arg Leu Ser Ile His
                405                 410                 415

Asp Thr Gln Ile Gly Thr His Phe Ile Pro Ala Gly Thr Thr Ala Met
            420                 425                 430

Val Asn Met Trp Ala Ile Thr His Asp Glu Lys Val Trp Pro Glu Ala
        435                 440                 445

His Glu Tyr Lys Pro Glu Arg Phe Leu Gly Ala Gln Glu Ser Asn Asn
    450                 455                 460

Phe Pro Ile Met Gly Ser Asp Leu Arg Leu Ala Pro Phe Gly Ala Gly
465                 470                 475                 480

Arg Arg Val Cys Pro Gly Lys Ser Met Gly Leu Ala Thr Val Glu Leu
                485                 490                 495

Trp Leu Ala Gln Leu Leu Gly Ser Tyr Lys Trp Val Ser Cys Gly Glu
                500                 505                 510

Val Asp Leu Ser Glu Thr Leu Lys Leu Ser Leu Glu Met Lys Asn Thr
            515                 520                 525

Leu Val Cys Lys Ala Ile Pro Arg Gly
        530                 535

<210> SEQ ID NO 48
<211> LENGTH: 555
<212> TYPE: PRT
<213> ORGANISM: Oryza sativa

<400> SEQUENCE: 48

Met Ala Met Ala Thr Ala Thr Ala Ser Ser Cys Val Asp Ala Thr Trp
1               5                   10                  15

Trp Ala Tyr Ala Leu Pro Ala Leu Leu Gly Ala Asp Thr Leu Cys Ala
            20                  25                  30

His Pro Ala Leu Leu Ala Gly Ala Val Leu Leu Ala Phe Ala Thr Ala
        35                  40                  45

Ala Val Leu Ala Trp Ala Ala Ser Pro Gly Gly Pro Ala Trp Ala His
    50                  55                  60

Gly Arg Gly Arg Leu Gly Ala Thr Pro Ile Glu Gly Pro Arg Gly Leu
65              70                  75                  80

Pro Val Phe Gly Ser Ile Phe Ala Leu Ser Arg Gly Leu Pro His Arg
            85                  90                  95

Ala Leu Asp Ala Met Ser Arg Asp Ala Ala Pro Arg Ala Arg Glu
            100                 105                 110

Leu Met Ala Phe Ser Val Gly Glu Thr Pro Ala Val Ser Ser Cys
        115                 120                 125

Pro Ala Thr Ala Arg Glu Val Leu Ala His Pro Ser Phe Ala Asp Arg
    130                 135                 140

Pro Leu Lys Arg Ser Ala Arg Glu Leu Leu Phe Ala Arg Ala Ile Gly
145                 150                 155                 160

Phe Ala Pro Ser Gly Glu Tyr Trp Arg Leu Leu Arg Arg Ile Ala Ser
                165                 170                 175

Thr His Leu Phe Ser Pro Arg Arg Val Ala Ala His Glu Pro Gly Arg
```

```
                    180                 185                 190
        Gln Ala Asp Ala Thr Ala Met Leu Ser Ala Met Ala Ala Glu Gln Ser
                    195                 200                 205
        Ala Thr Gly Ala Val Val Leu Arg Pro His Leu Gln Ala Ala Ala Leu
                    210                 215                 220
        Asn Asn Ile Met Gly Ser Val Phe Gly Arg Arg Tyr Asp Val Ser Ser
        225                 230                 235                 240
        Ser Ser Gly Ala Ala Asp Glu Ala Glu Gln Leu Lys Ser Met Val
                        245                 250                 255
        Arg Glu Gly Phe Glu Leu Leu Gly Ala Phe Asn Trp Ser Asp His Leu
                        260                 265                 270
        Pro Trp Leu Ala His Leu Tyr Asp Pro Asn His Val Ala Arg Arg Cys
                        275                 280                 285
        Ala Ala Leu Val Pro Arg Val Gln Ala Phe Val Arg Gly Val Ile Arg
                        290                 295                 300
        Asp His Arg Leu Arg Arg Asp Ser Ser Ser Thr Ala Ala Asp Asn Ala
        305                 310                 315                 320
        Asp Phe Val Asp Val Leu Leu Ser Leu Glu Ala His Glu Asn Leu Ala
                        325                 330                 335
        Glu Asp Asp Met Val Ala Val Leu Trp Glu Met Ile Phe Arg Gly Thr
                        340                 345                 350
        Asp Thr Thr Ala Leu Val Thr Glu Trp Cys Met Ala Glu Val Val Arg
                        355                 360                 365
        Asn Pro Ala Val Gln Ala Arg Leu Arg Ala Glu Val Asp Ala Ala Val
        370                 375                 380
        Gly Gly Asp Gly Cys Pro Ser Asp Gly Asp Val Ala Arg Met Pro Tyr
        385                 390                 395                 400
        Leu Gln Ala Val Val Lys Glu Thr Leu Arg Ala His Pro Pro Gly Pro
                        405                 410                 415
        Leu Leu Ser Trp Ala Arg Leu Ala Thr Ala Asp Val Gly Leu Ala Asn
                        420                 425                 430
        Gly Met Val Val Pro Ala Gly Thr Thr Ala Met Val Asn Met Trp Ala
                        435                 440                 445
        Ile Thr His Asp Gly Glu Val Trp Ala Asp Pro Glu Ala Phe Ala Pro
        450                 455                 460
        Glu Arg Phe Ile Pro Ser Glu Gly Gly Ala Asp Val Asp Val Arg Asp
        465                 470                 475                 480
        Gly Asp Leu Arg Leu Ala Pro Phe Gly Ala Gly Arg Arg Val Cys Pro
                        485                 490                 495
        Gly Lys Asn Leu Gly Leu Ala Thr Val Ser Leu Trp Val Ala Arg Leu
                        500                 505                 510
        Val His Ala Phe Asp Trp Phe Leu Pro Asp Gly Ser Pro Pro Val Ser
                        515                 520                 525
        Leu Asp Glu Val Leu Lys Leu Ser Leu Glu Met Lys Thr Pro Leu Ala
                        530                 535                 540
        Ala Ala Ala Thr Pro Arg Arg Arg Ala Ala
        545                 550                 555
```

<210> SEQ ID NO 49
<211> LENGTH: 547
<212> TYPE: PRT
<213> ORGANISM: Zea mays

<400> SEQUENCE: 49

```
Met Ala Met Ala Ser Ala Ala Cys Ser Cys Thr Asp Gly Thr Trp Trp
1               5                   10                  15

Val Tyr Ala Leu Pro Ala Leu Leu Gly Ser Asp Thr Leu Cys Ala His
        20                  25                  30

Pro Ala Leu Leu Ala Gly Leu Ile Phe Leu Ala Thr Val Ser Val Ala
        35                  40                  45

Leu Leu Ala Trp Ala Thr Ser Pro Gly Gly Pro Ala Trp Thr Asn Gly
50                  55                  60

Arg Gly Ala Ser Ala Ser Leu Leu Ser Trp Asp Pro Val Val Cys Pro
65                  70                  75                  80

Cys Ser Ala Ala Ser Arg Cys Pro Gly Ala Ala Pro Arg Pro
                85                  90                  95

Arg Arg Asp Gly Pro Arg Arg Pro Arg Ala Lys Glu Leu Met Ala
            100                 105                 110

Phe Ser Val Gly Asp Thr Pro Ala Val Val Ser Ser Cys Pro Ala Thr
        115                 120                 125

Ala Arg Glu Val Leu Ala His Pro Ser Phe Ala Asp Arg Pro Val Lys
        130                 135                 140

Arg Ser Ala Arg Glu Leu Met Phe Ala Arg Ala Ile Gly Phe Ala Pro
145                 150                 155                 160

Asn Gly Glu Tyr Trp Arg Arg Leu Arg Arg Val Ala Ser Thr His Leu
            165                 170                 175

Phe Ser Pro Arg Arg Val Ala Ser His Glu Pro Gly Arg Gln Gly Asp
            180                 185                 190

Ala Glu Ala Met Leu Arg Ser Ile Ala Ala Glu Gln Ser Ala Ser Gly
        195                 200                 205

Ala Val Ala Leu Arg Pro His Leu Gln Ala Ala Leu Asn Asn Ile
        210                 215                 220

Met Gly Ser Val Phe Gly Thr Arg Tyr Asp Val Thr Ser Gly Ala Gly
225                 230                 235                 240

Ala Ala Glu Ala Glu His Leu Lys Ser Met Val Arg Glu Gly Phe Glu
            245                 250                 255

Leu Leu Gly Ala Phe Asn Trp Ser Asp His Leu Pro Trp Leu Ala His
            260                 265                 270

Leu Tyr Asp Pro Ser Asn Val Thr Arg Arg Cys Ala Ala Leu Val Pro
        275                 280                 285

Arg Val Gln Thr Phe Val Arg Gly Val Ile Asp Glu His Arg Arg Arg
        290                 295                 300

Arg Gln Asn Ser Ala Ala Leu Asn Asp Asn Ala Asp Phe Val Asp Val
305                 310                 315                 320

Leu Leu Ser Leu Glu Gly Asp Glu Lys Leu Gly Asp Asp Met Val
                325                 330                 335

Ala Ile Leu Trp Glu Met Val Phe Arg Gly Thr Asp Thr Thr Ala Leu
            340                 345                 350

Leu Thr Glu Trp Cys Met Ala Glu Leu Val Arg His Pro Ala Val Gln
        355                 360                 365

Ala Arg Val Arg Ala Glu Val Asp Ala Ala Val Gly Ala Gly Gly Cys
        370                 375                 380

Pro Thr Asp Ala Asp Val Ala Arg Met Pro Tyr Leu Gln Ala Val Val
385                 390                 395                 400

Lys Glu Thr Leu Arg Ala His Pro Pro Gly Pro Leu Leu Ser Trp Ala
            405                 410                 415

Arg Leu Ala Thr Ala Asp Val Pro Leu Cys Asn Gly Met Val Val Pro
```

```
               420                 425                 430
Ala Gly Thr Thr Ala Met Val Asn Met Trp Ala Ile Thr His Asp Ala
            435                 440                 445

Ala Val Trp Ala Asp Pro Asp Ala Phe Ala Pro Glu Arg Phe Leu Pro
        450                 455                 460

Ser Glu Gly Gly Ala Asp Val Asp Val Arg Gly Val Asp Leu Arg Leu
465                 470                 475                 480

Ala Pro Phe Gly Ala Gly Arg Arg Val Cys Pro Gly Lys Asn Leu Gly
                485                 490                 495

Leu Thr Thr Val Gly Leu Trp Val Ala Arg Leu Val His Ala Phe Gln
            500                 505                 510

Trp Ala Leu Pro Asp Gly Ala Ala Val Cys Leu Asp Glu Val Leu
        515                 520                 525

Lys Leu Ser Leu Glu Met Lys Thr Pro Leu Val Ala Ala Ile Pro
530                 535                 540

Arg Thr Ala
545

<210> SEQ ID NO 50
<211> LENGTH: 426
<212> TYPE: PRT
<213> ORGANISM: Phalaenopsis sp. SM9108

<400> SEQUENCE: 50

Met Ala Phe Ser Val Gly Leu Thr Arg Phe Ile Val Ser Ser His Pro
1               5                   10                  15

Lys Thr Ala Lys Glu Ile Leu Ser Ser Pro Ala Phe Ala Asp Arg Pro
            20                  25                  30

Ile Lys Glu Ser Ala Tyr Glu Leu Leu Phe Asn Arg Ala Met Gly Phe
        35                  40                  45

Ala Pro Phe Gly Asp Tyr Trp Arg Asn Leu Arg Arg Ile Ser Ser Thr
    50                  55                  60

Tyr Leu Phe Ser Pro Arg Arg Val Ser Ser Phe Glu Lys Gln Arg Ser
65                  70                  75                  80

Glu Ile Gly Glu Gly Met Val Arg Asp Met Lys Arg Met Met Glu Arg
                85                  90                  95

Asn Gly Val Val Glu Val Arg Arg Met Leu His Tyr Gly Ser Leu Asn
            100                 105                 110

Asn Ile Met Leu Thr Val Phe Gly Lys Lys Phe Asp Phe Ala Lys Asp
        115                 120                 125

Glu Gly Leu Glu Leu Glu Leu Ile Leu Lys Glu Gly Tyr Glu Leu Leu
    130                 135                 140

Gly Ile Phe Asn Trp Gly Asp His Leu Pro Leu Leu Gly Trp Leu Asp
145                 150                 155                 160

Leu Gln Gly Val Arg Arg Arg Cys Arg Thr Leu Val Ala Lys Val Asn
                165                 170                 175

Val Phe Val Lys Lys Ile Ile Asp Glu His Lys Arg Arg Ala Asn Gly
            180                 185                 190

Val Gly Ile Asp Glu Gly Glu Gly Glu Asp Phe Val Asp Val Leu Leu
        195                 200                 205

Gly Leu Glu Glu Lys Asp Arg Leu Ser Glu Ser Asp Met Val Ala Val
    210                 215                 220

Leu Trp Glu Met Ile Phe Arg Gly Thr Asp Thr Val Ala Ile Leu Leu
225                 230                 235                 240
```

```
Glu Trp Thr Leu Ala Arg Met Val Leu His Pro Asp Ile Gln Ser Lys
                245                 250                 255

Ala Gln Val Glu Ile Asp Ser Val Val Asp Ser Ser Arg Pro Val Leu
            260                 265                 270

Asp Ser Asp Ile Gln Arg Leu Pro Tyr Leu Gln Ser Ile Val Lys Glu
        275                 280                 285

Thr Leu Arg Met His Pro Pro Gly Pro Leu Leu Ser Trp Ala Arg Leu
290                 295                 300

Ala Ile His Asp Val Pro Val Asp Gly His Met Ile Pro Ala Gly Thr
305                 310                 315                 320

Thr Ala Met Val Asn Met Trp Ala Ile Thr His Asp Glu Cys Asn Trp
                325                 330                 335

Ala Glu Pro Asn Lys Phe Asn Pro Asp Arg Phe Ile Asp Glu Asp Val
            340                 345                 350

Asn Ile Leu Gly Ser Asp Leu Arg Leu Ala Pro Phe Gly Ser Gly Lys
        355                 360                 365

Arg Val Cys Pro Gly Lys Thr Met Ala Leu Ala Val His Leu Trp
370                 375                 380

Leu Ala Gln Leu Leu Lys Ser Phe Lys Leu Leu Pro Ser Arg Asn Gly
385                 390                 395                 400

Val Asp Leu Ser Glu Cys Leu Lys Met Ser Leu Glu Met Lys Asn Pro
                405                 410                 415

Leu Val Cys Val Ala Val Pro Arg Phe Glu
            420                 425

<210> SEQ ID NO 51
<211> LENGTH: 523
<212> TYPE: PRT
<213> ORGANISM: Glycine max

<400> SEQUENCE: 51

Met Thr Ser His Ile Asp Asp Asn Leu Trp Ile Ile Ala Leu Thr Ser
1               5                   10                  15

Lys Cys Thr Gln Glu Asn Leu Ala Trp Val Leu Leu Ile Met Gly Ser
            20                  25                  30

Leu Trp Leu Thr Met Thr Phe Tyr Tyr Trp Ser His Pro Gly Gly Pro
        35                  40                  45

Ala Trp Gly Lys Tyr Tyr Thr Tyr Ser Pro Leu Ser Ile Ile Pro
    50                  55                  60

Gly Pro Lys Gly Phe Pro Leu Ile Gly Ser Met Gly Leu Met Thr Ser
65                  70                  75                  80

Leu Ala His His Arg Ile Ala Ala Ala Ala Thr Cys Arg Ala Lys
                85                  90                  95

Arg Leu Met Ala Phe Ser Leu Gly Asp Thr Arg Val Ile Val Thr Cys
            100                 105                 110

His Pro Asp Val Ala Lys Glu Ile Leu Asn Ser Ser Val Phe Ala Asp
        115                 120                 125

Arg Pro Val Lys Glu Ser Ala Tyr Ser Leu Met Phe Asn Arg Ala Ile
    130                 135                 140

Gly Phe Ala Ser Tyr Gly Val Tyr Trp Arg Ser Leu Arg Arg Ile Ala
145                 150                 155                 160

Ser Asn His Leu Phe Cys Pro Arg Gln Ile Lys Ala Ser Glu Leu Gln
                165                 170                 175

Arg Ser Gln Ile Ala Ala Gln Met Val His Ile Leu Asn Asn Lys Arg
            180                 185                 190
```

His Arg Ser Leu Arg Val Arg Gln Val Leu Lys Lys Ala Ser Leu Ser
            195                 200                 205

Asn Met Met Cys Ser Val Phe Gly Gln Glu Tyr Lys Leu His Asp Pro
210                 215                 220

Asn Ser Gly Met Glu Asp Leu Gly Ile Leu Val Asp Gln Gly Tyr Asp
225                 230                 235                 240

Leu Leu Gly Leu Phe Asn Trp Ala Asp His Leu Pro Phe Leu Ala His
                245                 250                 255

Phe Asp Ala Gln Asn Ile Arg Phe Arg Cys Ser Asn Leu Val Pro Met
            260                 265                 270

Val Asn Arg Phe Val Gly Thr Ile Ile Ala Glu His Arg Ala Ser Lys
        275                 280                 285

Thr Glu Thr Asn Arg Asp Phe Val Asp Val Leu Leu Ser Leu Pro Glu
    290                 295                 300

Pro Asp Gln Leu Ser Asp Ser Asp Met Ile Ala Val Leu Trp Glu Met
305                 310                 315                 320

Ile Phe Arg Gly Thr Asp Thr Val Ala Val Leu Ile Glu Trp Ile Leu
                325                 330                 335

Ala Arg Met Ala Leu His Pro His Val Gln Ser Lys Val Gln Glu Glu
            340                 345                 350

Leu Asp Ala Val Val Gly Lys Ala Arg Ala Val Ala Glu Asp Asp Val
        355                 360                 365

Ala Val Met Thr Tyr Leu Pro Ala Val Val Lys Glu Val Leu Arg Leu
    370                 375                 380

His Pro Pro Gly Pro Leu Leu Ser Trp Ala Arg Leu Ser Ile Asn Asp
385                 390                 395                 400

Thr Thr Ile Asp Gly Tyr His Val Pro Ala Gly Thr Thr Ala Met Val
                405                 410                 415

Asn Thr Trp Ala Ile Cys Arg Asp Pro His Val Trp Lys Asp Pro Leu
            420                 425                 430

Glu Phe Met Pro Glu Arg Phe Val Thr Ala Gly Gly Asp Ala Glu Phe
        435                 440                 445

Ser Ile Leu Gly Ser Asp Pro Arg Leu Ala Pro Phe Gly Ser Gly Arg
    450                 455                 460

Arg Ala Cys Pro Gly Lys Thr Leu Gly Trp Ala Thr Val Asn Phe Trp
465                 470                 475                 480

Val Ala Ser Leu Leu His Glu Phe Glu Trp Val Pro Ser Asp Glu Lys
                485                 490                 495

Gly Val Asp Leu Thr Glu Val Leu Lys Leu Ser Ser Glu Met Ala Asn
            500                 505                 510

Pro Leu Thr Val Lys Val Arg Pro Arg Arg Gly
        515                 520

<210> SEQ ID NO 52
<211> LENGTH: 553
<212> TYPE: PRT
<213> ORGANISM: Pinus radiata

<400> SEQUENCE: 52

Met Glu Asn Arg Arg Ser Ser Gly Gly Ser Gly Trp Trp Val Cys Val
1               5                   10                  15

Leu Pro Leu Phe Thr Lys Asp Gly Pro Ala Tyr Phe Leu His Ser Ser
            20                  25                  30

Ser Asp Asp Val Ser Ala Trp Arg Gln Trp Pro Leu Tyr Ile Ala Leu

-continued

```
                35                  40                  45
Leu Ile Val Ala Val Cys Ala Val Leu Val Ser Trp Leu Ser Pro Gly
 50                  55                  60

Gly Cys Ala Trp Ala Gly Arg His Lys Arg Gly Arg Val Ala Ile Pro
 65                  70                  75                  80

Gly Pro Lys Gly Trp Pro Ile Ile Gly Ser Leu Met Asp Met Ser Val
                 85                  90                  95

Gly Leu Pro His Arg Lys Leu Glu Ser Leu Ala Arg Leu His Gly Ala
                100                 105                 110

Lys Gln Leu Met Ser Phe Ser Leu Gly Cys Thr Pro Ala Val Ile Thr
                115                 120                 125

Ser Asp Pro Glu Val Ala Arg Glu Leu Leu Thr Ser Pro His Phe Ala
130                 135                 140

Asn Arg Pro Leu Lys Gln Ser Ala Gln Leu Leu Phe Gly Arg Ala
145                 150                 155                 160

Ile Gly Phe Ala Pro Asn Gly Gly Tyr Trp Arg Leu Leu Arg Arg Ile
                165                 170                 175

Ala Ser Ala His Leu Phe Ala Pro Arg Arg Ile Ala Ala His Glu Ala
                180                 185                 190

Gly Arg Gln Ala Asp Val Val Ala Met Leu Asp Asp Ile Gln Lys Glu
                195                 200                 205

Tyr His Ser Lys Gly Val Val Arg Val Arg Arg His Leu Gln Gly Ala
                210                 215                 220

Ala Leu Asn Asn Ile Met Gly Ser Val Phe Gly Arg Arg Phe Asp Met
225                 230                 235                 240

Ser His Glu Asn Glu Glu Val Lys Lys Leu Arg Glu Met Val Asp Glu
                245                 250                 255

Gly Phe Gln Leu Leu Gly Ala Phe Asn Trp Ala Asp His Leu Pro Trp
                260                 265                 270

Leu Arg Pro Leu Asp Pro Leu Arg Ile His Ala Arg Cys Ala Arg Leu
                275                 280                 285

Val Pro Arg Val Thr Thr Phe Val Ser Asn Ile Ile Glu Gln His Arg
290                 295                 300

Arg Glu Glu Gln Arg Arg Glu Ser Gly Asp Gln Cys Asp Phe Val Asp
305                 310                 315                 320

Val Leu Leu Ser Leu Gln Gly Glu Asp Lys Leu Asp Glu Glu Asp Met
                325                 330                 335

Ile Ala Val Leu Trp Glu Met Ile Phe Arg Gly Thr Asp Thr Thr Ala
                340                 345                 350

Leu Leu Thr Glu Trp Thr Met Ala Glu Leu Val Leu His Pro Glu Ala
                355                 360                 365

Gln Lys Lys Ala Gln Ala Glu Leu Asp Ala Val Val Gly His Asp Arg
                370                 375                 380

Ser Val Lys Asp Ser Asp Ile Pro Lys Leu Pro Tyr Ile Gln Ala Val
385                 390                 395                 400

Val Lys Glu Ala Leu Arg Met His Pro Pro Gly Pro Leu Leu Ser Trp
                405                 410                 415

Ala Arg Leu Ser Thr Glu Asp Val Asn Met Gly Asp Gly Met Cys Val
                420                 425                 430

Pro Ala Gly Thr Thr Ala Met Val Asn Met Trp Ser Ile Thr His Asp
                435                 440                 445

Pro Asn Ile Trp Glu Ser Pro Tyr Glu Phe Arg Pro Glu Arg Phe Val
                450                 455                 460
```

Val Phe Glu Gly Gly Glu Val Asp Val Arg Gly Asn Asp Leu Arg
465                 470                 475                 480

Leu Ala Pro Phe Gly Ala Arg Arg Val Cys Pro Gly Lys Ala Leu
                485                 490                 495

Gly Leu Ala Thr Val Asn Leu Trp Val Ala Lys Leu Leu His His Phe
                500                 505                 510

Glu Trp Leu Pro His Ala Glu His Pro Val Asp Leu Ser Glu Val Leu
            515                 520                 525

Lys Leu Ser Cys Glu Met Ala Arg Pro Leu His Cys Val Pro Val Thr
530                 535                 540

Arg Val Pro Phe Ala Lys Phe Ser Asp
545                 550

<210> SEQ ID NO 53
<211> LENGTH: 523
<212> TYPE: PRT
<213> ORGANISM: Glycine max

<400> SEQUENCE: 53

Met Thr Ser His Ile Asp Asp Asn Leu Trp Ile Ile Ala Leu Thr Ser
1               5                   10                  15

Lys Cys Thr Gln Glu Asn Leu Ala Trp Val Leu Leu Ile Met Gly Ser
                20                  25                  30

Leu Trp Leu Thr Met Thr Phe Tyr Tyr Trp Ser His Pro Gly Gly Pro
            35                  40                  45

Ala Trp Gly Lys Tyr Tyr Thr Tyr Ser Pro Pro Leu Ser Ile Ile Pro
50                  55                  60

Gly Pro Lys Gly Phe Pro Leu Ile Gly Ser Met Gly Leu Met Ile Ser
65                  70                  75                  80

Leu Ala His His Arg Ile Ala Ala Ala Ala Thr Cys Arg Ala Lys
                85                  90                  95

Arg Leu Met Ala Phe Ser Leu Gly Asp Thr Arg Val Ile Val Thr Cys
                100                 105                 110

His Pro Asp Val Ala Lys Glu Ile Leu Asn Ser Ser Val Phe Ala Asp
            115                 120                 125

Arg Pro Val Lys Glu Ser Ala Tyr Ser Leu Met Phe Asn Arg Ala Ile
        130                 135                 140

Gly Phe Ala Ser Tyr Gly Val Tyr Trp Arg Ser Leu Arg Arg Ile Ala
145                 150                 155                 160

Ser Asn His Phe Phe Cys Pro Arg Gln Ile Lys Ala Ser Glu Leu Gln
                165                 170                 175

Arg Ser Gln Ile Ala Ala Gln Met Val His Ile Leu Asn Asn Lys Arg
            180                 185                 190

His Arg Ser Leu Arg Val Arg Gln Val Leu Lys Lys Ala Ser Leu Ser
        195                 200                 205

Asn Met Met Cys Ser Val Phe Gly Gln Glu Tyr Lys Leu His Asp Pro
210                 215                 220

Asn Ser Gly Met Glu Asp Leu Gly Ile Leu Val Asp Gln Gly Tyr Asp
225                 230                 235                 240

Leu Leu Gly Leu Phe Asn Trp Ala Asp His Leu Pro Phe Leu Ala His
                245                 250                 255

Phe Asp Ala Gln Asn Ile Arg Phe Arg Cys Ser Asn Leu Val Pro Met
            260                 265                 270

Val Asn Arg Phe Val Gly Thr Ile Ile Ala Glu His Arg Ala Ser Lys

-continued

```
                275                 280                 285
Thr Glu Thr Asn Arg Asp Phe Val Asp Val Leu Leu Ser Leu Pro Glu
    290                 295                 300

Pro Asp Gln Leu Ser Asp Ser Asp Met Ile Ala Val Leu Trp Glu Met
305                 310                 315                 320

Ile Phe Arg Gly Thr Asp Thr Val Ala Val Leu Ile Glu Trp Ile Leu
                325                 330                 335

Ala Arg Met Ala Leu His Pro His Val Gln Ser Lys Val Gln Glu Glu
            340                 345                 350

Leu Asp Ala Val Val Gly Lys Ala Arg Ala Val Ala Glu Asp Asp Val
        355                 360                 365

Ala Val Met Thr Tyr Leu Pro Ala Val Val Lys Glu Val Leu Arg Leu
    370                 375                 380

His Pro Pro Gly Pro Leu Leu Ser Trp Ala Arg Leu Ser Ile Asn Asp
385                 390                 395                 400

Thr Thr Ile Asp Gly Tyr His Val Pro Ala Gly Thr Thr Ala Met Val
                405                 410                 415

Asn Met Trp Ala Ile Cys Arg Asp Pro His Val Trp Lys Asp Pro Leu
            420                 425                 430

Glu Phe Met Pro Glu Arg Phe Val Thr Ala Gly Gly Asp Ala Glu Phe
        435                 440                 445

Ser Ile Leu Gly Ser Asp Pro Arg Leu Ala Pro Phe Gly Ser Gly Arg
    450                 455                 460

Arg Ala Cys Pro Gly Lys Thr Leu Gly Trp Ala Thr Val Asn Phe Trp
465                 470                 475                 480

Val Ala Ser Leu Leu His Glu Phe Glu Trp Val Pro Ser Asp Glu Lys
                485                 490                 495

Gly Val Asp Leu Thr Glu Val Leu Lys Leu Ser Ser Glu Met Ala Asn
            500                 505                 510

Pro Leu Thr Val Lys Val Arg Pro Arg Gly
        515                 520

<210> SEQ ID NO 54
<211> LENGTH: 536
<212> TYPE: PRT
<213> ORGANISM: Glycine max

<400> SEQUENCE: 54

Met Ser Thr His Ile Glu Ser Leu Trp Val Leu Ala Leu Ala Ser Lys
1               5                   10                  15

Cys Ile Gln Glu Asn Ile Ala Trp Ser Leu Leu Ile Ile Met Val Thr
            20                  25                  30

Leu Trp Leu Thr Met Thr Phe Phe Tyr Trp Ser His Pro Gly Gly Pro
        35                  40                  45

Ala Trp Gly Lys Tyr Tyr Tyr Phe Asn Tyr Trp Lys Lys Thr Thr Ser
    50                  55                  60

Thr Asn Thr Asn Ile Asn Leu Lys Met Ile Ile Pro Gly Pro Arg Gly
65                  70                  75                  80

Tyr Pro Phe Ile Gly Ser Met Ser Leu Met Thr Ser Leu Ala His His
                85                  90                  95

Arg Ile Ala Ala Ala Gly Glu Ala Cys Asn Ala Thr Arg Leu Met Ala
            100                 105                 110

Phe Ser Met Gly Asp Thr Arg Ala Ile Val Thr Cys Asn Pro Asp Val
        115                 120                 125
```

```
Ala Lys Glu Ile Leu Asn Ser Ser Thr Phe Ala Asp Arg Pro Ile Lys
    130                 135                 140

Glu Ser Ala Tyr Ser Leu Met Phe Asn Arg Ala Ile Gly Phe Ala Pro
145                 150                 155                 160

Tyr Gly Val Tyr Trp Arg Thr Leu Arg Arg Ile Ala Ala Thr His Leu
                165                 170                 175

Phe Cys Pro Lys Gln Ile Lys Ala Ser Glu Leu Gln Arg Ala Glu Ile
            180                 185                 190

Ala Ala Gln Met Thr Asn Ser Phe Arg Asn His Arg Cys Ser Gly Gly
        195                 200                 205

Phe Gly Ile Arg Ser Val Leu Lys Arg Ala Ser Leu Asn Asn Met Met
210                 215                 220

Trp Ser Val Phe Gly Gln Lys Tyr Asn Leu Asp Glu Ile Asn Thr Ala
225                 230                 235                 240

Met Asp Glu Leu Ser Met Leu Val Glu Gln Gly Tyr Asp Leu Leu Gly
                245                 250                 255

Thr Leu Asn Trp Gly Asp His Ile Pro Phe Leu Lys Asp Phe Asp Leu
            260                 265                 270

Gln Lys Ile Arg Phe Thr Cys Ser Lys Leu Val Pro Gln Val Asn Arg
        275                 280                 285

Phe Val Gly Ser Ile Ile Ala Asp His Gln Ala Asp Thr Thr Gln Thr
290                 295                 300

Asn Arg Asp Phe Val His Val Leu Leu Ser Leu Gln Gly Pro Asp Lys
305                 310                 315                 320

Leu Ser His Ser Asp Met Ile Ala Val Leu Trp Glu Met Ile Phe Arg
                325                 330                 335

Gly Thr Asp Thr Val Ala Val Leu Ile Glu Trp Ile Leu Ala Arg Met
            340                 345                 350

Val Leu His Pro Glu Val Gln Arg Lys Val Gln Glu Glu Leu Asp Ala
        355                 360                 365

Val Val Arg Gly Gly Ala Leu Thr Glu Val Val Ala Ala Thr Ala
370                 375                 380

Tyr Leu Ala Ala Val Val Lys Glu Val Leu Arg Leu His Pro Pro Gly
385                 390                 395                 400

Pro Leu Leu Ser Trp Ala Arg Leu Ala Ile Thr Asp Thr Thr Ile Asp
                405                 410                 415

Gly Tyr His Val Pro Ala Gly Thr Thr Ala Met Val Asn Met Trp Ala
            420                 425                 430

Ile Ala Arg Asp Pro Glu Val Trp Leu Asp Pro Leu Glu Phe Lys Pro
        435                 440                 445

Glu Arg Phe Met Gly Leu Glu Asn Glu Phe Ser Val Phe Gly Ser Asp
450                 455                 460

Leu Arg Leu Ala Pro Phe Gly Ser Gly Arg Arg Thr Cys Pro Gly Lys
465                 470                 475                 480

Thr Leu Gly Leu Ser Thr Val Thr Phe Trp Val Ala Trp Leu Leu His
                485                 490                 495

Glu Phe Glu Trp Leu Pro Ser Asp Glu Ala Lys Val Asp Leu Thr Glu
            500                 505                 510

Val Leu Arg Leu Ser Cys Glu Met Ala Asn Pro Leu Ile Val Lys Val
        515                 520                 525

Arg Pro Arg His Gly Leu Ser Thr
530                 535
```

<210> SEQ ID NO 55
<211> LENGTH: 551
<212> TYPE: PRT
<213> ORGANISM: Oryza sativa

<400> SEQUENCE: 55

Met Asp Met Asp Ser Ser Pro Ser Thr Gln Asp Cys Gly Gly Trp Leu
1               5                   10                  15

Leu Tyr Val Ser Leu Ala Ala Lys Cys Gly Asp Pro Cys Arg Val
            20                  25                  30

Val Gly Phe Val Ala Val Ala Val Ala Phe Ala Val Thr Ser Leu
        35                  40                  45

Leu His Trp Leu Ser Pro Gly Gly Pro Ala Trp Gly Arg Tyr Trp Trp
    50                  55                  60

Asn Arg Arg Gly Gly Leu Gly Ile Ala Ala Ile Pro Gly Pro Arg
65                  70                  75                  80

Gly Leu Pro Val Leu Gly Ser Met Ser Leu Met Ala Gly Leu Ala His
                85                  90                  95

Arg Lys Leu Ala Ala Ala Gly Gly Ser Pro Ala Arg Arg Arg Leu
            100                 105                 110

Met Ala Leu Ser Leu Gly Glu Thr Arg Val Val Thr Ala Asp Pro
        115                 120                 125

Gly Val Ala Arg Glu Leu Leu Ala Ser Ala Phe Ala Asp Arg Pro
    130                 135                 140

Val Lys Glu Ser Ala Tyr Gly Met Leu Phe His Arg Ala Ile Gly Phe
145                 150                 155                 160

Ala Pro Tyr Gly Thr Tyr Trp Arg Ala Leu Arg Arg Val Ala Ser Thr
                165                 170                 175

His Leu Phe Ser Pro Arg Gln Val Ser Ala Ser Ala Gln Arg Ala
            180                 185                 190

Val Ile Ala Arg Gln Met Val Glu Ala Met Arg Ser Ala Ala Ala Ala
        195                 200                 205

Ala Ala Gly Gly Gly Val Ala Ala Arg Pro Phe Leu Lys Arg Ala Ser
    210                 215                 220

Leu His Asn Val Met Trp Ser Val Phe Gly Arg Lys Tyr Glu Leu Ala
225                 230                 235                 240

Ala Pro Glu Ser Glu Glu Thr Ala Glu Leu Arg Ser Met Val Asp Glu
                245                 250                 255

Gly Tyr Asp Leu Leu Gly Gln Leu Asn Trp Ser Asp His Leu Pro Trp
            260                 265                 270

Leu Ala Pro Phe Asp Leu Lys Lys Thr Arg Ser Arg Cys Ser Ser Leu
        275                 280                 285

Val Pro Arg Val Asn Arg Phe Val Thr Arg Ile Ile Asp Glu His Arg
    290                 295                 300

Ala Arg Leu Ser Leu Ala Val Asp Ala Ala Val Asp Phe Thr Asp Val
305                 310                 315                 320

Leu Leu Ser Leu His Gly Gly Asp Lys Leu Ser Asp Ala Asp Met Val
                325                 330                 335

Ala Val Leu Trp Glu Met Ile Phe Arg Gly Thr Asp Thr Val Ala Val
            340                 345                 350

Leu Ile Glu Trp Val Ala Ala Arg Leu Val Leu His Gln Asp Val Gln
        355                 360                 365

Ala Arg Val His Asp Glu Leu Asp Arg Val Val Gly Ser Asp Arg Ala
    370                 375                 380

Val Thr Glu Ser Asp Ala Ser Lys Leu Val Tyr Leu Gln Ala Val Ile
385                 390                 395                 400

Lys Glu Val Leu Arg Leu His Pro Pro Gly Pro Leu Leu Ser Trp Ala
            405                 410                 415

Arg Leu Ala Thr Ser Asp Val His Val Gly Gly Phe Leu Ile Pro Ser
            420                 425                 430

Gly Thr Thr Ala Met Val Asn Met Trp Ala Ile Thr His Asp Pro Ala
            435                 440                 445

Val Trp Pro Asp Pro Asn Glu Phe Lys Pro Glu Arg Phe Val Ala Gly
        450                 455                 460

Pro Ser Ser Asp Gln Ala Thr Glu Phe Pro Ile Met Gly Ser Asp Leu
465                 470                 475                 480

Arg Leu Ala Pro Phe Gly Ser Gly Arg Arg Ser Cys Pro Gly Lys Ser
            485                 490                 495

Leu Ala Ile Ala Thr Val Gly Phe Trp Val Ala Thr Leu Leu His Glu
            500                 505                 510

Phe Asp Trp Leu Pro Leu Ser Asp Lys Ser Arg Gly Val Asp Leu Ser
        515                 520                 525

Glu Val Leu Lys Leu Ser Cys Glu Met Ala Thr Pro Leu Glu Ala Arg
530                 535                 540

Leu Arg Pro Arg Arg Lys Val
545                 550

<210> SEQ ID NO 56
<211> LENGTH: 536
<212> TYPE: PRT
<213> ORGANISM: Brachypodium distachyon

<400> SEQUENCE: 56

Met Ala Thr Pro Glu Asp Cys Gly Ser Trp Leu Leu Tyr Leu Ser Leu
1               5                   10                  15

Ala Ala Lys Cys Gly Gly Asp Gly Asp His Pro Arg Arg Leu Ala Gly
            20                  25                  30

Leu Leu Ala Val Cys Ala Ala Phe Leu Val Thr Cys Leu Leu His
            35                  40                  45

Trp Cys Phe Pro Gly Gly Pro Ala Trp Gly Arg Trp Trp Thr Arg
50                  55                  60

Arg Gly Leu Gly Arg Gly Pro Val Val Pro Gly Pro Arg Gly Leu Pro
65                  70                  75                  80

Val Ile Gly Ser Met Trp Leu Met Thr Gly Leu Ala His Arg Lys Leu
            85                  90                  95

Ala Ala Glu Ala Ala Arg Leu Arg Gly Gly Arg Arg Leu Met Ala
            100                 105                 110

Phe Ser Leu Gly Glu Thr Arg Val Val Ala Gly His Pro Asp Val
            115                 120                 125

Ala Arg Glu Ile Leu Thr Ser Pro Ala Phe Ala Asp Arg Pro Val Lys
            130                 135                 140

Glu Ser Ala Tyr Gly Leu Met Phe His Arg Ala Ile Gly Phe Ala Arg
145                 150                 155                 160

His Gly Ala Tyr Trp Arg Ala Leu Arg Arg Val Ala Ser Thr His Leu
            165                 170                 175

Phe Ser Pro Trp Gln Val Ala Ala Ser Gly Ala Gln Arg Ala Val Ile
            180                 185                 190

Ala Arg Gln Met Val Ala Ala Leu Ala Gly Gly Ala Glu Val Arg Arg
            195                 200                 205

Val Leu Arg Arg Ala Ser Leu His Asn Val Met Trp Ser Val Phe Gly
            210                 215                 220

Arg Arg Tyr Asp Leu Glu Leu Asp Pro Gly Lys Glu Val Arg Glu Leu
225                 230                 235                 240

Gly Gln Leu Val Asp Glu Gly Tyr Asp Leu Leu Gly Gln Leu Asn Trp
                245                 250                 255

Ser Asp His Leu Pro Trp Leu Ala Arg Phe Asp Leu Gln Gly Thr Arg
            260                 265                 270

Ala Arg Cys Ala Ser Leu Val Pro Arg Val Asn Arg Phe Val Gly Gly
        275                 280                 285

Ile Ile Asp Asp His Arg Val Lys Ala Pro Ser Ala Val Lys Asp Phe
290                 295                 300

Thr Asp Val Leu Leu Gly Leu Gln Gly Gly Asp Arg Leu Ala Asp Ser
305                 310                 315                 320

Asp Met Val Ala Val Leu Trp Glu Met Val Phe Arg Gly Thr Asp Thr
                325                 330                 335

Val Ala Val Leu Met Glu Trp Val Leu Ala Arg Leu Val Leu His Gln
            340                 345                 350

Asp Val Gln Ala Arg Val His Glu Glu Leu Asp Arg Val Val Gly Arg
        355                 360                 365

Asp Arg Ala Val Ala Glu Ser Asp Ala Ala Ser Leu Ala Tyr Leu His
370                 375                 380

Ala Val Val Lys Glu Val Leu Arg Leu His Pro Pro Gly Pro Leu Leu
385                 390                 395                 400

Ser Trp Ala Arg Leu Ala Thr Ser Asp His Val Asp Gly Phe Leu
                405                 410                 415

Ile Pro Ala Gly Thr Thr Ala Met Val Asn Met Trp Ala Ile Thr His
            420                 425                 430

Asp Gly Asp Val Trp Ala Glu Pro Met Glu Phe Arg Pro Glu Arg Phe
        435                 440                 445

Val Gly Pro Gly Ala Glu Glu Phe Ser Val Met Gly Ser Asp Leu Arg
450                 455                 460

Leu Ala Pro Phe Gly Ala Gly Arg Arg Ser Cys Pro Gly Lys Ser Leu
465                 470                 475                 480

Ala Met Ala Thr Val Ala Phe Trp Leu Ala Thr Leu His Glu Phe
                485                 490                 495

Asp Leu Leu Pro Ser Ser Asp Pro Ala Arg Gly Val Gln Leu Ser Glu
            500                 505                 510

Thr Leu Arg Leu Ser Cys Glu Met Ala Thr Pro Leu Ala Leu Thr Pro
        515                 520                 525

Arg Ala Arg Arg Pro Ala Val
530                 535

<210> SEQ ID NO 57
<211> LENGTH: 542
<212> TYPE: PRT
<213> ORGANISM: Glycine max

<400> SEQUENCE: 57

Met Thr Thr His Ile Asp Asn Leu Trp Val Leu Ala Leu Val Ser Lys
1               5                   10                  15

Cys Thr Gln Glu Asn Ile Ala Trp Ser Leu Leu Thr Ile Met Val Thr
            20                  25                  30

Leu Trp Leu Ser Met Thr Phe Phe Cys Trp Ser His Pro Gly Gly Pro

```
                35                  40                  45
Ala Trp Gly Lys Tyr Tyr Ser Phe His Tyr Trp Lys Lys Thr Thr Thr
 50                  55                  60

Thr Thr Thr Ser Thr Ser Asn Asn Thr Asn Ser Asn Asn Leu Lys Met
 65                  70                  75                  80

Ile Pro Gly Pro Lys Gly Tyr Pro Phe Ile Gly Ser Met Ser Leu Met
                 85                  90                  95

Thr Ser Leu Ala His His Arg Ile Ala Ala Ala Gln Ala Cys Lys
            100                 105                 110

Ala Thr Arg Leu Met Ala Phe Ser Met Gly Asp Thr Arg Val Ile Val
            115                 120                 125

Thr Cys His Pro His Val Ala Lys Glu Ile Leu Asn Ser Ser Val Phe
            130                 135                 140

Ala Asp Arg Pro Ile Lys Glu Ser Ala Tyr Ser Leu Met Phe Asn Arg
145                 150                 155                 160

Ala Ile Gly Phe Ala Pro Tyr Gly Val Tyr Trp Arg Thr Leu Arg Arg
                165                 170                 175

Ile Ala Ala Thr His Leu Phe Cys Pro Lys Gln Ile Lys Ala Ser Glu
            180                 185                 190

Leu Gln Arg Ala Glu Ile Ala Ala Gln Met Thr His Ser Phe Arg Asn
            195                 200                 205

Arg Arg Gly Gly Phe Gly Ile Arg Ser Val Leu Lys Arg Ala Ser Leu
210                 215                 220

Asn Asn Met Met Trp Ser Val Phe Gly Gln Arg Tyr Asp Leu Asp Glu
225                 230                 235                 240

Thr Asn Thr Ser Val Asp Glu Leu Ser Arg Leu Val Glu Gln Gly Tyr
                245                 250                 255

Asp Leu Leu Gly Thr Leu Asn Trp Gly Asp His Ile Pro Phe Leu Lys
            260                 265                 270

Asp Phe Asp Leu Gln Lys Ile Arg Phe Thr Cys Ser Lys Leu Val Pro
            275                 280                 285

Gln Val Asn Arg Phe Val Gly Ser Ile Ile Ala Asp His Gln Thr Asp
            290                 295                 300

Thr Thr Gln Thr Asn Arg Asp Phe Val His Val Leu Leu Ser Leu Gln
305                 310                 315                 320

Gly Pro Asp Lys Leu Ser His Ser Asp Met Ile Ala Val Leu Trp Glu
                325                 330                 335

Met Ile Phe Arg Gly Thr Asp Thr Val Ala Val Leu Ile Glu Trp Ile
            340                 345                 350

Met Ala Arg Met Val Leu His Pro Glu Val Gln Arg Val Gln Glu
            355                 360                 365

Glu Leu Asp Ala Val Val Gly Gly Ala Arg Ala Leu Lys Glu Glu
            370                 375                 380

Asp Val Ala Ala Thr Ala Tyr Leu Leu Ala Val Val Lys Glu Val Leu
385                 390                 395                 400

Arg Leu His Pro Pro Gly Pro Leu Leu Ser Trp Ala Arg Leu Ala Ile
                405                 410                 415

Thr Asp Thr Thr Ile Asp Gly Tyr Asn Val Pro Ala Gly Thr Thr Ala
            420                 425                 430

Met Val Asn Met Trp Ala Ile Gly Arg Asp Pro Glu Val Trp Leu Asp
            435                 440                 445

Pro Leu Asp Phe Lys Pro Glu Arg Phe Met Gly Leu Glu Ala Glu Phe
            450                 455                 460
```

Ser Val Leu Gly Ser Asp Leu Arg Leu Ala Pro Phe Gly Ser Gly Arg
465                 470                 475                 480

Arg Thr Cys Pro Gly Lys Thr Leu Gly Leu Ser Thr Val Thr Phe Trp
                485                 490                 495

Val Ala Arg Leu Leu His Glu Phe Glu Trp Leu Pro Ser Asp Glu Gly
            500                 505                 510

Lys Val Asp Leu Thr Glu Val Leu Arg Leu Ser Cys Glu Met Ala Asn
        515                 520                 525

Pro Leu Tyr Val Lys Val Arg Pro Arg Gly Leu Ser Thr
    530                 535                 540

<210> SEQ ID NO 58
<211> LENGTH: 553
<212> TYPE: PRT
<213> ORGANISM: Oryza sativa

<400> SEQUENCE: 58

Met Ala Thr Pro Glu Asp Thr Gly Ser Trp Leu Leu Tyr Leu Ser Leu
1               5                   10                  15

Ala Ala Lys Cys Ser Gly Asp Gly Asp Gly Gln Pro His Arg Leu Leu
            20                  25                  30

Gly Phe Val Val Cys Ala Val Ala Gly Leu Val Thr Cys Leu Leu
            35                  40                  45

His Trp Ser Phe Pro Gly Gly Pro Ala Trp Gly Arg Trp Trp Trp Thr
        50                  55                  60

Arg Arg Arg Arg Arg Gly Ser Pro Cys Gly Val Ala Ala Val Pro Gly
65                  70                  75                  80

Leu Arg Gly Leu Pro Val Ile Gly Ser Met Trp Leu Met Thr Gly Leu
                85                  90                  95

Ala His Arg Lys Leu Ala Ala Ala Glu Ala Ala Gly Ala Gly Arg
            100                 105                 110

Leu Met Ala Leu Ser Leu Gly Glu Thr Arg Val Val Ala Ala His
            115                 120                 125

Pro Asp Val Ala Arg Glu Ile Leu His Gly Ala Ala Phe Ala Asp Arg
        130                 135                 140

Pro Val Lys Glu Ser Ala Tyr Gly Leu Leu Phe His Arg Ala Ile Gly
145                 150                 155                 160

Phe Ala Pro His Gly Ala Tyr Trp Arg Ala Leu Arg Arg Val Ala Ser
                165                 170                 175

Thr His Leu Phe Ser Pro Trp Gln Val Ala Ala Ser Ala Pro Gln Arg
            180                 185                 190

Ala Val Ile Ala Arg Gln Met Val Arg Ala Ile Lys Leu Gln Gln Arg
            195                 200                 205

Ser Arg Ser Gly Asp Ser Ala Ala Gly Ala Ala Val Glu Val Arg Arg
        210                 215                 220

Val Leu Arg Arg Ala Ser Leu His Asn Val Met Trp Ser Val Phe Gly
225                 230                 235                 240

Arg Arg Tyr Glu Leu Gln Leu Asp Pro Gly Lys Glu Ser Asp Glu Val
                245                 250                 255

Arg Glu Leu Arg Ala Leu Val Asp Glu Gly Tyr Asp Leu Leu Gly Gln
            260                 265                 270

Leu Asn Trp Ser Asp His Leu Pro Trp Leu Ala Arg Phe Asp Leu Gln
        275                 280                 285

Ser Thr Arg Ala Arg Cys Ser Arg Leu Val Pro Arg Val Asn Arg Phe

```
                290                 295                 300
Val Thr Arg Ile Ile Asp Glu His Arg Ser Ser Ala Pro Val Ala Ala
305                 310                 315                 320

Ala Ile Asp Phe Thr Asp Val Leu Leu Ser Leu Gln Gly Ser Asp Lys
                325                 330                 335

Leu Ala Asp Ser Asp Met Val Ala Val Leu Trp Glu Met Val Phe Arg
                340                 345                 350

Gly Thr Asp Thr Val Ala Val Leu Ile Glu Trp Val Leu Ala Arg Leu
                355                 360                 365

Val Leu Gln Gln Asp Val Gln Ala Arg Val His Asp Glu Leu Gly Arg
370                 375                 380

Val Val Gly Leu Asp Arg Asp Val Thr Glu Ser Asp Thr Ala Ser Leu
385                 390                 395                 400

Val Tyr Leu His Ala Val Ile Lys Glu Thr Leu Arg Leu His Pro Pro
                405                 410                 415

Gly Pro Leu Leu Ser Trp Ala Arg Leu Ala Thr Ser Asp Val His Val
                420                 425                 430

Asp Gly Tyr Leu Ile Pro Ala Gly Thr Thr Ala Met Val Asn Met Trp
                435                 440                 445

Ala Ile Ala His Asp Pro Asp Val Trp Ala Glu Pro Met Glu Phe Arg
450                 455                 460

Pro Glu Arg Phe Ile Gly Lys Ala Ala Glu Phe Ser Val Met Gly Ser
465                 470                 475                 480

Asp Leu Arg Leu Ala Pro Phe Gly Ser Gly Arg Arg Ser Cys Pro Gly
                485                 490                 495

Lys Ser Leu Ala Met Ala Thr Val Ala Phe Trp Leu Ala Thr Leu Leu
                500                 505                 510

His Glu Phe Ala Leu Leu Pro Ser Pro Asp Pro Ala His Gly Val Asp
                515                 520                 525

Leu Ser Glu Val Leu Arg Leu Ser Cys Glu Met Ala Thr Pro Leu Ala
                530                 535                 540

Val Thr Ala Trp Pro Arg Arg Val Val
545                 550

<210> SEQ ID NO 59
<211> LENGTH: 516
<212> TYPE: PRT
<213> ORGANISM: Glycine max

<400> SEQUENCE: 59

Met Ser Pro Asp Phe Thr Leu Leu Phe Phe Pro Glu Leu Met Gln Ser
1               5                   10                  15

Pro Met Ile Thr Phe Gln Ala Thr Leu Cys Val Leu Leu Phe Thr Leu
                20                  25                  30

Met Phe Thr Leu Leu Phe Thr Pro Gly Gly Leu Pro Trp Ala Trp Ala
                35                  40                  45

Arg Pro Arg Pro Ile Ile Pro Gly Pro Val Thr Ala Leu Leu Gly Ile
                50                  55                  60

Phe Thr Gly Ser Thr Pro His Arg Ala Leu Ser Lys Leu Ala Arg Asn
65                  70                  75                  80

Tyr His Ala Glu Lys Leu Met Ala Phe Ser Ile Gly Leu Thr Arg Phe
                85                  90                  95

Val Ile Ser Ser Glu Pro Glu Thr Ala Lys Glu Ile Leu Gly Ser Pro
                100                 105                 110
```

```
Ser Phe Ala Asp Arg Pro Val Lys Glu Ser Ala Tyr Glu Leu Leu Phe
            115                 120                 125

His Arg Ala Met Gly Phe Ala Pro Tyr Gly Glu Tyr Trp Arg Asn Leu
    130                 135                 140

Arg Arg Ile Ser Ala Leu His Leu Phe Ser Pro Lys Arg Ile Thr Gly
145                 150                 155                 160

Ser Glu Ser Phe Arg Ser Glu Val Gly Leu Lys Met Val Glu Gln Val
                165                 170                 175

Lys Lys Thr Met Ser Glu Asn Gln His Val Glu Val Lys Lys Ile Leu
            180                 185                 190

His Phe Ser Ser Leu Asn Asn Val Met Met Thr Val Phe Gly Lys Ser
            195                 200                 205

Tyr Glu Phe Tyr Glu Gly Glu Gly Leu Glu Leu Glu Gly Leu Val Ser
    210                 215                 220

Glu Gly Tyr Glu Leu Leu Gly Val Phe Asn Trp Ser Asp His Phe Pro
225                 230                 235                 240

Val Leu Gly Trp Leu Asp Leu Gln Gly Val Arg Lys Arg Cys Arg Cys
                245                 250                 255

Leu Val Glu Lys Val Asn Val Phe Val Gly Gly Val Ile Lys Glu His
            260                 265                 270

Arg Val Lys Arg Glu Arg Gly Glu Cys Val Lys Asp Glu Gly Thr Gly
    275                 280                 285

Asp Phe Val Asp Val Leu Leu Asp Leu Glu Lys Glu Asn Arg Leu Ser
    290                 295                 300

Glu Ala Asp Met Ile Ala Val Leu Trp Glu Met Ile Phe Arg Gly Thr
305                 310                 315                 320

Asp Thr Val Ala Ile Leu Leu Glu Trp Thr Leu Ala Arg Met Val Leu
                325                 330                 335

His Pro Glu Ile Gln Ala Lys Ala Gln Arg Glu Ile Asp Phe Val Cys
            340                 345                 350

Gly Ser Ser Arg Pro Val Ser Glu Ala Asp Ile Pro Asn Leu Arg Tyr
    355                 360                 365

Leu Gln Cys Ile Val Lys Glu Thr Leu Arg Val His Pro Pro Gly Pro
    370                 375                 380

Leu Leu Ser Trp Ala Arg Leu Ala Val His Asp Val Thr Val Gly Gly
385                 390                 395                 400

Lys His Val Ile Pro Lys Gly Thr Thr Ala Met Val Asn Met Trp Ala
                405                 410                 415

Ile Thr His Asp Glu Arg Val Trp Ala Glu Pro Glu Lys Phe Arg Pro
            420                 425                 430

Glu Arg Phe Val Glu Glu Asp Val Ser Ile Met Gly Ser Asp Leu Arg
            435                 440                 445

Leu Ala Pro Phe Gly Ser Gly Arg Arg Val Cys Pro Gly Lys Ala Leu
    450                 455                 460

Gly Leu Ala Ser Val His Leu Trp Leu Ala Gln Leu Leu Gln Asn Phe
465                 470                 475                 480

His Trp Val Ser Ser Asp Gly Val Ser Val Glu Leu Asp Glu Phe Leu
                485                 490                 495

Lys Leu Ser Met Glu Met Lys Lys Pro Leu Ser Cys Lys Ala Val Pro
            500                 505                 510

Arg Val Ser Val
            515
```

```
<210> SEQ ID NO 60
<211> LENGTH: 516
<212> TYPE: PRT
<213> ORGANISM: Glycine max

<400> SEQUENCE: 60
```

| | | | | | | | | | | | | | | | |
|---|---|---|---|---|---|---|---|---|---|---|---|---|---|---|---|
| Met | Ser | Pro | Asp | Phe | Thr | Leu | Leu | Phe | Ser | Pro | Glu | Leu | Met | Gln | Ser |
| 1 | | | | 5 | | | | | 10 | | | | | 15 | |
| Pro | Ile | Ile | Thr | Phe | Gln | Ala | Thr | Phe | Cys | Val | Leu | Leu | Phe | Thr | Leu |
| | | | 20 | | | | | 25 | | | | | 30 | | |
| Met | Phe | Thr | Pro | Phe | Phe | Thr | Pro | Gly | Gly | Leu | Pro | Trp | Ala | Trp | Ala |
| | | | 35 | | | | | 40 | | | | | 45 | | |
| Arg | Pro | Arg | Thr | Ile | Ile | Pro | Gly | Pro | Val | Thr | Ala | Leu | Leu | Gly | Val |
| | 50 | | | | | 55 | | | | | 60 | | | | |
| Phe | Thr | Gly | Ser | Thr | Pro | His | Ser | Ala | Leu | Ser | Lys | Leu | Ala | Arg | Thr |
| 65 | | | | | 70 | | | | | 75 | | | | | 80 |
| Tyr | His | Ala | Glu | Lys | Leu | Met | Ala | Phe | Ser | Ile | Gly | Leu | Thr | Arg | Phe |
| | | | | 85 | | | | | 90 | | | | | 95 | |
| Val | Ile | Ser | Ser | Glu | Pro | Glu | Thr | Ala | Lys | Glu | Ile | Leu | Gly | Ser | Pro |
| | | | 100 | | | | | 105 | | | | | 110 | | |
| Gly | Phe | Ala | Asp | Arg | Pro | Val | Lys | Glu | Ser | Ala | Tyr | Glu | Leu | Leu | Phe |
| | | | 115 | | | | | 120 | | | | | 125 | | |
| His | Arg | Ala | Met | Gly | Phe | Ala | Pro | Tyr | Gly | Glu | Tyr | Trp | Arg | Asn | Leu |
| | 130 | | | | | 135 | | | | | 140 | | | | |
| Arg | Arg | Ile | Ser | Ala | Leu | His | Leu | Phe | Ser | Pro | Lys | Arg | Ile | Thr | Ser |
| 145 | | | | | 150 | | | | | 155 | | | | | 160 |
| Ser | Glu | Ser | Phe | Arg | Ser | Lys | Val | Gly | Leu | Lys | Met | Val | Glu | Gln | Val |
| | | | | 165 | | | | | 170 | | | | | 175 | |
| Lys | Lys | Thr | Met | Ser | Glu | Asn | Gln | His | Val | Glu | Val | Lys | Lys | Ile | Leu |
| | | | 180 | | | | | 185 | | | | | 190 | | |
| His | Phe | Ser | Ser | Leu | Asn | Asn | Val | Met | Met | Thr | Val | Phe | Gly | Lys | Cys |
| | | | 195 | | | | | 200 | | | | | 205 | | |
| Tyr | Glu | Phe | Tyr | Glu | Gly | Glu | Gly | Leu | Glu | Leu | Glu | Gly | Leu | Val | Ser |
| | 210 | | | | | 215 | | | | | 220 | | | | |
| Glu | Gly | Tyr | Glu | Leu | Leu | Gly | Val | Phe | Asn | Trp | Ser | Asp | His | Phe | Pro |
| 225 | | | | | 230 | | | | | 235 | | | | | 240 |
| Val | Leu | Gly | Trp | Leu | Asp | Leu | Gln | Gly | Val | Arg | Lys | Arg | Cys | Arg | Cys |
| | | | | 245 | | | | | 250 | | | | | 255 | |
| Leu | Val | Glu | Lys | Val | Asn | Val | Phe | Val | Gly | Gly | Val | Ile | Lys | Glu | His |
| | | | 260 | | | | | 265 | | | | | 270 | | |
| Arg | Val | Lys | Arg | Glu | Arg | Gly | Asp | Cys | Val | Lys | Asp | Glu | Gly | Ala | Glu |
| | | | 275 | | | | | 280 | | | | | 285 | | |
| Asp | Phe | Val | Asp | Val | Leu | Leu | Asp | Leu | Glu | Lys | Glu | Asn | Arg | Leu | Ser |
| | 290 | | | | | 295 | | | | | 300 | | | | |
| Glu | Ala | Asp | Met | Ile | Ala | Val | Leu | Trp | Glu | Met | Ile | Phe | Arg | Gly | Thr |
| 305 | | | | | 310 | | | | | 315 | | | | | 320 |
| Asp | Thr | Val | Ala | Ile | Leu | Leu | Glu | Trp | Ile | Leu | Ala | Arg | Met | Val | Leu |
| | | | | 325 | | | | | 330 | | | | | 335 | |
| His | Pro | Glu | Ile | Gln | Ala | Lys | Ala | Gln | Arg | Glu | Ile | Asp | Phe | Val | Cys |
| | | | 340 | | | | | 345 | | | | | 350 | | |
| Gly | Ser | Ser | Arg | Leu | Val | Ser | Glu | Ala | Asp | Ile | Pro | Asn | Leu | Arg | Tyr |
| | | | 355 | | | | | 360 | | | | | 365 | | |
| Leu | Gln | Cys | Ile | Val | Lys | Glu | Thr | Leu | Arg | Val | His | Pro | Pro | Gly | Pro |
| | 370 | | | | | 375 | | | | | 380 | | | | |

```
Leu Leu Ser Trp Ala Arg Leu Ala Val His Asp Val Thr Val Gly Gly
385                 390                 395                 400

Lys His Val Ile Pro Lys Gly Thr Thr Ala Met Val Asn Met Trp Ala
            405                 410                 415

Ile Thr His Asp Glu Arg Val Trp Ala Glu Pro Glu Lys Phe Arg Pro
            420                 425                 430

Glu Arg Phe Val Glu Glu Asp Val Ser Ile Met Gly Ser Asp Leu Arg
        435                 440                 445

Leu Ala Pro Phe Gly Ser Arg Arg Val Cys Pro Gly Lys Ala Leu
    450                 455                 460

Gly Leu Ala Ser Val His Leu Trp Leu Ala Gln Leu Leu Gln Asn Phe
465                 470                 475                 480

His Trp Val Ser Ser Asp Gly Val Ser Val Glu Leu Asp Glu Phe Leu
                485                 490                 495

Lys Leu Ser Met Glu Met Lys Lys Pro Leu Ser Cys Lys Ala Val Pro
                500                 505                 510

Arg Val Ser Val
            515

<210> SEQ ID NO 61
<211> LENGTH: 543
<212> TYPE: PRT
<213> ORGANISM: Zea mays

<400> SEQUENCE: 61

Met Ala Pro Pro Thr Glu Asp Cys Gly Trp Leu Leu Tyr Leu Ser Leu
1               5                   10                  15

Ala Ala Lys Cys Gly Asp Pro Gln Arg Leu Leu Gly Phe Ala Ala Val
            20                  25                  30

Phe Val Ala Ala Cys Val Val Thr Ser Leu Leu His Trp Ala Ser Pro
        35                  40                  45

Gly Gly Pro Ala Trp Gly Trp Tyr Trp Trp Thr Arg Arg Ala Gly Leu
    50                  55                  60

Gly Ile Val Arg Ala Ala Ile Pro Gly Pro Arg Gly Leu Pro Val Val
65                  70                  75                  80

Gly Ser Met Gly Leu Met Thr Gly Leu Ala His Arg Lys Leu Ser Ala
                85                  90                  95

Ala Ala Glu Arg Gln Ala Ser Arg Arg Leu Met Ala Phe Ser Leu
            100                 105                 110

Gly Glu Thr Arg Val Val Thr Ala Asp Pro Asp Val Ala Arg Glu
        115                 120                 125

Leu Leu Ala Ser Ala Ala Phe Ala Asp Arg Pro Val Lys Glu Ser Ala
    130                 135                 140

Tyr Gly Leu Leu Phe His Arg Ala Ile Gly Phe Ala Pro His Gly Ala
145                 150                 155                 160

Tyr Trp Arg Ala Leu Arg Arg Val Ala Ser Ala His Leu Phe Ser Pro
                165                 170                 175

Arg Gln Ile Ala Ala Ser Ala Ala Gln Arg Ala Ala Ile Ala Arg Gln
            180                 185                 190

Met Val Asp Ala Thr Thr Thr Ala Ala His Ala Pro Val Val Val
        195                 200                 205

Ala Arg Arg Phe Leu Lys Arg Ala Ser Leu His Asn Val Met Trp Ser
    210                 215                 220

Val Phe Gly Arg Arg Tyr Asp Leu Met Ala Asp Ser Arg Glu Ala Glu
225                 230                 235                 240
```

```
Glu Leu Lys Ala Leu Val Asp Glu Gly Tyr Asp Leu Gly Gln Leu
                245                 250                 255

Asn Trp Ser Asp His Leu Pro Trp Leu Ala Arg Phe Asp Leu Gln Lys
            260                 265                 270

Thr Arg Ala Arg Cys Cys Ala Leu Val Pro Arg Val Asn Arg Phe Val
        275                 280                 285

Gly Asn Ile Ile Gly Glu His Arg Ala Arg Leu Gly Arg Gly Val Asp
    290                 295                 300

Thr Ala Val Met Asp Phe Thr Asp Val Leu Leu Ser Leu Gln Gly Asp
305                 310                 315                 320

Asp Lys Leu Ser Asp Ala Asp Met Ile Ala Val Leu Trp Glu Met Ile
                325                 330                 335

Phe Arg Gly Thr Asp Thr Val Ala Val Leu Ile Glu Trp Val Leu Ala
            340                 345                 350

Arg Leu Val Leu His Gln Asp Val Gln Ser Lys Val Gln Glu Glu Leu
        355                 360                 365

Asp Arg Val Val Gly Leu Gly Gln Ala Val Thr Glu Ser Asp Thr Ala
    370                 375                 380

Ser Leu Pro Tyr Leu Gln Ala Val Ile Lys Glu Val Leu Arg Leu His
385                 390                 395                 400

Pro Pro Gly Pro Leu Leu Ser Trp Ala Arg Leu Ala Thr Ser Asp Val
                405                 410                 415

His Val Gly Gly Tyr Leu Val Pro Ala Gly Thr Thr Ala Met Val Asn
            420                 425                 430

Met Trp Ala Ile Thr His Asp Pro Ser Leu Trp Pro Glu Pro Met Glu
        435                 440                 445

Phe Arg Pro Glu Arg Phe Met Gly Pro Ala Ala Glu Asp Val Pro Ile
    450                 455                 460

Met Gly Ser Asp Leu Arg Leu Ala Pro Phe Gly Ser Gly Arg Arg Ser
465                 470                 475                 480

Cys Pro Gly Lys Ser Leu Ala Val Ala Thr Val Gly Phe Trp Val Ala
                485                 490                 495

Thr Leu Leu Tyr Glu Phe Lys Trp Leu Pro Pro Ser Glu Pro Arg
            500                 505                 510

Gly Gly Gly Val Asp Leu Ser Glu Val Leu Arg Leu Ser Cys Glu Met
        515                 520                 525

Ala Ala Pro Leu Glu Ala Arg Val Pro Arg His Ala Val Cys
    530                 535                 540

<210> SEQ ID NO 62
<211> LENGTH: 551
<212> TYPE: PRT
<213> ORGANISM: Sorghum bicolor

<400> SEQUENCE: 62

Met Ala Val Ala Ala Thr Pro Asp Asp Cys Gly Ser Trp Leu Leu Tyr
1               5                   10                  15

Leu Ser Leu Ala Ala Lys Cys Ala Gly Gly Asp Gln Pro His Arg Leu
            20                  25                  30

Ala Gly Phe Leu Ala Val Cys Ala Val Ala Phe Val Val Thr Cys Leu
        35                  40                  45

Leu His Trp Cys Phe Pro Gly Gly Pro Ala Trp Gly Arg Trp Trp Trp
    50                  55                  60

Thr Thr Gln Ala Arg Arg Val Ala Ala Ala Val Pro Gly Pro Arg
```

```
                65                  70                  75                  80
        Gly Leu Pro Val Val Gly Ser Met Trp Leu Met Thr Gly Leu Ala His
                            85                  90                  95

Arg Lys Leu Ala Ala Ala Ala Asp Ser Leu Arg Ala Arg Arg Leu Met
                            100                 105                 110

Ala Phe Ser Leu Gly Gly Thr Arg Val Val Ala Ala His Pro Asp
                        115                 120                 125

Val Ala Arg Glu Ile Leu Asn Ser Pro Ala Phe Ala Asp Arg Pro Ile
                    130                 135                 140

Lys Glu Ser Ala Tyr Gly Leu Leu Phe His Arg Ala Ile Gly Phe Ala
        145                 150                 155                 160

Pro Tyr Gly Ala Tyr Trp Arg Ala Leu Arg Arg Val Ala Ser Thr His
                            165                 170                 175

Leu Phe Ser Pro Trp Gln Val Ala Ala Ser Ala Ala Gln Arg Ala Val
                        180                 185                 190

Ile Ala Arg Gln Met Val Ala Ala Met Lys Gln Glu Leu Ser Ser Ser
                    195                 200                 205

Ser Ser Ala Ser Ala Gly Phe Glu Val Arg Arg Val Leu Arg Arg Gly
                210                 215                 220

Ser Leu His Asn Val Met Trp Ser Val Phe Gly Arg Arg Tyr Asp Leu
        225                 230                 235                 240

Glu Leu Asp Pro Ala Lys Glu Ser Pro Glu Thr Arg Glu Leu Arg Ser
                            245                 250                 255

Leu Val Asp Glu Gly Tyr Asp Leu Leu Gly Gln Leu Asn Trp Ser Asp
                        260                 265                 270

His Leu Pro Trp Leu Ala Arg Phe Asp Leu Gln Ser Thr Arg Ser Arg
                    275                 280                 285

Cys Asp Arg Leu Val Pro Leu Val Asn Arg Phe Val Gly Gly Ile Ile
        290                 295                 300

Asp Ala His Arg Ala Arg Asn Asp Leu Arg Ser Ala Pro Pro His Ala
        305                 310                 315                 320

Val Met Asp Phe Thr Asp Val Leu Leu Ser Leu Pro Ala Asp Asp Arg
                        325                 330                 335

Leu Thr Asp Ser Asp Met Ile Ala Val Leu Trp Glu Met Val Phe Arg
                    340                 345                 350

Gly Thr Asp Thr Val Ala Val Leu Ile Glu Trp Val Leu Ala Arg Leu
                355                 360                 365

Val Leu His Pro Asp Val Gln Ala Arg Val His Asp Glu Leu Asp Arg
                370                 375                 380

Val Val Gly Arg Asp Arg Ala Val Thr Glu Ser Asp Ser Gly Ser Leu
        385                 390                 395                 400

Val Tyr Leu His Ala Val Ile Lys Glu Val Leu Arg Met His Pro Pro
                            405                 410                 415

Gly Pro Leu Leu Ser Trp Ala Arg Leu Ala Thr Ser Asp Val Gln Val
                        420                 425                 430

Asp Gly His Leu Ile Pro Ala Gly Thr Thr Ala Met Val Asn Met Trp
                    435                 440                 445

Ala Ile Thr His Asp Pro Asp Val Trp Ala Glu Pro Ala Glu Phe Gln
        450                 455                 460

Pro Glu Arg Phe Met Gly Ser Thr Thr Gly Gly Glu Phe Pro Ile Met
        465                 470                 475                 480

Gly Ser Asp Leu Arg Leu Ala Pro Phe Gly Ala Gly Arg Arg Ser Cys
                        485                 490                 495
```

```
Pro Gly Lys Ser Leu Ala Met Ala Thr Val Ala Leu Trp Leu Ala Thr
                500                 505                 510

Leu Leu His Glu Phe Glu Leu Pro Ala Arg Gly Val Tyr Leu Ser
            515                 520                 525

Glu Val Leu Lys Leu Ser Cys Glu Met Ala Val Pro Leu Ala Val Thr
530                 535                 540

Ala Arg Pro Arg Gln Ala Val
545                 550

<210> SEQ ID NO 63
<211> LENGTH: 528
<212> TYPE: PRT
<213> ORGANISM: Glycine max

<400> SEQUENCE: 63

Met Ser Ser Ser Glu Leu Ser Ser Phe Phe Leu Leu Arg Leu Ser Asp
1               5                   10                  15

Ile Leu Ser Phe Asp Val Leu Leu Gly Val Met Phe Leu Val Ala Val
            20                  25                  30

Phe Gly Tyr Trp Leu Val Pro Gly Gly Leu Ala Trp Ala Phe Ser Lys
        35                  40                  45

Phe Lys Pro Ala Ile Pro Gly Pro Ser Gly Tyr Pro Val Val Gly Leu
    50                  55                  60

Val Trp Ala Phe Ile Gly Pro Leu Thr His Arg Val Leu Ala Lys Leu
65                  70                  75                  80

Ala Glu Thr Phe Asp Ala Lys Pro Leu Met Ala Phe Ser Val Gly Phe
                85                  90                  95

Thr Arg Phe Ile Ile Ser Ser His Pro Asp Thr Ala Lys Glu Ile Leu
            100                 105                 110

Asn Ser Ser Ala Phe Ala Asp Arg Pro Val Lys Glu Ser Ala Tyr Glu
        115                 120                 125

Leu Leu Phe His Arg Ala Met Gly Phe Ala Pro Tyr Gly Glu Tyr Trp
    130                 135                 140

Arg Asn Leu Arg Arg Ile Ser Ala Thr His Met Phe Ser Pro Arg Arg
145                 150                 155                 160

Ile Ala Ala Gln Gly Val Phe Arg Ala Arg Ile Gly Ala Gln Met Val
                165                 170                 175

Arg Asp Ile Val Gly Leu Met Gly Arg Asp Gly Val Val Glu Val Arg
            180                 185                 190

Lys Val Leu His Phe Gly Ser Leu Asn Asn Val Met Lys Ser Val Phe
        195                 200                 205

Gly Arg Ser Tyr Val Phe Gly Glu Gly Gly Asp Gly Cys Glu Leu Glu
    210                 215                 220

Gly Leu Val Ser Glu Gly Tyr His Leu Leu Gly Val Phe Asn Trp Ser
225                 230                 235                 240

Asp His Phe Pro Leu Leu Gly Trp Leu Asp Leu Gln Gly Val Arg Lys
                245                 250                 255

Ser Cys Arg Ser Leu Val Asp Arg Val Asn Val Tyr Val Gly Lys Ile
            260                 265                 270

Ile Leu Glu His Arg Val Lys Arg Val Ala Gln Gly Glu Asp Asn Lys
        275                 280                 285

Ala Ile Asp Thr Asp Ser Ser Gly Asp Phe Val Asp Val Leu Leu Asp
    290                 295                 300

Leu Glu Lys Glu Asn Arg Leu Asn His Ser Asp Met Val Ala Val Leu
```

```
                305                 310                 315                 320
Trp Glu Met Ile Phe Arg Gly Thr Asp Thr Val Ala Ile Leu Leu Glu
                    325                 330                 335

Trp Ile Leu Ala Arg Met Val Leu His Pro Glu Ile Gln Ala Lys Ala
                    340                 345                 350

Gln Ser Glu Ile Asp Ser Val Gly Ser Gly Arg Ser Val Ser Asp
                    355                 360                 365

Asp Asp Leu Pro Asn Leu Pro Tyr Val Arg Ala Ile Val Lys Glu Thr
            370                 375                 380

Leu Arg Met His Pro Pro Gly Pro Leu Leu Ser Trp Ala Arg Leu Ser
385                 390                 395                 400

Ile His Asp Thr Gln Ile Gly Asn His Phe Val Pro Ala Gly Thr Thr
                    405                 410                 415

Ala Met Val Asn Met Trp Ala Ile Thr His Asp Gln Glu Val Trp Tyr
                    420                 425                 430

Glu Pro Lys Gln Phe Lys Pro Glu Arg Phe Leu Lys Asp Glu Asp Val
                    435                 440                 445

Pro Ile Met Gly Ser Asp Leu Arg Leu Ala Pro Phe Gly Ser Gly Arg
            450                 455                 460

Arg Val Cys Pro Gly Lys Ala Met Gly Leu Ala Thr Val Glu Leu Trp
465                 470                 475                 480

Leu Ala Met Phe Leu Gln Lys Phe Lys Trp Met Pro Cys Asp Asp Ser
                    485                 490                 495

Gly Val Asp Leu Ser Glu Cys Leu Lys Leu Ser Met Glu Met Lys His
                    500                 505                 510

Ser Leu Lys Thr Lys Val Val Ala Arg Pro Val Val Ser Leu Ala Met
                    515                 520                 525

<210> SEQ ID NO 64
<211> LENGTH: 557
<212> TYPE: PRT
<213> ORGANISM: Zea mays

<400> SEQUENCE: 64

Met Ala Ala Pro Pro Thr Glu Asp Cys Gly Trp Leu Leu Tyr Leu Ser
1               5                   10                  15

Leu Ala Ala Lys Cys Gly Asp Pro Ser Arg Leu Leu Gly Leu Ala Ala
                    20                  25                  30

Val Phe Val Gly Ala Cys Val Val Thr Ser Leu Leu His Trp Ala Cys
                    35                  40                  45

Pro Gly Gly Pro Ala Trp Gly Arg Tyr Trp Trp Thr Arg Arg Gly Gly
            50                  55                  60

Leu Gly Ile Val Arg Ala Ala Ile Pro Gly Pro Arg Gly Leu Pro Val
65                  70                  75                  80

Val Gly Ser Met Gly Leu Met Thr Gly Leu Ala His Arg Lys Leu Ala
                    85                  90                  95

Ala Ala Ala Ala Ala Gly Gly Gln Gly Ser Ser Arg Arg Arg
                    100                 105                 110

Leu Met Ala Leu Ser Leu Gly Glu Thr Arg Ala Val Val Thr Gly Asp
                    115                 120                 125

Pro Asp Val Ala Arg Glu Leu Leu Gly Ser Ala Ala Phe Ala Asp Arg
            130                 135                 140

Pro Val Lys Glu Ser Ala Tyr Gly Leu Leu Phe His Arg Ala Ile Gly
145                 150                 155                 160
```

```
Phe Ala Pro His Gly Ala Tyr Trp Arg Ala Leu Arg Arg Val Ala Ser
                165                 170                 175

Ala His Leu Phe Ser Pro Arg Gln Val Ala Ala Ser Ser Ala Gln Arg
        180                 185                 190

Ala Val Ile Ala Arg Gln Met Val Asp Ala Val Thr Thr Ala Ala Pro
    195                 200                 205

Ala Pro Ala Pro Ala Val Val Val Ala Arg Arg Phe Leu Lys Arg Ala
210                 215                 220

Ser Leu His Asn Val Met Trp Ser Val Phe Gly Arg Arg Tyr Asp Leu
225                 230                 235                 240

Leu Leu Leu Ala Ala Asp Gly Glu Glu Leu Lys Ala Leu Val Asp Glu
                245                 250                 255

Gly Tyr Asp Leu Leu Gly Gln Leu Asn Trp Ser Asp His Leu Pro Trp
            260                 265                 270

Leu Ala Arg Phe Asp Leu Gln Arg Thr Arg Ala Arg Cys Ser Ala Leu
        275                 280                 285

Val Pro Arg Val Asn Arg Phe Val Gly Asn Ile Ile Asp Glu His Arg
    290                 295                 300

Ala Arg Leu Gly Leu Gly Asp Thr Gly Gly Val Thr Asp Phe Thr Asp
305                 310                 315                 320

Val Leu Leu Ser Leu Gln Gly Val Asp Lys Leu Ser Asp Ala Asp Met
                325                 330                 335

Val Ala Val Leu Trp Glu Met Ile Phe Arg Gly Thr Asp Thr Val Ala
            340                 345                 350

Val Leu Met Glu Trp Val Leu Ala Arg Leu Val Leu His Gln Asp Val
        355                 360                 365

Gln Ser Lys Val Gln Glu Glu Leu Asp Arg Val Val Gly Pro Pro Gly
    370                 375                 380

Gln Ala Ala Ser Val Thr Glu Ser Asp Thr Ala Ser Leu Val Tyr Leu
385                 390                 395                 400

Gln Ala Val Ile Lys Glu Val Leu Arg Leu His Pro Pro Gly Pro Leu
                405                 410                 415

Leu Ser Trp Ala Arg Leu Ala Thr Ser Asp Ala Arg Val Gly Gly Tyr
            420                 425                 430

His Val Pro Ala Gly Thr Thr Ala Met Val Asn Met Trp Ala Ile Thr
        435                 440                 445

His Asp Pro Ser Val Trp Ala Glu Pro Thr Glu Phe Arg Pro Glu Arg
    450                 455                 460

Phe Val Gly Ala Ser Ala Gly Ala Gly Ala Gly Ala Gly Ala Glu Asp
465                 470                 475                 480

Val Pro Met Ile Met Gly Ser Asp Leu Arg Leu Ala Pro Phe Gly Ser
                485                 490                 495

Gly Arg Arg Ser Cys Pro Gly Lys Ser Leu Ala Leu Ala Thr Val Gly
            500                 505                 510

Phe Trp Val Ala Thr Leu Leu His Glu Phe Lys Trp Leu Pro Pro Cys
        515                 520                 525

Arg Gly Val Asp Leu Ser Glu Val Leu Arg Leu Ser Cys Glu Met Ala
    530                 535                 540

Ala Pro Leu Glu Ala Arg Val Val Pro Arg His Ala Val
545                 550                 555

<210> SEQ ID NO 65
<211> LENGTH: 572
<212> TYPE: PRT
```

<213> ORGANISM: Brachypodium distachyon

<400> SEQUENCE: 65

```
Met Ala Pro Ala Thr Ser Ala Ser Glu Asp Cys Ala Gly Trp Leu Leu
1               5                   10                  15

Tyr Ala Ser Leu Ala Ala Arg Cys Asn Asp Gly Gly Glu Ala Tyr Arg
            20                  25                  30

Ala Ala Val Phe Ala Met Ala Leu Leu Ala Thr Ser Phe Ile Leu Thr
        35                  40                  45

Ser Leu Leu His Trp Ala Ser Thr Pro Gly Gly Pro Ala Trp Gly Arg
    50                  55                  60

Tyr Arg Trp Thr Ser Thr Thr Ser Arg Ala Ala Ile Ser Thr Ser Pro
65                  70                  75                  80

Arg Ile Pro Gly Pro Arg Gly Leu Pro Val Val Gly Ser Met Gly Leu
                85                  90                  95

Met Thr Gly Leu Ala His Arg Lys Leu Ala Ala Val Ala Ala Ala Gly
            100                 105                 110

Gly Asp Asp Glu Glu Arg Ser Gln Arg Arg Leu Met Ala Phe
        115                 120                 125

Ser Met Gly Glu Thr Arg Ala Val Val Ser Ser Asp Pro Ala Val Ala
    130                 135                 140

Arg Glu Leu Leu Ser Ser Pro Ala Phe Ala Asp Arg Pro Val Lys Glu
145                 150                 155                 160

Ser Ala Tyr Gly Leu Leu Phe His Arg Ala Ile Gly Phe Ala Pro His
                165                 170                 175

Gly Ala Tyr Trp Arg Ser Leu Arg Arg Val Ala Ser Ala His Leu Phe
            180                 185                 190

Ser Pro Arg Gln Val Ala Ala Ser Ala Ala His Arg Ala Ala Ile Ala
        195                 200                 205

Arg Ser Met Val Gly Ser Val Ser Ala Ile Ala Met Gly Ser Gly Glu
    210                 215                 220

Val Glu Val Arg Arg Phe Leu Lys Arg Ala Ala Leu His Gly Val Met
225                 230                 235                 240

Trp Ser Val Phe Gly Arg Arg Tyr Asp Gly Thr Ala Ala Pro Glu Leu
                245                 250                 255

Gly Lys Lys Glu Glu Glu Leu Arg Ser Met Val Glu Gly Tyr
            260                 265                 270

Glu Leu Leu Gly Lys Leu Asn Trp Ala Asp His Leu Pro Trp Leu Ala
        275                 280                 285

Arg Phe Asp Leu Gln Gly Ile Arg Ala Arg Cys Ala Ala Leu Val Pro
    290                 295                 300

Arg Val Asn Arg Phe Val Gly Lys Ile Val Asp Asp His Arg Ala Ala
305                 310                 315                 320

Ala Ala Ala Asp Ala Gly Asp Arg Val Val Asp Phe Thr Asp Val Leu
                325                 330                 335

Leu Ser Leu Gln Gly Ala Asp Lys Leu Ser Asp Ala Asp Met Ile Ala
            340                 345                 350

Val Leu Trp Glu Met Val Phe Arg Gly Thr Asp Thr Met Ala Val Val
        355                 360                 365

Met Glu Trp Val Leu Ala Arg Leu Val Met His Gln Asp Val Gln Ala
    370                 375                 380

Arg Val Gln Glu Glu Leu Asp Arg Val Val Gly Pro Gly Gln Ala Val
385                 390                 395                 400
```

-continued

```
Ser Glu Ser Asp Ala Ala Arg Leu Val Tyr Leu Gln Ala Val Ile Lys
                405                 410                 415
Glu Thr Met Arg Leu His Pro Pro Gly Pro Leu Leu Ser Trp Ala Arg
            420                 425                 430
Leu Ala Thr Ser Asp Val His Val Gly Gly Phe Leu Val Pro Ala Gly
        435                 440                 445
Thr Thr Ala Met Val Asn Met Trp Ala Ile Thr His Asp Pro Thr Val
    450                 455                 460
Trp Ala Asp Pro Leu Glu Phe Asn Pro Asp Arg Phe Ile Val Gly Ala
465                 470                 475                 480
Val Pro Leu Ser Glu Gly His His Asn Ala Val Pro Gly Ala Glu Phe
                485                 490                 495
Ser Ile Met Gly Ser Asp Leu Arg Leu Ala Pro Phe Gly Ser Gly Arg
            500                 505                 510
Arg Ile Cys Pro Gly Lys Pro Leu Ala Met Ala Ser Ile Gly Phe Trp
        515                 520                 525
Val Ala Thr Leu Leu His Glu Phe Lys Trp Thr Ser Ala Pro Arg Gly
    530                 535                 540
Asp Val Asp Leu Ser Glu Val Leu Arg Leu Ser Cys Glu Met Ala Ala
545                 550                 555                 560
Pro Leu Lys Ala Arg Leu Thr Pro Arg Arg Pro Val
                565                 570

<210> SEQ ID NO 66
<211> LENGTH: 517
<212> TYPE: PRT
<213> ORGANISM: Glycine max

<400> SEQUENCE: 66

Met Ser Ser Ser Glu Leu Ser Ser Phe Phe Leu Leu Pro Leu Ser Ala
1               5                   10                  15
Ile Leu Ser Phe Asp Ala Leu Leu Gly Val Met Phe Leu Val Ala Val
                20                  25                  30
Phe Gly Tyr Trp Leu Val Pro Gly Gly Leu Ala Trp Ala Leu Ser Lys
            35                  40                  45
Phe Lys Pro Ala Ile Pro Gly Pro Cys Gly Tyr Pro Val Val Gly Leu
        50                  55                  60
Val Trp Ala Phe Ile Gly Pro Leu Thr His Arg Val Leu Ala Lys Leu
65                  70                  75                  80
Ala Glu Thr Phe Asp Ala Lys Pro Leu Met Ala Phe Ser Val Gly Phe
                85                  90                  95
Thr Arg Phe Ile Ile Ser Ser His Pro Asp Thr Ala Lys Glu Ile Leu
            100                 105                 110
Asn Ser Ser Ala Phe Ala Asp Arg Pro Val Lys Glu Ser Ala Tyr Glu
        115                 120                 125
Leu Leu Phe His Arg Ala Met Gly Phe Ala Pro Tyr Gly Glu Tyr Trp
    130                 135                 140
Arg Asn Leu Arg Arg Ile Ser Ala Thr His Met Phe Ser Pro Lys Arg
145                 150                 155                 160
Ile Ala Ala Gln Gly Val Phe Arg Ala Arg Val Gly Ala Gln Met Val
                165                 170                 175
Arg Glu Ile Val Gly Leu Met Gly Lys Asn Asp Val Val Glu Val Arg
            180                 185                 190
Lys Val Leu His Phe Gly Ser Leu Asn Asn Val Met Lys Ser Val Phe
        195                 200                 205
```

Gly Arg Ser Tyr Val Phe Gly Glu Gly Gly Asp Gly Cys Glu Leu Glu
            210                 215                 220

Glu Leu Val Ser Glu Gly Tyr Asp Leu Leu Gly Leu Phe Asn Trp Ser
225                 230                 235                 240

Asp His Phe Pro Leu Leu Gly Trp Leu Asp Phe Gln Gly Val Arg Lys
                245                 250                 255

Arg Cys Arg Ser Leu Val Asp Arg Val Asn Val Phe Val Gly Lys Ile
            260                 265                 270

Ile Met Glu His Arg Val Lys Arg Asp Ala Glu Ser Gly Asp Phe Val
        275                 280                 285

Asp Val Leu Leu Asp Leu Glu Lys Glu Asp Arg Leu Asn His Ser Asp
290                 295                 300

Met Val Ala Val Leu Trp Glu Met Ile Phe Arg Gly Thr Asp Thr Val
305                 310                 315                 320

Ala Ile Leu Leu Glu Trp Ile Leu Ala Arg Met Val Leu His Pro Glu
                325                 330                 335

Ile Gln Ala Lys Ala Gln Cys Glu Ile Asp Ser Val Val Gly Ser Gly
            340                 345                 350

Cys Ser Val Thr Asp Asp Leu Pro Asn Leu Pro Tyr Val Arg Ala
        355                 360                 365

Ile Val Lys Glu Thr Leu Arg Met His Pro Gly Pro Leu Leu Ser
370                 375                 380

Trp Ala Arg Leu Ser Ile His Glu Thr Gln Ile Gly Asn His Phe Val
385                 390                 395                 400

Pro Ala Gly Thr Thr Ala Met Val Asn Leu Trp Ala Ile Thr His Asp
                405                 410                 415

Gln Gln Val Trp Ser Glu Pro Glu Gln Phe Lys Pro Glu Arg Phe Leu
            420                 425                 430

Lys Asp Glu Asp Val Pro Ile Met Gly Ser Asp Leu Arg Leu Ala Pro
        435                 440                 445

Phe Gly Ala Gly Arg Arg Val Cys Pro Gly Lys Ala Met Gly Leu Ala
450                 455                 460

Thr Val Glu Leu Trp Leu Ala Val Phe Leu Gln Lys Phe Lys Trp Met
465                 470                 475                 480

Pro Cys Asp Asp Ser Gly Val Asp Leu Ser Glu Cys Leu Lys Leu Ser
                485                 490                 495

Met Glu Met Lys His Ser Leu Ile Thr Lys Ala Val Ala Arg Pro Thr
            500                 505                 510

Ser Ser Leu Ala Met
        515

<210> SEQ ID NO 67
<211> LENGTH: 525
<212> TYPE: PRT
<213> ORGANISM: Oryza sativa

<400> SEQUENCE: 67

Met Ala Leu Ser Ser Met Ala Ala Gln Glu Ser Ser Leu Leu Leu
1               5                   10                  15

Phe Leu Leu Pro Thr Ser Ala Ala Ser Val Phe Pro Leu Ile Ser
                20                  25                  30

Val Val Val Leu Ala Ala Leu Leu Trp Leu Ser Pro Gly Gly Pro
            35                  40                  45

Ala Trp Ala Leu Ser Arg Cys Arg Gly Thr Pro Pro Pro Gly Val

-continued

```
            50                  55                  60
    Ala Gly Gly Ala Ala Ser Ala Leu Ser Gly Pro Ala Ala His Arg Val
65                      70                  75                  80

Leu Ala Gly Ile Ser Arg Ala Val Glu Gly Ala Ala Val Met Ser
                        85                  90                  95

Leu Ser Val Gly Leu Thr Arg Leu Val Val Ala Ser Arg Pro Glu Thr
                        100                 105                 110

Ala Arg Glu Ile Leu Val Ser Pro Ala Phe Gly Asp Arg Pro Val Lys
                        115                 120                 125

Asp Ala Ala Arg Gln Leu Leu Phe His Arg Ala Met Gly Phe Ala Pro
                130                 135                 140

Ser Gly Asp Ala His Trp Arg Gly Leu Arg Arg Ala Ser Ala Ala His
145                     150                 155                 160

Leu Phe Gly Pro Arg Arg Val Ala Gly Ser Ala Pro Glu Arg Glu Ala
                        165                 170                 175

Ile Gly Ala Arg Ile Val Gly Asp Val Ala Ser Leu Met Ser Arg Arg
                        180                 185                 190

Gly Glu Val Pro Leu Arg Arg Val Leu His Ala Ala Ser Leu Gly His
                        195                 200                 205

Val Met Ala Thr Val Phe Gly Lys Arg His Gly Asp Ile Ser Ile Gln
                210                 215                 220

Asp Gly Glu Leu Leu Glu Glu Met Val Thr Glu Gly Tyr Asp Leu Leu
225                     230                 235                 240

Gly Lys Phe Asn Trp Ala Asp His Leu Pro Leu Leu Arg Trp Leu Asp
                        245                 250                 255

Leu Gln Gly Ile Arg Arg Arg Cys Asn Arg Leu Val Gln Lys Val Glu
                        260                 265                 270

Val Phe Val Gly Lys Ile Ile Gln Glu His Lys Ala Lys Arg Ala Ala
                        275                 280                 285

Gly Gly Val Ala Val Ala Asp Gly Val Leu Gly Asp Phe Val Asp Val
                290                 295                 300

Leu Leu Asp Leu Gln Gly Glu Glu Lys Met Ser Asp Ser Asp Met Ile
305                     310                 315                 320

Ala Val Leu Trp Glu Met Ile Phe Arg Gly Thr Asp Thr Val Ala Ile
                        325                 330                 335

Leu Met Glu Trp Val Met Ala Arg Met Val Met His Pro Glu Ile Gln
                        340                 345                 350

Ala Lys Ala Gln Ala Glu Val Asp Ala Ala Val Gly Gly Arg Arg Gly
                        355                 360                 365

Arg Val Ala Asp Gly Asp Val Ala Ser Leu Pro Tyr Ile Gln Ser Ile
                370                 375                 380

Val Lys Glu Thr Leu Arg Met His Pro Pro Gly Pro Leu Leu Ser Trp
385                     390                 395                 400

Ala Arg Leu Ala Val His Asp Ala Arg Val Gly Gly His Ala Val Pro
                        405                 410                 415

Ala Gly Thr Thr Ala Met Val Asn Met Trp Ala Ile Ala His Asp Ala
                        420                 425                 430

Ala Val Trp Pro Glu Pro Asp Ala Phe Arg Pro Glu Arg Phe Ser Glu
                        435                 440                 445

Gly Glu Asp Val Gly Val Leu Gly Gly Asp Leu Arg Leu Ala Pro Phe
                450                 455                 460

Gly Ala Gly Arg Arg Val Cys Pro Gly Arg Met Leu Ala Leu Ala Thr
465                     470                 475                 480
```

Ala His Leu Trp Leu Ala Gln Leu Leu His Ala Phe Asp Trp Ser Pro
            485                 490                 495

Thr Ala Ala Gly Val Asp Leu Ser Glu Arg Leu Gly Met Ser Leu Glu
        500                 505                 510

Met Ala Ala Pro Leu Val Cys Lys Ala Val Ala Arg Ala
        515                 520                 525

<210> SEQ ID NO 68
<211> LENGTH: 520
<212> TYPE: PRT
<213> ORGANISM: Glycine max

<400> SEQUENCE: 68

Met Ser Pro Asp Phe Thr Leu Leu Phe Phe Pro Glu Leu Ile Gln Pro
1               5                   10                  15

Pro Ile Val Thr Leu Gln Ala Ala Leu Cys Ile Leu Leu Leu Thr Phe
            20                  25                  30

Leu Leu Thr Phe Phe Leu Thr Pro Gly Gly Leu Ala Trp Ala Trp Ala
        35                  40                  45

Thr Lys Ser Ser Thr Arg Pro Ile Ile Pro Gly Pro Val Met Ala Leu
    50                  55                  60

Leu Ser Val Phe Thr Gly Ser Thr Pro His Arg Arg Leu Ser Met Leu
65                  70                  75                  80

Ala Arg Ser Tyr His Ala Glu Lys Leu Met Ala Phe Ser Ile Gly Leu
                85                  90                  95

Thr Arg Phe Val Ile Ser Ser Glu Pro Glu Thr Ala Lys Glu Ile Leu
            100                 105                 110

Gly Ser Pro Gly Phe Ala Asp Arg Pro Val Lys Glu Ser Ala Tyr Gln
        115                 120                 125

Leu Leu Phe His Arg Ala Met Gly Phe Ala Pro Tyr Gly Glu Tyr Trp
    130                 135                 140

Arg Asn Leu Arg Arg Ile Ser Ala Leu His Leu Phe Ser Pro Lys Arg
145                 150                 155                 160

Ile Thr Gly Ser Glu Ala Phe Arg Asn Glu Val Gly Leu Lys Met Val
                165                 170                 175

Asp Glu Val Lys Lys Val Met Lys Asp Asn Arg His Val Glu Val Lys
            180                 185                 190

Arg Ile Leu His Tyr Gly Ser Leu Asn Asn Val Met Met Thr Val Phe
        195                 200                 205

Gly Lys Cys Tyr Glu Phe Tyr Glu Gly Glu Gly Val Glu Leu Glu Ala
    210                 215                 220

Leu Val Ser Glu Gly Tyr Glu Leu Leu Gly Val Phe Asn Trp Ser Asp
225                 230                 235                 240

His Phe Pro Val Leu Gly Trp Leu Asp Leu Gln Gly Val Arg Lys Arg
                245                 250                 255

Cys Arg Cys Leu Val Glu Lys Val Asn Ala Phe Val Gly Gly Val Ile
            260                 265                 270

Glu Glu His Arg Val Lys Arg Val Arg Gly Gly Cys Val Lys Asp Glu
        275                 280                 285

Gly Thr Gly Asp Phe Val Asp Val Leu Leu Asp Leu Glu Asn Glu Asn
    290                 295                 300

Lys Leu Ser Glu Ala Asp Met Ile Ala Val Leu Trp Glu Met Ile Phe
305                 310                 315                 320

Arg Gly Thr Asp Thr Val Ala Ile Leu Leu Glu Trp Ile Leu Ala Arg

```
                       325                 330                 335
Met Val Leu His Pro Asp Ile Gln Ala Lys Ala Gln Arg Glu Ile Asp
                340                 345                 350

Ser Val Cys Gly Pro Tyr Arg Leu Val Ser Glu Ala Asp Met Pro Asn
                355                 360                 365

Leu Arg Tyr Leu Gln Gly Ile Val Lys Glu Thr Leu Arg Val His Pro
            370                 375                 380

Pro Gly Pro Leu Leu Ser Trp Ala Arg Leu Ala Val His Asp Val Thr
385                 390                 395                 400

Val Gly Gly Lys His Val Ile Pro Lys Gly Thr Thr Ala Met Val Asn
                405                 410                 415

Met Trp Ala Ile Thr His Asp Glu Arg Phe Trp Ala Glu Pro Glu Arg
                420                 425                 430

Phe Arg Pro Glu Arg Phe Val Glu Glu Asp Val Asn Ile Met Gly
            435                 440                 445

Ser Asp Leu Arg Leu Ala Pro Phe Gly Ser Gly Arg Arg Val Cys Pro
            450                 455                 460

Gly Lys Ala Leu Gly Leu Ala Ser Val His Leu Trp Leu Ala Gln Leu
465                 470                 475                 480

Leu Gln Asn Phe His Trp Val Gln Phe Asp Gly Val Ser Val Glu Leu
                485                 490                 495

Asp Glu Cys Leu Lys Leu Ser Met Glu Met Lys Lys Pro Leu Ala Cys
                500                 505                 510

Lys Ala Val Pro Arg Val Ala Val
            515                 520

<210> SEQ ID NO 69
<211> LENGTH: 445
<212> TYPE: PRT
<213> ORGANISM: Sorghum bicolor

<400> SEQUENCE: 69

Met Asp Ala Thr Thr Gln Asp Ser Leu Leu Phe Leu Phe Pro Ala Ala
1               5                   10                  15

Ala Thr Phe Leu Ser Pro Leu Leu Ala Val Leu Leu Val Ala Leu Ser
                20                  25                  30

Leu Leu Trp Leu Val Pro Gly Gly Pro Ala Trp Ala Leu Ile Ser Thr
            35                  40                  45

Ser Arg Ser Arg Ala Thr Pro Pro Gly Ala Pro Gly Val Val Thr
        50                  55                  60

Ala Leu Ser Gly Pro Ala Ala His Arg Ala Leu Ala Ser Leu Ser Arg
65                  70                  75                  80

Ser Leu Pro Gly Gly Ala Ala Leu Ser Ala Phe Ser Val Gly Leu Thr
                85                  90                  95

Arg Leu Val Val Ala Ser Gln Pro Asp Thr Ala Arg Glu Leu Leu Ala
            100                 105                 110

Ser Ala Ala Phe Ala Asp Arg Pro Val Lys Asp Ala Ala Arg Gly Leu
        115                 120                 125

Leu Phe His Arg Ala Met Gly Phe Ala Pro Ser Gly Asp Tyr Trp Arg
    130                 135                 140

Ala Leu Cys Arg Ile Ser Ser Ala Tyr Leu Phe Ser Pro Arg Ser Glu
145                 150                 155                 160

Ser Ala Thr Ala Pro Arg Arg Val Thr Ile Gly Glu Arg Met Leu Arg
                165                 170                 175
```

-continued

Asp Leu Ser Asp Ala Ile Gly Arg Leu Arg Arg Ser Leu Val Ser Arg
                180                 185                 190

Val Asn Val Phe Val Ala Arg Ile Ile Glu Glu His Arg Gln Lys Lys
            195                 200                 205

Lys Asp Asp Val Ala Asn Asn Gly Glu Ser Ala Ala Gly Asp Phe Val
        210                 215                 220

Asp Val Leu Leu Gly Leu Glu Gly Glu Lys Leu Ser Asp Ser Asp
225                 230                 235                 240

Met Ile Ala Val Leu Trp Glu Met Ile Phe Arg Gly Thr Asp Thr Val
                245                 250                 255

Ala Ile Leu Leu Glu Trp Val Met Ala Arg Met Val Leu His Pro Gly
            260                 265                 270

Ile Gln Ser Lys Ala Gln Ala Glu Leu Asp Ala Val Val Gly Arg Gly
        275                 280                 285

Gly Ala Val Ser Asp Ala Asp Val Ser Arg Leu Pro Tyr Leu Gln Arg
    290                 295                 300

Val Val Lys Glu Thr Leu Arg Val His Pro Pro Gly Pro Leu Leu Ser
305                 310                 315                 320

Trp Ala Arg Leu Ala Val His Asp Ala Val Val Gly His Leu Val
                325                 330                 335

Pro Ala Gly Thr Thr Ala Met Val Asn Met Trp Ala Ile Ala Arg Asp
            340                 345                 350

Pro Ala Val Trp Ala Asp Pro Thr Ala Phe Arg Pro Glu Arg Phe Glu
        355                 360                 365

Glu Glu Asp Val Ser Val Leu Gly Gly Asp Leu Arg Leu Ala Pro Phe
    370                 375                 380

Gly Ala Gly Arg Arg Val Cys Pro Gly Lys Thr Leu Ala Leu Ala Thr
385                 390                 395                 400

Val His Leu Trp Leu Ala Gln Leu Leu His Arg Phe Gln Trp Ala Pro
                405                 410                 415

Ala Asp Gly Gly Val Asp Leu Ala Glu Arg Leu Gly Met Ser Leu Glu
            420                 425                 430

Met Glu Lys Pro Leu Val Cys Lys Pro Thr Pro Arg Trp
        435                 440                 445

<210> SEQ ID NO 70
<211> LENGTH: 548
<212> TYPE: PRT
<213> ORGANISM: Oryza sativa

<400> SEQUENCE: 70

Met Asp Ala Thr Leu Gly Ala Ser Thr Thr His Gly Tyr Leu Leu Leu
1               5                   10                  15

Leu Pro Ala Asn Ser Thr Thr Phe Phe Ser Pro Leu Leu Ala Ala Leu
                20                  25                  30

Leu Ala Val Thr Ser Leu Leu Trp Leu Val Pro Gly Gly Pro Ala Trp
            35                  40                  45

Ala Leu Ser Arg Cys Arg Arg Pro Pro Gly Ala Pro Gly Ala Leu
        50                  55                  60

Ala Ala Leu Ala Gly Pro Ala His Arg Ala Leu Ala Ala Met Ser
65                  70                  75                  80

Arg Ser Val Pro Gly Gly Ala Ala Leu Ala Ser Phe Ser Val Gly Leu
                85                  90                  95

Thr Arg Phe Val Val Ala Ser Arg Pro Asp Thr Ala Arg Glu Leu Leu
            100                 105                 110

-continued

```
Ser Ser Ala Ala Phe Ala Asp Arg Pro Val Lys Asp Ala Arg Gly
        115                 120                 125

Leu Leu Phe His Arg Ala Met Gly Phe Ala Pro Ser Gly Asp Tyr Trp
130                 135                 140

Arg Ala Leu Arg Arg Val Ser Ala Asn His Leu Phe Thr Pro Arg Arg
145                 150                 155                 160

Val Ala Ala Ser Ala Pro Arg Arg Leu Ala Ile Gly Glu Arg Met Leu
                165                 170                 175

Asp Arg Leu Ser Ala Leu Ala Gly Gly Glu Ile Gly Met Arg Arg Val
            180                 185                 190

Leu His Ala Ala Ser Leu Asp His Val Met Asp Thr Val Phe Gly Thr
        195                 200                 205

Arg Tyr Asp Gly Asp Ser Gln Glu Gly Ala Glu Leu Glu Ala Met Val
210                 215                 220

Lys Glu Gly Tyr Asp Leu Leu Gly Met Phe Asn Trp Gly Asp His Leu
225                 230                 235                 240

Pro Leu Leu Lys Trp Leu Asp Leu Gln Gly Val Arg Arg Cys Arg
                245                 250                 255

Thr Leu Val Gln Arg Val Asp Val Phe Val Arg Ser Ile Ile Asp Glu
        260                 265                 270

His Arg Gln Arg Lys Arg Arg Thr Gly Gly Asn Gly Gly Gly Glu Glu
        275                 280                 285

Leu Pro Gly Asp Phe Val Asp Val Leu Leu Gly Leu Gln Gly Glu Glu
        290                 295                 300

Lys Met Thr Glu Ser Asp Met Val Ala Val Leu Trp Val Thr Lys Asp
305                 310                 315                 320

Pro Ser Asp Met His Ala Ser Ile Arg Ser Ile Leu Cys Ile Ala Ile
                325                 330                 335

Asn Gly Phe Met Asp Ile Phe Asp Leu Ala Arg Val Gln Glu Met Ile
            340                 345                 350

Phe Arg Gly Thr Asp Thr Val Ala Ile Leu Leu Glu Trp Ile Met Ala
        355                 360                 365

Arg Met Val Leu His Pro Asp Ile Gln Ala Lys Ala Gln Ala Glu Leu
        370                 375                 380

Asp Ala Val Val Gly Arg Gly Arg Ala Val Ser Asp Gly Asp Val Ala
385                 390                 395                 400

Gly Leu Arg Tyr Leu Gln Cys Val Val Lys Glu Ala Leu Arg Val His
                405                 410                 415

Pro Pro Gly Pro Leu Leu Ser Trp Ala Arg Leu Ala Val Arg Asp Ala
            420                 425                 430

His Val Gly Gly His Val Val Pro Ala Gly Thr Thr Ala Met Val Asn
        435                 440                 445

Met Trp Ala Ile Ala His Asp Pro Glu Leu Trp Pro Glu Pro Asp Glu
        450                 455                 460

Phe Arg Pro Glu Arg Phe Ala Glu Glu Asp Val Ser Val Leu Gly Gly
465                 470                 475                 480

Asp Leu Arg Leu Ala Pro Phe Gly Ala Gly Arg Arg Ala Cys Pro Gly
                485                 490                 495

Lys Thr Leu Ala Leu Ala Thr Val His Leu Trp Leu Ala Gln Leu Leu
            500                 505                 510

His Arg Phe Glu Trp Ala Pro Val Gly Gly Gly Val His Leu Leu Glu
        515                 520                 525
```

```
Arg Leu Asn Met Ser Leu Glu Met Glu Lys Pro Leu Val Cys Lys Ala
            530                 535                 540

Lys Pro Arg Trp
545

<210> SEQ ID NO 71
<211> LENGTH: 522
<212> TYPE: PRT
<213> ORGANISM: Glycine max

<400> SEQUENCE: 71

Met Ile Pro Thr Leu Val Cys Ile Gly Thr Thr Ile Phe Gln Ser Thr
1               5                   10                  15

Leu Ser Ser Tyr Ser Leu Ser Phe Ile Ser Leu Phe Leu Ser Thr Ser
            20                  25                  30

Leu Ala Leu Leu Ala Ile Ser Leu Asn Tyr Trp Leu Val Pro Gly Gly
        35                  40                  45

Phe Ala Trp Arg Lys Tyr His Ser Arg Tyr Lys Gly His Ala Lys Val
50                  55                  60

Ser Gly Pro Met Gly Trp Pro Ile Leu Gly Thr Leu Pro Ala Met Gly
65                  70                  75                  80

Pro Leu Ala His Arg Lys Leu Ala Ala Met Ala Thr Ser Pro Lys Ala
                85                  90                  95

Lys Lys Leu Met Thr Leu Ser Leu Gly Thr Asn Pro Val Ile Ser
            100                 105                 110

Ser His Pro Glu Thr Ala Arg Glu Ile Leu Cys Gly Ser Asn Phe Ala
        115                 120                 125

Asp Arg Pro Val Lys Glu Ser Ala Arg Met Leu Met Phe Glu Arg Ala
130                 135                 140

Ile Gly Phe Ala Pro Tyr Gly Thr Tyr Trp Arg His Leu Arg Lys Val
145                 150                 155                 160

Ala Ile Thr His Met Phe Ser Pro Arg Ile Ser Asp Leu Glu Ser
                165                 170                 175

Leu Arg Gln His Val Val Gly Glu Met Val Met Arg Ile Trp Lys Glu
        180                 185                 190

Met Gly Asp Lys Gly Val Val Glu Val Arg Gly Ile Leu Tyr Glu Gly
            195                 200                 205

Ser Leu Ser His Met Leu Glu Cys Val Phe Gly Ile Asn Asn Ser Leu
210                 215                 220

Gly Ser Gln Thr Lys Glu Ala Leu Gly Asp Met Val Glu Glu Gly Tyr
225                 230                 235                 240

Asp Leu Ile Ala Lys Phe Asn Trp Ala Asp Tyr Phe Pro Phe Gly Phe
                245                 250                 255

Leu Asp Phe His Gly Val Lys Arg Arg Cys His Lys Leu Ala Thr Lys
        260                 265                 270

Val Asn Ser Val Val Gly Lys Ile Val Glu Glu Arg Lys Asn Ser Gly
            275                 280                 285

Lys Tyr Val Gly Gln Asn Asp Phe Leu Ser Ala Leu Leu Leu Leu Pro
290                 295                 300

Lys Glu Glu Ser Ile Gly Asp Ser Asp Val Val Ala Ile Leu Trp Glu
305                 310                 315                 320

Met Ile Phe Arg Gly Thr Asp Thr Ile Ala Ile Leu Leu Glu Trp Ile
                325                 330                 335

Met Ala Met Met Val Leu His Gln Asp Val Gln Met Lys Ala Arg Gln
        340                 345                 350
```

Glu Ile Asp Ser Cys Ile Lys Gln Asn Gly Tyr Met Arg Asp Ser Asp
            355                 360                 365

Ile Pro Asn Leu Pro Tyr Leu Gln Ala Ile Val Lys Glu Val Leu Arg
    370                 375                 380

Leu His Pro Pro Gly Pro Leu Leu Ser Trp Ala Arg Leu Ala Ile His
385                 390                 395                 400

Asp Val His Val Asp Lys Val Ile Val Pro Ala Gly Thr Thr Ala Met
                405                 410                 415

Val Asn Met Trp Ala Ile Ser His Asp Ser Ser Ile Trp Glu Asp Pro
            420                 425                 430

Trp Ala Phe Lys Pro Glu Arg Phe Met Lys Asp Val Ser Ile Met
        435                 440                 445

Gly Ser Asp Met Arg Leu Ala Pro Phe Gly Ala Gly Arg Arg Val Cys
450                 455                 460

Pro Gly Lys Thr Leu Gly Leu Ala Thr Val His Leu Trp Leu Ala Gln
465                 470                 475                 480

Leu Leu His His Phe Ile Trp Ile Pro Val Gln Pro Val Asp Leu Ser
                485                 490                 495

Glu Cys Leu Lys Leu Ser Leu Glu Met Lys Lys Pro Leu Arg Cys Gln
            500                 505                 510

Val Ile Arg Arg Phe Asn Thr Ile Ser Ser
            515                 520

<210> SEQ ID NO 72
<211> LENGTH: 534
<212> TYPE: PRT
<213> ORGANISM: Zea mays

<400> SEQUENCE: 72

Met Thr Leu Ile Pro Ala Ile Ser Gly Glu Gln His Gly Asn Met Ala
1               5                   10                  15

Thr Val Ala Thr Ser Phe Ala Tyr Leu Ala Ile Phe Ala Cys Leu Ala
            20                  25                  30

Trp Val Gly Ala Ser Leu Leu Tyr Trp Ala His Pro Gly Gly Pro Ala
        35                  40                  45

Trp Gly Lys Tyr Trp Arg Ala Arg Gly Lys Lys Pro Ser Ala Ala Ile
    50                  55                  60

Pro Gly Pro Lys Gly Leu Pro Val Val Gly Ser Leu Gly Leu Met Ser
65                  70                  75                  80

Gly Leu Ala His Arg Ser Leu Ala Asp Glu Ala Ser Arg Arg Pro Gly
                85                  90                  95

Ala Lys Arg Leu Met Ala Leu Ser Leu Gly Pro Val Arg Ala Val Val
            100                 105                 110

Thr Ser His Pro Asp Val Ala Lys Glu Ile Leu Asp Ser Pro Ala Phe
        115                 120                 125

Ala Ala Arg Pro Leu Asn His Ala Ala Tyr Gly Leu Met Phe His Arg
    130                 135                 140

Ser Ile Gly Phe Ala Glu His Gly Pro Tyr Trp Arg Ala Leu Arg Arg
145                 150                 155                 160

Val Ala Ala Gly His Leu Phe Gly Pro Arg Gln Val Glu Ala Phe Ala
                165                 170                 175

Pro Tyr Arg Ala Ala Val Ala Glu Gly Ile Val Ala Leu Leu Arg
            180                 185                 190

Ala Gly Ser Gly Gly Ala Val Val Gln Val Arg Gly Leu Leu Arg Arg

```
            195                 200                 205
Ala Ser Leu Tyr Tyr Ile Met Arg Phe Val Phe Gly Lys Glu Tyr Asp
    210                 215                 220

Val Ser Arg Val Val Pro Pro Ser Gly Gly Glu Val Glu Glu Leu
225                 230                 235                 240

Leu Glu Met Val His Glu Gly Tyr Glu Leu Leu Gly Met Glu Asn Leu
                245                 250                 255

Cys Asp Tyr Phe Pro Gly Leu Ala Ala Leu Asp Pro Gln Gly Val Gly
            260                 265                 270

Ala Arg Cys Ala Glu Leu Met Pro Arg Val Asn Arg Phe Val His Gly
        275                 280                 285

Val Ile Gln Glu His Arg Ala Lys Ala Val Ala Gly Gly Asp Ala Arg
    290                 295                 300

Asp Phe Val Asp Ile Leu Leu Ser Leu Gln Ser Glu Gly Leu Ala
305                 310                 315                 320

Asp Ala Asp Ile Ala Ser Val Leu Trp Glu Met Ile Phe Arg Gly Thr
                325                 330                 335

Asp Ala Met Ala Val Leu Met Glu Trp Thr Leu Ala Arg Leu Val Leu
            340                 345                 350

His Arg Asp Val Gln Ala Lys Ala His Arg Glu Leu Asp Lys Val Val
        355                 360                 365

Gly Ala Asp Ser Gln Thr Thr Glu Ser Ala Ala Pro Tyr Leu Gln Ala
370                 375                 380

Leu Leu Lys Glu Ala Leu Arg Met His Pro Pro Gly Pro Leu Leu Ser
385                 390                 395                 400

Trp Arg His Arg Ala Ile Ser Asp Thr Tyr Val Asp Gly His Leu Val
                405                 410                 415

Pro Ala Gly Thr Thr Ala Met Val Asn Gln Trp Ala Ile Ser Arg Asp
            420                 425                 430

Pro Glu Val Trp Asp Ala Pro Leu Glu Phe Arg Pro Glu Arg Phe Leu
        435                 440                 445

Pro Gly Gly Glu Gly Gln Asp Val Ser Val Leu Gly Ala Asp Gly Arg
    450                 455                 460

Leu Val Pro Phe Gly Ser Gly Arg Arg Ser Cys Pro Gly Lys Ser Leu
465                 470                 475                 480

Ala Met Thr Thr Val Thr Ser Trp Met Ala Thr Leu Leu His Glu Phe
                485                 490                 495

Glu Trp Leu Pro Ala Ser Asp Asp Thr Gly Asp Val Asp Leu Ser Glu
            500                 505                 510

Val Leu Arg Leu Ser Cys Glu Met Ala Val Pro Leu Glu Val Arg Val
        515                 520                 525

Arg Pro Arg Ser Ser Val
    530

<210> SEQ ID NO 73
<211> LENGTH: 514
<212> TYPE: PRT
<213> ORGANISM: Glycine max

<400> SEQUENCE: 73

Met Lys Pro Thr Ala Thr Phe Phe Phe Leu Leu Ser Thr Thr Thr Leu
1               5                   10                  15

Leu Val Cys Leu Cys Leu Gly Thr Thr Thr Phe Gln Thr Thr Leu Phe
            20                  25                  30
```

-continued

```
Ile Thr Phe Phe Thr Ile Ser Leu Asn Tyr Trp Leu Val Pro Gly Gly
         35                  40                  45

Phe Ala Trp Arg Asn Tyr His Ser Tyr His Thr Asn Glu Lys Pro Asn
 50                  55                  60

Lys Lys Leu Thr Gly Pro Met Gly Trp Pro Ile Leu Gly Ser Leu Pro
 65                  70                  75                  80

Leu Met Gly Ser Leu Ala His Gln Lys Leu Ala Ala Leu Ala Ala Thr
                 85                  90                  95

Leu Asn Ala Lys Arg Leu Met Ala Leu Ser Leu Gly Pro Thr Pro Val
            100                 105                 110

Val Ile Ser Ser His Pro Glu Thr Ala Arg Glu Ile Leu Leu Gly Ser
        115                 120                 125

Ser Phe Ser Asp Arg Pro Ile Lys Glu Ser Ala Arg Ala Leu Met Phe
130                 135                 140

Glu Arg Ala Ile Gly Phe Ala Pro Ser Gly Thr Tyr Trp Arg His Leu
145                 150                 155                 160

Arg Arg Ile Ala Ala Phe His Met Phe Ser Pro Arg Arg Ile Gln Gly
                165                 170                 175

Leu Glu Gly Leu Arg Gln Arg Val Gly Asp Asp Met Val Lys Ser Ala
            180                 185                 190

Trp Lys Glu Met Glu Met Lys Gly Val Val Glu Val Arg Gly Val Phe
        195                 200                 205

Gln Glu Gly Ser Leu Cys Asn Ile Leu Glu Ser Val Phe Gly Ser Asn
210                 215                 220

Asp Lys Ser Glu Glu Leu Gly Asp Met Val Arg Glu Gly Tyr Glu Leu
225                 230                 235                 240

Ile Ala Met Leu Asn Leu Glu Asp Tyr Phe Pro Leu Lys Phe Leu Asp
                245                 250                 255

Phe His Gly Val Lys Arg Arg Cys His Lys Leu Ala Ala Lys Val Gly
            260                 265                 270

Ser Val Val Gly Gln Ile Val Glu Asp Arg Lys Arg Glu Gly Ser Phe
        275                 280                 285

Val Val Lys Asn Asp Phe Leu Ser Thr Leu Leu Ser Leu Pro Lys Glu
290                 295                 300

Glu Arg Leu Ala Asp Ser Asp Met Ala Ala Ile Leu Trp Glu Met Val
305                 310                 315                 320

Phe Arg Gly Thr Asp Thr Val Ala Ile Leu Leu Glu Trp Val Met Ala
                325                 330                 335

Arg Met Val Leu His Gln Asp Val Gln Lys Lys Ala Arg Glu Glu Ile
            340                 345                 350

Asp Thr Cys Ile Gly Gln Asn Ser His Val Arg Asp Ser Asp Ile Ala
        355                 360                 365

Asn Leu Pro Tyr Leu Gln Ala Ile Val Lys Glu Val Leu Arg Leu His
370                 375                 380

Pro Pro Gly Pro Leu Leu Ser Trp Ala Arg Leu Ala Val Asn Asp Val
385                 390                 395                 400

His Val Asp Lys Val Leu Val Pro Ala Gly Thr Thr Ala Met Val Asn
                405                 410                 415

Met Trp Ala Ile Ser His Asp Ser Ser Ile Trp Glu Asp Pro Trp Ala
            420                 425                 430

Phe Lys Pro Glu Arg Phe Leu Lys Glu Asp Val Ser Ile Met Gly Ser
        435                 440                 445

Asp Leu Arg Leu Ala Pro Phe Gly Ala Gly Arg Arg Val Cys Pro Gly
```

```
                450                 455                 460
Arg Ala Leu Gly Leu Ala Thr Thr His Leu Trp Leu Ala Gln Leu Leu
465                 470                 475                 480

Arg His Phe Ile Trp Leu Pro Ala Gln Pro Val Asp Leu Ser Glu Cys
                485                 490                 495

Leu Arg Leu Ser Met Glu Met Lys Thr Pro Leu Arg Cys Leu Val Val
                500                 505                 510

Arg Arg

<210> SEQ ID NO 74
<211> LENGTH: 235
<212> TYPE: PRT
<213> ORGANISM: Sorghum bicolor

<400> SEQUENCE: 74

Met Asp Phe Thr Asp Val Leu Leu Ser Leu Asn Gly Asp Asp Lys Leu
1               5                   10                  15

Ser Asp Ala Asp Met Ile Ala Val Leu Trp Glu Met Ile Phe Arg Gly
                20                  25                  30

Thr Asp Thr Val Ala Val Leu Ile Glu Trp Val Leu Ala Arg Leu Val
            35                  40                  45

Leu His Gln Asp Val Gln Arg Lys Val His Asp Glu Leu Asp Arg Val
50                  55                  60

Val Gly Pro Gly Glu Ala Val Thr Glu Ser Asp Thr Ala Ser Leu Val
65                  70                  75                  80

Tyr Leu Gln Ala Val Ile Lys Glu Val Leu Arg Leu His Pro Pro Gly
                85                  90                  95

Pro Leu Leu Ser Trp Ala Arg Leu Ala Thr Ser Asp Val Asn Val Gly
                100                 105                 110

Gly His Leu Val Pro Ala Gly Thr Thr Ala Met Val Asn Met Trp Ala
            115                 120                 125

Ile Thr His Asp Ala Ser Val Trp Pro Glu Pro Thr Glu Phe Arg Pro
            130                 135                 140

Glu Arg Phe Val Ala Ala Ala Gly Gly Glu Asp Val Val Pro Ile Met
145                 150                 155                 160

Gly Ser Asp Leu Arg Leu Ala Pro Phe Gly Ser Gly Arg Arg Ser Cys
                165                 170                 175

Pro Gly Lys Ser Leu Ala Val Ala Thr Val Gly Phe Trp Val Ala Thr
                180                 185                 190

Leu Leu His Glu Phe Glu Trp Leu Pro Cys Gly Gly Gly Gly Gly Val
            195                 200                 205

Asp Leu Ser Glu Val Leu Arg Leu Ser Cys Glu Met Ala Ala Pro Leu
210                 215                 220

Glu Ala Arg Val Val Pro Arg Arg His Ala Val
225                 230                 235

<210> SEQ ID NO 75
<211> LENGTH: 508
<212> TYPE: PRT
<213> ORGANISM: Glycine max

<400> SEQUENCE: 75

Met Lys Pro Thr Ala Thr Phe Phe Leu Leu Pro Ser Thr Thr Leu
1               5                   10                  15

Val Val Cys Leu Cys Leu Gly Ile Gly Thr Thr Thr Leu Phe Ile Thr
                20                  25                  30
```

```
Leu Leu Ala Ile Ser Leu Asn Tyr Trp Leu Val Pro Gly Gly Phe Ala
        35                  40                  45

Trp Arg Asn Tyr Asp Tyr Tyr Gln Thr Lys Lys Leu Thr Gly Pro
 50                  55                  60

Met Gly Trp Pro Ile Leu Gly Thr Leu Pro Leu Met Gly Ser Leu Ala
 65                  70                  75                  80

His Gln Lys Leu Ala Ala Leu Ala Thr Ser Leu Asn Ala Lys Arg Leu
                85                  90                  95

Met Ala Leu Ser Leu Gly Pro Thr Pro Val Val Ile Ser Ser His Pro
                100                 105                 110

Glu Thr Ala Arg Glu Ile Leu Leu Gly Ser Ser Phe Ser Asp Arg Pro
                115                 120                 125

Ile Lys Glu Ser Ala Arg Ala Leu Met Phe Glu Arg Ala Ile Gly Phe
                130                 135                 140

Ala His Ser Gly Thr Tyr Trp Arg His Leu Arg Arg Ile Ala Ala Phe
145                 150                 155                 160

His Met Phe Ser Pro Arg Arg Ile His Gly Leu Glu Gly Leu Arg Gln
                165                 170                 175

Arg Val Gly Asp Asp Met Val Lys Ser Ala Trp Arg Glu Met Gly Glu
                180                 185                 190

Lys Gly Val Val Glu Val Arg Arg Val Phe Gln Glu Gly Ser Leu Cys
                195                 200                 205

Asn Ile Leu Glu Ser Val Phe Gly Ser Asn Asp Lys Ser Glu Glu Leu
                210                 215                 220

Arg Asp Met Val Arg Glu Gly Tyr Glu Leu Ile Ala Met Phe Asn Leu
225                 230                 235                 240

Glu Asp Tyr Phe Pro Phe Lys Phe Leu Asp Phe His Gly Val Lys Arg
                245                 250                 255

Arg Cys His Lys Leu Ala Ala Lys Val Gly Ser Val Val Gly Gln Ile
                260                 265                 270

Val Glu Glu Arg Lys Arg Asp Gly Gly Phe Val Gly Lys Asn Asp Phe
                275                 280                 285

Leu Ser Thr Leu Leu Ser Leu Pro Lys Glu Glu Arg Leu Ala Asp Ser
                290                 295                 300

Asp Leu Val Ala Ile Leu Trp Glu Met Val Phe Arg Gly Thr Asp Thr
305                 310                 315                 320

Val Ala Ile Leu Leu Glu Trp Val Met Ala Arg Met Val Leu His Gln
                325                 330                 335

Asp Leu Gln Lys Lys Ala Arg Glu Glu Ile Asp Thr Cys Val Gly Gln
                340                 345                 350

Asn Ser His Val Arg Asp Ser Asp Ile Ala Asn Leu Pro Tyr Leu Gln
                355                 360                 365

Ala Ile Val Lys Glu Val Leu Arg Leu His Pro Pro Gly Pro Leu Leu
                370                 375                 380

Ser Trp Ala Arg Leu Ala Val His Asp Val His Ala Asp Lys Val Leu
385                 390                 395                 400

Val Pro Ala Gly Thr Thr Ala Met Val Asn Met Trp Ala Ile Ser His
                405                 410                 415

Asp Ser Ser Ile Trp Glu Asp Pro Trp Ala Phe Lys Pro Glu Arg Phe
                420                 425                 430

Leu Lys Glu Asp Val Ser Ile Met Gly Ser Asp Leu Arg Leu Ala Pro
                435                 440                 445
```

```
Phe Gly Ala Gly Arg Arg Val Cys Pro Gly Arg Ala Leu Gly Leu Ala
    450                 455                 460

Thr Ala His Leu Trp Leu Ala Gln Leu Leu Arg His Phe Ile Trp Leu
465                 470                 475                 480

Pro Ala Gln Thr Val Asp Leu Ser Glu Cys Leu Arg Leu Ser Met Glu
                485                 490                 495

Met Lys Thr Pro Leu Arg Cys Leu Val Val Arg Arg
                500                 505

<210> SEQ ID NO 76
<211> LENGTH: 517
<212> TYPE: PRT
<213> ORGANISM: Sorghum bicolor

<400> SEQUENCE: 76

Met Val Leu Thr Met Ala Thr Gly Gln Glu Asp Ser Leu Leu Leu Leu
1               5                   10                  15

Leu Leu Pro Thr Thr Ser Pro Leu Pro Pro Leu Met Ala Val Phe Ile
            20                  25                  30

Leu Ala Ala Val Leu Leu Trp Leu Ser Pro Gly Gly Pro Ala Trp Ala
        35                  40                  45

Leu Ser Arg Cys Arg Arg Pro Pro Ser Gly Pro Thr Gly Val Val Thr
50                  55                  60

Ala Leu Ser Ser Pro Val Ala His Arg Thr Leu Ala Ala Leu Ser His
65                  70                  75                  80

Ala Val Asp Gly Gly Lys Ala Leu Met Ala Phe Ser Val Gly Leu Thr
                85                  90                  95

Arg Leu Val Val Ser Ser Gln Pro Asp Thr Ala Arg Glu Ile Leu Val
            100                 105                 110

Asn Pro Ala Phe Ser Asp Arg Pro Ile Lys Asp Ala Ala Arg His Leu
        115                 120                 125

Leu Phe His Arg Ala Met Gly Phe Ala Pro Ser Gly Asp Ala His Trp
130                 135                 140

Arg Gly Leu Arg Arg Leu Ala Ala Asn His Leu Phe Gly Pro Arg Arg
145                 150                 155                 160

Val Ala Ala Ala His His Arg Val Ser Ile Gly Glu Ala Met Val
                165                 170                 175

Ala Asp Val Ala Ala Met Ala Arg His Gly Glu Val Ser Leu Lys
            180                 185                 190

Arg Val Leu His Ile Ala Ser Leu Asn His Ile Met Ala Thr Val Phe
            195                 200                 205

Gly Lys His Tyr Asp Met Asp Ser Gln Glu Gly Val Leu Glu Glu
    210                 215                 220

Met Val Thr Glu Gly Tyr Asp Leu Leu Gly Thr Phe Asn Trp Ala Asp
225                 230                 235                 240

His Leu Pro Leu Ile Lys His Leu Asp Leu Gln Gly Val Arg Arg
                245                 250                 255

Cys Asn Arg Leu Val Gln Lys Val Glu Val Phe Val Gly Lys Ile Ile
            260                 265                 270

Gln Glu His Arg Ala Arg Arg Ala Asn Gly Gly Val Asp Asp Glu Tyr
        275                 280                 285

Met Gly Asp Phe Val Asp Val Leu Leu Asp Leu Glu Gly Glu Glu Lys
    290                 295                 300

Leu Ser Glu Ser Asp Met Ile Ala Val Leu Trp Glu Met Ile Phe Arg
305                 310                 315                 320
```

```
Gly Ala Asp Thr Val Ala Ile Leu Met Glu Trp Ile Met Ala Arg Met
            325                 330                 335

Ala Leu His Pro Glu Ile Gln Ser Lys Ala Gln Ala Glu Leu Asp Gly
        340                 345                 350

Val Val Val Gly Gly Val Ala Asp Ala Asp Val Gly Asn Leu Pro Tyr
            355                 360                 365

Ile Gln Cys Ile Val Lys Glu Thr Leu Arg Met His Pro Pro Gly Pro
370                 375                 380

Leu Leu Ser Trp Ala Arg Leu Ala Ile His Asp Ala His Val Gly Gly
385                 390                 395                 400

His Leu Val Pro Ala Gly Thr Thr Ala Met Val Asn Met Trp Ser Ile
            405                 410                 415

Ala His Asp Pro Ala Ile Trp Ala Glu Pro Glu Lys Phe Arg Pro Glu
            420                 425                 430

Arg Phe Gln Glu Glu Asp Val Ser Val Leu Gly Ser Asp Leu Arg Leu
        435                 440                 445

Ala Pro Phe Gly Ala Gly Arg Arg Val Cys Pro Gly Lys Met Leu Ala
    450                 455                 460

Leu Ala Thr Thr His Leu Trp Ile Ala Gln Leu Leu His Glu Phe Glu
465                 470                 475                 480

Trp Ala Pro Ala Ala Ala Asn Gly Gly Val Asp Leu Ser Glu Arg Leu
                485                 490                 495

Asn Met Ser Leu Glu Met Ala Thr Pro Leu Val Cys Lys Ala Val Pro
            500                 505                 510

Arg Ala Gln Leu Ala
        515

<210> SEQ ID NO 77
<211> LENGTH: 549
<212> TYPE: PRT
<213> ORGANISM: Sorghum bicolor

<400> SEQUENCE: 77

Met Glu Ser Ser Val Glu Ser Trp Trp Val Leu Pro Met Thr Leu Ile
1               5                   10                  15

Pro Ala Ile Ser Gly Gln Gln His Glu Asn Met Ala Thr Ile Ala Thr
            20                  25                  30

Ser Phe Val Tyr Leu Ala Ile Phe Ala Cys Leu Ala Trp Ala Gly Ala
        35                  40                  45

Ser Leu Leu Tyr Trp Ala His Pro Gly Pro Ala Trp Gly Lys Tyr
    50                  55                  60

Trp Arg Ala Lys Gly Lys Pro Ser Ser Thr Ile Pro Gly Pro Lys Gly
65                  70                  75                  80

Leu Pro Val Val Gly Ser Leu Gly Leu Met Ser Gly Leu Ala His Cys
                85                  90                  95

Ser Leu Ala Asp Glu Ala Ser Arg Arg Pro Gly Ala Lys Arg Leu Met
            100                 105                 110

Ala Leu Ser Leu Gly Pro Val Arg Ala Val Val Thr Ser His Pro Asp
        115                 120                 125

Val Ala Lys Glu Ile Leu Asp Asn Pro Ala Phe Ala Asp Arg Pro Leu
    130                 135                 140

Asn His Ala Ala Tyr Gly Leu Met Phe His Arg Ser Ile Gly Phe Ala
145                 150                 155                 160

Glu His Gly Pro Tyr Trp Arg Ala Leu Arg Arg Val Ala Ala Gly His
```

```
                    165                 170                 175
Leu Phe Gly Pro Arg Gln Val Glu Ala Phe Ala Pro Tyr Arg Ala Ala
                180                 185                 190

Val Gly Glu Gly Ile Val Ala Ala Leu His Gly Ala Gly Gly Val
            195                 200                 205

Val Gln Val Arg Gly Leu Leu Arg Ala Ser Leu Tyr Tyr Ile Met
        210                 215                 220

Arg Phe Val Phe Gly Lys Glu Tyr Asp Val Ser Arg Ala Val Pro Ala
225                 230                 235                 240

Ser Gly Lys Glu Glu Val Glu Glu Leu Glu Met Val His Glu Gly
                245                 250                 255

Tyr Glu Leu Leu Gly Met Glu Asn Trp Cys Asp Tyr Phe Pro Gly Leu
            260                 265                 270

Ala Ala Leu Asp Pro Gln Gly Val Gly Ala Arg Cys Ala Glu Leu Met
        275                 280                 285

Pro Arg Val Asn Arg Phe Val His Gly Ile Ile Gln Glu Arg Arg Ala
    290                 295                 300

Lys Ala Ile Ala Gly Gly Asp Ala Arg Asp Phe Val Asp Ile Leu Leu
305                 310                 315                 320

Ser Leu Gln Glu Ser Glu Arg Leu Ala Asp Ala Asp Ile Ala Ala Val
                325                 330                 335

Leu Trp Glu Met Ile Phe Arg Gly Thr Asp Ala Met Ala Val Leu Met
            340                 345                 350

Glu Trp Thr Leu Ala Arg Leu Val Leu His Arg Asp Val Gln Ala Lys
        355                 360                 365

Ala His Arg Glu Leu Asp Glu Val Val Gly Gly Asn Ser Gln Val Val
    370                 375                 380

Thr Glu Ser Ala Ala Ala Pro Ser Leu Pro Tyr Leu Gln Ala Leu Leu
385                 390                 395                 400

Lys Glu Ala Leu Arg Met His Pro Pro Gly Pro Leu Leu Ser Trp Arg
                405                 410                 415

His Arg Ala Ile Ser Asp Thr Tyr Val Asp Gly His Leu Val Pro Ala
            420                 425                 430

Gly Thr Thr Ala Met Val Asn Gln Trp Ala Ile Ser Arg Asp Pro Glu
        435                 440                 445

Val Trp Asp Ala Pro Leu Glu Phe Arg Pro Glu Arg Phe Leu Pro Gly
    450                 455                 460

Gly Glu Gly Gln Asp Val Ser Val Leu Gly Ala Asp Gly Arg Leu Val
465                 470                 475                 480

Pro Phe Gly Ser Gly Arg Arg Ser Cys Pro Gly Lys Ser Leu Ala Met
                485                 490                 495

Thr Thr Val Thr Thr Trp Met Ala Thr Leu Leu Asn Glu Phe Glu Trp
            500                 505                 510

Leu Pro Ala Ser Asp Asp Thr Gly Gly Asp Val Asp Leu Ser Glu Val
        515                 520                 525

Leu Arg Leu Ser Cys Glu Met Ala Val Pro Leu Glu Val Arg Val Arg
    530                 535                 540

Pro Arg Ser Gly Met
545

<210> SEQ ID NO 78
<211> LENGTH: 539
<212> TYPE: PRT
<213> ORGANISM: Sorghum bicolor
```

<400> SEQUENCE: 78

```
Met Lys Thr Glu Val Ile Thr Thr Met Ile Ser Leu Val Phe Leu Val
1               5                   10                  15

His Phe Ala Ile Thr Ile Ser Pro Asn Ala Gln Pro Ser Trp Leu Phe
            20                  25                  30

Ser Leu Met Ser Leu Ser Leu Ala Val Val Ala Val Ile Val Pro Leu
        35                  40                  45

Val Val Thr Thr Thr Cys His Ala Arg Lys Asn Thr Asp Ala Thr Thr
    50                  55                  60

Thr Ile Pro Gly Pro Arg Gly Trp Pro Leu Val Gly Ser Leu Leu Val
65                  70                  75                  80

Val Ser Gly Pro Leu Met His Arg Arg Leu Ala Ala Leu Ala Asp Ala
                85                  90                  95

His Ser Ala Arg Arg Leu Met Ser Leu Thr Leu Gly Ala Thr Pro Val
            100                 105                 110

Val Ile Ser Ser His Pro Glu Thr Ala Arg Asp Ile Leu Ser Gly Ala
        115                 120                 125

Ala Phe Val Asp Arg Pro Pro Lys Ala Ala Arg Glu Leu Met Phe
130                 135                 140

Cys Arg Ala Ile Gly Phe Ala Pro Thr Gly Glu Tyr Trp Arg Arg Leu
145                 150                 155                 160

Arg Arg Ile Thr Gly Ala Gly Met Leu Ser Pro Arg Arg Met Ala Met
                165                 170                 175

Leu Arg Gly Leu Arg Cys Arg Val Ala Asp Ser Met Ile Gln Arg Val
            180                 185                 190

Ala Asp Gln Met Glu Arg Ser Gly Glu Val Ala Met Arg Ala Leu Leu
        195                 200                 205

Gln Arg Ala Ser Leu Glu Ser Met Val Gly Ser Val Leu Gly Leu Glu
    210                 215                 220

Gly Asp Ala Val Cys Glu Glu Leu Gly Glu Met Val Arg Glu Gly Tyr
225                 230                 235                 240

Glu Leu Val Gly Met Phe Asn Leu Glu Asp His Tyr Tyr Lys Thr Ser
                245                 250                 255

Trp Gly Pro Leu Met Asp Leu Trp Gly Val Arg Pro Met Cys Arg Glu
            260                 265                 270

Leu Ala Ala Met Val Arg Gly Tyr Phe Gly Lys Ile Ile Gln Glu Arg
        275                 280                 285

Arg Leu Ala Gly Asp Cys His Glu Arg Ala Asp Leu Leu Ser Tyr Met
    290                 295                 300

Leu Ser Leu Pro Glu Glu Lys Leu Glu Asp Ser Asp Val Ile Ala
305                 310                 315                 320

Val Leu Trp Glu Met Ile Phe Arg Gly Val Asp Val Ala Ile Leu
                325                 330                 335

Leu Glu Trp Ala Met Ala Arg Met Ser Leu His Pro Ile Gln Ser
            340                 345                 350

Lys Ala Gln Glu Glu Met Asp Ala Ala Val Gly Val Arg Arg Arg Arg
        355                 360                 365

Ala Ile Thr Asp Ser Asp Val Pro Asn Leu Ala Phe Leu Gln Trp Ile
    370                 375                 380

Leu Lys Glu Thr Leu Arg Met His Pro Pro Gly Pro Leu Leu Ser Trp
385                 390                 395                 400

Ala Arg Leu Ala Val Gln Asp Ala Arg Val Gly Lys His Val Val Pro
```

```
                            405                 410                 415
Ala Gly Thr Thr Ala Met Val Asn Met Trp Ala Ile Ser His Asp Glu
            420                 425                 430

Ala Ile Trp Gly Asp Pro Trp Val Phe Arg Pro Glu Arg Phe Ala Ala
            435                 440                 445

Ala Ala Ala Gly Glu Glu Val Ser Val Leu Gly Ser Asp Leu Arg Leu
450                 455                 460

Ala Pro Phe Gly Ser Gly Arg Arg Val Cys Pro Gly Arg Met Met Gly
465                 470                 475                 480

Leu Ala Thr Ala Gln Leu Trp Leu Gly Arg Leu Leu Gln Glu Tyr Arg
            485                 490                 495

Trp Leu Pro Pro Pro Ala Asn Lys Pro Val Glu Leu Ala Glu Cys Leu
            500                 505                 510

Arg Leu Ser Met Glu Met Lys Thr Pro Leu Val Cys Arg Ala Val Pro
            515                 520                 525

Arg Arg Arg Gly Gly Arg Pro Pro Ala Ala Ala
            530                 535

<210> SEQ ID NO 79
<211> LENGTH: 499
<212> TYPE: PRT
<213> ORGANISM: Oryza sativa

<400> SEQUENCE: 79

Met Ala Val Val Ala Leu Pro Pro Leu Leu Ala Lys Arg His Gly His
1               5                   10                  15

Ala Arg Arg Val Asn Gly Gly Gly Ala Ala Ile Pro Gly Pro Arg Gly
            20                  25                  30

Trp Pro Leu Leu Gly Ser Leu Pro Val Val Ser Gly Pro Leu Met His
        35                  40                  45

Arg Arg Leu Ala Ala Leu Ala Asp Ala His Gly Gly Gly Ala Arg Arg
    50                  55                  60

Leu Met Ser Leu Thr Leu Gly Ala Thr Pro Val Val Ser Ser His
65                  70                  75                  80

Pro Asp Thr Val Arg Glu Ile Leu Ala Gly Ala Ala Phe Arg Asp Arg
                85                  90                  95

Pro Ala Arg Ala Ala Ala Arg Glu Leu Met Phe Leu Arg Ala Val Gly
            100                 105                 110

Phe Ala Pro Ala Ser Gly Asp Asp Gly Gly Ala Tyr Trp Arg Arg Leu
        115                 120                 125

Arg Arg Ala Ala Gly Ala Gly Met Leu Ser Pro Arg Arg Ala Ala Ala
    130                 135                 140

Leu Ala Ala Leu Arg Ala Arg Val Ala Arg Arg Thr Ser Glu Ala Val
145                 150                 155                 160

Ser Arg Gly Met Ala Val Pro Pro Gly Arg Val Ala Met Arg Ala Leu
                165                 170                 175

Leu His Ala Ala Ser Leu Asp Asn Met Val Gly Ser Val Leu Gly Leu
            180                 185                 190

Glu His His Asp His His Gly Gly Val Ile Ser Asp Met Gly Asp Met
        195                 200                 205

Val Arg Glu Gly Tyr Glu Leu Val Gly Lys Phe Asn Leu Gly Asp Tyr
    210                 215                 220

Tyr Ser Thr Thr Gln Tyr Gln Cys Leu Trp Gly Leu Leu Asp Phe His
225                 230                 235                 240
```

Gly Val Gly Pro Arg Cys Gln Arg Leu Ala Arg Val Arg Glu Gln
                245                 250                 255

Phe Gly Arg Val Met Glu Glu Arg Lys Val Ser Asp Leu His Lys
            260                 265                 270

Arg Asp Asp Leu Leu Ser Tyr Met Leu Ser Met Pro Gln Glu Glu Arg
            275                 280                 285

Ile Glu Asp Ser Asp Val Ile Ala Val Leu Trp Glu Met Ile Phe Arg
    290                 295                 300

Gly Thr Asp Val Val Ala Ile Leu Leu Glu Trp Ala Met Ala Arg Met
305                 310                 315                 320

Val Leu His Pro Asp Ile Gln Ser Lys Val Gln Glu Glu Leu Asp Arg
                325                 330                 335

Ala Val Gly His Arg Pro Met Thr Asp Ser Asp Ile Pro Asn Leu Arg
            340                 345                 350

Phe Leu His Cys Val Ile Lys Glu Thr Leu Arg Met His Pro Pro Gly
            355                 360                 365

Pro Leu Leu Ser Trp Ala Arg Leu Ala Val His Asp Thr Tyr Val Gly
    370                 375                 380

Lys His Leu Val Pro Ala Gly Thr Thr Ala Met Val Asn Met Trp Ala
385                 390                 395                 400

Ile Ser His Asp Glu Thr Ile Trp Gly Asp Pro Trp Val Phe Arg Pro
                405                 410                 415

Glu Arg Phe Met Glu Asp Ile Asn Val Leu Gly Ser Asp Leu Arg
            420                 425                 430

Leu Ala Pro Phe Gly Ser Gly Arg Arg Val Cys Pro Gly Arg Met Met
            435                 440                 445

Gly Leu Ser Thr Ala Tyr Leu Trp Phe Gly Arg Met Leu Gln Glu Tyr
    450                 455                 460

Lys Trp Ala Ala Ala Gln Pro Val Lys Leu Thr Glu Cys Leu Arg Leu
465                 470                 475                 480

Ser Met Glu Met Lys Lys Pro Leu Val Cys His Ala Val Pro Arg Ser
                485                 490                 495

Lys Thr Gly

<210> SEQ ID NO 80
<211> LENGTH: 555
<212> TYPE: PRT
<213> ORGANISM: Oryza sativa

<400> SEQUENCE: 80

Met Ala Met Ala Thr Ala Thr Ala Ser Ser Cys Val Asp Ala Thr Trp
1               5                   10                  15

Trp Ala Tyr Ala Leu Pro Ala Leu Leu Gly Ala Asp Thr Leu Cys Ala
                20                  25                  30

His Pro Ala Leu Leu Ala Gly Ala Val Leu Leu Ala Phe Ala Thr Ala
            35                  40                  45

Ala Val Leu Ala Trp Ala Ala Ser Pro Gly Gly Pro Ala Trp Ala His
    50                  55                  60

Gly Arg Gly Arg Leu Gly Ala Thr Pro Ile Glu Gly Pro Arg Gly Leu
65                  70                  75                  80

Pro Val Phe Gly Ser Ile Phe Ala Leu Ser Arg Gly Leu Pro His Arg
                85                  90                  95

Ala Leu Asp Ala Met Ser Arg Asp Ala Ala Pro Arg Ala Arg Glu
            100                 105                 110

-continued

```
Leu Met Ala Phe Ser Val Gly Glu Thr Pro Ala Val Ser Ser Cys
        115                 120                 125

Pro Ala Thr Ala Arg Glu Val Leu Ala His Pro Ser Phe Ala Asp Arg
        130                 135                 140

Pro Leu Lys Arg Ser Ala Arg Glu Leu Leu Phe Ala Arg Ala Ile Gly
145                 150                 155                 160

Phe Ala Pro Ser Gly Glu Tyr Trp Arg Leu Leu Arg Arg Ile Ala Ser
                165                 170                 175

Thr His Leu Phe Ser Pro Arg Arg Val Ala Ala His Glu Pro Gly Arg
                180                 185                 190

Gln Ala Asp Ala Thr Ala Met Leu Ser Ala Met Ala Glu Gln Ser
        195                 200                 205

Ala Thr Gly Ala Val Val Leu Arg Pro His Leu Gln Ala Ala Ala Leu
        210                 215                 220

Asn Asn Ile Met Gly Ser Val Phe Gly Arg Arg Tyr Asp Val Ser Ser
225                 230                 235                 240

Ser Ser Gly Ala Ala Ala Asp Glu Ala Glu Gln Leu Lys Ser Met Val
                245                 250                 255

Arg Glu Gly Phe Glu Leu Leu Gly Ala Phe Asn Trp Ser Asp His Leu
                260                 265                 270

Pro Trp Leu Ala His Leu Tyr Asp Pro Asn His Val Ala Arg Arg Cys
        275                 280                 285

Ala Ala Leu Val Pro Arg Val Gln Ala Phe Val Arg Gly Val Ile Arg
        290                 295                 300

Asp His Arg Leu Arg Arg Asp Ser Ser Ser Thr Ala Ala Asp Asn Ala
305                 310                 315                 320

Asp Phe Val Asp Val Leu Leu Ser Leu Glu Ala His Glu Asn Leu Ala
                325                 330                 335

Glu Asp Asp Met Val Ala Val Leu Trp Glu Met Ile Phe Arg Gly Thr
                340                 345                 350

Asp Thr Thr Ala Leu Val Thr Glu Trp Cys Met Ala Glu Val Val Arg
        355                 360                 365

Asn Pro Ala Val Gln Ala Arg Leu Arg Ala Glu Val Asp Ala Ala Val
        370                 375                 380

Gly Gly Asp Gly Cys Pro Ser Asp Gly Asp Val Ala Arg Met Pro Tyr
385                 390                 395                 400

Leu Gln Ala Val Val Lys Glu Thr Leu Arg Ala His Pro Pro Gly Pro
                405                 410                 415

Leu Leu Ser Trp Ala Arg Leu Ala Thr Ala Asp Val Gly Leu Ala Asn
                420                 425                 430

Gly Met Val Val Pro Ala Gly Thr Thr Ala Met Val Asn Met Trp Ala
        435                 440                 445

Ile Thr His Asp Gly Glu Val Trp Ala Asp Pro Glu Ala Phe Ala Pro
        450                 455                 460

Glu Arg Phe Ile Pro Ser Glu Gly Gly Ala Asp Val Asp Val Arg Gly
465                 470                 475                 480

Gly Asp Leu Arg Leu Ala Pro Phe Gly Ala Gly Arg Arg Val Cys Pro
                485                 490                 495

Gly Lys Asn Leu Gly Leu Ala Thr Val Thr Leu Trp Val Ala Arg Leu
                500                 505                 510

Val His Ala Phe Asp Trp Phe Leu Pro Asp Gly Ser Pro Pro Val Ser
        515                 520                 525

Leu Asp Glu Val Leu Lys Leu Ser Leu Glu Met Lys Thr Pro Leu Ala
```

```
                    530                 535                 540

Ala Ala Ala Thr Pro Arg Arg Arg Ala Ala
545                 550                 555

<210> SEQ ID NO 81
<211> LENGTH: 174
<212> TYPE: PRT
<213> ORGANISM: Sorghum bicolor

<400> SEQUENCE: 81

Arg Asp Gly Arg Arg Gly Glu Pro Pro Leu Arg Ala Glu Arg Arg
1               5                   10                  15

Glu Gly Asp Ala Ala His Ala Pro Ala Arg Ala Arg Cys Cys Arg Gly
                20                  25                  30

Arg Ala Trp Pro Ser Thr Thr Arg Thr Ser Ala Ala Thr Leu Val Pro
            35                  40                  45

Ala Gly Thr Thr Ala Met Val Asn Met Trp Ala Ile Ala His Asp Pro
        50                  55                  60

Ala Ile Trp Ala Glu Pro Glu Glu Phe Arg Pro Glu Arg Phe Gln Glu
65                  70                  75                  80

Glu Glu Glu Asp Val Ser Val Leu Gly Gly Asp Leu Arg Leu Ala Pro
                85                  90                  95

Phe Gly Ala Gly Arg Arg Val Cys Pro Asp Lys Met Leu Ala Leu Ala
                100                 105                 110

Thr Thr His Leu Trp Val Ala Gln Leu Leu His Arg Phe Glu Trp Ala
            115                 120                 125

Pro Ala Gly Ala Ala Ser Ser Gly Gly Gly Val Asp Leu Ser Glu
        130                 135                 140

Arg Leu Asn Met Ser Leu Glu Met Ala Thr Pro Leu Val Cys Lys Ala
145                 150                 155                 160

Val Pro Arg Ser Ala Pro Gln Leu His Ala Gly Leu Ala Ser
                165                 170

<210> SEQ ID NO 82
<211> LENGTH: 552
<212> TYPE: PRT
<213> ORGANISM: Sorghum bicolor

<400> SEQUENCE: 82

Met Ala Met Ala Ser Ala Val Ser Ser Cys Thr Asp Ser Thr Trp Trp
1               5                   10                  15

Val Tyr Ala Leu Pro Thr Leu Leu Gly Ser Asp Thr Leu Cys Ala His
                20                  25                  30

Pro Ala Leu Leu Ala Gly Leu Leu Phe Leu Thr Thr Val Thr Ala Ala
            35                  40                  45

Leu Leu Ala Trp Ala Ala Ser Pro Gly Gly Pro Ala Trp Ala His Gly
        50                  55                  60

Arg Gly Arg Leu Gly Ala Thr Pro Ile Val Gly Pro Arg Gly Leu Pro
65                  70                  75                  80

Val Phe Gly Ser Ile Phe Ala Leu Ser Arg Gly Leu Pro His Arg Thr
                85                  90                  95

Leu Ala Ala Met Ala Arg Ala Ala Gly Pro Arg Ala Lys Glu Leu Met
                100                 105                 110

Ala Phe Ser Val Gly Asp Thr Pro Ala Val Val Ser Ser Cys Pro Ala
            115                 120                 125

Thr Ala Arg Glu Val Leu Ala His Pro Ser Phe Ala Asp Arg Pro Val
```

-continued

```
            130                 135                 140
Lys Arg Ser Ala Arg Glu Leu Met Phe Ala Arg Ala Ile Gly Phe Ala
145                 150                 155                 160

Pro Asn Gly Glu Tyr Trp Arg Leu Arg Arg Val Ala Ser Thr His
                165                 170                 175

Leu Phe Ser Pro Arg Arg Val Ala Ala His Glu Pro Gly Arg Gln Gly
                180                 185                 190

Asp Ala Glu Ala Met Leu Arg Ser Val Ala Ala Glu Gln Ser Ala Ser
                195                 200                 205

Gly Thr Val Val Leu Arg Pro His Leu Gln Ala Ala Leu Asn Asn
    210                 215                 220

Ile Met Gly Ser Val Phe Gly Thr Arg Tyr Asp Val Thr Ser Gly Ala
225                 230                 235                 240

Thr Ala Gly Ala Ala Glu Ala Glu Gln Leu Lys Ser Met Val Arg Glu
                245                 250                 255

Gly Phe Glu Leu Leu Gly Ala Phe Asn Trp Ser Asp His Leu Pro Trp
                260                 265                 270

Leu Ala His Leu Tyr Asp Pro Ser Asn Val Thr Arg Arg Cys Ala Ala
                275                 280                 285

Leu Val Pro Arg Val Gln Thr Phe Val Arg Gly Val Ile Asp Glu His
                290                 295                 300

Arg Arg Arg Arg Gln Asn Ser Ala Ala Leu Asp Leu Asn Asp Asn Ala
305                 310                 315                 320

Asp Phe Val Tyr Val Leu Leu Ser Leu Asp Gly Asp Glu Lys Leu Arg
                325                 330                 335

Asp Asp Asp Met Val Ala Ile Leu Trp Glu Met Ile Phe Arg Gly Thr
                340                 345                 350

Asp Thr Thr Ala Leu Leu Thr Glu Trp Cys Met Ala Glu Leu Val Arg
                355                 360                 365

His Pro Ala Val Gln Ala Arg Leu Arg Ala Glu Val Asp Ala Ala Val
                370                 375                 380

Gly Ala Gly Gly Arg Pro Thr Asp Ala Asp Val Ala Arg Met Pro Tyr
385                 390                 395                 400

Leu Gln Ala Val Val Lys Glu Thr Leu Arg Ala His Pro Pro Gly Pro
                405                 410                 415

Leu Leu Ser Trp Ala Arg Leu Ala Thr Ala Asp Val Pro Leu Ser Asn
                420                 425                 430

Gly Met Val Val Pro Ala Gly Thr Thr Ala Met Val Asn Met Trp Ala
                435                 440                 445

Ile Thr His Asp Ala Gly Val Trp Ala Asp Pro Asp Ala Phe Ala Pro
450                 455                 460

Glu Arg Phe Leu Pro Ser Glu Gly Gly Ala Asp Val Asp Val Arg Gly
465                 470                 475                 480

Val Asp Leu Arg Leu Ala Pro Phe Gly Ala Gly Arg Arg Val Cys Pro
                485                 490                 495

Gly Lys Asn Leu Gly Leu Thr Thr Val Gly Leu Trp Val Ala Arg Leu
                500                 505                 510

Val His Ala Phe Glu Trp Ala Leu Pro Asp Gly Ala Pro Pro Val Cys
                515                 520                 525

Leu Asp Glu Val Leu Lys Leu Ser Leu Glu Met Lys Thr Pro Leu Ala
                530                 535                 540

Ala Ala Ala Ile Pro Arg Thr Ala
545                 550
```

<210> SEQ ID NO 83
<211> LENGTH: 561
<212> TYPE: PRT
<213> ORGANISM: Brachypodium distachyon

<400> SEQUENCE: 83

```
Met Glu Ser Ser Val Glu Ser Ser Trp Trp Val Leu Pro Leu Thr Leu
1               5                   10                  15

Ile Pro Ala Ile Ser Gly Gln Gln Gln His Asp Gln Ser Thr Ala
            20                  25                  30

Ala Ala Ile Ala Thr Ser Phe Val Tyr Leu Ala Ile Leu Ala Cys Leu
            35                  40                  45

Ala Trp Ala Ala Lys Ser Leu Leu Tyr Trp Ala His Pro Gly Gly Pro
50                  55                  60

Ala Trp Gly Arg Arg Tyr Trp Thr Ser Pro Cys Ala Lys Thr Ala Pro
65                  70                  75                  80

Ala Pro Ala Pro Ile Pro Gly Pro Arg Gly Leu Pro Val Val Gly Ser
                85                  90                  95

Leu Gly Leu Met Ser Gly Leu Ala His Ser Thr Leu Ala Ala Glu Ala
            100                 105                 110

Ala Arg Thr Pro Gly Ala Lys Arg Leu Met Ala Leu Ser Leu Gly Pro
            115                 120                 125

Val Pro Ala Val Val Thr Ala His Pro Asp Val Ala Lys Glu Ile Leu
130                 135                 140

Asp Asn Pro Ala Phe Ala Asp Arg Pro Val Asn His Ala Ala Tyr Gly
145                 150                 155                 160

Leu Met Phe His Arg Ser Ile Gly Phe Ala Glu His Gly Pro Tyr Trp
                165                 170                 175

Arg Ala Leu Arg Arg Val Ala Ser Ala His Leu Phe Ala Pro Arg Gln
            180                 185                 190

Val Asp Ala Phe Ala Pro Tyr Arg Ala Arg Val Gly Glu Asp Val Val
            195                 200                 205

Ala Ala Leu Arg His Ala Gly Gly Val Val Asn Val Arg Gly Val
210                 215                 220

Leu Arg Arg Ala Ser Leu Tyr Tyr Ile Met Arg Phe Val Phe Gly Lys
225                 230                 235                 240

Glu Tyr Asp Val Ser Ser Asp Ser Gly Lys Lys Asp Gln Gly Glu Val
                245                 250                 255

Glu Glu Leu Leu Glu Met Val His Glu Gly Tyr Glu Leu Leu Gly Lys
            260                 265                 270

Glu Asn Trp Cys Asp Tyr Phe Pro Gly Leu Ala Gly Phe Asp Pro Gln
            275                 280                 285

Gly Val Gly Ala Arg Cys Ala Glu Leu Met Pro Arg Val Asn Arg Phe
290                 295                 300

Val His Gly Ile Ile Asp Glu His Arg Gly Lys Ala Met Ile Ala Gly
305                 310                 315                 320

Gly Glu Gly Glu Ala Gln Pro Leu Asp Phe Val Asp Ile Leu Leu Ser
                325                 330                 335

Leu Gln Glu Ser Glu Gly Leu Ala Asp Ala Asp Ile Ala Ala Val Leu
            340                 345                 350

Trp Glu Met Ile Phe Arg Gly Thr Asp Ala Met Ala Val Leu Met Glu
            355                 360                 365

Trp Thr Met Ala Arg Leu Val Leu His Pro Gly Val Gln Ala Asn Val
```

```
                    370             375             380
His Lys Glu Leu Asp Glu Val Val Gly Lys Ser Ser His Val Thr Glu
385                 390                 395                 400

Ser Ala Val Leu Ser Leu Pro Tyr Leu Gln Ala Leu Leu Lys Glu Ala
                405                 410                 415

Leu Arg Val His Pro Pro Gly Pro Leu Leu Ser Trp Arg His Arg Ala
            420                 425                 430

Met Trp Asp Thr Tyr Val Asp Gly His Leu Val Pro Ala Gly Thr Thr
        435                 440                 445

Ala Met Val Asn Gln Trp Ala Met Ser Arg Asp Pro Glu Val Trp Ala
450                 455                 460

Glu Pro Leu Glu Phe Arg Pro Glu Arg Phe Leu Pro Gly Gly Glu Ala
465                 470                 475                 480

Gly Pro Gly Val Ser Val Leu Gly Ser Asp Gly Arg Leu Val Pro Phe
                485                 490                 495

Gly Ser Gly Arg Arg Ser Cys Pro Gly Lys Asn Leu Ala Met Thr Thr
            500                 505                 510

Val Thr Ala Trp Met Ala Thr Leu Met His Glu Phe Glu Trp Met Pro
        515                 520                 525

Ala Lys Thr Gly Ala Pro Val Asp Met Ser Glu Val Leu Arg Leu Ser
530                 535                 540

Cys Glu Met Ala Thr Pro Leu Gln Val Arg Val Arg Pro Arg Arg Gly
545                 550                 555                 560

Val

<210> SEQ ID NO 84
<211> LENGTH: 9
<212> TYPE: PRT
<213> ORGANISM: Artificial sequence
<220> FEATURE:
<223> OTHER INFORMATION: Synthetic sequence: CYP78A6-clade polypeptide
      amino acid sequence motif
<220> FEATURE:
<221> NAME/KEY: VARIANT
<222> LOCATION: (8)..(8)
<223> OTHER INFORMATION: Xaa is any amino acid, preferably Gly, His or
      Thr

<400> SEQUENCE: 84

Gly Gly Ala Trp Gly Lys Tyr Xaa Arg
1               5

<210> SEQ ID NO 85
<211> LENGTH: 17
<212> TYPE: PRT
<213> ORGANISM: Artificial sequence
<220> FEATURE:
<223> OTHER INFORMATION: Synthetic sequence: CYP78A6-clade polypeptide
      amino acid sequence motif
<220> FEATURE:
<221> NAME/KEY: VARIANT
<222> LOCATION: (1)..(1)
<223> OTHER INFORMATION: Xaa is any amino acid, preferably Val or Asn
<220> FEATURE:
<221> NAME/KEY: VARIANT
<222> LOCATION: (3)..(3)
<223> OTHER INFORMATION: Xaa is any amino acid, preferably Lys or Arg
<220> FEATURE:
<221> NAME/KEY: VARIANT
<222> LOCATION: (10)..(10)
<223> OTHER INFORMATION: Xaa may be present or absent. If present, Xaa
      is any amino acid, preferably Arg
<220> FEATURE:
<221> NAME/KEY: VARIANT
```

```
<222> LOCATION: (11)..(11)
<223> OTHER INFORMATION: Xaa is any amino acid, preferably Met or Ser
<220> FEATURE:
<221> NAME/KEY: VARIANT
<222> LOCATION: (13)..(13)
<223> OTHER INFORMATION: Xaa is any amino acid, preferably Ser, Asn or
      His
<220> FEATURE:
<221> NAME/KEY: VARIANT
<222> LOCATION: (14)..(14)
<223> OTHER INFORMATION: Xaa is any amino acid, preferably Thr or Val

<400> SEQUENCE: 85

Xaa Gly Xaa Gly Val Gly Ser Met Ser Xaa Xaa Ser Xaa Xaa Ala His
1               5                   10                  15

Arg

<210> SEQ ID NO 86
<211> LENGTH: 25
<212> TYPE: PRT
<213> ORGANISM: Artificial sequence
<220> FEATURE:
<223> OTHER INFORMATION: Synthetic sequence: CYP78A6-clade polypeptide
      amino acid sequence motif
<220> FEATURE:
<221> NAME/KEY: VARIANT
<222> LOCATION: (5)..(5)
<223> OTHER INFORMATION: Xaa is any amino acid, preferably Thr or Asp
<220> FEATURE:
<221> NAME/KEY: VARIANT
<222> LOCATION: (6)..(6)
<223> OTHER INFORMATION: Xaa is any amino acid, preferably Thr or Arg
<220> FEATURE:
<221> NAME/KEY: VARIANT
<222> LOCATION: (7)..(7)
<223> OTHER INFORMATION: Xaa may be present or absent. If present, Xaa
      is any amino acid, preferably Lys
<220> FEATURE:
<221> NAME/KEY: VARIANT
<222> LOCATION: (8)..(8)
<223> OTHER INFORMATION: Xaa may be present or absent. If present, Xaa
      is any amino acid, preferably Val
<220> FEATURE:
<221> NAME/KEY: VARIANT
<222> LOCATION: (13)..(13)
<223> OTHER INFORMATION: Xaa is any amino acid, preferably Asn or His
<220> FEATURE:
<221> NAME/KEY: VARIANT
<222> LOCATION: (14)..(14)
<223> OTHER INFORMATION: Xaa is any amino acid, preferably Asp or Ala
<220> FEATURE:
<221> NAME/KEY: VARIANT
<222> LOCATION: (19)..(19)
<223> OTHER INFORMATION: Xaa may be present or absent. If present, Xaa
      is any amino acid, preferably Ser

<400> SEQUENCE: 86

Met Ala Ser Gly Xaa Xaa Xaa Xaa Val Val Thr Cys Xaa Xaa Val Ala
1               5                   10                  15

Lys Asn Xaa Ser Val Ala Asp Arg Val
            20                  25

<210> SEQ ID NO 87
<211> LENGTH: 12
<212> TYPE: PRT
<213> ORGANISM: Artificial sequence
<220> FEATURE:
<223> OTHER INFORMATION: Synthetic sequence: CYP78A6-clade polypeptide
      amino acid sequence motif

<400> SEQUENCE: 87

Val Gly Tyr Asp Gly Thr Asn Trp Thr Asp His Trp
```

```
<210> SEQ ID NO 88
<211> LENGTH: 10
<212> TYPE: PRT
<213> ORGANISM: Artificial sequence
<220> FEATURE:
<223> OTHER INFORMATION: Synthetic sequence: CYP78A6-clade polypeptide
      amino acid sequence motif

<400> SEQUENCE: 88

Ala Val Trp Met Arg Gly Thr Asp Val Ala
1               5                   10

<210> SEQ ID NO 89
<211> LENGTH: 13
<212> TYPE: PRT
<213> ORGANISM: Artificial sequence
<220> FEATURE:
<223> OTHER INFORMATION: Synthetic sequence: CYP78A6-clade polypeptide
      amino acid sequence motif
<220> FEATURE:
<221> NAME/KEY: VARIANT
<222> LOCATION: (10)..(10)
<223> OTHER INFORMATION: Xaa is any amino acid, preferably Ala or Ser

<400> SEQUENCE: 89

Lys Val Arg His Gly Ser Trp Ala Arg Xaa Thr Asp Thr
1               5                   10

<210> SEQ ID NO 90
<211> LENGTH: 49
<212> TYPE: PRT
<213> ORGANISM: Artificial sequence
<220> FEATURE:
<223> OTHER INFORMATION: Synthetic sequence: CYP78A6-clade polypeptide
      amino acid sequence motif
<220> FEATURE:
<221> NAME/KEY: VARIANT
<222> LOCATION: (13)..(13)
<223> OTHER INFORMATION: Xaa is any amino acid, preferably Ala or Val
<220> FEATURE:
<221> NAME/KEY: VARIANT
<222> LOCATION: (14)..(14)
<223> OTHER INFORMATION: Xaa may be present or absent. If present, Xaa
      is any amino acid, preferably Ser
<220> FEATURE:
<221> NAME/KEY: VARIANT
<222> LOCATION: (15)..(15)
<223> OTHER INFORMATION: Xaa is any amino acid, preferably His or Arg
<220> FEATURE:
<221> NAME/KEY: VARIANT
<222> LOCATION: (20)..(20)
<223> OTHER INFORMATION: Xaa is any amino acid, preferably Val, Asn or
      Asp
<220> FEATURE:
<221> NAME/KEY: VARIANT
<222> LOCATION: (21)..(21)
<223> OTHER INFORMATION: Xaa may be present or absent. If present, Xaa
      is any amino acid, preferably Asp
<220> FEATURE:
<221> NAME/KEY: VARIANT
<222> LOCATION: (28)..(28)
<223> OTHER INFORMATION: Xaa is any amino acid, preferably Ala or Val
<220> FEATURE:
<221> NAME/KEY: VARIANT
<222> LOCATION: (39)..(39)
<223> OTHER INFORMATION: Xaa is any amino acid, preferably Arg or Lys
<220> FEATURE:
<221> NAME/KEY: VARIANT
<222> LOCATION: (41)..(41)
<223> OTHER INFORMATION: Xaa may be present or absent. If present, Xaa
      is any amino acid, preferably Val
```

```
<400> SEQUENCE: 90

Val Ala Gly Thr Thr Ala Met Val Asn Met Trp Ala Xaa Xaa Xaa Asp
1               5                   10                  15

His Val Trp Xaa Xaa Lys Arg Val Ala Lys Gly Xaa Ser Val Gly Ser
                20                  25                  30

Asp Arg Ala Gly Ser Gly Xaa Arg Xaa Cys Gly Lys Asn Gly Thr Thr
            35                  40                  45

Val

<210> SEQ ID NO 91
<211> LENGTH: 17
<212> TYPE: PRT
<213> ORGANISM: Arabidopsis thaliana

<400> SEQUENCE: 91

Gly Gly Ala Trp Gly Lys Tyr Gly Arg Ser Gly Ser Tyr Lys Thr Gly
1               5                   10                  15

Asn

<210> SEQ ID NO 92
<211> LENGTH: 16
<212> TYPE: PRT
<213> ORGANISM: Arabidopsis thaliana

<400> SEQUENCE: 92

Val Gly Lys Gly Val Gly Ser Met Ser Met Ser Ser Thr Ala His Arg
1               5                   10                  15

<210> SEQ ID NO 93
<211> LENGTH: 22
<212> TYPE: PRT
<213> ORGANISM: Arabidopsis thaliana

<400> SEQUENCE: 93

Met Ala Ser Gly Thr Arg Val Val Thr Cys Asn Asp Val Ala Lys Asn
1               5                   10                  15

Ser Val Ala Asp Arg Val
            20

<210> SEQ ID NO 94
<211> LENGTH: 13
<212> TYPE: PRT
<213> ORGANISM: Arabidopsis thaliana

<400> SEQUENCE: 94

Lys Val Arg His Gly Ser Trp Ala Arg Ala Thr Asp Thr
1               5                   10

<210> SEQ ID NO 95
<211> LENGTH: 48
<212> TYPE: PRT
<213> ORGANISM: Arabidopsis thaliana

<400> SEQUENCE: 95

Val Ala Gly Thr Thr Ala Met Val Asn Met Trp Ala Val Ser His Asp
1               5                   10                  15

His Val Trp Val Asp Lys Arg Val Ala Lys Gly Val Ser Val Gly Ser
                20                  25                  30

Asp Arg Ala Gly Ser Gly Arg Arg Cys Gly Lys Asn Gly Thr Thr Val
            35                  40                  45
```

<210> SEQ ID NO 96
<211> LENGTH: 1229
<212> TYPE: DNA
<213> ORGANISM: Arabidopsis thaliana

<400> SEQUENCE: 96

```
acactctttc ctctctcttt cttctctctt tcttttctct ctctctcctc tgctcctccg      60
tctctcgtct acagtgccct ccgcatcacc tttttccttg tcctatgaat ttggtcgaaa     120
tgcccttctc ctcctcctcc ttccactaat ctcaaaagat atatccttcg agactctccc     180
ttgccgtctc caattgccac tcaccgctcc aactctcttc gaattagctg aaatgaatgg     240
agataataga ccagtggaag atgctcatta cacggagaca ggtttccctt atgctgctac     300
tggaagttac atggactttt atggtggtgc ggctcagggg cctcttaact acgatcatgc     360
cgcaactatg catcctcagg acaatctgta ctggaccatg aataccaatg catacaagtt     420
tgggttttca ggatcagata atgcttcttt ctatggttca tatgacatga acgatcattt     480
atcgaggatg tccataggga gaacaaattg ggactatcat cccatggtga acgttgctga     540
tgatcctgaa aacacagttg cacgttccgt ccaaatcgga gacacagatg agcactctga     600
agctgaagaa tgcattgcaa atgagcatga tcccgacagt cctcaggtat cctggcaaga     660
tgacattgat cctgatacaa tgacctatga ggaattagta gagctggggg aagcagtagg     720
aacagaaagc agggggttgt ctcaggaact catagaaacg cttcccacta aaagtataa     780
gtttgggagc atcttctcca ggaaaagagc tggggagagg tgtgtgatat gccagctcaa     840
gtacaagata ggggagaggc aaatgaatct gccgtgcaag catgtgtatc attctgaatg     900
catttccaaa tggctaagca tcaacaaggt ttgcccggtg tgtaacagcg aggtctttgg     960
ggagcccagc attcattgat cggcacaagg ggctcctcct cttcttttct ttttggcttt    1020
ttatatcgag gctcatcaag taattgtttt agtgtagtga aaaccccaaa aaatagtcta    1080
aaagatgtcc acactatact ctctcatgtt cagtccttct ctgtacatgt aattttttctt   1140
ctagttccat tttcgcttgt gtgtgcttta agtttaacag tcactcgtat tgtatactaa    1200
atgctaagtc aaaaacgctg aatccatat                                      1229
```

<210> SEQ ID NO 97
<211> LENGTH: 248
<212> TYPE: PRT
<213> ORGANISM: Arabidopsis thaliana

<400> SEQUENCE: 97

```
Met Asn Gly Asp Asn Arg Pro Val Glu Asp Ala His Tyr Thr Glu Thr
1               5                   10                  15

Gly Phe Pro Tyr Ala Ala Thr Gly Ser Tyr Met Asp Phe Tyr Gly Gly
                20                  25                  30

Ala Ala Gln Gly Pro Leu Asn Tyr Asp His Ala Ala Thr Met His Pro
            35                  40                  45

Gln Asp Asn Leu Tyr Trp Thr Met Asn Thr Asn Ala Tyr Lys Phe Gly
        50                  55                  60

Phe Ser Gly Ser Asp Asn Ala Ser Phe Tyr Gly Ser Tyr Asp Met Asn
65                  70                  75                  80

Asp His Leu Ser Arg Met Ser Ile Gly Arg Thr Asn Trp Asp Tyr His
                85                  90                  95

Pro Met Val Asn Val Ala Asp Asp Pro Glu Asn Thr Val Ala Arg Ser
            100                 105                 110
```

Val Gln Ile Gly Asp Thr Asp Glu His Ser Glu Ala Glu Glu Cys Ile
            115                 120                 125

Ala Asn Glu His Asp Pro Asp Ser Pro Gln Val Ser Trp Gln Asp Asp
    130                 135                 140

Ile Asp Pro Asp Thr Met Thr Tyr Glu Glu Leu Val Glu Leu Gly Glu
145                 150                 155                 160

Ala Val Gly Thr Glu Ser Arg Gly Leu Ser Gln Glu Leu Ile Glu Thr
                165                 170                 175

Leu Pro Thr Lys Lys Tyr Lys Phe Gly Ser Ile Phe Ser Arg Lys Arg
            180                 185                 190

Ala Gly Glu Arg Cys Val Ile Cys Gln Leu Lys Tyr Lys Ile Gly Glu
        195                 200                 205

Arg Gln Met Asn Leu Pro Cys Lys His Val Tyr His Ser Glu Cys Ile
    210                 215                 220

Ser Lys Trp Leu Ser Ile Asn Lys Val Cys Pro Val Cys Asn Ser Glu
225                 230                 235                 240

Val Phe Gly Glu Pro Ser Ile His
                245

<210> SEQ ID NO 98
<211> LENGTH: 22
<212> TYPE: DNA
<213> ORGANISM: Artificial sequence
<220> FEATURE:
<223> OTHER INFORMATION: Synthetic sequence: Primer for verifying T-DNA

<400> SEQUENCE: 98
ggtctaagat ttctctcgtg tc                                          22

<210> SEQ ID NO 99
<211> LENGTH: 22
<212> TYPE: DNA
<213> ORGANISM: Artificial sequence
<220> FEATURE:
<223> OTHER INFORMATION: Synthetic sequence: Primer for verifying T-DNA

<400> SEQUENCE: 99
cgtacgtctt ctattactcc ac                                          22

<210> SEQ ID NO 100
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 100
aactccaaag gatcaaccca c                                           21

<210> SEQ ID NO 101
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 101
ccggttaaag aatcggctta c                                           21

<210> SEQ ID NO 102
<211> LENGTH: 21
<212> TYPE: DNA

```
<213> ORGANISM: Artificial sequence
<220> FEATURE:
<223> OTHER INFORMATION: Synthetic sequence: Primer for verifying T-DNA

<400> SEQUENCE: 102
gacttgcaaa gatcgttcac c                                              21

<210> SEQ ID NO 103
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 103
actcaatgtg acgtgttgtg g                                              21

<210> SEQ ID NO 104
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 104
tttgatcgag tggattcttg c                                              21

<210> SEQ ID NO 105
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 105
atatttgctt gtaatcgggg c                                              21

<210> SEQ ID NO 106
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 106
taaaaccaaa cgacaccgtt c                                              21

<210> SEQ ID NO 107
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 107
tccaagtttg ttgacgattc c                                              21

<210> SEQ ID NO 108
<211> LENGTH: 24
<212> TYPE: DNA
<213> ORGANISM: Artificial sequence
<220> FEATURE:
<223> OTHER INFORMATION: Synthetic sequence: Primer for verifying T-DNA

<400> SEQUENCE: 108
cgagtatcaa tggaaactta accg                                           24
```

<210> SEQ ID NO 109
<211> LENGTH: 20
<212> TYPE: DNA
<213> ORGANISM: Artificial sequence
<220> FEATURE:
<223> OTHER INFORMATION: Synthetic sequence: Primer for verifying T-DNA

<400> SEQUENCE: 109
aacggagagt ggcttgagat                                            20

<210> SEQ ID NO 110
<211> LENGTH: 20
<212> TYPE: DNA
<213> ORGANISM: Artificial sequence
<220> FEATURE:
<223> OTHER INFORMATION: Synthetic sequence: Primer for verifying T-DNA

<400> SEQUENCE: 110
tggcccttat ggtttctgca                                            20

<210> SEQ ID NO 111
<211> LENGTH: 15
<212> TYPE: DNA
<213> ORGANISM: Artificial sequence
<220> FEATURE:
<223> OTHER INFORMATION: Synthetic sequence: Primer for verifying T-DNA
<220> FEATURE:
<221> NAME/KEY: misc_feature
<222> LOCATION: (1)..(1)
<223> OTHER INFORMATION: n is a or g or c or t

<400> SEQUENCE: 111
ntcgastwts gwgtt                                                 15

<210> SEQ ID NO 112
<211> LENGTH: 22
<212> TYPE: DNA
<213> ORGANISM: Artificial sequence
<220> FEATURE:
<223> OTHER INFORMATION: Synthetic sequence: Primer for verifying T-DNA

<400> SEQUENCE: 112
tggttcacgt agtgggccat cg                                         22

<210> SEQ ID NO 113
<211> LENGTH: 34
<212> TYPE: DNA
<213> ORGANISM: Artificial sequence
<220> FEATURE:
<223> OTHER INFORMATION: Synthetic sequence: Primer for verifying T-DNA

<400> SEQUENCE: 113
gcttcctatt atatcttccc aaattaccaa taca                            34

<210> SEQ ID NO 114
<211> LENGTH: 30
<212> TYPE: DNA
<213> ORGANISM: Artificial sequence
<220> FEATURE:
<223> OTHER INFORMATION: Synthetic sequence: Primer for constructs

<400> SEQUENCE: 114
ctgcagatgg ctacgaaact cgaaagctcc                                 30

<210> SEQ ID NO 115

```
<211> LENGTH: 30
<212> TYPE: DNA
<213> ORGANISM: Artificial sequence
<220> FEATURE:
<223> OTHER INFORMATION: Synthetic sequence: Primer for constructs

<400> SEQUENCE: 115
ctgcagttaa ctgcgcctac ggcgcaattt                                    30

<210> SEQ ID NO 116
<211> LENGTH: 24
<212> TYPE: DNA
<213> ORGANISM: Artificial sequence
<220> FEATURE:
<223> OTHER INFORMATION: Synthetic sequence: Primer for constructs

<400> SEQUENCE: 116
gagctctgtc tcgtggataa gtag                                          24

<210> SEQ ID NO 117
<211> LENGTH: 27
<212> TYPE: DNA
<213> ORGANISM: Artificial sequence
<220> FEATURE:
<223> OTHER INFORMATION: Synthetic sequence: Primer for constructs

<400> SEQUENCE: 117
ccatggggcg gatcaaagca aagtaag                                       27

<210> SEQ ID NO 118
<211> LENGTH: 18
<212> TYPE: DNA
<213> ORGANISM: Artificial sequence
<220> FEATURE:
<223> OTHER INFORMATION: Synthetic sequence: Primer for RT-PCR

<400> SEQUENCE: 118
accaaccttg ccttctcc                                                 18

<210> SEQ ID NO 119
<211> LENGTH: 19
<212> TYPE: DNA
<213> ORGANISM: Artificial sequence
<220> FEATURE:
<223> OTHER INFORMATION: Synthetic sequence: Primer for RT-PCR

<400> SEQUENCE: 119
cgtctcggct cttctgatt                                                19

<210> SEQ ID NO 120
<211> LENGTH: 17
<212> TYPE: DNA
<213> ORGANISM: Artificial sequence
<220> FEATURE:
<223> OTHER INFORMATION: Synthetic sequence: Primer for RT-PCR

<400> SEQUENCE: 120
acaacgagca gcaacca                                                  17

<210> SEQ ID NO 121
<211> LENGTH: 19
<212> TYPE: DNA
<213> ORGANISM: Artificial sequence
<220> FEATURE:
<223> OTHER INFORMATION: Synthetic sequence: Primer for RT-PCR

<400> SEQUENCE: 121
```

-continued tcttcaaccg gaacttcat                                              19

<210> SEQ ID NO 122
<211> LENGTH: 18
<212> TYPE: DNA
<213> ORGANISM: Artificial sequence
<220> FEATURE:
<223> OTHER INFORMATION: Synthetic sequence: Primer for RT-PCR

<400> SEQUENCE: 122
atccttcctg atatcgac                                               18

<210> SEQ ID NO 123
<211> LENGTH: 18
<212> TYPE: DNA
<213> ORGANISM: Artificial sequence
<220> FEATURE:
<223> OTHER INFORMATION: Synthetic sequence: Primer for RT-PCR

<400> SEQUENCE: 123
gagaagatga ctcagatc                                               18

<210> SEQ ID NO 124
<211> LENGTH: 20
<212> TYPE: DNA
<213> ORGANISM: Artificial sequence
<220> FEATURE:
<223> OTHER INFORMATION: Synthetic sequence: Primer for quantitative
      real-time RT-PCR

<400> SEQUENCE: 124
ccggttaaag aatcggctta                                             20

<210> SEQ ID NO 125
<211> LENGTH: 20
<212> TYPE: DNA
<213> ORGANISM: Artificial sequence
<220> FEATURE:
<223> OTHER INFORMATION: Synthetic sequence: Primer for quantitative
      real-time RT-PCR

<400> SEQUENCE: 125
ttgagatcac tcgtcgttgc                                             20

<210> SEQ ID NO 126
<211> LENGTH: 20
<212> TYPE: DNA
<213> ORGANISM: Artificial sequence
<220> FEATURE:
<223> OTHER INFORMATION: Synthetic sequence: Primer for quantitative
      real-time RT-PCR

<400> SEQUENCE: 126
gaaatcacag cacttgcacc                                             20

<210> SEQ ID NO 127
<211> LENGTH: 20
<212> TYPE: DNA
<213> ORGANISM: Artificial sequence
<220> FEATURE:
<223> OTHER INFORMATION: Synthetic sequence: Primer for quantitative
      real-time RT-PCR

<400> SEQUENCE: 127
aagcctttga tcttgagagc                                             20

```
<210> SEQ ID NO 128
<211> LENGTH: 22
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 128
aaagaagctc atatgagaat ta                                              22

<210> SEQ ID NO 129
<211> LENGTH: 23
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 129
tggtgtaaat ataaattgaa act                                             23

<210> SEQ ID NO 130
<211> LENGTH: 24
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 130
ttagtgtatg ataaggctaa ggct                                            24

<210> SEQ ID NO 131
<211> LENGTH: 22
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 131 gtattaacttt tctttgtga ca                                              22
```

METHODS OF CONTROLLING SEED SIZE IN PLANTS

CROSS-REFERENCE TO RELATED APPLICATIONS

This is a divisional application of U.S. Ser. No. 14/372,582 filed Jul. 16, 2014, which is a National Phase application claiming priority to PCT/GB2013/050072 filed Jan. 15, 2013, which claims priority to GB 1202258.8 filed Feb. 9, 2012 and U.S. Provisional Application Ser. No. 61/588,792 filed Jan. 20, 2012, all of which are herein incorporated by reference in their entirety.

FIELD OF INVENTION

This invention relates to the control of the size of the seeds which are produced by plants.

BACKGROUND OF THE INVENTIONS

Seed size is a key determinant of evolutionary fitness in plants and is also an important agronomic trait during crop domestication (Orsi and Tanksley, 2009). Several studies suggest that seedlings of large-seeded plants are better able to tolerate many of the stresses encountered during seedling establishment, whereas small-seeded plants are considered to have superior colonization abilities because they produce large numbers of seeds (Westoby et al., 2002; Moles et al., 2005). At the same time, seed size is negatively associated with the number of seeds produced by a plant due to the limited resources of the mother plant (Harper et al., 1970). Scientific interest in seed size relates not only to its importance in plant fitness, but also to crop domestication. Crops domesticated for consumption of their seeds (e.g. rice and wheat) often produce seeds significantly larger than their wild ancestors (Fan et al., 2006; Song et al., 2007; Gegas et al., 2010).

A seed consists of three major components; the embryo, the endosperm and the seed coat, that originate from different cells of the ovule and possess different complements of maternal and paternal genomes. In angiosperms, seed development involves a double fertilization process in which one sperm nucleus fuses with the egg to produce the diploid embryo, while the other sperm nucleus fuses with two polar nuclei to form the triploid endosperm (Lopes and Larkins, 1993). The seed coat differentiates after fertilization from maternally derived integuments. The embryo is surrounded by the endosperm, which, in turn, is enclosed within the maternal seed coat. Therefore, the size of a seed is determined by the coordinated growth of maternal sporophytic and zygotic tissues.

The size of seeds is influenced by a variety of cellular processes. Seed size is known to be influenced by parent-of-origin effects. The cross between a diploid female parent and tetraploid male parent produces larger $F_1$ seeds, whereas the reciprocal cross generates smaller $F_1$ seeds, suggesting that maternal or paternal excess of genome has a dramatic effect on seed size (Scott et al., 1998). Similar to interploidy crosses, crosses between wild type and met1 mutant with hypomethylated genomes show that larger $F_1$ seeds are generated when the maternal parent is met1, while smaller $F_1$ seeds are produced when the paternal parent is met1 (Xiao et al., 2006), suggesting that parent-of-origin effects may involve DNA methylation. In addition, the size of seeds is affected by the maternal and/or zygotic tissues. Several factors that influence seed size by the zygotic tissues have been recently identified in Arabidopsis. haiku (iku) and miniseed3 (mini3) mutants form small seeds due to the reduced growth and early cellularization of the endosperm (Garcia et al., 2003; Luo et al., 2005). IKU1, IKU2 and MINI3 function in the same pathway to promote endosperm growth in Arabidopsis (Garcia et al., 2003; Luo et al., 2005; Wang et al., 2010). SHORT HYPOCOTYL UNDER BLUE1 (SHB1) associates with both MINI3 and IKU2 promoters in vivo and may act with other proteins that bind to MINI3 and IKU2 promoters to promote endosperm growth in the early phase of seed development (Zhou et al., 2009). Seed size is also influenced by maternal tissues. Several factors that act in maternal tissues to influence seed size have been isolated. Arabidopsis TRANSPARENT TESTA GLABRA 2 (TTG2) promotes seed growth by increasing cell expansion in the integuments (Garcia et al., 2005; Ohto et al., 2009). APETALA2 (AP2) may restrict seed growth by limiting cell expansion in the integuments (Jofuku et al., 2005; Ohto et al., 2005; Ohto et al., 2009). By contrast, AUXIN RESPONSE FACTOR 2 (ARF2) and the predicted ubiquitin receptor CYP78A61 limit seed size by restricting cell proliferation in the integuments (Schruff et al., 2006; Li et al., 2008). However, CYP78A5/KLU promotes seed growth by increasing cell proliferation in the integuments of ovules (Adamski et al., 2009). Therefore, the integument or seed coat plays a key role in maternal control of seed size. In addition, many quantitative trait loci (QTLs) for seed size have been mapped in Arabidopsis and crops (Alonso-Blanco et al., 1999; Li et al., 2004; Fan et al., 2006; Song et al., 2007; Shomura et al., 2008; Weng et al., 2008). Three grain size QTLs have been recently cloned in rice, including GS3, GW2 and qSW5/GW5 (Fan et al., 2006; Song et al., 2007; Shomura et al., 2008; Weng et al., 2008). However, it is not clear whether these three factors act in maternal and/or zygotic tissues in rice.

Despite the importance of seed size, relatively little is known about the genetic and molecular mechanisms that control seed size.

Identification of factors that control the final size of seeds will not only advance understanding of the mechanisms of size control in plants, but may also have substantial practical applications for example in improving crop yield.

SUMMARY OF INVENTION

The present inventors have identified and characterized a genetic factor which alters seed size in plants. This may be useful, for example, in modulating seed size and improving yields in crop plants.

An aspect of the invention provides a method of modulating seed size in a plant which comprises;
  altering the expression of a CYP78A polypeptide within cells of said plant.

Another aspect of the invention provides a method of producing a plant with an altered seed size comprising:
  incorporating a heterologous nucleic acid which alters the expression of a CYP78A polypeptide into a plant cell by means of transformation, and;
  regenerating the plant from one or more transformed cells.

Other aspects of the invention relate to plant cells with altered expression of a CYP78A polypeptide relative to controls, for example plant cells produced by a method described above; plants comprising such cells, and the seeds and progeny of such plants.

The CYP78A polypeptide may be a CYP78A6 polypeptide.

The expression of two or more CYP78A polypeptides may be altered in the plant cells.

The expression of one or more other growth factors, such as DA or BB may additionally be altered in the plant cells.

BRIEF DESCRIPTION OF DRAWINGS

FIG. 1(A) shows seeds from wild-type, da1-1 and eod3-1D da1-1 plants (from left to right). FIG. 1(B) shows mature embryos of wild type, da1-1 and eod3-1D da1-1 (from left to right). FIG. 1(C) shows 10-d-old-seedlings of wild type, da1-1 and eod3-1D da1-1 (from left to right). FIG. 1(D) shows projective area of wild-type, da1-1 and eod3-1D da1-1 seeds. FIG. 1(E) shows seed weight of wild type, da1-1 and eod3-1D da1-1. FIG. 1(F) shows cotyledon area of 10-d-old wild-type, da1-1 and eod3-1D da1-1 seedlings. Values (D-F) are given as mean±SE relative to the respective wild-type values, set at 100%. Bars: A, B, 0.5 mm; C, 5 mm.

Table 1 shows phenotypes of wild-type, eod3-ko1, cyp78a9-ko1, eod3-ko1 cyp78a9-ko1 and eod3-1D plants.

Table 2 shows developmental stages of embryogenesis.

Table 3 shows primers.

DETAILED DESCRIPTION OF EMBODIMENTS OF THE INVENTION

In various aspects, the invention provides methods which relate to the modulation of CYP78A expression in plant cells. This modulation may be useful in altering, for example increasing or decreasing, seed size in plants.

CYP78A polypeptides are a sub-family of cytochrome p450 (CYP) dependent monooxygenases which are found only in plants. CYP78A polypeptides may be defined by phylogenetic analysis on the basis of overall identity and sequence conservation within domains (Chapple Annu. Rev. Plant Physiol. Plant Mol. Biol. (1998) 49:311-43)

Figure 18:
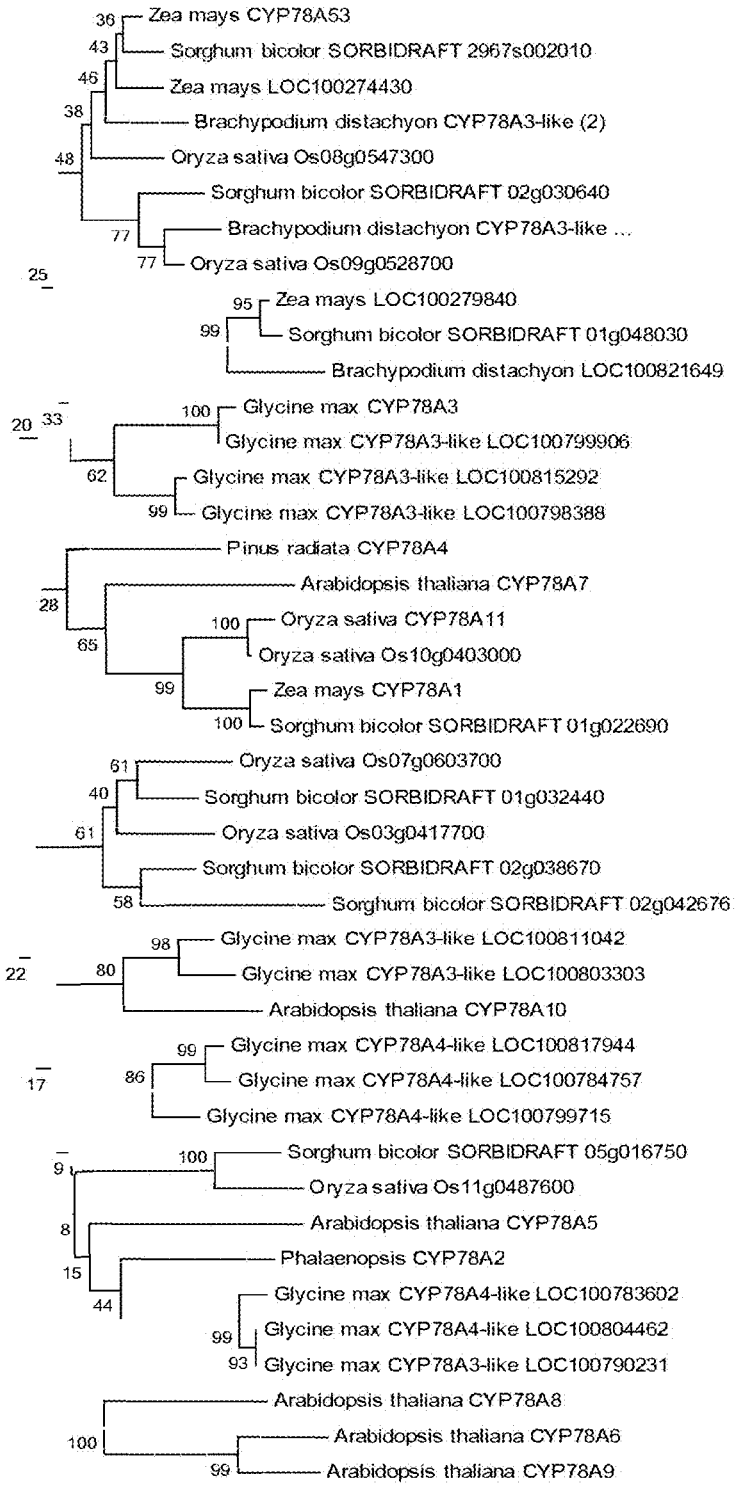
FIG. 18 shows phylogenic analysis of *Arabidopsis* CYP78A6 and its orthologues.

A CYP78A polypeptide may comprise an amino acid sequence which is shown in FIG. 18 or an amino acid sequence which is selected from the group consisting of SEQ ID NOS: 42 to 83 or an amino acid sequence which is a variant or fragment of one of these sequences which retains CYP78A activity.

Other CYP78A polypeptide sequences which include the characteristic features set out above may be identified using standard sequence analysis tools.

Figure 3:
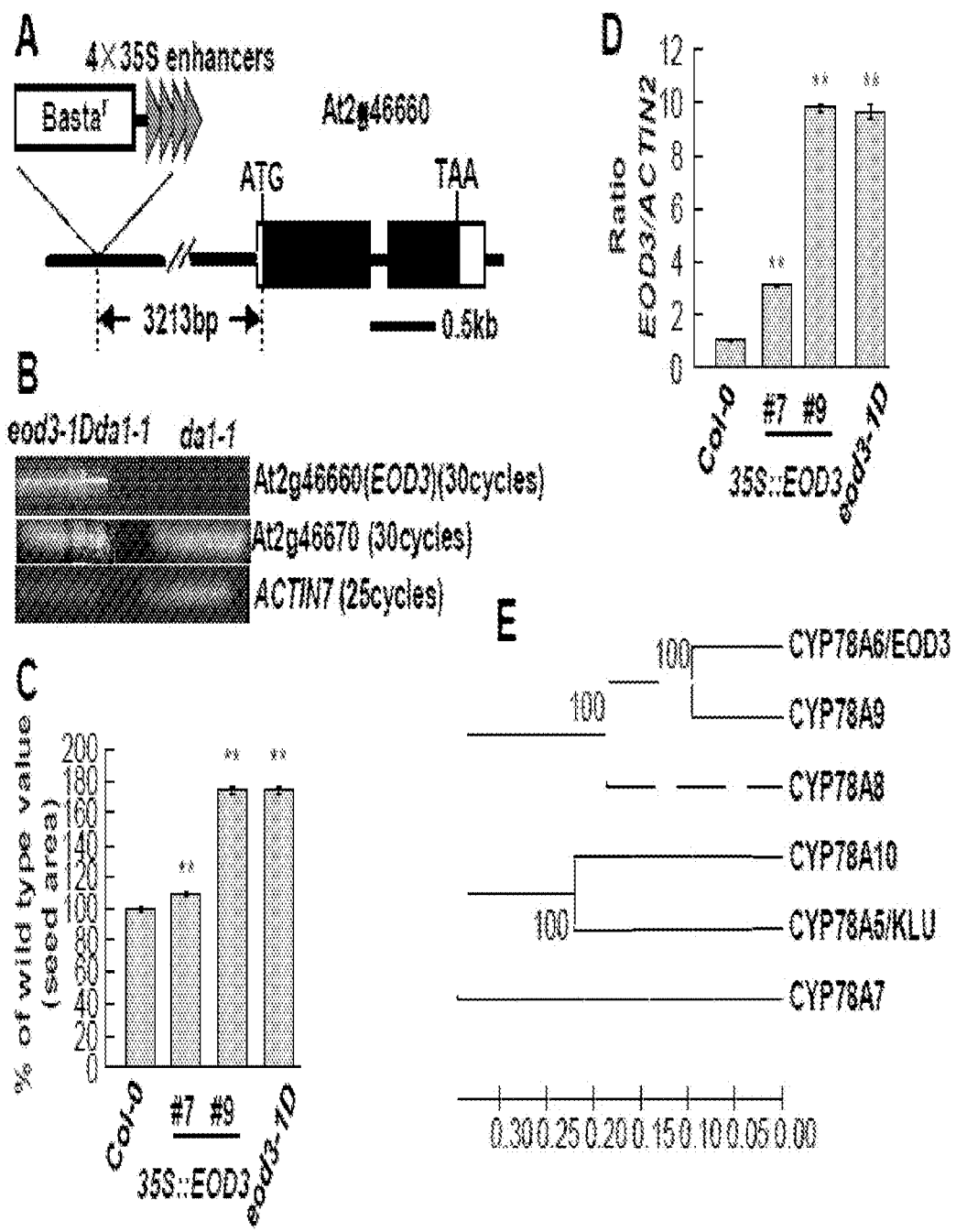
FIG. 3 shows the cloning of the EOD3 gene. 3(A) shows thes tructure of T-DNA insertion in the eod3-1D mutant. 3(B) shows expression levels of At2g46660 (EOD3) and At2g46670 in da1-1 and eod3-1D da1-1 seedlings. 3(C) shows projective area of wild-type, 35S::EOD3#7, 35S::EOD3#9 and eod3-1D seeds. 3(D) shows expression levels of EOD3 in wild-type, 35S::EOD3#7, 35S::EOD3#9 and eod3-1D seedlings. 3(E) shows phylogenetic tree of the CYP78A family members in *Arabidopsis thaliana*. Values (C and D) are given as mean±SE relative to the wild-type value, set at 100%. **, P<0.01 compared with the wild type (Student's t-test).

In some preferred embodiments, the CYP78A polypeptide may be a member of the phylogenetic grouping of CYP78A polypeptides which comprises CYP78A6, CYP78A8 and CYP78A9 and excludes CYP78A7, CYP78A5 and CYP78A10, as shown in FIG. 3E (i.e. a CYP78A6-clade polypeptide).

For example, a CYP78A6-clade polypeptide may comprise 1, 2, 3, 4, 5, 6 or all 7 of the amino acid sequence motifs of SEQ ID NOS: 84 to 90;

GGAWGKYX$_1$R (SEQ ID NO: 84), wherein X$_1$ is any amino acid, preferably G, H or T, most preferably G.

X$_2$G X$_3$GVGSMSX$_4$ X$_5$S X$_6$X$_7$AHR (SEQ ID NO: 85), wherein X$_2$ is any amino acid, preferably V or N, most preferably V; wherein X$_3$ is any amino acid, preferably K or R, most preferably K; wherein X$_4$ is absent or any amino acid, preferably absent or R, most preferably absent; wherein X$_5$ is any amino acid, preferably M or S, most preferably M; wherein X$_6$ is any amino acid, preferably S, N or H, most preferably S; and wherein X$_7$ is any amino acid, preferably T or V, most preferably T.

MASGX$_8$X$_9$X$_{10}$X$_{11}$VVTCX$_{12}$X$_{13}$VAKNX$_{14}$SVADRV (SEQ ID NO: 86), wherein X$_8$ is any amino acid, preferably T or D, most preferably T; wherein X$_9$ is any amino acid, preferably T or R, most preferably R; wherein X$_{10}$ is absent or any amino acid, preferably absent or K, most preferably absent; wherein X$_{11}$ is absent or any amino acid, preferably absent or V, most preferably absent; wherein X$_{12}$ is any amino acid, preferably N or H, most preferably N; wherein X$_{13}$ is any amino acid, preferably D or A, most preferably D; wherein X$_{14}$ is absent or any amino acid, preferably absent or S, most preferably absent.

VGYDGTNWTDHW (SEQ ID NO: 87)

AVWMRGTDVA (SEQ ID NO: 88)

KVRHGSWARX$_{15}$TDT (SEQ ID NO: 89), wherein X$_{15}$ is any amino acid, preferably A or S, most preferably A.

VAGTTAMVNMWAX$_{16}$X$_{17}$X$_{18}$DHVWX$_{19}$X$_{20}$ KRVAKGX$_{21}$SVGSDRAGSGX$_{22}$RX$_{23}$CG KNGTTV (SEQ ID NO: 90); wherein independently, X$_{16}$ is any amino acid, preferably A or V, most preferably V; X$_{17}$ is absent or any amino acid, preferably absent or S, most preferably S; X$_{18}$ is any amino acid, preferably H or R, most preferably H; X$_{19}$ is any amino acid, preferably V, N or D, most preferably V; X$_{20}$ is absent or any amino acid, preferably absent or D, most preferably D; X$_{21}$ is any amino acid, preferably A or V, most preferably V; X$_{22}$ is any amino acid, preferably R or K, most preferably R; and X$_{23}$ is absent or any amino acid, preferably absent or V, most preferably absent.

For example, a CYP78A6-clade polypeptide may comprise SEQ NO:84 in combination with any 1, 2, 3, 4, 5 or all 6 of SEQ ID NOS: 85 to 90; a CYP78A6-clade polypeptide may comprise SEQ NO:85 in combination with any 1, 2, 3, 4, 5 or all 6 of SEQ ID NOS: 84 and 86 to 90; a CYP78A6-clade polypeptide may comprise SEQ NO:86 in combination with any 1, 2, 3, 4, 5 or all 6 of SEQ ID NOS: 84, 85 and 87 to 90; a CYP78A6-clade polypeptide may comprise SEQ NO:87 in combination with any 1, 2, 3, 4, 5 or all 6 of SEQ ID NOS: 84 to 86 and 88 to 90; a CYP78A6-clade polypeptide may comprise SEQ NO:88 in combination with any 1, 2, 3, 4, 5 or all 6 of SEQ ID NOS: 84 to 87, 89 or 90; a CYP78A6-clade polypeptide may comprise SEQ NO:89 in combination with any 1, 2, 3, 4, 5 or all 6 of SEQ ID NOS: 84 to 88 and 90; or a CYP78A6-clade polypeptide may comprise SEQ NO:90 in combination with any 1, 2, 3, 4, 5 or all 6 of SEQ ID NOS: 84 to 89.

In some preferred embodiments, a CYP78A6-clade polypeptide may comprise an amino acid sequence selected from the group consisting of SEQ ID NOS:42 to 44, or may be variant or a fragment of one of these sequences which retains CYP78A activity.

Preferably, the CYP78A6-clade polypeptide is a CYP78A6 polypeptide or a functional homologue thereof, as described herein. A CYP78A6 polypeptide may comprise 1, 2, 3, 4, 5, 6 or all 7 of the amino acid sequence motifs of SEQ ID NOS: 87, 88 and 91 to 95;

```
                              (SEQ ID NO: 91)
GGAWGKYGRSGSYKTGN (SEQ ID NO: 92)
VGKGVGSMSMSSTAHR (SEQ ID NO: 93)
MASGTRVVTCNDVAKNSVADRV (SEQ ID NO: 94)
KVRHGSWARATDT (SEQ ID NO: 95)
VAGTTAMVNMWAVSHDHVWVDKRVAKGVSVGSDRAGSGRRCGKNGTTV.
```

For example, a CYP78A6 polypeptide may comprise the amino acid sequence of *A. thaliana* CYP78A6 (At2g46660) (SEQ ID NO: 42) or may be a fragment or variant of this sequence which retains CYP78A activity. Other CYP78A6 polypeptides may comprise the amino acid sequence of any one of SEQ ID NOS: 42 to 83 or may be a fragment or variant of the sequence which retains CYP78A activity.

A CYP78A polypeptide which is a variant of a reference CYP78A sequence, such as any one of SEQ ID NOS: 42 to 83, preferably SEQ ID NOS: 42 to 44, most preferably SEQ ID NO:42, may comprise an amino acid sequence having at least 20%, at least 30%, at least 40%, at least 50%, at least 55%, at least 60%, at least 70%, at least 80%, at least 90%, at least 95%, or at least 98% sequence identity to the reference sequence.

Particular amino acid sequence variants may differ from the reference CYP78A sequence, such as any one of SEQ ID NOS: 42 to 83, by insertion, addition, substitution or deletion of 1 amino acid, 2, 3, 4, 5-10, 10-20 20-30, 30-50, or more than 50 amino acids.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4.

Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used.

Sequence comparison may be made over the full-length of the relevant sequence described herein.

A CYP78A polypeptide which is a fragment of a reference CYP78A sequence, such as any one of SEQ ID NOS: 42 to 83, may consist of fewer amino acid residues than the full-length sequence. A CYP78A polypeptide fragment retains CYP78A activity and may, for example, comprise 100 or more, 150 or more, 200 or more or 250 or more amino acids.

Methods of increasing seed size in plants as described herein may comprise increasing expression of a CYP78A polypeptide in one or more cells of the plant relative to controls.

CYP78A expression may be increased by mutation. For example, a nucleic acid sequence which represses expression of a CYP78A coding sequence may be mutated. Suitable mutation methods, such as insertional activation using a heterologous nucleic acid, are well known in the art.

Alternatively, CYP78A expression may be increased by over-expression of a CYP78A coding sequence. For example, a heterologous nucleic acid encoding the CYP78A polypeptide may be expressed within the cells of a plant or a heterologous nucleic acid which promotes or increases expression of an endogenous CYP78A coding sequence may be inserted into the cells of a plant.

In some preferred embodiments, a nucleic acid encoding a CYP78A polypeptide may comprise the nucleotide sequence of SEQ ID NO: 1 or any one of SEQ ID NOS: 2 to 41 or may be a variant or fragment of this sequence which encodes a polypeptide which retains CYP78A activity.

Other nucleic acid sequences which encode CYP78A polypeptides are available on public databases.

A variant sequence may be a mutant, homologue, or allele of a reference CYP78A nucleotide sequence, such as any one of SEQ ID NOS: 1 to 41, or a reference BB sequence, such as SEQ ID NO: 96 and may differ from the reference CYP78A or BB sequence by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included. A nucleic acid encoding a CYP78A polypeptide may comprise a sequence having at least 20% or at least 30% sequence identity with the reference CYP78A nucleic acid sequence, preferably at least 40%, at least 50%, at least 60%, at least 65%, at least 70%, at least 80%, at least 90%, at least 95% or at least 98%. A nucleic acid encoding a BB polypeptide may comprise a sequence having at least 20% or at least 30% sequence identity with the reference BB nucleic acid sequence, preferably at least 40%, at least 50%, at least 60%, at least 65%, at least 70%, at least 80%, at least 90%, at least 95% or at least 98%. Sequence identity is described above.

A fragment or variant may comprise a sequence which encodes a functional CYP78A polypeptide i.e. a polypeptide which retains one or more functional characteristics of the polypeptide encoded by the wild-type CYP78A gene, for example, cytochrome p450 monooxygenase activity.

A nucleic acid comprising a nucleotide sequence which is a variant of a reference CYP78A6 nucleic acid sequence, such as any one of SEQ ID NOS: 1 to 41, may selectively hybridise under stringent conditions with this nucleic acid sequence or the complement thereof.

Stringent conditions include, e.g. for hybridization of sequences that are about 80 to 90% identical, hybridization overnight at 42° C. in 0.25M Na$_2$HPO$_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na$_2$HPO$_4$, pH 7.2, 6.5% SDS, 10% dextran sulfate and a final wash at 60° C. in 0.1×SSC, 0.1% SDS.

An alternative, which may be particularly appropriate with plant nucleic acid preparations, is a solution of 5×SSPE (final 0.9 M NaCl, 0.05M sodium phosphate, 0.005M EDTA pH 7.7), 5×Denhardt's solution, 0.5% SDS, at 50° C. or 65° C. overnight. Washes may be performed in 0.2×SSC/0.1% SDS at 65° C. or at 50-60° C. in 1×SSC/0.1% SDS, as required.

Nucleic acids as described herein may be wholly or partially synthetic. In particular, they may be recombinant in that nucleic acid sequences which are not found together in nature (do not run contiguously) have been ligated or otherwise combined artificially. Alternatively, they may have been synthesised directly e.g. using an automated synthesiser.

The nucleic acid may of course be double- or single-stranded, cDNA or genomic DNA, or RNA. The nucleic acid may be wholly or partially synthetic, depending on design. Naturally, the skilled person will understand that where the nucleic acid includes RNA, reference to the sequence shown should be construed as reference to the RNA equivalent, with U substituted for T.

Nucleic acid encoding a CYP78A polypeptide may be expressed in the same plant species or variety from which it was originally isolated or in a different plant species or variety (i.e. a heterologous plant).

"Heterologous" indicates that the gene/sequence of nucleotides in question or a sequence regulating the gene/sequence in question, has been introduced into said cells of the plant or an ancestor thereof, using genetic engineering or recombinant means, i.e. by human intervention. Nucleotide sequences which are heterologous to a plant cell may be non-naturally occurring in cells of that type, variety or species (i.e. exogenous or foreign) or may be sequences which are non-naturally occurring in that sub-cellular or genomic environment of the cells or may be sequences which are non-naturally regulated in the cells i.e. operably linked to a non-natural regulatory element. "Isolated" indicates that the isolated molecule (e.g. polypeptide or nucleic acid) exists in an environment which is distinct from the environment in which it occurs in nature. For example, an isolated nucleic acid may be substantially isolated with respect to the genomic environment in which it naturally occurs. An isolated nucleic acid may exist in an environment other than the environment in which it occurs in nature.

Methods of reducing seed size in plants as described herein may comprise reducing or abolishing expression of a CYP78A polypeptide in one or more cells of the plant relative to controls.

CYP78A expression may be reduced or abolished by mutation. For example, nucleic acid sequence encoding a CYP78A polypeptide within cells of said plant may be mutated, for example by insertion of a heterologous nucleic acid, within the plant cells. Alternatively, nucleic acid which regulates the expression of a CYP78A coding sequence within cells of said plant, such as a promoter or enhancer sequence, may be mutated, for example by insertion of a heterologous nucleic acid, within the plant cells.

The expression of CYP78A polypeptide may be reduced or abolished by mutating the nucleic acid sequences in the plant cell which encode the active protein and regenerating a plant from the mutated cell. The nucleic acids may be mutated by insertion or deletion of one or more nucleotides. Techniques for the inactivation or knockout of target genes are well-known in the art.

CYP78A expression may be reduced or abolished by suppression. For example, a heterologous nucleic encoding a suppressor nucleic acid which suppresses expression of a CYP78A polypeptide may be expressed within the plant cells.

The suppression of the expression of target polypeptides in plant cells is well-known in the art. Suitable suppressor nucleic acids may be copies of all or part of the target CYP78A gene inserted in antisense or sense orientation or both relative to the CYP78A gene, to achieve reduction in expression of the CYP78A gene. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of this approach may be found in WO95/34668 (Biosource); Angell & Baulcombe (1997) The EMBO Journal 16, 12:3675-3684; and Voinnet & Baulcombe (1997) Nature 389: pg 553.

In some embodiments, the suppressor nucleic acids may be sense suppressors of expression of active CYP78A protein.

A suitable sense suppressor nucleic acid may be a double stranded RNA (Fire A. et al Nature, Vol 391, (1998)). dsRNA mediated silencing is gene specific and is often termed RNA interference (RNAi). RNAi is a two step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

siRNAs (sometimes called microRNAs) down-regulate gene expression by binding to complementary RNAs and either triggering mRNA elimination (RNAi) or arresting mRNA translation into protein. siRNA may be derived by processing of long double stranded RNAs and when found in nature are typically of exogenous origin. Micro-interfering RNAs (miRNA) are endogenously encoded small noncoding RNAs, derived by processing of short hairpins. Both siRNA and miRNA can inhibit the translation of mRNAs bearing partially complementary target sequences without RNA cleavage and degrade mRNAs bearing fully complementary sequences.

Accordingly, the present invention provides the use of RNAi sequences based on the CYP78A nucleic acid sequence for suppression of the expression of the CYP78A polypeptide. For example, an RNAi sequence may correspond to a fragment of any one of SEQ ID NOS: 1 to 41 or other CYP78A nucleic acid sequence referred to above, or a variant thereof.

siRNA molecules are typically double stranded and, in order to optimise the effectiveness of RNA mediated down-regulation of the function of a target gene, it is preferred that the length and sequence of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA sequences which are transcribed from DNA, but are not translated into protein. A DNA sequence that codes for a miRNA is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed on John et al, PLoS Biology, 11(2), 1862-1879, 2004.

Typically, the RNA molecules intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using one of the numerous publically available on-line siRNA finders, such as GenScript siRNA Target Finder, GenScript USA Inc. siRNA and miRNA sequences can be synthetically produced and added exogenously to cause gene downregulation or produced using expression systems (e.g. vectors). In a preferred embodiment, the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo) nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complementary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of SHR. For example, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of any one of SEQ ID NOS: 1 to 41 or a variant thereof, preferably any one of SEQ ID NOS: 1, 2, or 3 or a variant thereof, most preferably SEQ ID NO: 1 or a variant thereof.

In other embodiments, the suppressor nucleic acid may be an anti-sense suppressor of expression of a CYP78A6 polypeptide. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) Nature 334, 724-726; Zhang et al, (1992) The Plant Cell 4, 1575-1588, English et al., (1996) The Plant Cell 8, 179-188. Antisense technology is also reviewed in Bourque, (1995), Plant Science 105, 125-149, and Flavell (1994) PNAS USA 91, 3490-3496.

An anti-sense suppressor nucleic acid may comprise an anti-sense sequence of at least 10 nucleotides from a nucleotide sequence is a fragment of any one of SEQ ID NOS: 1 to 41 or other CYP78A sequence referred to above, or a variant thereof.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

A nucleic acid encoding a CYP78A polypeptide or a CYP78A suppressor as described herein may be operably linked to a heterologous regulatory sequence, such as a promoter, for example a constitutive, inducible, tissue-specific or developmental specific promoter.

Many suitable regulatory sequences are known in the art and may be used in accordance with the invention. Examples of suitable regulatory sequences may be derived from a plant virus, for example the Cauliflower Mosaic Virus 35S (CaMV 35S) gene promoter that is expressed at a high level in virtually all plant tissues (Benfey et al, (1990) EMBO J 9: 1677-1684). Other suitable constitutive regulatory elements include the cauliflower mosaic virus 19S promoter; the Figwort mosaic virus promoter; and the nopaline synthase (nos) gene promoter (Singer et al., Plant Mol. Biol. 14:433 (1990); An, Plant Physiol. 81:86 (1986)).

Constructs for expression of the CYP78A genes or CYP78A suppressors under the control of a strong constitutive promoter (the 35S promoter) are exemplified below but those skilled in the art will appreciate that a wide variety of other promoters may be employed to advantage in particular contexts.

A tissue-specific promoter may be employed to express the CYP78A polypeptide or CYP78A suppressor in a specific tissue or organ.

For example, a seed-, seed-coat- or integument-specific promoter may be used to express the CYP78A polypeptide or CYP78A suppressor in seeds. Suitable promoters include, for example *Phaseolus vulgaris* phas promoter, *Vicia faba* leB4-, usp- or sbp-promoters, Soybean β-conglycinin α-subunit promoter, *Brassica* FAE1 promoter and At4g12960 promoter (AtGILTpro) (Wu et al Plant Cell Rep (2011) 30:75-80).

Alternatively, or in addition, one might select an inducible promoter. In this way, for example, the CYP78A polypeptide or suppressor may be expressed at specific times or places in order to obtain desired changes in organ growth. Inducible promoters include the alcohol inducible AlcA gene-expression system (Roslan et al., Plant Journal; 2001 October; 28(2):225-35) may be employed.

The nucleic acid encoding the CYP78A polypeptide or CYP78A suppressor may be contained on a nucleic acid construct or vector. The construct or vector is preferably suitable for transformation into and/or expression within a plant cell. A vector is, inter alia, any plasmid, cosmid, phage or *Agrobacterium* binary vector in double or single stranded linear or circular form, which may or may not be self transmissible or mobilizable, and which can transform prokaryotic or eukaryotic host, in particular a plant host, either by integration into the cellular genome or exist extrachromasomally (e.g. autonomous replicating plasmid with an origin of replication).

Specifically included are shuttle vectors by which is meant a DNA vehicle capable, naturally or by design, of replication in two different organisms, which may be selected from Actinomyces and related species, bacteria and eukaryotic (e.g. higher plant, mammalia, yeast or fungal) cells.

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, imidazolinones, glyphosate and d-amino acids.

Those skilled in the art can construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and *Protocols in Molecular Biology*, Second Edition, Ausubel et al. eds. John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy R R D ed) Oxford, BIOS Scientific Publishers, pp 121-148.

When introducing a chosen nucleic acid construct into a cell, certain considerations must be taken into account, well known to those skilled in the art. The nucleic acid to be inserted should be assembled within a construct that contains effective regulatory elements that will drive transcription. There must be available a method of transporting the construct into the cell. Once the construct is within the cell membrane, integration into the endogenous chromosomal material either will or will not occur. Finally, the target cell type is preferably such that cells can be regenerated into whole plants.

Those skilled in the art will also appreciate that in producing constructs for achieving expression of the genes according to this invention, it is desirable to use a construct and transformation method which enhances expression of the nucleic acid encoding the CYP78A polypeptide or CYP78A suppressor. Integration of a single copy of the gene into the genome of the plant cell may be beneficial to minimize gene silencing effects. Likewise, control of the complexity of integration may be beneficial in this regard. Of particular interest in this regard is transformation of plant cells utilizing a minimal gene expression construct according to, for example, EP1407000B1, herein incorporated by reference for this purpose.

Techniques well known to those skilled in the art may be used to introduce nucleic acid constructs and vectors into plant cells to produce transgenic plants with the properties described herein.

*Agrobacterium* transformation is one method widely used by those skilled in the art to transform plant species. Production of stable, fertile transgenic plants is now routine in the art (see for example Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; CYP78A6tta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828; Nilsson, O. et al (1992) *Transgenic Research* 1, 209-220).

Other methods, such as microprojectile or particle bombardment (U.S. Pat No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press), direct DNA uptake (DE 4005152, WO 9012096, U.S. Pat. No. 4,684,611), liposome mediated DNA uptake (e.g. Freeman et al. *Plant Cell Physiol.* 29: 1353 (1984)) or the vortexing method (e.g. Kindle, *PNAS U.S.A.* 87: 1228 (1990d)) may be preferred where *Agrobacterium* transformation is inefficient or ineffective, for example in some gymnosperm species.

Physical methods for the transformation of plant cells are reviewed in Oard, 1991, *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

In some embodiments, the plant cell may further comprise altered expression of a DA protein, such as DA-1, and/or EOD1/BB protein. For example, expression of a DA and/or EOD1/BB protein may be reduced or abolished in plant cells in which CYP78A expression is increased, or dominant negative forms of DA and/or EOD1/BB proteins may be expressed. Expression of a DA and/or EOD1/BB protein may be increased in plant cells in which CYP78A expression is reduced.

DA proteins possess a characteristic domain structure comprising a LIM domain, a UIM1 domain and a UIM2 domain (Li et al Genes & Dev, 2008, 22: 1331-1336; WO2009/04752). ADA polypeptide may comprise the amino acid sequence of SEQ ID NO: 42 (AT1G19270; NP_173361.1 GI: 15221983) or may be a fragment or variant of this sequence which retains DA activity.

Big Brother (EOD1/BB) is an E3 ubiquitin ligase which is known to repress plant organ growth (Disch Curr Biol 16 272-279 (2006)). A BB protein may comprise the amino acid sequence of At3g63530 NP_001030922.1 GI: 79316205 (SEQ ID NO: 97), or may be a fragment or variant which retains BB activity or is capable of interfering with the function of BB.

A BB protein or DA protein which is a variant of a reference BB or DA sequence described above may comprise an amino acid sequence having at least 20%, at least 30%, at least 40%, at least 50%, at least 60%, at least 70%, at least 80%, at least 90%, at least 95%, or at least 98% sequence identity to the reference sequence. Sequence identity is described in more detail above.

DA proteins and EOD1/BB proteins, which may include AtDA1 (At1G19270) and AtBB (At3g63530), respectively, and variants thereof, are described and defined in detail in WO2009/04752, which is incorporated herein by reference for all purposes.

Particular amino acid sequence variants may differ from the DA polypeptide of SEQ ID NO: 42 or the BB polypeptide of SEQ ID NO: 97 (At3g63530) by insertion, addition, substitution or deletion of 1 amino acid, 2, 3, 4, 5-10, 10-20 20-30, 30-50, or more than 50 amino acids.

Plant as described herein having altered CYP78A expression in one or more cells therein, for example abolished, reduced, or increased CYP78A expression relative to controls, may be sexually or asexually propagated or off-spring or descendants may be grown.

Another aspect of the invention provides a method of producing a plant with an altered seed size comprising:
  incorporating a heterologous nucleic acid which alters the expression of a CYP78A polypeptide into a plant cell by means of transformation, and;
  regenerating the plant from one or more transformed cells.

As described above, the heterologous nucleic acid may encode a CYP78A polypeptide or a CYP78A suppressor molecule or may inactivate the endogenous CYP78A coding sequence of the plant or a regulatory sequence thereof, for example a repressor or enhancer.

The altered phenotype of the plant produced by the method is described in more detail above. The method may be useful, for example, in producing plants having increased yields, for example, crop plants having improved grain yield, relative to control plants.

In some embodiments, a method may further comprise reducing or abolishing the expression or activity of a DA polypeptide and/or EOD1/BB protein in the plant cell or plant.

This may be carried out before, at the same time or after the incorporation of the nucleic acid which encodes the CYP78A polypeptide. For example, in some embodiments, the expression or activity of a DA polypeptide and/or EOD1/BB protein may be abolished or reduced in one or more plant cells which already incorporate the nucleic acid encoding the CYP78A polypeptide. In other embodiments, the nucleic acid encoding the CYP78A polypeptide may be incorporated into one or more plant cells which have abolished or reduced expression of a DA polypeptide and/or EOD1/BB protein.

A plant thus produced may comprise a heterologous nucleic acid which encodes a CYP78A polypeptide and may possess abolished or reduced expression or activity of a DA polypeptide and/or EOD1/BB protein in one or more of its plant cells.

The expression or activity of a DA polypeptide and/or EOD1/BB protein may be reduced or abolished as described above. For example, a method may comprise incorporating a heterologous nucleic acid into a plant cell by means of transformation, wherein the nucleic acid encodes a suppressor nucleic acid, such as a siRNA or shRNA, which reduces the expression of a DA polypeptide and/or EOD1/BB protein.

The heterologous nucleic acids encoding the CYP78A polypeptide and Da and/or EOD1/BB suppressor nucleic acid may be on the same or different expression vectors and may be incorporated into the plant cell by conventional techniques.

CYP78A6 polypeptides and CYP78A suppressor nucleic acids are described in more detail above.

In some embodiments, the the expression or activity of two or more CYP78A polypeptides, such as CYP78A6 and CYP78A9, may be abolished or reduced to produce a plant having reduced seed size.

A plant produced as described above may be sexually or asexually propagated or grown to produce off-spring or descendants. Off-spring or descendants of the plant regenerated from the one or more cells may be sexually or asexually propagated or grown. The plant or its off-spring or descendents may be crossed with other plants or with itself.

A plant suitable for use in the present methods is preferably a higher plant, for example an agricultural plant selected from the group consisting of *Lithospermum erythrorhizon, Taxus* spp, tobacco, cucurbits, carrot, vegetable brassica, melons, capsicums, grape vines, lettuce, strawberry, oilseed brassica, sugar beet, wheat, barley, maize, rice, soyabeans, peas, sorghum, sunflower, tomato, potato, pepper, chrysanthemum, carnation, linseed, hemp and rye.

In some embodiments, the plant may be a flowering plant (angiosperm). Flowering plants may include monocotyledons or dicotyledons, such as eudicots, in particular members of the Rosid clade, including Brasicaceae, such as broccoli, horseradish, cabbage, and cauliflower. In some embodiments, a plant may be other than *Arabidopsis thaliana*.

Another aspect of the invention provides a plant which comprises a heterologous nucleic acid which alters expression of a CYP78A polypeptide, as described above, and optionally has reduced or abolished expression of a DA polypeptide and/or EOD1/BB polypeptide.

The plant may display an altered seed size phenotype relative to controls (e.g. non-transgenic plants of the same species). For example, a plant which displays increased expression of a CYP78A polypeptide may display increased seed size relative to controls.

A plant which displays increased expression of the CYP78A6 polypeptide may also display one or more of; increased flower and leaf size, increased stem thickness, and increased height relative to control plants (e.g. identical plants which do not display increased expression of the CYP78A6 polypeptide).

A plant which displays reduced expression of a CYP78A polypeptide may display reduced seed size relative to controls.

A suitable plant with altered expression of a CYP78A polypeptide may be produced by a method described herein In some embodiments, the plant may have normal fertility relative to control plants.

In some embodiments, a plant may not display increased organ size relative to controls.

In addition to a plant comprising a heterologous nucleic acid which alters CYP78A expression, for example a nucleic acid which encodes a CYP78A polypeptide or CYP78A suppressor molecule, as described herein, the invention encompasses any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Having generally described the invention above, certain aspects and embodiments of the invention will now be illustrated by way of example to extend the written description and enablement of the invention, and to ensure adequate disclosure of the best mode of practicing the invention. Those skilled in the art will appreciate, however, that the scope of this invention should not be interpreted as being limited by the specifics of these examples. Rather, variations, extensions, modifications and equivalents of these specifics and generic extensions of these details may be made without departing from the scope of the invention comprehended by this disclosure. Therefore, for an appreciation of the scope of this invention and the exclusive rights claimed herein, reference should be had to the claims appended to this disclosure, including equivalents thereof.

All documents mentioned in this specification are incorporated herein by reference in their entirety for all purposes.

The contents of all database entries mentioned in this specification are also incorporated herein by reference in their entirety. This includes the versions of any sequences which are current at the filing date of this application.

EXAMPLES

Methods
Activation Tagging Screening

The *Agrobacterium tumefaciens* strain GV3101 was transformed with the activation tagging vector pJFAT260 (Fan et al., 2009), and the resulting strain was used for floral dip transformation of *Arabidopsis* da1-1 mutant plants (Li et al., 2008). $T_1$ plants were selected by using the herbicide Basta. Seeds produced from $T_1$ plants were passed through a fine wire sieve (425 µm) (Fisher Scientific). Seeds retained by the sieve were kept for further characterization.

Plant Materials and Growth Conditions *Arabidopsis thaliana* Columbia (Col-0) was the wild type line used. All mutants were in the Col-0 background. Plant materials and growth conditions are available in the Supporting Information.

Morphological and Cellular Analysis

Area measurements of fully expanded cotyledons, petals (stage 14), and leaves were made by flattening the organs, scanning to produce a digital image, and then calculating area by using Image J software. Embryo cell sizes were measured on the adaxial side of cotyledons from DIC images.

For analysis of whole-mount seeds, seeds were dissected from siliques and placed in a drop of clearing solution [30 ml $H_2O$, 80 g Chloral hydrate (Sigma, C8383), 10 ml 100% Glycerol (Sigma, G6279)]. Samples were photographed under a Leica microscope (LEICA DM2500) with differential interference contrast optics using a SPOT FLEX Cooled CCD Digital Imaging System.

Seed Size and Seed Mass Analysis

Average seed mass was determined by weighing mature dry seeds in batches of 500 using an electronic analytical balance (METTLER TOLEDO AL104, China). The weights of five sample batches were measured for each seed lot. The wild-type and mutant seeds were photographed under a Leica microscope (LEICA S8APO) using Leica CCD (DFC420). The length, width and projective area of wild-type and mutant seeds were measured by using Image J software.

Cloning of the EOD3 gene

The flanking region of the T-DNA insertion of the eod3-1 D mutant was isolated by the thermal asymmetric interlaced PCR (TAIL-PCR) (Liu et al., 1995). Detailed protocols are described in the Supporting Information.

Constructs and Transformation

The EOD3 CDS was subcloned into the PstI site of the binary vector 35S::pGreen to generate the transformation plasmid 35S::EOD3. The specific primers for the EOD3 CDS are EOD3CDS-F and EOD3CDS-R.

The 1878 bp EOD3 promoter was subcloned into SaI and NcoI sites of the binary vector pGreen-GUS to generate the transformation plasmid pEOD3::GUS. The specific primers for the EOD3 promoter are EOD3PROM-F and EOD3PROM-R.

GUS Staining

Samples (pEOD3::GUS) were stained in a solution of 1 mM X-gluc, 50 mM NaPO4 buffer, 0.4 mM each $K_3Fe(CN)_6$/$K_4Fe(CN)_6$, 0.1% (v/v) Triton X-100 and incubated at 37° C. for 8 hrs. After GUS staining chlorophyll was removed using 70% ethanol.

RT-PCR, Quantitative Real-Time RT-PCR, and RNA in situ Hybridization

Total RNA was extracted from *Arabidopsis* seedlings using an RNAprep pure Plant kit (TIANGEN). Reverse transcription (RT)-PCR was performed as described (Li et al., 2006). cDNA samples were standardized on actin transcript amount using the primers ACTIN7-F and ACTIN7-R. Quantitative real-time RT-PCR analysis was performed with a Lightcycler 480 machine (Roche) using the Lightcycler 480 SYBR Green I Master (Roche). ACTIN2 mRNA was used as an internal control, and relative amounts of mRNA were calculated using the comparative threshold cycle method. RNA in situ hybridization method is described in the Supporting Information. The primers used for RT-PCR, quantitative real-time RT-PCR, and RNA in situ hybridization are described herein.

Plant materials and Growth Conditions *Arabidopsis thaliana* Columbia (Col-0) was the wild type line used. All mutants were in the Col-0 background. eod3-1D was identified as an enhancer of da1-1 by using T-DNA activation tagging method. The eod3-ko1 (CS833552), eod3-ko2 (CS806696), cyp78a9-ko1 (SALK_121278) and ttg2-3 (SALK_148838) were identified in AtIDB (*Arabidopsis Thaliana* Integrated Database) and obtained from *Arabidopsis* Stock Centre ABRC collection. The eod3-ko1, eod3-ko2, cyp78a9-ko1 and ttg2-3 mutants were backcrossed into Col-0 for three times. T-DNA insertions were confirmed by PCR and sequencing by using the primers described in Supplementary Table 3. Seeds were surface-sterilized with 100% isopropanol for 1 min and 10% (v/v) household bleach for 10 mins, washed at least five times with sterile water, stratified at 4° C. for 2 d in the dark, dispersed on Murashige and Skoog medium (Sigma) supplemented with 0.9% agar and 1% glucose, and then grown at 22° C.

Cloning of the EOD3 Gene

The flanking region of the T-DNA insertion of the eod3-1D mutant was isolated by the thermal asymmetric interlaced PCR (TAIL-PCR) (Liu et al., 1995). Genomic DNA was prepared by using buffer containing 50 mM Tris-HCL (pH8.0), 25 mM EDTA, 250 mM NaCl and 0.5% SDS. Approximately 100 ng of the genomic DNA of the eod3-1D da1-1 mutant was used to perform TAIL-PCR analysis according to a previously reported method (Liu et al., 1995). Briefly, TAIL-PCR utilizes three nested specific primers (OJF22, OJF23 and OJF24) within the T-DNA region of the pJFAT260 vector together with a shorter arbitrary degenerate primer (AD1) so that the relative amplification efficiencies of specific and non-specific products can be thermally controlled. The specific primers OJF22, OJF23 and OJF24 and an arbitrary degenerate (AD1) primer are described in Table S3. TAIL-PCR products were sequenced by using the primer OJF24.

Cellular Analysis

For resin sections, siliques were cut transversely into four pieces and fixed in 4% paraformaldehyde. The tissues were embedded in Technovit 7100 resin (Heraeus Kulzer, Germany), sectioned at 5 μm thickness and stained with 0.05% toluidine blue.

RNA In Situ Hybridization

In situ hybridization was performed as described (Li et al., 2003). DIG-labeled RNA transcripts were generated by transcription of EOD3 and CYP78A9 in sense or antisense orientation using SP6 or T7 RNA polymerase (Roche). After hybridization, washing and blocking, DIG-labeled RNA transcripts reacting with alkaline phosphatase-conjugated anti-DIG Fab fragment (1:3000 [v/v], Roche) were detected using 5-bromo-4-chloro-3-indolyl phosphate/nitroblue tetrazolium. The slides were observed with a microscope (LEICA DM2500) and photographed using a SPOT FLEX Cooled CCD Digital Imaging System.

Expression of *Arabidopsis* EOD3 in *Oryza sativa*

Figure 19:
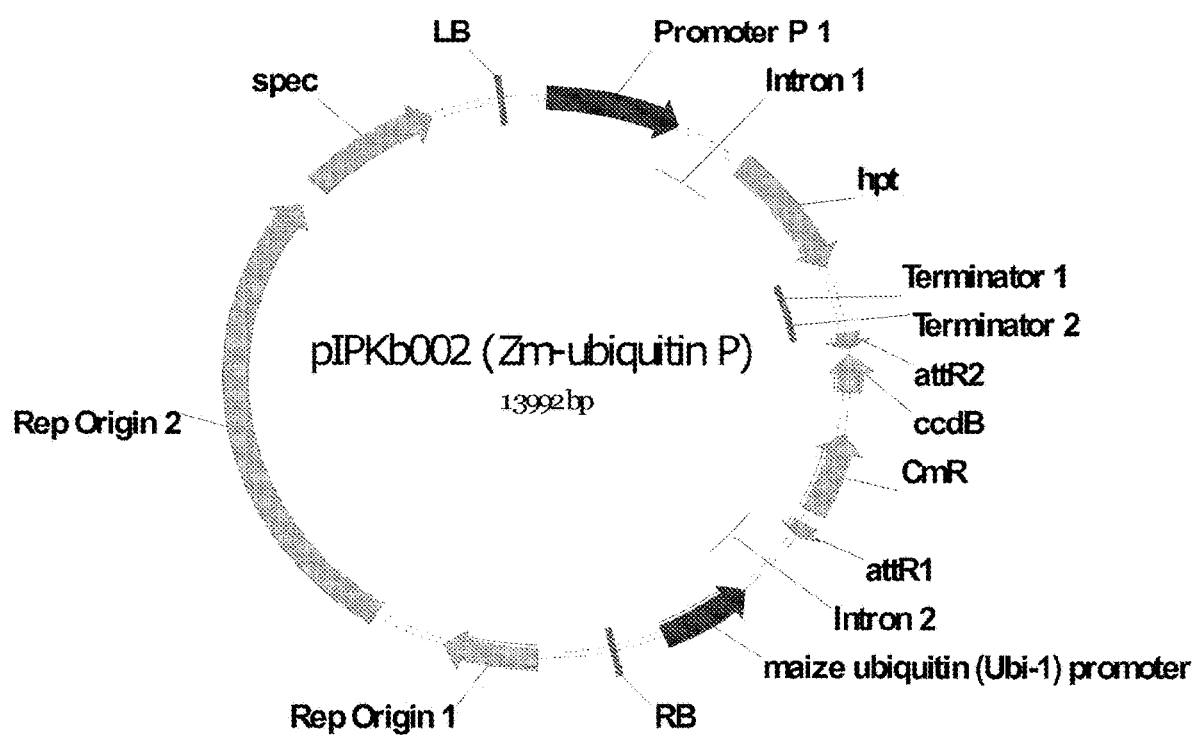
FIG. 19 shows the Gateway Binary Vector pIPKb002 containing the Zm-ubiqutin promoter used to expresss EOD3 in *Oryza sativa*.

For overexpression of *Arabidopsis* EOD3 in *Oryza sativa*, the full length CDS of EOD3 was subcloned into pCR8/GW/TOPO TA cloning vector (Invitrogen) using TOPO enzyme and sequenced. The EOD3 CDS was then subcloned into Gateway Binary Vector pIPKb002 containing the Zm-ubiquitin promoter (FIG. 19). The construct was then introduced into callus of *Oryza sativa L. japonica*. cv. *Nipponbare* and selected on hygromycin-containing medium. The detailed methods were described in Hiei et al (1994) Plant J 6 271-282.

The areas of 24 seeds from each line of T0 transgene plants were scanned to produce digital images, and then the average area per seed was calculated using Image J software as an indicator of seed size. The average area per seeds from each transgenic line was then determined.

Results

Figure 1:
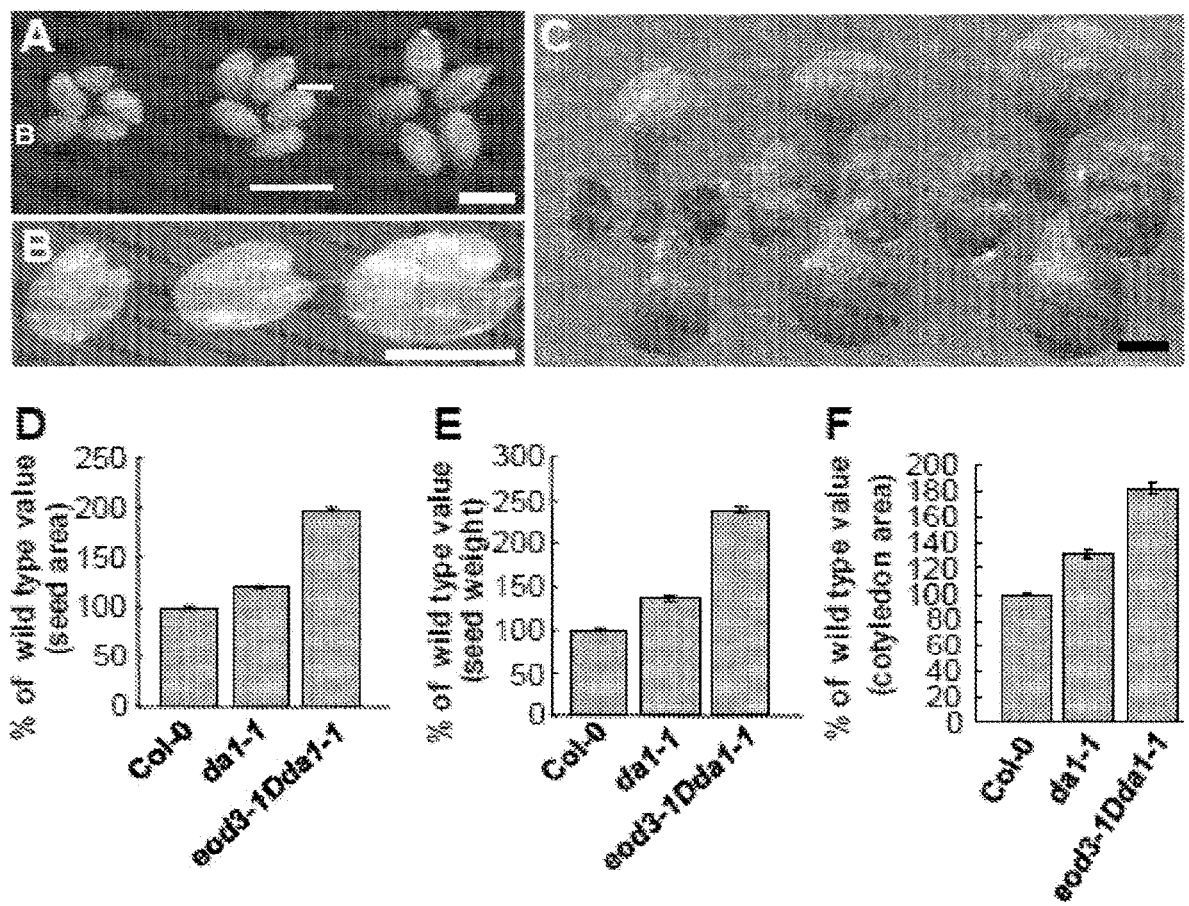
FIG. 1 shows the isolation of an enhancer of da1-1 (eod3-1D).
Figure 10:
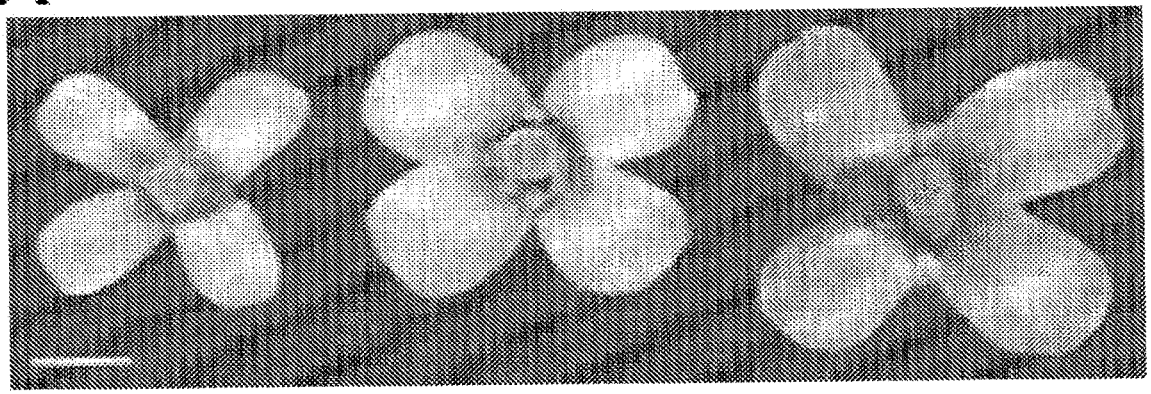
FIG. 10 shows eod3-1D enhances the organ size phenotype of da1-1. 10A shows flowers of wild type, da1-1 and eod3-1D da1-1. 10(b) shows area of the fifth leaves in wild type, da1-1 and eod3-1D da1-1. Values (B) are given as mean±SE relative to the respective wild-type values, set at 100%. Bar: A, 1 mm.
Figure 10:
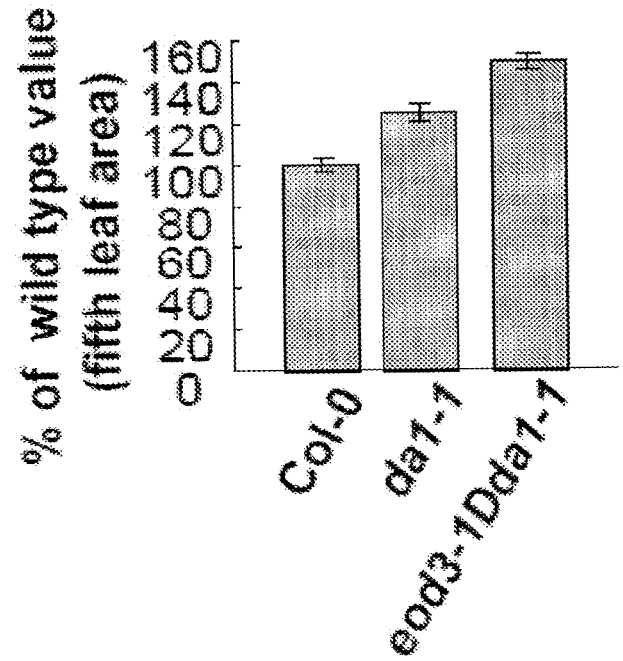

We previously characterized the *Arabidopsis* da1-1 mutant, which had larger seeds than wild type (Li et al., 2008). DA1, encoding a predicted ubiquitin receptor, sets final seed size by restricting cell proliferation (Li et al., 2008). To identify other components in the DA1 pathway or additional factors of seed size control, we initiated a T-DNA activation tagging screen in a da1-1 homozygous genetic background. Seeds produced from approximate 16,000 $T_1$ plants were screened for mutations affecting the seed size phenotype of da1-1. A dominant enhancer of da1-1 (eod3-1D), which enhanced the seed size phenotype of da1-1, was identified (FIGS. 1A and D). Seeds of the eod3-1D da1-1 double mutant were dramatically larger and heavier than those of the da1-1 mutant (FIG. 1D an E). The embryo constitutes the major volume of a mature seed in *Arabidopsis*. The size of eod3-1D da1-1 embryos was substantially increased, compared with that of Col-0 and da1-1 embryos (FIG. 1B). The changes in seed size were also reflected in the size of seedlings (FIG. 1C). Cotyledons of eod3-1D da1-1 seedlings were significantly larger than those of Col-0 and da1-1 seedlings (FIGS. 1C and F). In addition, eod3-1D da1-1 double mutant had larger flowers and leaves than da1-1 (FIG. 10).

eod3-1D Sets Large Seeds

Figure 2:
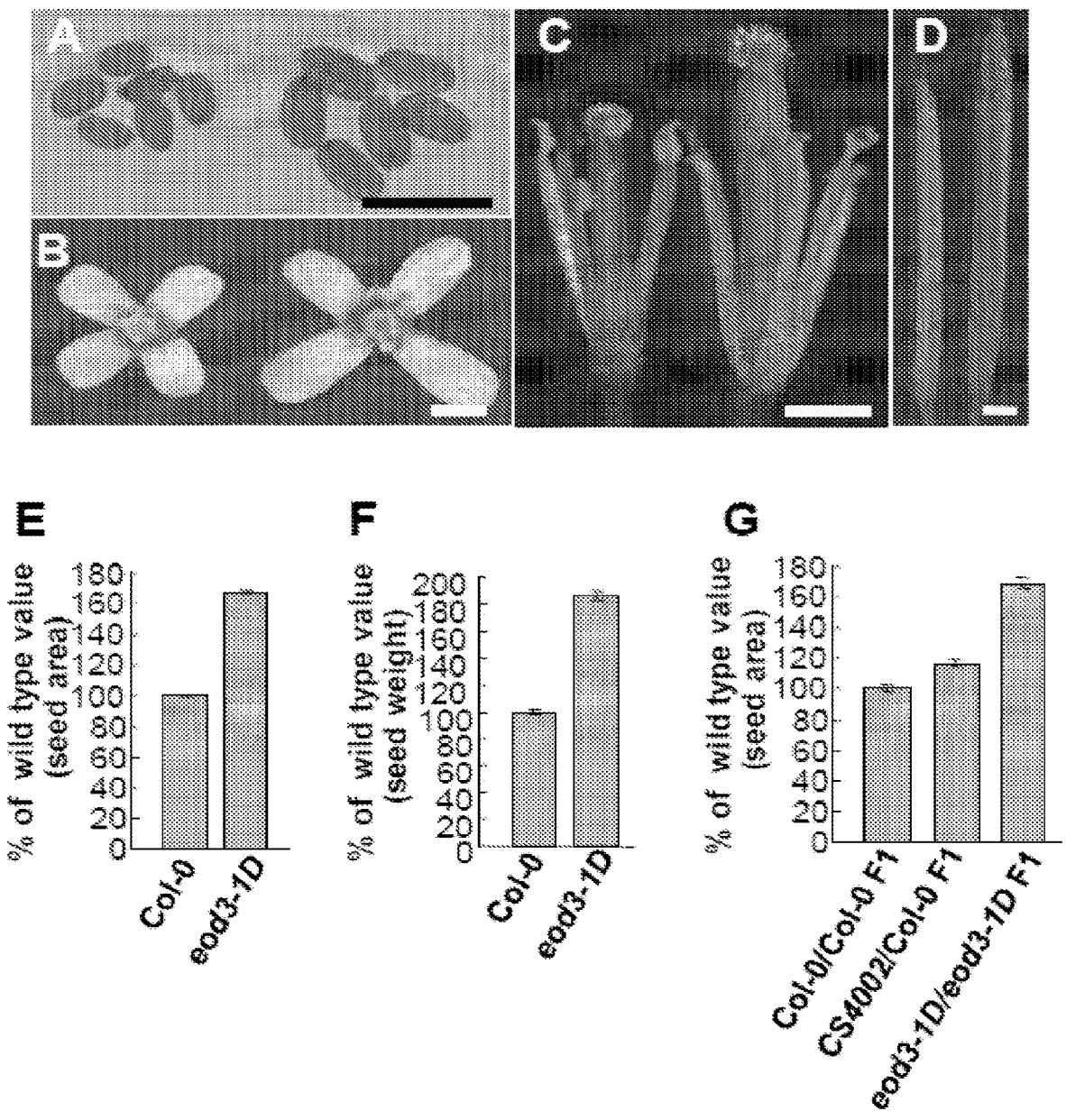
FIG. 2 shows seed and organ size in the eod3-1D mutant. 2(A-D) show seeds (A), flowers (B), stamens and carpels (C), and siliques (D) of wild type (left) and eod3-1D (right). 2(E) shows projective area of wild-type and eod3-1D seeds. 2(F) shows seed weight of wild type and eod3-1D. 2(G) shows projective area of Col-0×Col-0 $F_1$, CS4002×Col-0 $F_1$ and eod3-1D×eod3-1D $F_1$ seeds. Values (E-G) are given as mean±SE relative to the respective wild-type values, set at 100%. Bars: A, B, C, D, 1 mm.
Figure 11:
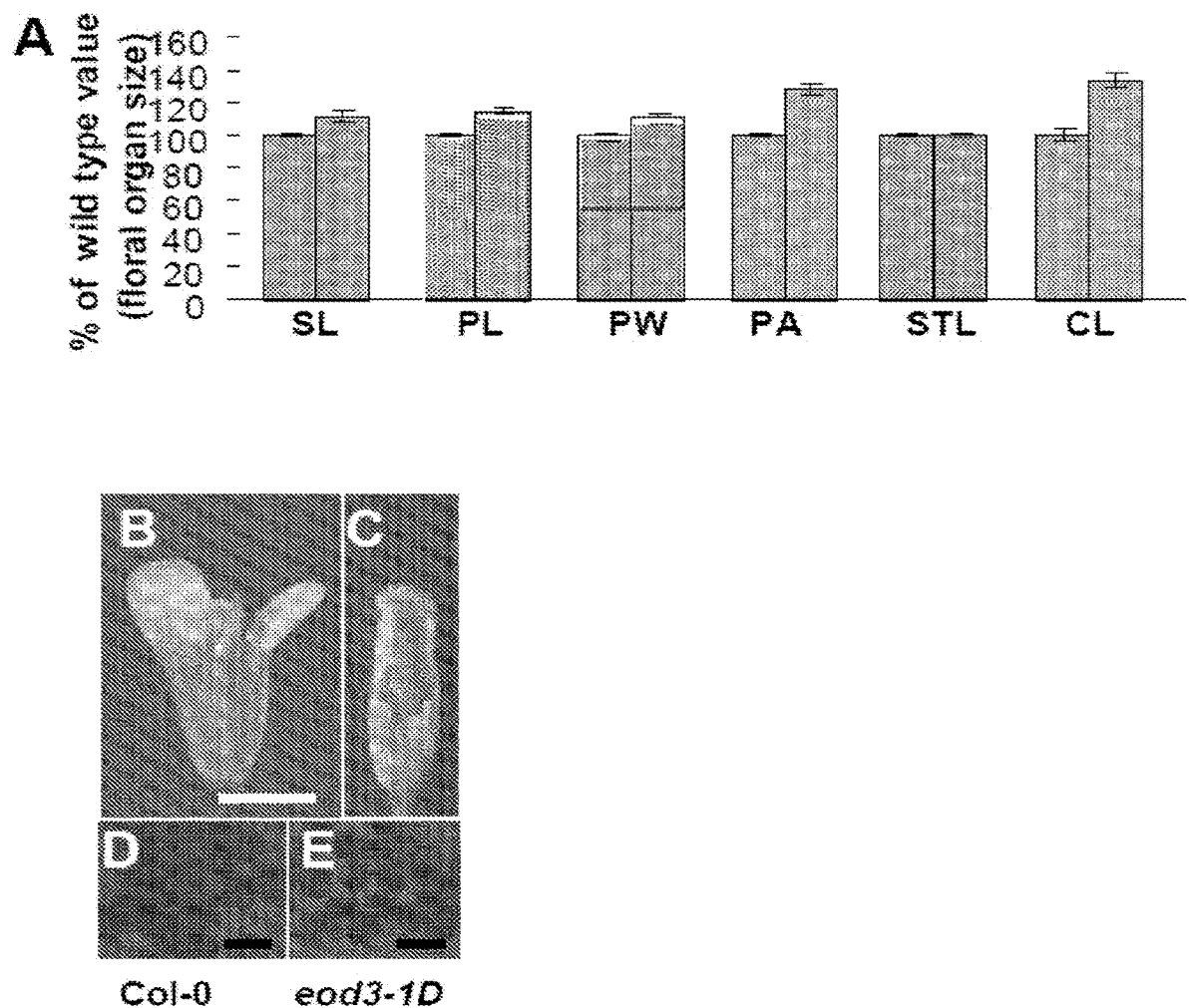
FIG. 11 shows organ size and reproductive development in eod3-1D. 11(A) shows sepal length (SL), petal length (PL), petal width (PW), petal area (PA), stamen length (STL) and carpel length (CL) of wild-type (left) and eod3-1D (right) flowers. 11(B and C) show the earliest-arising flowers on the primary inflorescences of wild type (B) and eod3-1D (C). 11(D and E) show pollens from the earliest-arising flowers were stained by using Alexander staining buffer. Values (A) are given as mean±SE relative to the respective wild-type values, set at 100%. Bars: B, C, 1 mm; D,E, 100 μm.

To determine whether the single eod3-1D mutant has the altered seed size, we identified the eod3-1D mutant among $F_2$ progeny derived from a cross between the eod3-1D da1-1 double mutant and wild type (Col-0). Seeds produced by eod3-1D were larger and heavier than the wild-type seeds (FIGS. 2A, E and F). In addition to the seed phenotype, eod3-1D plants showed larger flowers and leaves, thicker stems, and higher plants than wild type (FIG. 2B; FIG. 11A; Table 1). However, the number of rosette and cauline leaves was similar in wild type and eod3-1D, and the number of rosette and cauline branches in eod3-1D was also comparable with that in wild type (Table 1).

The eod3-1D mutation also caused defects in reproductive development. For example, eod3-1D mutant produced fewer elongated siliques than wild type (Table 1). First several flowers on the primary inflorescences of eod3-1D did not open normally (FIGS. 11B and C). Their stamens were much shorter than those of wild type (FIGS. 11B and C). The dehiscence of eod3-1D anthers was much delayed (FIG. 11C), but their pollens were functional (FIGS. 11D and E). The enlarged siliques were more frequently observed in the latest-arising flowers of old plants. In general, the enlarged siliques contained few seeds although the number of ovules per silique in eod3-1D was not reduced (Table 1). We observed that carpels of the late developing eod3-1D flowers were longer than those of wild-type flowers, whereas the length of stamens was similar to that of wild-type stamens (FIG. 2C; FIG. 11A), such that eod3-1D pollen is not able to directly reach stigmatic papillae; this could, in part, explain the decreased fertility. Fully elongated eod3-1D mutant siliques were longer and wider than wild-type siliques (FIG. 2D).

To determine whether the large seed size phenotype could result from allocation of extra resources to the few seeds produced, we hand-pollinated six flowers on primary inflorescences of wild-type plants, eod3-1D, and a male-sterile mutant (CS4002). For this set of experiments, flowers were pollinated with pollens of the same genotypes, with the exception of male-sterile plants for which wild-type pollens were used. Thus, each male-sterile plant produced only six siliques. The average seed size from male-sterile maternal plants was increased to 116% of that from wild-type maternal plants (FIG. 2G), indicating that seed size increased under condition of reduced fertility. By contrast, the average seed size from the eod3-1D mutant were approximate 170% of that from wild type (FIG. 2G), indicating that the effect of eod3-1D on seed size is not primarily due to its effect on fertility.

EOD3 Encodes a Cytochrome P450 Monooxygenase

To test whether this T-DNA insertion might cause the eod3-1D phenotypes, we analyzed the genetic linkage of the mutant phenotype with Basta resistance, which is conferred by the selectable marker of the activation tagging vector (Fan et al., 2009). All 101 plants with eod3-1D da1-1 phenotypes in $T_2$ population were resistant, whereas the 36 plants with da1-1 phenotypes were sensitive, indicating that the insertion is responsible for the eod3-1D mutation. To identify the EOD3 gene, the DNA flanking the T-DNA insertion was isolated by thermal asymmetric interlaced PCR (Liu et al., 1995). Sequence analysis indicated that the insertion was in an intergenic region on chromosome II between the genes At2g46660 and At2g46670. The T-DNA had inserted approximately 3.2 kb upstream of the At2g46660 gene and about 6.5 kb downstream of the At2g46670 gene (FIG. 3A). The mRNA levels of these two genes were determined by reverse transcription-polymerase chain reaction (RT-PCR). Expression levels of the At2g46670 gene were similar in da1-1 and eod3-1D da1-1 plants (FIG. 3B), indicating that At2g46670 was unlikely to be the EOD3 gene. The mRNA of At2g46660 accumulated at a higher level in eod3-1D da1-1 than in da1-1 (FIG. 3B), strongly indicating that At2g46660 is likely to be the EOD3 gene. To demonstrate that this gene corresponded to EOD3, we overexpressed the At2g46660 gene in Col-0 wild-type plants and isolated 41 transgenic plants. Most transgenic plants showed large seeds and increased plant height (FIGS. 3C and D; FIG. 12A), as had been seen in the eod3-1D single mutant, confirming At2g46660 is the EOD3 gene. Importantly, the 35S::EOD3#7 transgenic plants exhibited normal growth and fertility, but produced significantly large seeds compared with wild type (FIG. 3C; FIGS. 12B and C).

The EOD3 gene encodes the putative cytochrome P450 monooxygenase CYP78A6, one of six members of the CYP78A family in *Arabidopsis*. Genes in the CYP78A class belong to the group A cytochrome P450 in plants and seem to perform plant-specific functions (Zondlo and Irish, 1999; Ito and Meyerowitz, 2000; Anastasiou et al., 2007). EOD3/CYP78A6 exhibits the highest similarity to *Arabidopsis* CYP78A9 (FIG. 3E) (Ito and Meyerowitz, 2000).

EOD3/CYP78A6 Acts Redundantly with CYP78A9 to Control Seed Size

Figure 4:
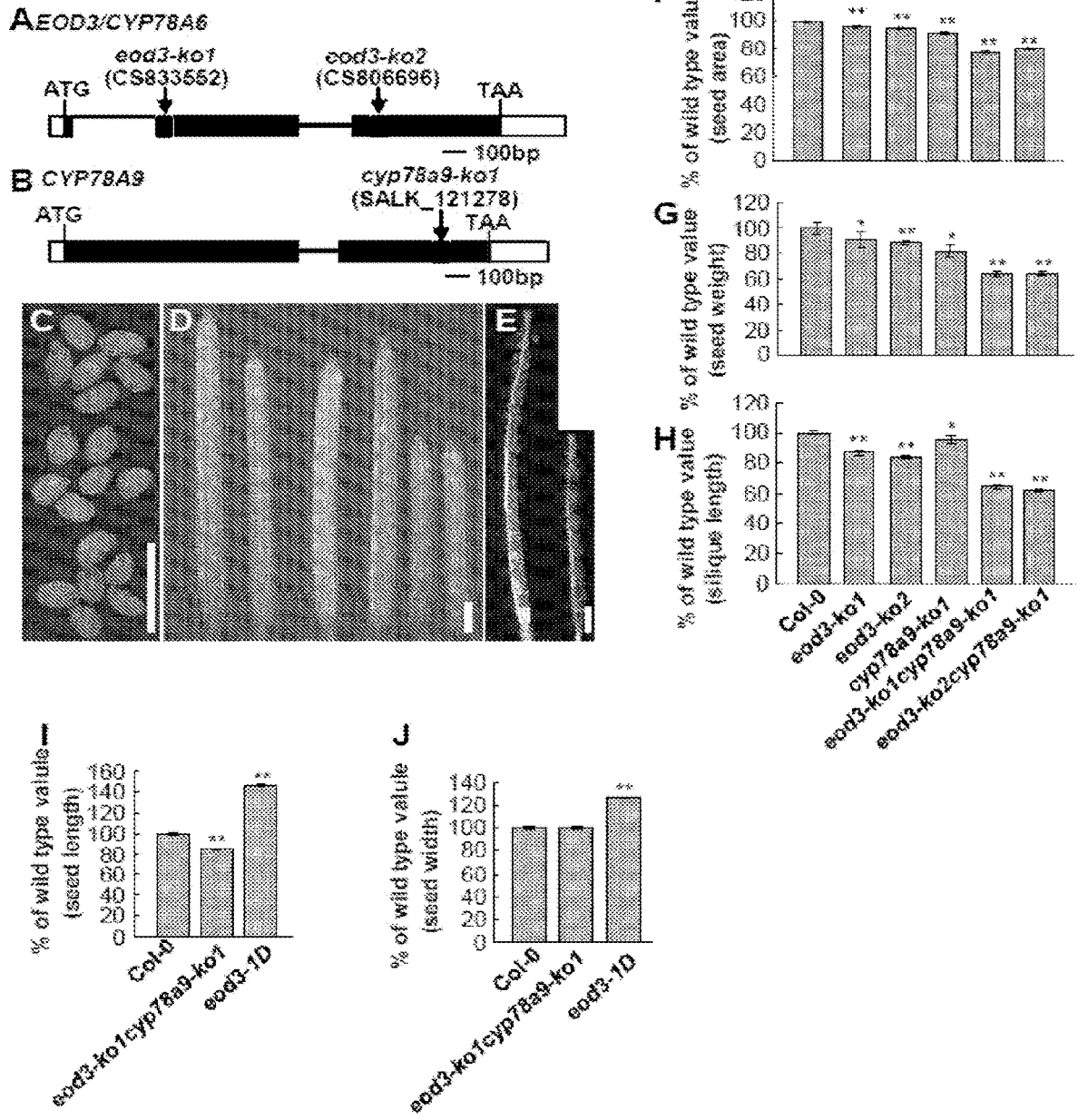
FIG. 4 shows that EOD3 acts redundantly with CYP78A9 to influence seed size. 4(A) shows EOD3 gene structure. The start codon (ATG) and the stop codon (TAA) are indicated. Closed boxes indicate the coding sequence, and the line between boxes indicates intron. T-DNA insertion sites (eod3-ko1 and eod3-ko2) in the EOD3 gene were shown. 4(B) shows CYP78A9 gene structure. The start codon (ATG) and the stop codon (TAA) are indicated. Closed boxes indicate the coding sequence, and the line between boxes indicates intron. The T-DNA insertion site (cyp78a9-ko1) in the CYP78A9 gene was shown. 4(C) shows seeds from wild-type, eod3-ko1 cyp78a9-ko1 and eod3-ko2 cyp78a9-ko1 plants (from top to bottom). 4(D) Siliques from wild-type, eod3-ko1, eod3-ko2, cyp78a9-ko1, eod3-ko1 cyp78a9-ko1 and eod3-ko2 cyp78a9-ko1 plants (from left to right). 4(E) shows opened siliques from wild-type and eod3-ko1 cyp78a9-ko1 plants (from left to right). 4(F) shows projective area of wild-type, eod3-ko1, eod3-ko2, cyp78a9-ko1, eod3-ko1 cyp78a9-ko1 and eod3-ko2 cyp78a9-ko1 seeds. 4(G) shows seed weight of wild type, eod3-ko1, eod3-ko2, cyp78a9-ko1, eod3-ko1 cyp78a9-ko1 and eod3-ko2 cyp78a9-ko1. 4(H) shows silique length of wild type, eod3-ko1, eod3-ko2, cyp78a9-ko1, eod3-ko1 cyp78a9-ko1 and eod3-ko2 cyp78a9-ko1. 4(I and J) show seed length (I) and seed width (J) of wild type, eod3-ko1, cyp78a9-ko1 and eod3-ko1 cyp78a9-ko1. Values (F-J) are given as mean±SE relative to the respective wild-type values, set at 100%. **, P<0.01 and *, P<0.05 compared with the wild type (Student's t-test). Bars: C, D, E, 1 mm.
Figure 13:
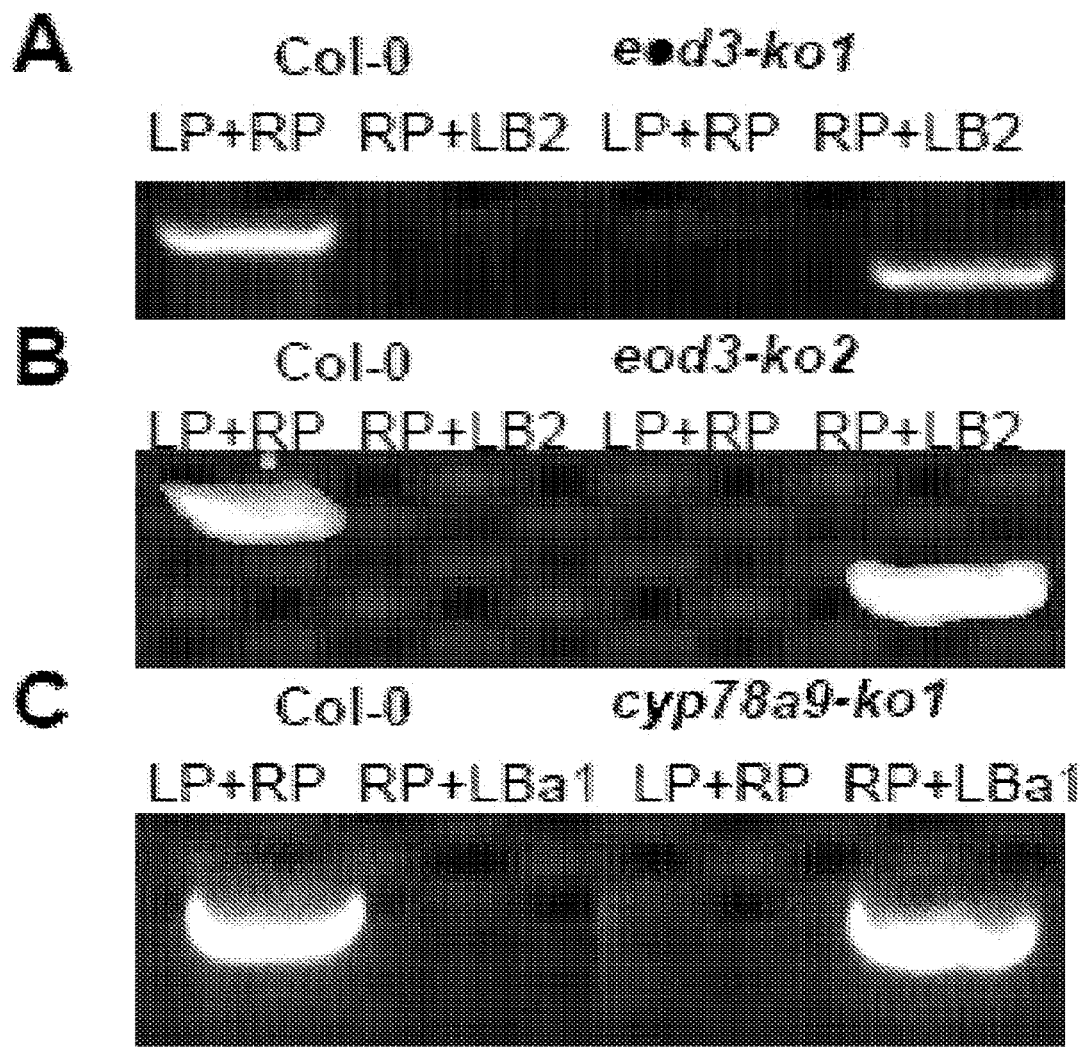
FIG. 13 shows identification of eod3-ko1, eod3-ko2 and cyp78a9-ko1 mutants. 13(A-C) show PCR identification of T-DNA insertions in eod3-ko1 (A), eod3-ko2 (B), cyp78a9-ko1 (C) mutants with T-DNA specific primers and flanking primers.

In order to further understand the function of EOD3, we isolated T-DNA inserted loss-of-function mutants for EOD3/CYP78A6 and CYP78A9, the most closely related family member. eod3-ko1 and eod3-ko2 were identified with T-DNA insertions in the first and second exons of the EOD3/CYP78A6 gene, respectively (FIG. 4A). cyp78a9-ko1 had T-DNA insertion in the second exon of CYP78A9 (FIG. 4B). The T-DNA insertion sites were confirmed by PCR using T-DNA specific and flanking primers and sequencing PCR products (FIG. 13). The eod3-ko1, eod3-ko2 and cyp78a9-ko1 mutants were further backcrossed into Col-0 for three times.

Seeds from eod3-ko1, eod3-ko2 and cyp78a9-ko1 mutants were smaller and lighter than seeds from wild-type plants (FIGS. 4F and G). Silique length in eod3-ko1, eod3-ko2 and cyp78a9-ko1 was reduced, compared with that in wild type (FIGS. 4D and H). By contrast, the size of leaves and petals, stem thickness and plant height in eod3-ko1 and cyp78a9-ko1 were comparable with those in wild type (Table 1). In addition, the number of rosette and cauline leaves, rosette and cauline branches, siliques per plant and ovules per silique in eod3-ko1 and cyp78a9-ko1 was similar to that in wild type (Table 1). As EOD3/CYP78A6 shows the highest similarity to the *Arabidopsis* CYP78A9, we postulated that EOD3 may act redundantly with CYP78A9 to control seed size. To test this, we generated the double knockout mutants, eod3-ko1 cyp78a9-ko1 and eod3-ko2 cyp78a9-ko1. The seed size and weight phenotype of eod3-ko mutants was synergistically enhanced by the disruption of CYP78A9 (FIGS. 4F and G), indicating that EOD3 functions redundantly with CYP78A9 to control seed growth. The eod3-ko cyp78a9-ko mutations also caused a significant change in seed shape (FIG. 4C). eod3-ko cyp78a9-ko seeds were shorter than wild-type seeds, whereas seed width was comparable with that of wild type (FIGS. 4C, I and J), indicating that eod3-ko cyp78a9-ko seeds are more round in shape than wild type. eod3-ko cyp78a9-ko produced fewer siliques per plant than wild type (Table 1). The length of siliques in eod3-ko cyp78a9-ko was dramatically reduced, compared with their parental lines (FIGS. 4D and H). Surprisingly, the number of ovules per silique in eod3-ko1 cyp78a9-ko1 was similar to that in wild type, resulting in a higher density of seeds within siliques (FIG. 4E; Table 1). In addition, the primary inflorescence stem of eod3-ko1 cyp78a9-ko1 was shorter than that of wild type, and the size of petals and leaves was slightly reduced compared with wild type (Table 1). However, the number of leaves and branches in eod3-ko1 cyp78a9-ko1 was comparable with that observed in wild type (Table 1).

EOD3 Acts Maternally to Influence Seed Size

Figure 14:
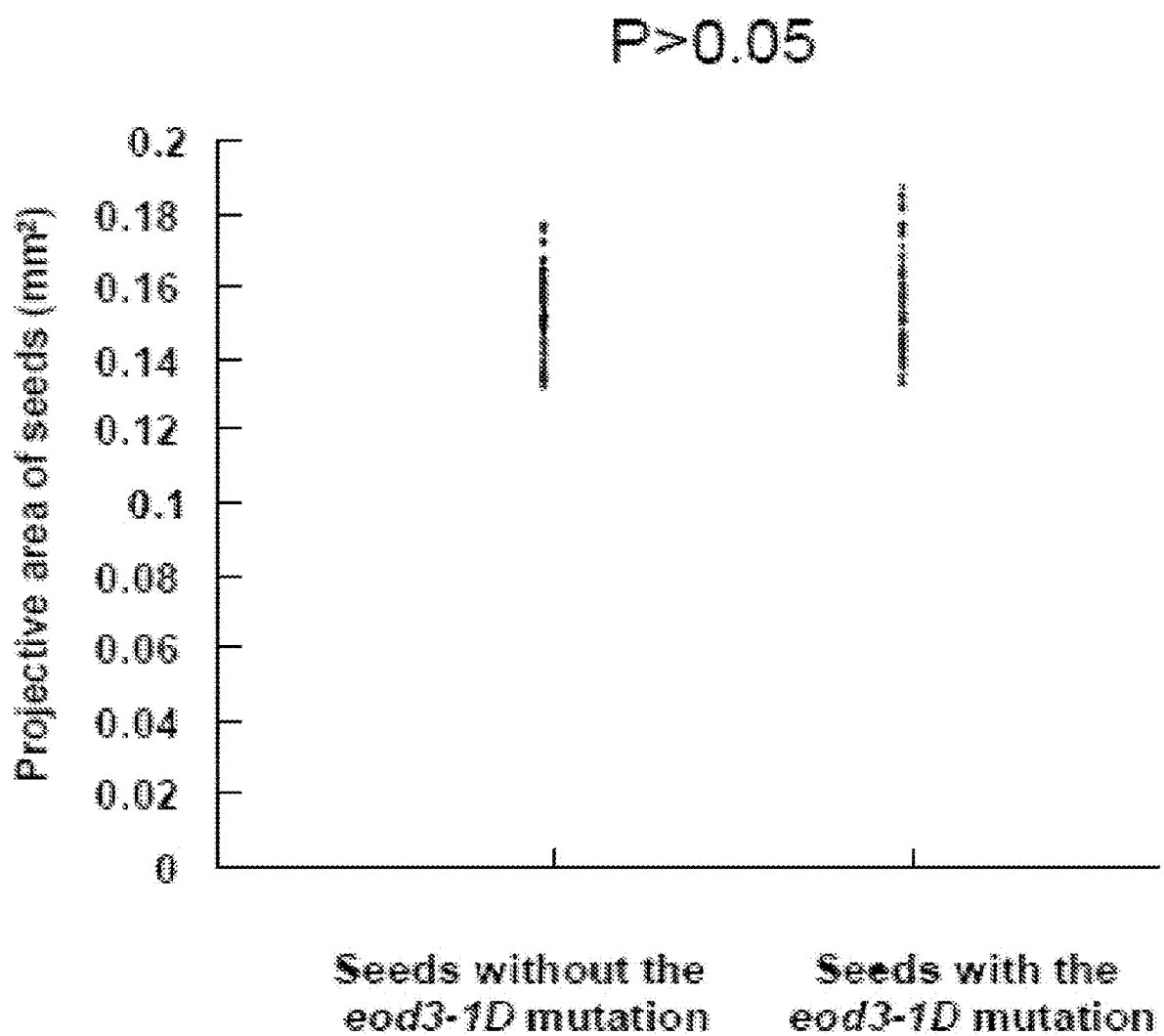
FIG. 14 shows EOD3 acts maternally to influence seed size. Projective area of individual seeds from eod3-1D/+ plants fertilized with wild-type pollen was measured. These seeds were further genotyped for the eod3-1D mutation. The data shows that the eod3-1D mutation is not associated with variation in the size of these seeds (P>0.05, Student's t-test).

To obtain clues about the genetic control of seed size, we asked whether EOD3 functions maternally or zygotically. Reciprocal cross experiments between wild type and eod3-ko1 cyp78a9-ko1 were performed. The effect of eod3-ko1 cyp78a9-ko1 on seed size was observed only when maternal plants are eod3-ko1 cyp78a9-ko1 mutant. Seeds produced by an eod3-ko1 cyp78a9-ko1 mother, regardless of the genotype of the pollen donor, were consistently smaller than those produced by maternal wild-type plants, and eod3-ko1 cyp78a9-ko1 mutant pollen in a wild-type mother produced seeds with wild-type size (FIG. 5A). This indicates that eod3-ko1 cyp78a9-ko1 can act maternally to control seed size. We further did reciprocal cross experiments between wild type and eod3-1D. Pollinating wild-type plants with eod3-1D pollen leads to the development of eod3-1D/+ embryos within a wild-type seed coat. However, the size of the resulting seeds was comparable with that of self-pollinated wild type seeds (FIG. 5B). In contrast, we could not observed the wild-type sized seeds from eod3-1D/+ plants fertilized with wild-type pollen, although half of them contained wild-type embryos. We further measured the size of individual seeds from eod3-1D/+ plants fertilized with wild-type pollen and genotyped the eod3-1D mutation. Our results show that the eod3-1D mutation is not associated with variation in the size of these seeds (FIG. 14). Together, these analyses indicate that the embryo and endosperm genotype for EOD3 do not influence seed size, and EOD3 is required in the sporophytic tissue of the mother plant to promote seed growth.

eod3-ko1 cyp78a9-ko1 Reduces Cell Expansion in the Integuments of Developing Seeds The reciprocal crosses indicate that EOD3 acts maternally to influence seed growth. The integuments surrounding the ovule form the seed coat after fertilization, which may physically restrict seed growth. The integument size of ovules is known to influence seed size (Garcia et al., 2005; Schruff et al., 2006). We therefore asked whether EOD3 functions through the maternal integument to affect seed size. To test this, we characterized mature ovules from wild type and eod3-ko1 cyp78a9-ko1 at 2 days after emasculation.

Figure 15:
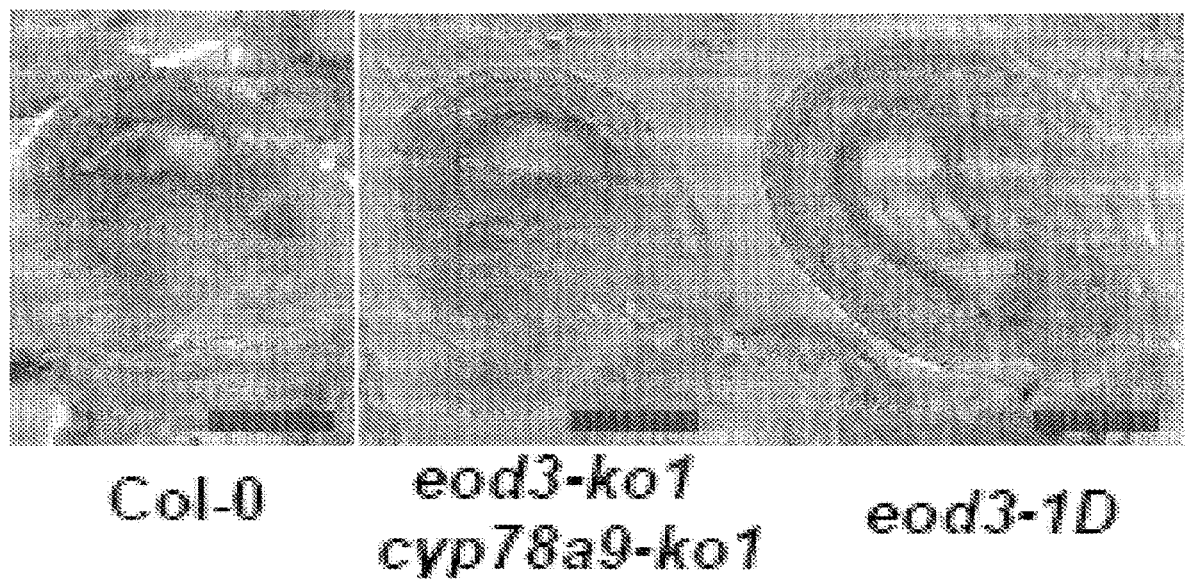
FIG. 15 shows mature ovules from Col-0, eod3-ko1 cyp78a9-ko1 and eod3-1D plants. Bars: A, B, C, 50 μm.
Figure 16:
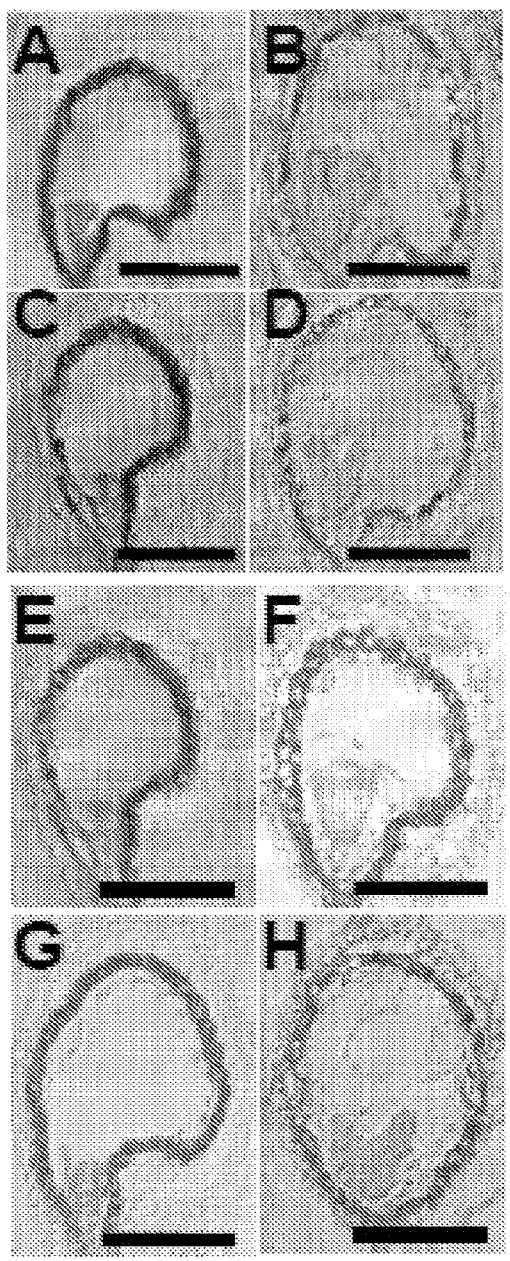
FIG. 16 shows EOD3 and CYP78A9 expression in developing seeds. 16(A and B) show results of in situ hybridization with EOD3 antisense probe. 16(C and D) show results of in situ hybridization with EOD3 sense probe. 16(E and F) show results of in situ hybridization with CYP78A9 antisense probe. 16(G and H) show results of in situ hybridization with CYP78A9 sense probe. Bars: A, B, C, D, E, F, G, H, 50 μm.

Surprisingly, the size of eod3-ko1 cyp78a9-ko1 ovules was not significantly altered, compared with that of wild-type ovules (FIG. 6A and FIG. 15). We further investigated the outer integument length of wild-type and eod3-ko1 cyp78a9-ko1 seeds at specific times after pollination. The size of wild-type and eod3-ko1 cyp78a9-ko1 outer integuments showed a significant difference at 2 days after pollination (DAP) and subsequent time points (FIG. 6B). Previous study showed that the integument of a developing seed could completely stop cell division at 4 d after pollination (Garcia et al., 2005). To assess the contribution of cell proliferation and cell expansion in the integuments of developing seeds to eod3-ko1 cyp78a9-ko1, we measured outer integument cell number and cell size at 6 DAP. Outer integument cell number in eod3-ko1 cyp78a9-ko1 was similar to that in wild type (FIG. 6C), whereas cells in eod3-ko1 cyp78a9-ko1 outer integuments were significantly smaller than those in wild-type outer integuments (FIG. 6D). These results indicate that eod3-ko1 cyp78a9-ko1 restricts cell expansion in the integuments of developing seeds.

eod3-1D Promotes Both Cell Proliferation and Cell Expansion in the Integuments

As the gain-of-function eod3-1D mutant had large seeds, we further asked whether eod3-1D mutant affects the integument size of ovules and developing seeds. The size of eod3-1D ovules was significantly larger than wild-type ovules (FIG. 6A and FIG. S6). eod3-1D also had dramatically larger outer integuments than wild type during the whole process of seed development (FIG. 6B). We further investigated outer integument cell number and cell size of developing seeds at 6 DAP and found that eod3-1D had more and larger outer integument cells than wild type (FIGS. 6C and D).

Effects of eod3-ko1 cyp78a9-ko1 and eod3-1D Mutations on Embryo Development eod3-ko1 cyp78a9-ko1 and eod3-1D had smaller and larger seed coats, respectively. The maternal integument or seed coat acts as a physical constraint on embryo growth. We therefore investigated whether eod3-ko1 cyp78a9-ko1 and eod3-1D integuments could indirectly influence embryo development. To test this, we manually pollinated wild-type, eod3-ko1 cyp78a9-ko1 and eod3-1D plants with their own pollen grains and examined developing embryos at specific times after pollination. In the siliques of wild-type plants, the majority of embryos reached the globular stage at 2DAP, the heart and torpedo stages at 4DAP, the bent-cotyledon stage at 6 DAP, and the stage of the fully filled seed cavity from 10 DAP onward (Table 2). Developmental progresses of eod3-ko1 cyp78a9-ko1 embryos were almost similar to those of wild type. However, morphological development of eod3-1D embryos was slightly slower than wild type at 4 DAP. At 6 DAP, most embryos reached the bent-cotyledon stage, as seen in wild-type plants (Table 2). This phenomenon of embryo development has also been observed in other Arabidopsis mutants (Schruff et al., 2006; Ohto et al., 2009; Zhou et al., 2009). Interestingly, the majority of wild-type embryos fully filled the seed cavity at 12 DAP, while most eod3-1D embryos completely filled the seed cavity at 14 DAP. It is plausible that eod3-1D forms a larger seed cavity than wild type; therefore eod3-1D embryos need to grow for a longer period of time to fill the large seed cavity than wild-type embryos.

Figure 5:
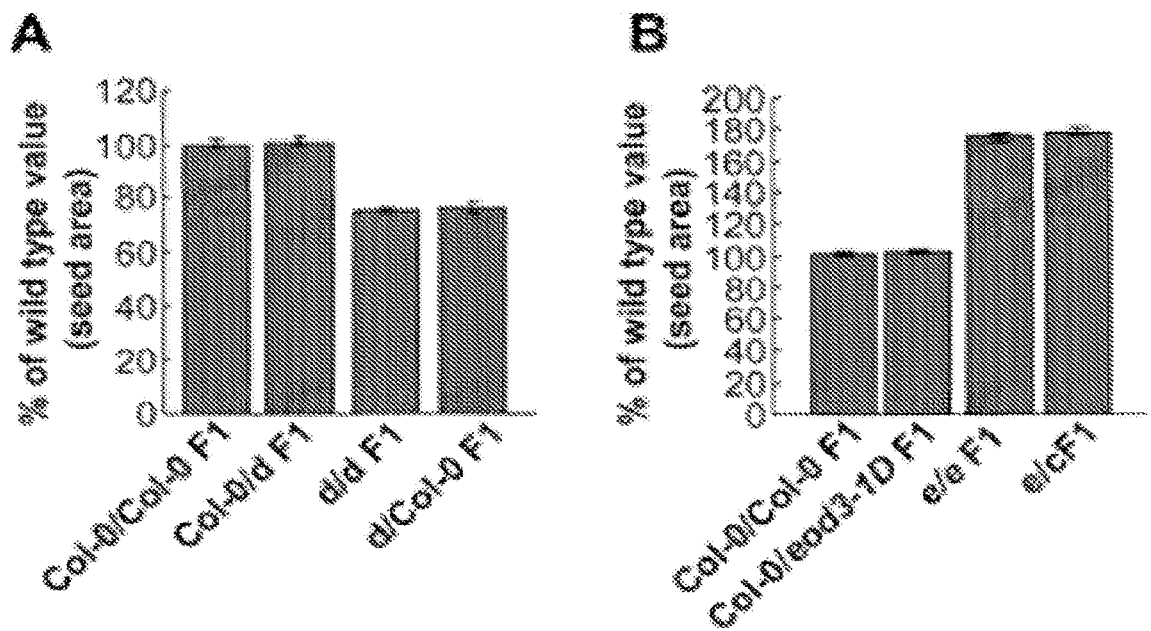
FIG. 5 shows EOD3 acts maternally to control seed size. 5(A) shows projective area of Col-0×Col-0×$F_1$, Col-0× eod3-ko1 cyp78a9-ko1 (d) $F_1$, eod3-ko1 cyp78a9-ko1(d)× eod3-ko1 cyp78a9-ko1(d) $F_1$ and eod3-ko1 cyp78a9-ko1 (d)×Col-0×$F_1$ seeds. 5(B) shows projective area of Col-0× Col-0 $F_1$, Col-0×eod3-1D $F_1$, eod3-1D/+×eod3-1D/+(e/e) $F_1$, eod3-1D/+×Col-0 (e/c) $F_1$ seeds. Values (A and B) are given as mean±SE relative to the respective wild-type values, set at 100%.

Effects of eod3-ko1 cyp78a9-ko1 and eod3-1D Mutations on Embryo Cell Number and Cell Size We isolated and visualized embryos from mature eod3-ko1 cyp78a9-ko1 and eod3-1D seeds. eod3-ko1 cyp78a9-ko1 embryos were significantly smaller than those of wild type, whereas eod3-1D produced large mature embryos compared with wild type (FIG. 7A). The average cotyledon area of eod3-ko1 cyp78a9-ko1 and eod3-1D embryos was about 72% and 196% that of wild-type embryos, respectively (FIG. 7B). The size of embryos is determined by both cell number and cell size. We measured palisade cells in the central regions of wild-type, eod3-ko1 cyp78a9-ko1 and eod3-1D cotyledons to learn which parameter is affected. The average size of eod3-ko1 cyp78a9-ko1 cotyledon cells was 79% that of wild-type cotyledon cells, while the average size of eod3-1D cotyledon cells was 1.36-fold that of the wild-type cotyledon cells (FIG. 7C). The magnitude of the changes in the areas of eod3-ko1 cyp78a9-ko1 and wild-type cotyledons (0.72 times) closely parallels the differences in the areas of cotyledon cells (0.79 times), indicating that eod3-ko1 cyp78a9-ko1 mainly affects embryo cell expansion. Given differences in the areas of eod3-1D and wild-type cotyledons (1.96 times) and cells (1.36 times), we conclude that eod3-1D had approximate 1.44 times more cells than wild type (1.96/1.36=1.44). These results indicate that eod3-ko1 cyp78a9-ko1 formed small embryos as a result of the reduced embryo cell expansion, and eod3-1D had large embryos due to increases in both embryo cell proliferation and cell expansion. Thus, EOD3 could act maternally to influence embryo cell proliferation and cell expansion because EOD3 is solely required in the sporophytic tissue of the mother plant to control seed growth (FIG. 5).

Expression Pattern of EOD3/CYP78A6

Figure 8:
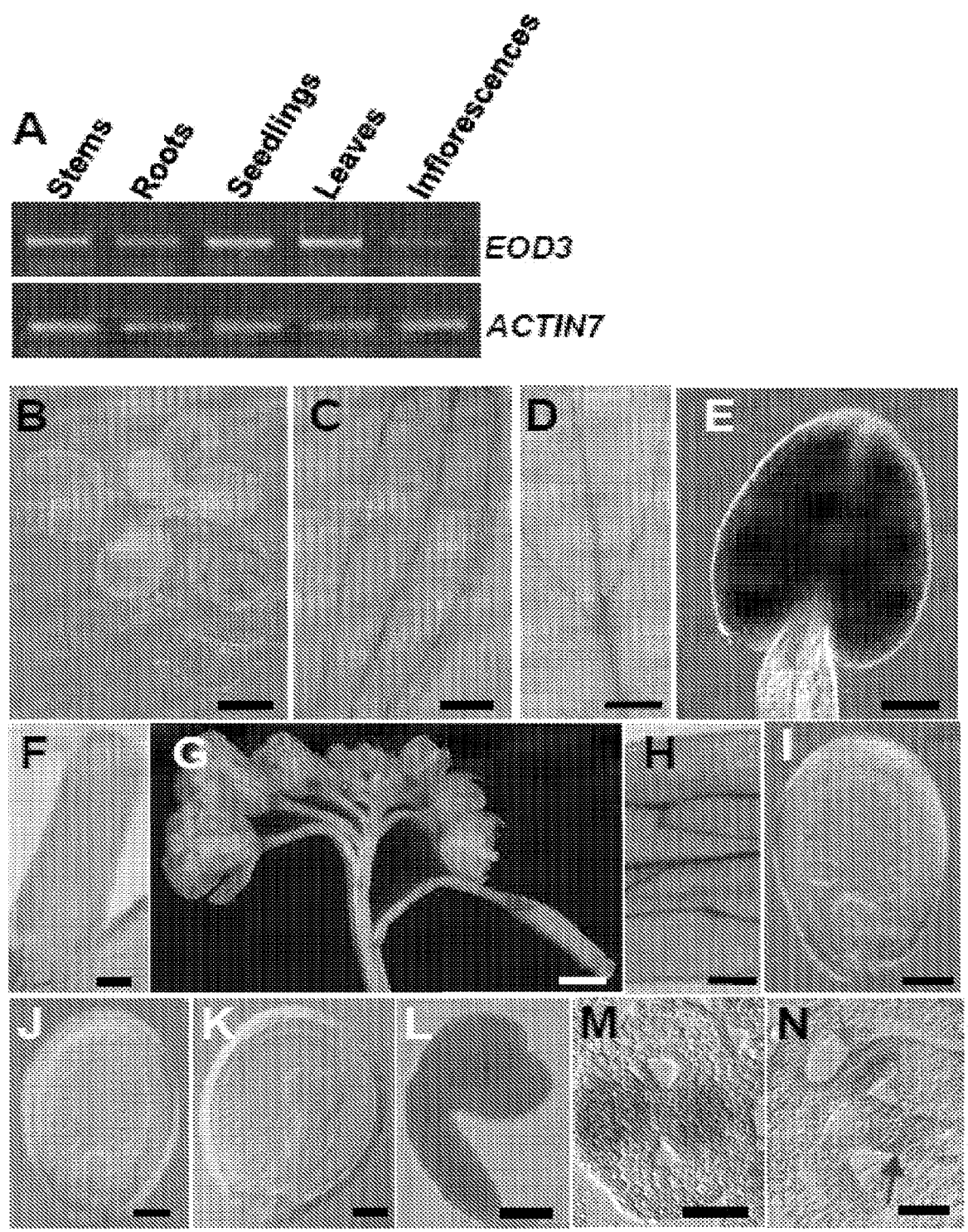
FIG. 8 shows the expression pattern of EOD3. 8(A) shows RT-PCR analysis of the EOD3 gene expression. Total RNA was isolated from stems, roots, 10-d-old seedlings, leaves and inflorescences. 8(B-L) show EOD3 expression activity monitored by pEOD3::GUS transgene expression. Three GUS-expressing lines were observed and all showed a similar pattern, although they differed slightly in the intensity of the staining. Histochemical analysis of GUS activity in a 14-d-old seedling (B), a sepal (C), a petal (D), a stamen (E), a carpel (F), an inflorescence (G), the valve of a silique (H) and embryos (I-L). No GUS activity was detected in developing seeds. 8(M and N) show results of in situ hybridization with EOD3 antisense probe. Cross-section of the carpel of a stage 8 flower (M). Cross-section of the carpel of a stage 12 flower (N). The blue arrow indicates the central region of the septum, and the red arrow shows the funiculus. Bars: B, 2 mm; G, 1 mm; C, E, F, I, J, K, L, 100 µm; D, M, N, 50 µm. H, 200 µm.
Figure 17:
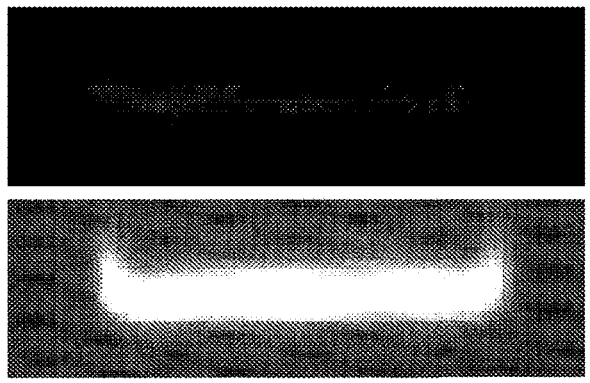
FIG. 17 shows expression of EOD3 in developing seeds using RT-PCR analysis of the EOD3 gene expression. Total RNA was isolated from developing seeds within elongated siliques.

To examine the expression pattern of EOD3, RT-PCR were performed with total RNA from various tissues with EOD3-specific primers, including roots, stems, leaves, seedlings and inflorescences. EOD3 mRNA can be detected in all plant organs tested (FIG. 8A). To monitor EOD3 expression pattern during development, the pEOD3::GUS vector was constructed and transformed to wild-type plants. Tissues at different development stages were stained with GUS solution. In 14-d-old seedlings, GUS activity was detected in leaves. Relatively high GUS activity was observed in old leaves than in young ones (FIG. 8B). In flowers, GUS expression was detected in sepals, petals, stamens and carpels (FIG. 8C-H). Surprisingly, there was no EOD3 expression during the development of seeds (FIG. 8I-L; FIG. 17). We further performed in situ hybridization experiments to investigate expression of EOD3. EOD3 accumulated in the medial gynoecial domains at stage 8 (FIG. 8M). During stage 12, the EOD3 transcript was found within the central region of the septum (FIG. 8N). Expression was also seen in the funiculus (FIG. 8N). However, EOD3 expression was not detected in integuments, embryos, and endosperms during seed development (FIG. 16A-D), consistent with the GUS staining results. Similarly, CYP78A9 was also not observed in developing seeds (FIG. 16E-H). These analyses indicate that EOD3 is a temporally and spatially expressed gene.

Figure 9:
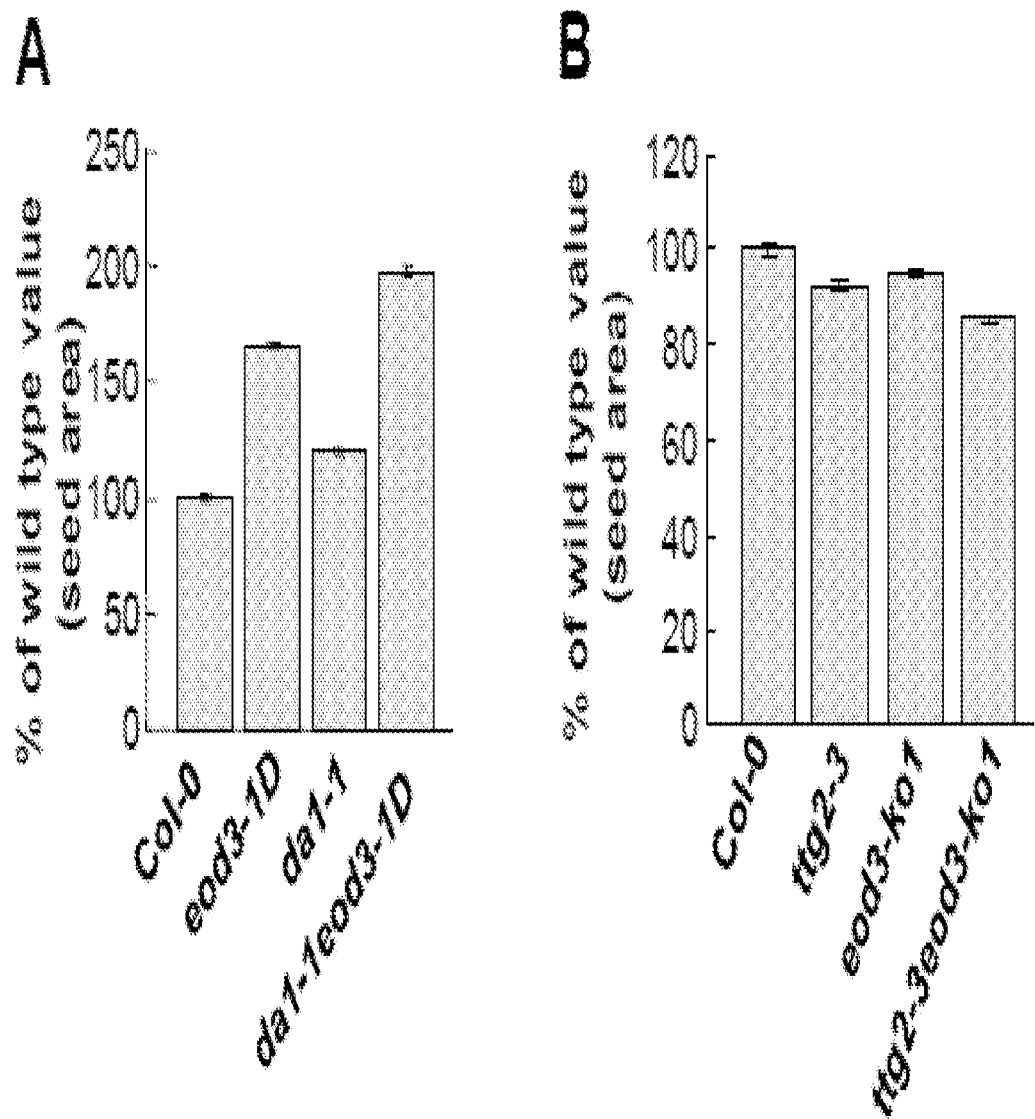
FIG. 9 shows genetic interactions of eod3 with da1-1 and ttg2-3 mutants. 9(A) shows the projective area of wild-type, eod3-1D, da1-1 and da1-1 eod3-1D seeds. 9(B) shows projective area of wild-type, ttg2-3, eod3-ko1 and ttg2-3 eod3-ko1 seeds. Values (A-B) are given as mean±SE relative to the respective wild-type values, set at 100%.

EOD3 May Function Independently of DA1 and TTG2 to Influence Seed Size da1-1 mutant had large seeds due to the increased cell proliferation in maternal integuments (Li et al., 2008), while eod3-ko mutants produced small seeds as a result of the reduced cell expansion in the integuments after fertilization, providing indication that EOD3 and DA1 might function in different pathways. However, the gain-of-function eod3-1D mutant promotes both cell proliferation and cell expansion in the integuments. We therefore asked whether there are any genetic interactions between eod3-1D and da1-1. To test this, we measured the size of seeds in wild-type, da1-1, eod3-1D and eod3-1D da1-1 plants. The genetic interaction between eod3-1D and da1-1 was essentially additive for seed size, compared with their parental lines (FIG. 9A), further indicating that EOD3 might function independently of DA1 to control seed size.

The TTG2 gene acts maternally to promote cell expansion in the integuments. ttg2 mutants produced small seeds as a result of the reduced cell elongation in the integuments (Garcia et al., 2005). To determine the genetic interaction between EOD3 and TTG2, we generated ttg2-3 eod3-ko1 double mutant. The genetic interaction between eod3-ko1 and ttg2-3 was additive for seed size, compared with their parental lines (FIG. 9B), providing indication that EOD3 functions to control seed growth separately from TTG2.

EOD3 Promotes Seed Growth by Increasing Maternal Integument Size

In this study, we identified the role of EOD3/CYP78A6 in seed size control. eod3-1D gain-of-function mutant formed larger seeds, while eod3-ko loss-of-function mutants exhibited smaller seeds. In addition, mutations in its most closely related family member CYP78A9 synergistically enhanced the seed size phenotype of eod3-ko mutants (FIGS. 4C, F and G), indicating that EOD3/CYP78A6 acts redundantly with CYP78A9 to influence seed growth. However, the eod3-1D mutant exhibited partial sterility although eod3-ko mutants had normal fertility. The tradeoff between seed number and size in many species (Harper et al., 1970), including Arabidopsis (Alonso-Blanco et al., 1999), has been observed. Our results show that the effect of eod3-1D on seed size is not primarily due to its effect on fertility. Similarly, recent studies show that ap2 and arf2 mutations increase seed size partly because of reduced fertility but also through a separate maternal effect on seed growth (Jofuku et al., 2005; Ohto et al., 2005; Schruff et al., 2006).

Reciprocal cross experiments show that EOD3 acts maternally to affect seed growth. The integuments surrounding the ovule are maternal tissues and form the seed coat after fertilization. Altered maternal integument size such as those seen in arf2, da1-1 and klu ovules is known to contribute to changes in seed size (Schruff et al., 2006; Li et al., 2008; Adamski et al., 2009). However, the size of mature eod3-ko1 cyp78a9-ko1 ovules was similar to that of wild-type ovules, indicating that the size difference between the wild-type and eod3-ko1 cyp78a9-ko1 seeds happens after fertilization. Consistent with this idea, eod3-ko1 cyp78a9-ko1 integuments were smaller than wild-type integuments from 2DAP onward (FIG. 6B). By contrast, eod3-1D formed large integuments in mature ovules and developing seeds (FIGS. 6A and B). Thus, a general theme emerging from these studies is that the control of maternal integument size is one of critical mechanisms for determining final seed size.

Figure 6:
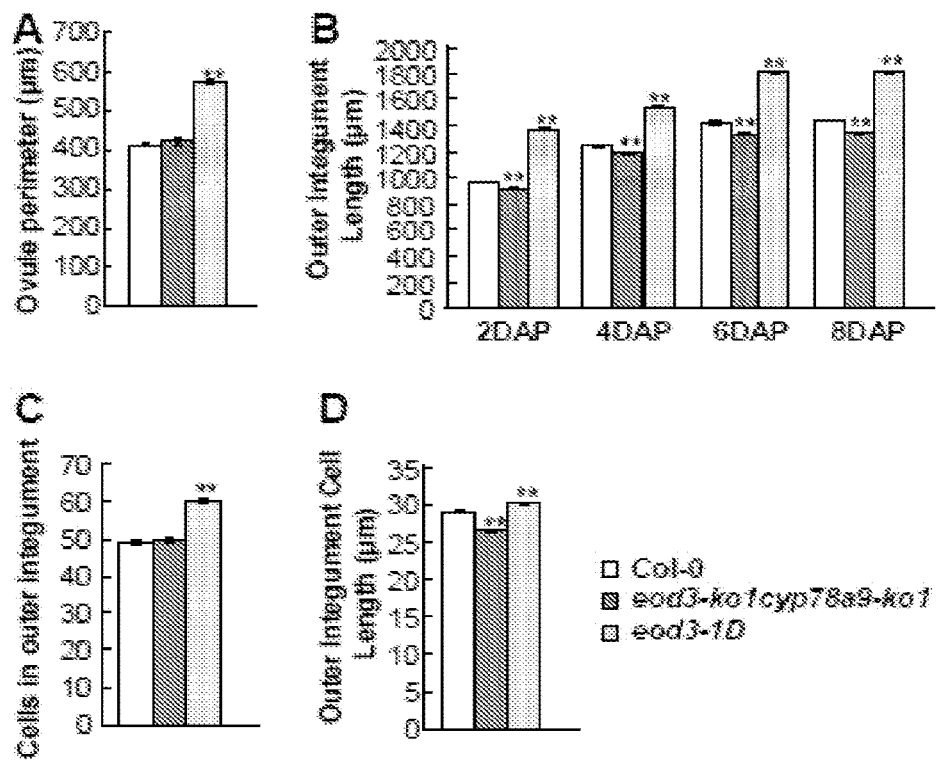
FIG. 6 shows cell size and cell number in the integuments of wild-type, eod3-ko1 cyp78a9-ko1 and eod3-1D developing seeds. (A) shows mature ovule perimeter. 6(B) shows the outer integument length at specific times after pollination, as measured from the insertion point at the funiculus to the tip at the micropyle. 6(C) shows the number of cells in the outer integument at 6DAP. 6(D) shows the average length of cells in the outer integument at 6DAP calculated from the outer integument length and cell number for individual seeds. Values (A-D) are given as mean±SE. **, P<0.01 compared with the wild type (Student's t-test).
Figure 7:
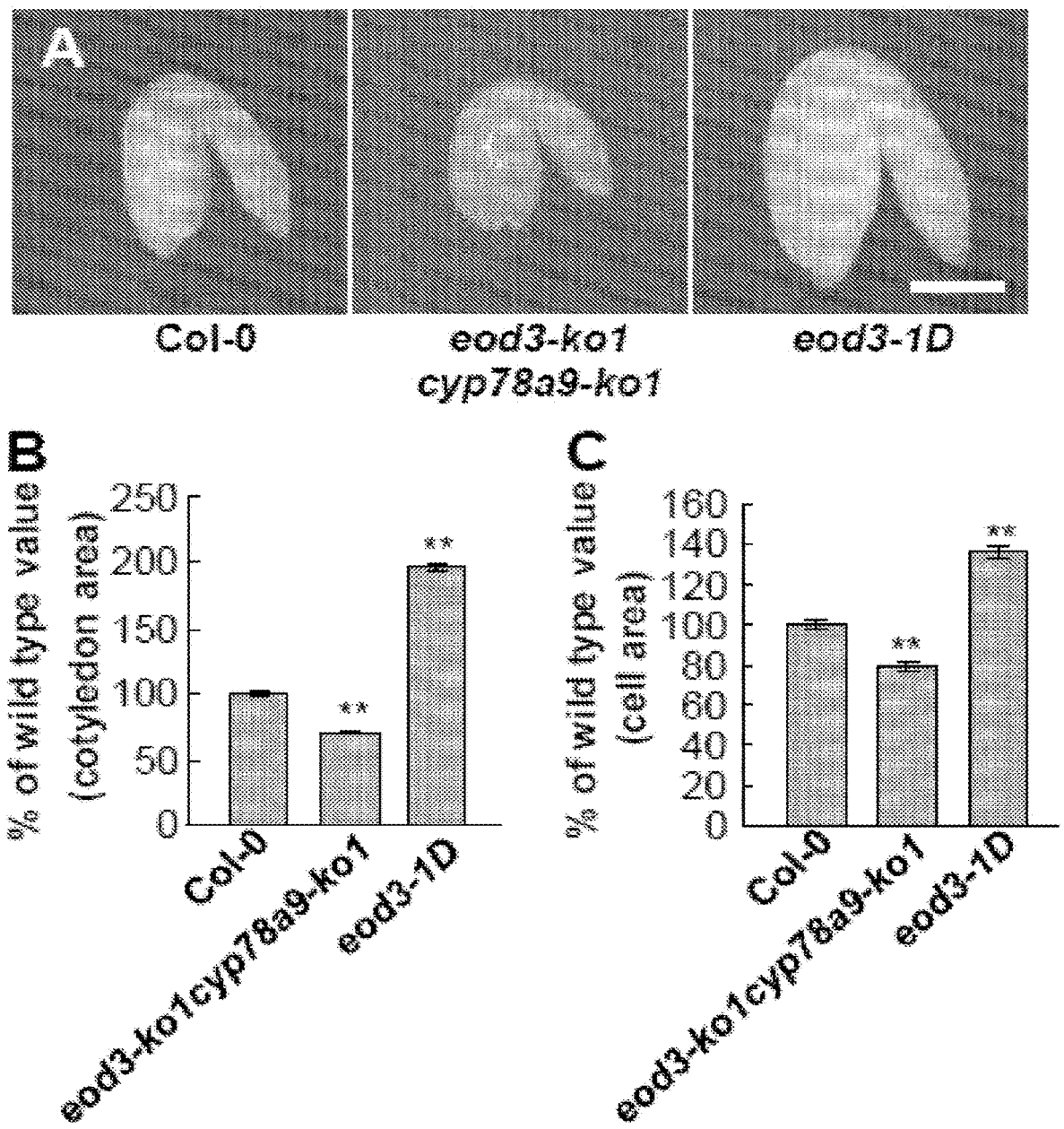
FIG. 7 shows cell size and cell number in cotyledons of mature wild-type, eod3-ko1 cyp78a9-ko1 and eod3-1D embryos. 7(A) shows mature embryos of wild type, eod3-ko1 cyp78a9-ko1 and eod3-1D. 7(B) shows cotyledon area of wild-type, eod3-ko1 cyp78a9-ko1 and eod3-1D embryos. 7(C) Average area of palisade cells in cotyledons of wild-type, eod3-ko1 cyp78a9-ko1 and eod3-1D embryos. Values (B and C) are given as mean±SE relative to the respective wild-type values, set at 100%. **, P<0.01 compared with the wild type (Student's t-test). Bar: A, 0.25 mm.

The size of the integument or seed coat is determined by cell proliferation and cell expansion. The cell number in the integuments of the mature ovule sets the growth potential of the seed coat after fertilization. For example, arf2 and da1-1 mutants had large ovules with more cells, resulting in large seeds (Schruff et al., 2006; Li et al., 2008), whereas klu mutants formed small ovules with less cells, leading to small seeds (Adamski et al., 2009). After fertilization, cells in integuments mainly undergo expansion. Our results indicate that eod3-ko1 cyp78a9-ko1 mutant formed normal-sized ovules, but smaller developing seeds as a result of the reduced cell expansion in the integuments after fertilization (FIG. 6). However, eod3-1D promoted both cell proliferation and cell elongation in the integuments of developing seeds, resulting in large volume of a seed cavity. Therefore, integument growth is driven by both cell proliferation and cell expansion; these two processes are assumed to be coordinated. In addition, our reciprocal cross experiments provide a demonstration of maternal sporophytic control of embryo growth (FIG. 5; FIG. 7; FIG. 14). The maternal integument or seed coat, which acts as a physical constraint on embryo and endosperm growth, may set an upper limit to final seed size.

The CYP78A Family Members have Overlapping and Distinct Functions in Seed Growth EOD3 encodes a cytochrome P450 CYP78A6, one of the CYP78A family members. The other CYP78A subfamily member genes have been isolated as growth regulators. Overexpression of CYP78A9, which is most closely related to EOD3/CYP78A6, induced large and seedless silique in Arabidopsis (Ito and Meyerowitz, 2000). To a certain extent, plants overexpressing EOD3/CYP78A6 and CYP78A9 exhibited similar growth phenotypes, such as large siliques and short stamens (FIGS. 2C and D) (Ito and Meyerowitz, 2000), indicating that these two genes might affect the same or related metabolic network. In line with this idea, our genetic analyses demonstrate that the cyp78a9-ko1 mutation synergistically enhanced the seed size phenotype of eod3-ko mutants (FIGS. 4C and F). This provides indication that EOD3 and CYP78A9 may have overlapping functions in seed size control.

Another CYP78A subfamily member KLU/CYP78A5 also affects seed size by promoting cell proliferation in the integuments of ovules (Adamski et al., 2009). klu mutants produced smaller seeds than wild type due to small ovules with less cells (Adamski et al., 2009). By contrast, eod3-ko1 cyp78a9-ko1 mutants did not significantly affect the size of ovules, but restricted cell expansion in the integuments of developing seeds. These findings provide indication that KLU may act in the cell proliferation phase at the early stages of integument development, and EOD3 mainly functions in the cell expansion phase at the later stages of integument growth.

EOD3 and CYP78A9 May Control Seed Growth in a Non-Cell-Autonomous Manner

Figure 12:
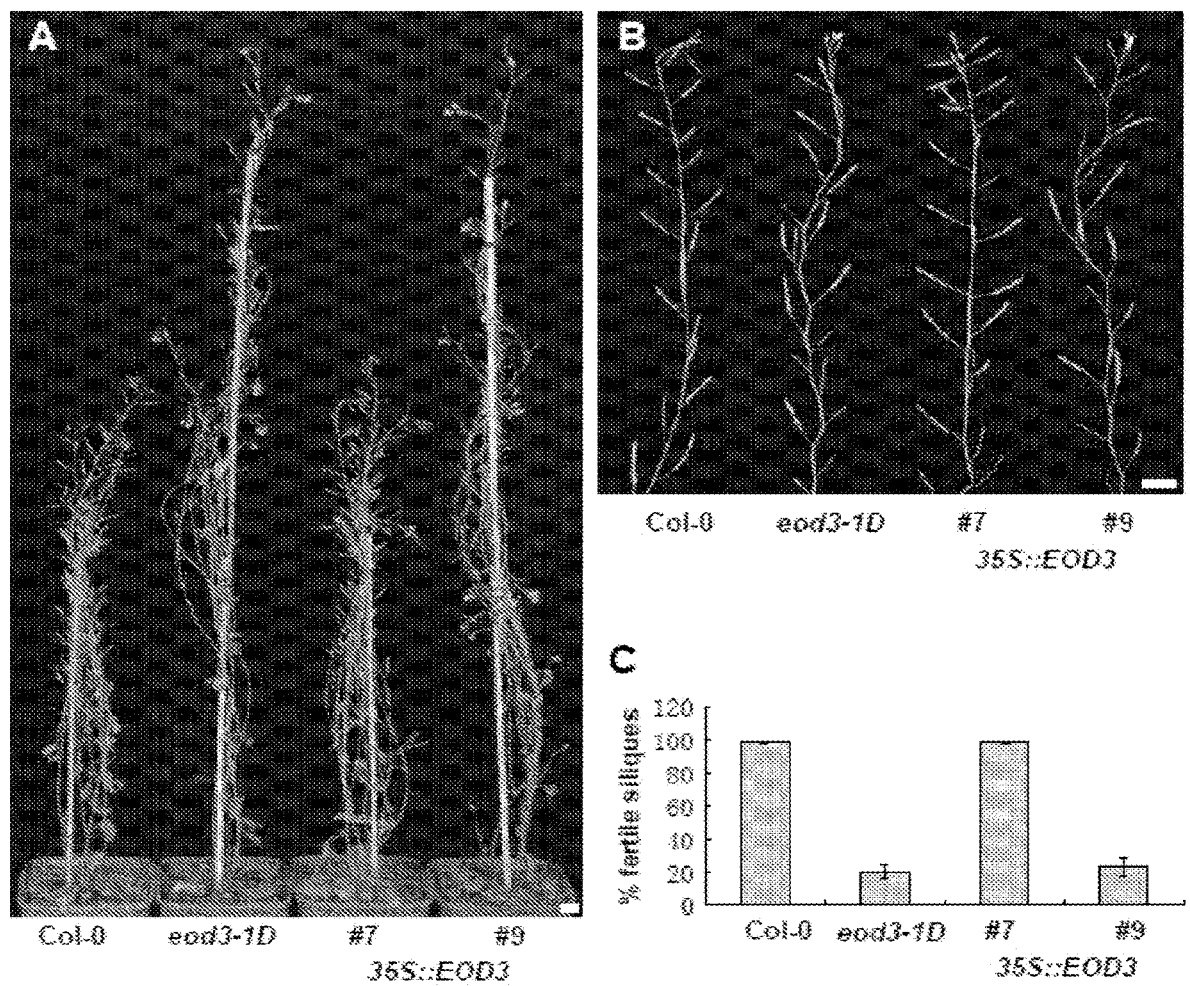
FIG. 12 shows phenotypes of wild-type, eod3-1D and 35S::EOD3 plants. 12A shows 56-d-old wild-type, eod3-1D, 35S::EOD3#7 and 35S::EOD3#9 plants. 12B shows primary inflorescence stems of wild-type, eod3-1D, 35S::EOD3#7 and 3.5S::EOD3#9 plants. 12C shows percent of fertile siliques on the primary inflorescence. Values (C) are given as mean±SE. Bars: A, B, 1 cm.

Another interesting feature of the CYP78A subfamily members is to generate mobile factors mediating organ growth (Miyoshi et al., 2004; Anastasiou et al., 2007). Rice PLA1/CYP78A11 affected cell division in the shoot apical meristem (SAM), but CYP78A11 expression was not detected in the shoot apical meristem, suggesting that CYP78A11 most likely acts through its non-cell-autonomous function (Miyoshi et al., 2004). *Arabidopsis* CYP78A5 has been proposed to be involved in generating a mobile signal distinct from the classical phytohormones (Anastasiou et al., 2007). However, mobile growth substances remain to be discovered. Interestingly, EOD3 and CYP78A9 were not detected in the maternal integuments of developing seeds (FIG. S7) (Ito and Meyerowitz, 2000), but eod3-ko, cyp78a9-ko and eod3-ko cyp78a9-ko mutants produced small seeds (FIGS. 4C and F). This suggests that EOD3 and CYP78A9 might control seed growth in a non-cell-autonomous manner, as proposed for other CYP78A subfamily members (Miyoshi et al., 2004; Anastasiou et al., 2007). However, EOD3 expression was detected in other organs, such as leaves and carpels (FIGS. 8B and F), providing indication that EOD3 might promote leaf and carpel growth in a cell-autonomous manner. Several *Arabidopsis* mutants with large organs also exhibited large seeds (Schruff et al., 2006; Li et al., 2008), suggesting a possible link between organ size and seed growth. By contrast, several other mutants with large organs produced normal-sized seeds (Szecsi et al., 2006; White, 2006), indicating that organ size is not always positively related to seed growth. 35S::EOD3#7 plants exhibited normal growth and fertility, but produced significantly larger seeds than wild type (FIGS. 3C and D; FIG. 12), providing indication that the effect of EOD3 on seed size might not be due to its effect on organ size. CYP78A9 has been suggested to be involved in producing an undiscovered plant growth substance (Ito and Meyerowitz, 2000). One of the functions of EOD3 might be production of a signal that promotes integument growth. Eventually, the elucidation of the biochemical function of these gene products may lead to the discovery of one or more new plant growth substances with use in control of seed size.

EOD3 Controls Seed Growth in *Oryza sativa*

The *Arabidopsis* EOD3 coding sequence was sub-cloned and overexpressed in *Oryza sativa*. The areas of the seeds from T0 transgenic *Oryza sativa* plants were then determined.

Figure 20:
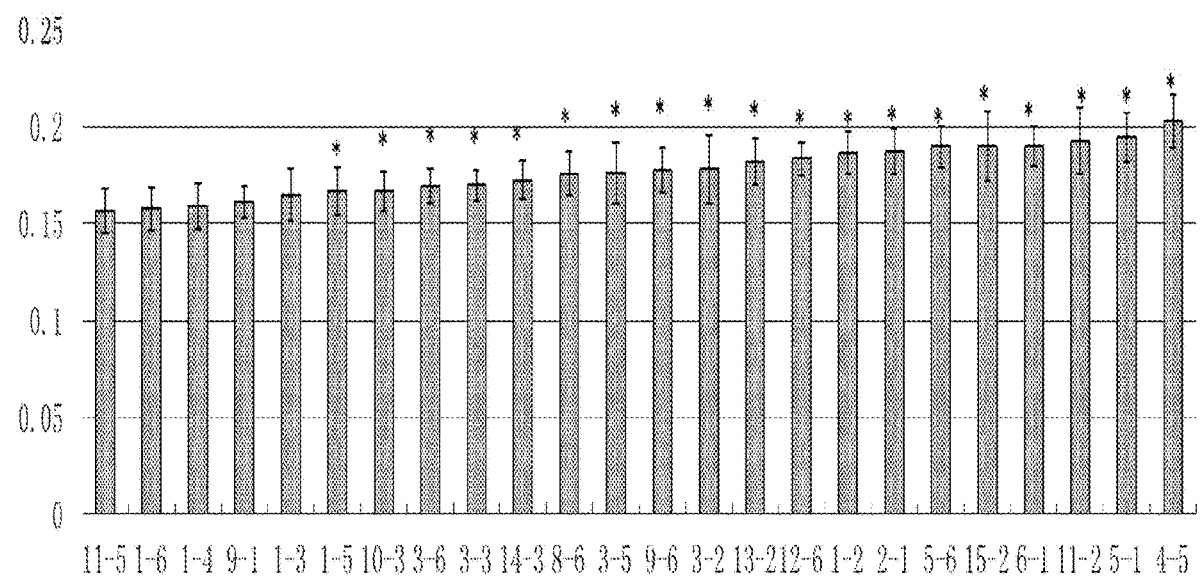
FIG. 20 shows seed size in T0 transgenic *Oryza sativa* overexpressing EOD3. *represents p<0.01 in t-test with the smallest seed line (11-5).

The transgenic rice plant lines (To) showed a range of different average seed sizes (FIG. 20), as expected from variations in insertion site, expression levels and other factors. However, statistically significant differences in seed size were found between a number of the To lines and the smallest seed line (11-5) (FIG. 20; $P<0.01$). These statistically significant differences show that that Eod3 overexpression increases seed size in rice.

REFERENCES

Adamski, N. M. et al. (2009) *Proc Natl Acad Sci USA*, 106, 20115-20120
Alonso-Blanco, C. et al (1999) *Proc Natl Acad Sci USA*, 96, 4710-4717
Anastasiou, E. et al (2007) *Dev Cell*, 13, 843-856.
Fan, C. et al (2006) *Theor Appl Genet*, 112, 1164-1171.
Fan, J. et al (2009) *Plant Physiol*, 150, 1750-1761.
Garcia, D. et al 2003) *Plant Physiol*, 131, 1661-1670.
Garcia, D. et al (2005) *Plant Cell*, 17, 52-60.
Gegas, V. C. et al (2010). *Plant Cell*, 22, 1046-1056.
Harper, J. L. et al (1970) *Annual Review of Ecology and Systematics*, 1, 327-356
Ito, T. et al (2000) *Plant Cell*, 12, 1541-1550.
Jofuku, K. D. et al (2005). *Proc Natl Acad Sci USA*, 102, 3117-3122.
Li, J. et al (2004). *Genetics*, 168, 2187-2195.
Li, Y. et al (2006). *Genome Res*, 16, 414-427.
Li, Y., Zheng et al (2008) *Genes Dev*, 22, 1331-1336.
Li, Y. et al (2003). *Plant Cell*, 15, 2020-2031.
Liu, Y. G. et al (1995) *Plant J*, 8, 457-463.
Lopes, M. A et al (1993). *Plant Cell*, 5, 1383-1399.
Luo, M. et al (2005) *Proc Natl Acad Sci USA*, 102, 17531-17536.
Miyoshi, K. et al (2004) *Proc Natl Acad Sci USA*, 101, 875-880.
Moles, A. T. et al (2005) *Science*, 307, 576-580.
Ohto, M. A. et al (2005) *Proc Natl Acad Sci USA*, 102, 3123-3128.
Ohto, M. A. et al (2009) *Sex Plant Reprod*, 22, 277-289.
Orsi, C. H. et al (2009) *PLoS Genet*, 5, e1000347.
Schruff, M. C. et al (2006) 133, 251-261.
Scott, R. J. et al (1998). *Development*, 125, 3329-3341.
Shomura, A. et al (2008) *Nat Genet*, 40, 1023-1028.
Song, X. J. et al (2007) *Nat Genet*, 39, 623-630.
Szecsi, J. et al (2006) *Embo J*, 25, 3912-3920.
Wang, A. et al (2010) *Plant J*, 64, 670-679.
Weng, J. et al (2008) *Cell Res*, 18, 1199-1209.
Westoby, M. et al (2002) *Annual Review of Ecology and Systematics*, 33, 125-159.
White, D. W. (2006) *Proc Natl Acad Sci USA*, 103, 13238-13243.
Xiao, W. et al (2006) *Plant Physiol*, 142, 1160-1168.
Zhou, Y. et al. (2009) *Plant Cell*, 21, 106-117.
Zondlo, S. C. et al (1999) *Plant J*, 19, 259-268.

| Phenotypes of wild-type, eod3-ko1, eyp78a9-ko1, eod3-ko1 cyp78a9-ko1 and eod3-1D plants | | | | | |
| --- | --- | --- | --- | --- | --- |
| | Col-0 | eod3-ko1 | cyp78a9-ko1 | eod3-ko1cyp78a9-ko1 | eod3-1D |
| Petal area (mm$^2$) | 1.99 ± 0.11 | 1.99 ± 0.09 | 1.95 ± 0.10 | 1.86 ± 0.09** | 2.48 ± 0.16** |
| Petal length (mm) | 3.08 ± 0.10 | 3.08 ± 0.09 | 3.05 ± 0.12 | 3.02 ± 0.08** | 3.32 ± 0.11** |
| Petal width (mm) | 1.03 ± 0.04 | 1.03 ± 0.04 | 1.02 ± 0.04 | 1.01 ± 0.03** | 1.18 ± 0.05** |
| Leaf area (cm$^2$) | 1.02 ± 0.07 | 1.01 ± 0.07 | 0.99 ± 0.08 | 0.91 ± 0.08** | 1.34 ± 0.11** |
| Leaf length (cm) | 1.29 ± 0.05 | 1.28 ± 0.04 | 1.27 ± 0.05 | 1.24 ± 0.07* | 1.40 ± 0.09** |
| Leaf width (cm) | 1.01 ± 0.05 | 1.00 ± 0.04 | 0.99 ± 0.03 | 0.92 ± 0.04** | 1.16 ± 0.05** |
| Plant height (cm) | 36.8 ± 1.9 | 36.7 ± 1.7 | 36.6 ± 1.5 | 33.5 ± 1.8** | 64.8 ± 3.0** |
| Stem thickness (mm) | 0.88 ± 0.03 | 0.87 ± 0.03 | 0.87 ± 0.02 | 0.87 ± 0.04 | 0.99 ± 0.03** |
| Number of RI | 3.0 ± 0.7 | 3.0 ± 0.6 | 2.9 ± 0.6 | 2.9 ± 0.6 | 3.0 ± 0.6 |
| Number of RII | 4.0 ± 1.3 | 4.0 ± 0.9 | 3.9 ± 1.3 | 3.9 ± 1.1 | 4.0 ± 0.9 |
| Number of CI | 2.5 ± 0.5 | 2.5 ± 0.5 | 2.4 ± 0.5 | 2.4 ± 0.5 | 2.5 ± 0.5 |
| Number of CII | 5.0 ± 0.8 | 5.0 ± 1.0 | 4.9 ± 1.0 | 4.9 ± 1.1 | 5.0 ± 0.8 |
| Leaf number | 12.7 ± 0.8 | 12.6 ± 0.7 | 12.6 ± 0.7 | 12.6 ± 0.5 | 12.8 ± 0.7 |

-continued

Phenotypes of wild-type, eod3-ko1, eyp78a9-ko1, eod3-ko1 cyp78a9-ko1 and eod3-1D plants

|  | Col-0 | eod3-ko1 | cyp78a9-ko1 | eod3-ko1cyp78a9-ko1 | eod3-1D |
|---|---|---|---|---|---|
| Elongated siliques | 328 ± 28 | 326 ± 32 | 324 ± 34 | 269 ± 22** | 87 ± 18** |
| % fertile siliques | 99.1 ± 1.6 | 99.0 ± 1.5 | 98.9 ± 1.7 | 99.0 ± 1.8 | 21.1 ± 11.8** |
| Ovule number per silique | 53.9 ± 2.3 | 53.7 ± 2.6 | 53.4 ± 2.3 | 52.9 ± 2.1 | 53.1 ± 2.9 |
| Silique fertility | 98.4 ± 4.2% | 98.2 ± 4.8% | 98.2 ± 4.3% | 98.1 ± 3.9% | 51.8 ± 26.0%** |

Number of primary rosette branches (RI), second rosette branches (RII), primary cauline branches (CI), and second cauline branches (CII) were counted at 30 d after bolting. Primary rosette branches (RI) are axillary branches from rosette leaves, and second rosette branches (RII) are axillary branches from RI. Similarly, primary cauline branches (CI) are axillary branches from cauline leaves, and second cauline branches (CII) are axillary branches from CI. Opened flowers on the primary inflorescence were used to investigate ovules per silique. The elongated siliques on the primary inflorescence were used to investigate fertility. All values are given as mean ± SD. **, $P < 0.01$ and *, $P < 0.05$ compared with the wild type (Student's t-test).

TABLE 2

Developmental stages of embryogenesis

| DAP | Genotype | Quadrant or octant | Dermatogen | Globular | Transition | Heart | Torpedo | Bent cotyledon | The stage of the fully filled seed cavity |
|---|---|---|---|---|---|---|---|---|---|
| 2 | Col-0 | 9 | 23 | 67 | | | | | |
|   | e3a9 | 8 | 21 | 65 | | | | | |
|   | eod3-1D | 14 | 29 | 52 | | | | | |
| 4 | Col-0 | | | | 5 | 36 | 72 | | |
|   | e3a9 | | | | 9 | 39 | 62 | | |
|   | eod3-1D | | | 17 | 28 | 40 | 13 | | |
| 6 | Col-0 | | | | | | 41 | 88 | |
|   | e3a9 | | | | | | 29 | 97 | |
|   | eod3-1D | | | | | | 34 | 86 | |
| 8 | Col-0 | | | | | | 7 | 70 | |
|   | e3a9 | | | | | | 4 | 72 | |
|   | eod3-1D | | | | | | 18 | 80 | |
| 10 | Col-0 | | | | | | | 80 | 28 |
|   | e3a9 | | | | | | | 77 | 13 |
|   | eod3-1D | | | | | | | 98 | |
| 12 | Col-0 | | | | | | | 10 | 90 |
|   | e3a9 | | | | | | | 17 | 70 |
|   | eod3-1D | | | | | | | 89 | |
| 14 | Col-0 | | | | | | | | 96 |
|   | e3a9 | | | | | | | | 124 |
|   | eod3-1D | | | | | | | 26 | 68 |

Siliques from the wild-type (Col-0), eod3-ko1cyp78a9-ko1 (e3a9) and eod3-1D plants were dissected. The number of embryos at each developmental stage was recorded.

TABLE 3

| Name | Primers |
|---|---|
| | Primers for verifying T-DNA |
| eod3-1D-LP | GGTCTAAGATTTCTCTCGTGTC (SEQ ID NO: 98) |
| eod3-1D-RP | CGTACGTCTTCTATTACTCCAC (SEQ ID NO: 99) |
| CS833552LP | AACTCCAAAGGATCAACCCAC (SEQ ID NO: 100) |
| CS833552RP | CCGGTTAAAGAATCGGCTTAC (SEQ ID NO: 101) |
| CS806696LP | GACTTGCAAAGATCGTTCACC (SEQ ID NO: 102) |
| CS806696RP | ACTCAATGTGACGTGTTGTGG (SEQ ID NO: 103) |
| SALK121278LP | TTTGATCGAGTGGATTCTTGC (SEQ ID NO: 104) |
| SALK121278RP | ATATTTGCTTGTAATCGGGGC (SEQ ID NO: 105) |
| SALK148838LP(TTG2) | TAAAACCAAACGACACCGTTC (SEQ ID NO: 106) |
| SALK148838RP(TTG2) | TCCAAGTTTGTTGACGATTCC (SEQ ID NO: 107) |
| OJF22 | CGAGTATCAATGGAAACTTAACCG (SEQ ID NO: 108) |
| OJF23 | AACGGAGAGTGGCTTGAGAT (SEQ ID NO: 109) |
| OJF24 | TGGCCCTTATGGTTTCTGCA (SEQ ID NO: 110) |
| AD1 | NTCGA(G/C)T(A/T)T(G/C)G(A/T)GTT (SEQ ID NO: 111) |
| SALK_LBa1 | TGGTTCACGTAGTGGGCCATCG (SEQ ID NO: 112) |
| SAIL_LB2 | GCTTCCTATTATATCTTCCCAAATTACCAATACA (SEQ ID NO: 113) |

TABLE 3 -continued

| Name | Primers |
|---|---|
| Primers for constructs | |
| EOD3CDS-F | *CTGCAG*ATGGCTACGAAACTCGAAAGCTCC (SEQ ID NO: 114) |
| EOD3CDS-R | *CTGCAG*TTAACTGCGCCTACGGCGCAATTT (SEQ ID NO: 115) |
| EOD3PROM-F | *GAGCTC*TGTCTCGTGGATAAGTAG (SEQ ID NO: 116) |
| EOD3PROM-R | *CCATGG*GGCGGATCAAAGCAAAGTAAG (SEQ ID NO: 117) |
| Primers for RT-PCR | |
| EOD3RT-F | ACCAACCTTGCCTTCTCC (SEQ ID NO: 118) |
| EOD3RT-R | CGTCTCGGCTCTTCTGATT (SEQ ID NO: 119) |
| AT2G46670RT-F | ACAACGAGCAGCAACCA (SEQ ID NO: 120) |
| AT2G46670RT-R | TCTTCAACCGGAACTTCAT (SEQ ID NO: 121) |
| ACTIN7-F | ATCCTTCCTGATATCGAC (SEQ ID NO: 122) |
| ACTIN7-R | GAGAAGATGACTCAGATC (SEQ ID NO: 123) |
| Primers for quantitative real-time RT-PCR | |
| EOD3QRT-F | CCGGTTAAAGAATCGGCTTA (SEQ ID NO: 124) |
| EOD3QRT-R | TTGAGATCACTCGTCGTTGC (SEQ ID NO: 125) |
| ACTIN2-F | GAAATCACAGCACTTGCACC (SEQ ID NO: 126) |
| ACTIN2-R | AAGCCTTTGATCTTGAGAGC (SEQ ID NO: 127) |
| Primers for in situ hybridization | |
| EOD3INSITU-F | AAAGAAGCTCATATGAGAATTA (SEQ ID NO: 128) |
| EOD3INSITU-R | TGGTGTAAATATAAATTGAAACT (SEQ ID NO: 129) |
| CYP78A9INSITU-F | TTAGTGTATGATAAGGCTAAGGCT (SEQ ID NO: 130) |
| CYP78A9INSITU-R | GTATTAACTTTTCTTTGTGACA (SEQ ID NO: 131) |

The invention claimed is:

1. A method of increasing seed size in a plant comprising: introducing a heterologous nucleic acid molecule encoding a CYP78A6 polypeptide which increases the expression of the CYP78A6 polypeptide within cells of a plant having reduced or abolished expression of a DA polypeptide, wherein the CYP78A6 polypeptide comprises an amino acid sequence having at least 95% sequence identity to SEQ ID NO: 42, wherein the plant having reduced or abolished expression of the DA polypeptide comprises a) a mutation in the nucleic acid sequence encoding the DA polypeptide which reduces or abolishes expression of the DA polypeptide or b) a heterologous nucleic acid which reduces or abolishes expression of the DA polypeptide;

wherein the seed size is increased relative to a control plant having reduced or abolished expression of the DA polypeptide without the heterologous nucleic acid encoding the CYP78A6 polypeptide.

2. A method of producing a plant with an increased seed size comprising:

introducing into a plant cell one or more nucleic acid constructs which increase expression of a CYP78A6 polypeptide and reduce or abolish expression of a DA polypeptide, wherein the one or more nucleic acid constructs comprise a) a heterologous nucleic acid encoding a CYP78A6 polypeptide, wherein said CYP78A6 polypeptide comprises an amino acid sequence having at least 95% sequence identity to SEQ ID NO 42; and b) a heterologous nucleic acid which reduces or abolishes expression of the DA polypeptide; and regenerating the plant from one or more transformed cells;

wherein the seed size is increased relative to a control plant having reduced or abolished expression of the DA polypeptide without the heterologous nucleic acid encoding the CYP78A6 polypeptide.

3. The method according to claim 2 wherein the CYP78A6 polypeptide comprises the amino acid sequence encoded by SEQ ID NO: 1.

4. The method according to claim 2 wherein the heterologous nucleic acid which reduces or abolishes expression of the DA polypeptide expresses a suppressor nucleic acid.

5. The method according to claim 2 wherein the heterologous nucleic acid encoding the CYP78A polypeptide is operably linked to a heterologous promoter.

6. The method according to claim 1 wherein the CYP78A6 polypeptide comprises the amino acid sequence encoded by SEQ ID NO: 1.

7. The method according to claim 1 wherein the heterologous nucleic acid encoding the CYP78A polypeptide is operably linked to a heterologous promoter.

8. The method according to claim 1 wherein the plant is a higher plant.

9. The method according to claim 1, wherein the plant is an agricultural plant selected from the group consisting of *Lithospermum erythrorhizon, Taxus* spp, tobacco, cucurbits, carrot, vegetable brassica, melons, capsicums, grape vines, lettuce, strawberry, oilseed brassica, sugar beet, wheat, barley, maize, rice, soyabeans, peas, sorghum, sunflower, tomato, potato, pepper, chrysanthemum, carnation, linseed, hemp and rye.

10. A method of increasing seed size in a plant comprising:
   obtaining a plant having reduced or abolished expression of a DA polypeptide, wherein the plant comprises a) a mutation in the nucleic acid sequence encoding the DA polypeptide which reduces or abolishes expression of the DA polypeptide or b) a heterologous nucleic acid which reduces or abolishes expression of the DA polypeptide; and
   introducing into the plant a heterologous nucleic acid molecule encoding a CYP78A6 polypeptide, wherein the CYP78A6 polypeptide comprises an amino acid sequence having at least 95% sequence identity to SEQ ID NO: 42;
   wherein the seed size is increased relative to a control plant having reduced or abolished expression of the DA polypeptide without the heterologous nucleic acid encoding the CYP78A6 polypeptide.

11. The method according to claim 10 wherein the plant having reduced or abolished expression of the DA polypeptide comprises a heterologous nucleic acid which expresses a suppressor nucleic acid which reduces expression of the DA polypeptide.

12. The method according to claim 10 wherein the plant having reduced or abolished expression of the DA polypeptide comprises a mutation in the nucleic acid sequence encoding the DA polypeptide.

13. The method according to claim 1 wherein the plant having reduced or abolished expression of the DA polypeptide comprises a heterologous nucleic acid which expresses a suppressor nucleic acid which reduces expression of the DA polypeptide.

14. The method according to claim 1 wherein the plant having reduced or abolished expression of the DA polypeptide comprises a mutation in the nucleic acid sequence encoding the DA polypeptide.

15. The method according to claim 4 wherein the suppressor nucleic acid is a short interfering RNA (siRNA), a short hairpin RNA (shRNA), or a micro-interfering RNA (miRNA).

* * * * *